United States Patent [19]

Arai et al.

[11] Patent Number: 4,832,038

[45] Date of Patent: May 23, 1989

[54] APPARATUS FOR MONITORING CARDIOVASCULAR REGULATION USING HEART RATE POWER SPECTRAL ANALYSIS

[75] Inventors: Makoto R. Arai; David Gordon; Laura E. McAlpine, all of Chicago, Ill.

[73] Assignee: The Board of Trustees of University of Illinois, Urbana, Ill.

[21] Appl. No.: 9,099

[22] Filed: Jan. 20, 1987

Related U.S. Application Data

[63] Continuation of Ser. No. 742,088, Jun. 5, 1985, abandoned.

[51] Int. Cl.[4] .................................... A61B 5/02
[52] U.S. Cl. ..................... 128/670; 128/702; 128/706
[58] Field of Search ........... 128/630, 670–671, 128/687–689, 695–697, 699–700, 702–705, 723–725; 364/415, 417

[56] References Cited

U.S. PATENT DOCUMENTS

| | | | |
|---|---|---|---|
| 3,612,041 | 10/1971 | Ragsdale | 128/705 |
| 3,698,386 | 10/1972 | Fried | 128/705 |
| 4,170,992 | 10/1979 | Dillman | 128/702 |
| 4,289,141 | 9/1981 | Covmier | 128/713 |
| 4,379,460 | 4/1983 | Judell | 128/671 |
| 4,422,458 | 12/1983 | Kravath | 128/671 |
| 4,432,375 | 2/1984 | Angel et al. | 128/706 |
| 4,463,764 | 8/1984 | Anderson et al. | 128/671 |
| 4,506,678 | 3/1985 | Russell et al. | 128/723 |
| 4,519,395 | 5/1985 | Hruskesky | 128/671 |
| 4,545,387 | 10/1985 | Balique | 128/667 |
| 4,549,551 | 10/1985 | Dyck et al. | 128/689 |
| 4,570,225 | 2/1986 | Lundy | 128/700 |
| 4,573,478 | 3/1986 | Arnold | 128/706 |

OTHER PUBLICATIONS

Does Aging Differentially Reduce Heart Rate Variablity Related to Respiration, Exp. Ag. Res., vol. 10, 1984.

Eur. J. Clin. Invest. 14 (2 part 2) 19 (1984), Spectral Anal. of Resting Variability of Some Circulatory Par. in Man, vol. 27, 1978, Physiolog. Bohemslovaca.

(List continued on next page.)

Primary Examiner—Francis Jaworski
Assistant Examiner—George Manuel
Attorney, Agent, or Firm—Marshall, O'Toole, Gerstein, Murray & Bicknell

[57] ABSTRACT

Apparatus for heart rate fluctuation power spectrum analysis obtains an electrocardiogram signal from an electrocardiograph machine and a respiratory rate signal from an electroplethysmograph machine. These signals are processed by a data acquisition system to provide output suitable for heart rate fluctuation power spectrum analysis by a mini-micro-computer.

Data manipulation includes correction of artifacts by substituting an appropriate heartbeat interval for detected heartbeat intervals for which the variance exceeds a preselected range of slewing rates. Trending of data and overlapping data analysis increase the analytical capabilities of the apparatus.

Methods of treatment for conditions manifested by abnormalities in a heart rate fluctuation power spectrum involve applying treatments when spectral abnormalities are observed. Specific abnormalities indicating the need for treatment include: a level below about 0.1 (beats/min.)$^2$ in the power spectrum of heart rate fluctuations at a frequency between about 0.04 and about 0.10 Hz; a marked increase to above about 10 (beats/min.)$^2$ in heart rate fluctuations at a frequency between 0.04 and about 0.10 Hz; and a ratio of the area under a heart rate fluctuation power spectrum of a peak at a frequency between about 0.04 and about 0.10 Hz to the area under a peak in the respiratory heart rate fluctuation power spectrum centered at the mean respiratory rate (as measured by the apparatus) at about 0.1 Hz as having a value less than 2.0 for longer than or equal to about one hour or as having an absolute value greater than about 50.

16 Claims, 17 Drawing Sheets

OTHER PUBLICATIONS

Power Spectra of Spontan. Var. of Indirect. Recorded B.P., Heart Rate and Aoral Blood Flow, Automedia, 1978, vol. 2, pp. 143–147.

Ident. Tech. Applied to Proc. of Sigs. from Cardiovascular Sys.; Med. Infor., vol. 10, No. 3223–3225.

Myocardial Infarction Diminishesboth Low and High Freq. QRS Pot.: Power Spec. Anal. of Lead II J. Electrocardiology 14(1), 1981, 57–60.

Highlights, Comp. Electrocardiographic Process, Aug. 1972.

Measurement of Heart-Rate Var.: Part II Hardware Digital Device for the Assessment of Heart Rate Variability, Med. Biol., Eng. & Comp. 1977, 15, 412–420.

Relationships Bet. Short-Term Blood-Pres., Med. & Biol. Eng. & Comp., 1985, 23352–358.

Automedica 1984, vol. 5, pp. 77–90, Sleep State Related Dynamics of Neonatal Heart Rate Fluctuations and Respiration Rhythms within Several Freq.

Non-Invasive Monitoring Tech. in New Surgical Intensive Care, Jour. of Clinical Engineering, Oct.–Dec. '79.

Putnam et al., "Journal of Clinical Engineering", vol. 5, No. 1, Jan.–Mar. 1980, pp. 56–58.

Kuo et al., "Computers in Cardiology", Sep. 1978, pp. 347–349.

Nygards et al., "Recognition of Ventricular Fibrillations Utilizing the Power.Spectrom of the ECG", pp. 393–396, no date available.

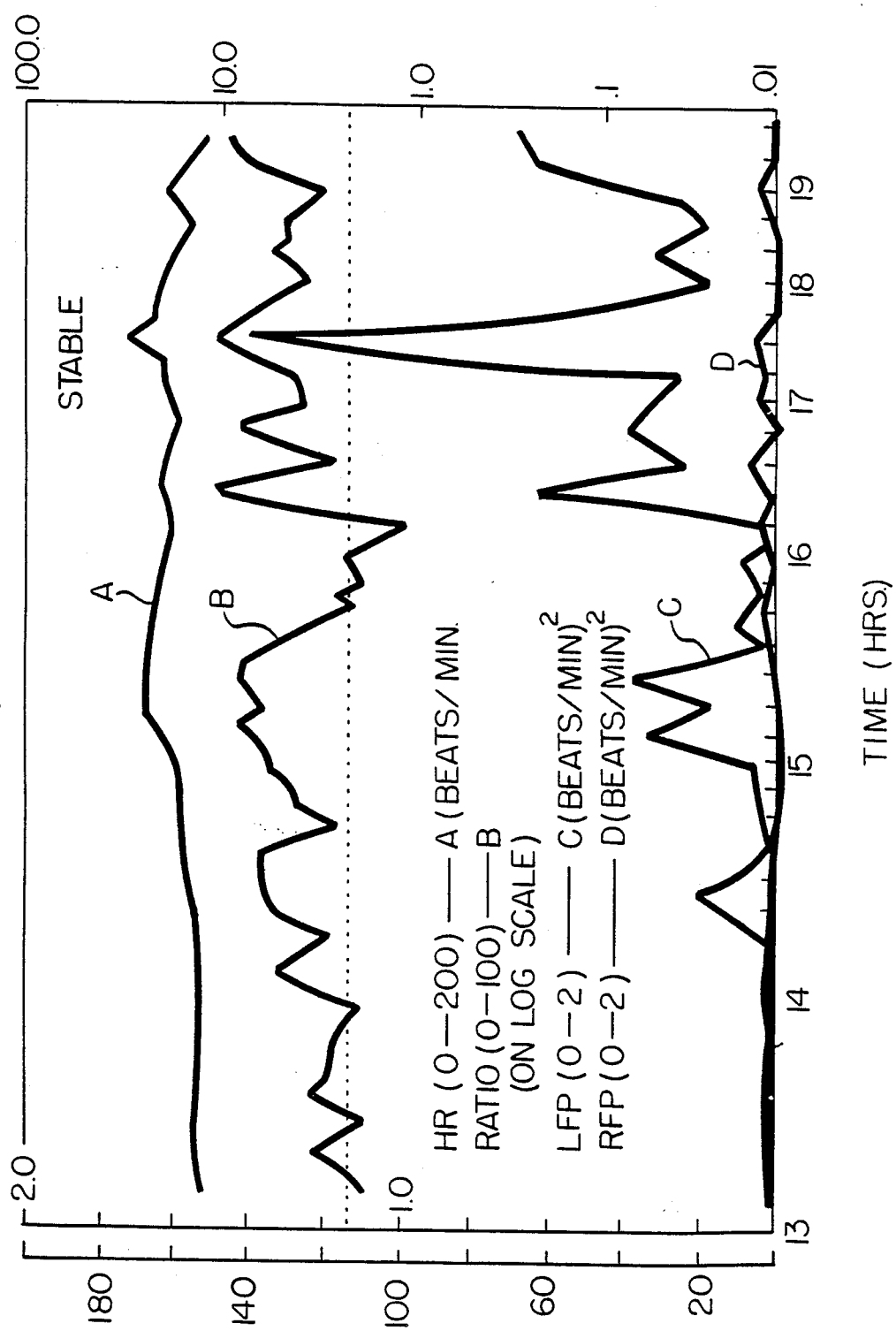

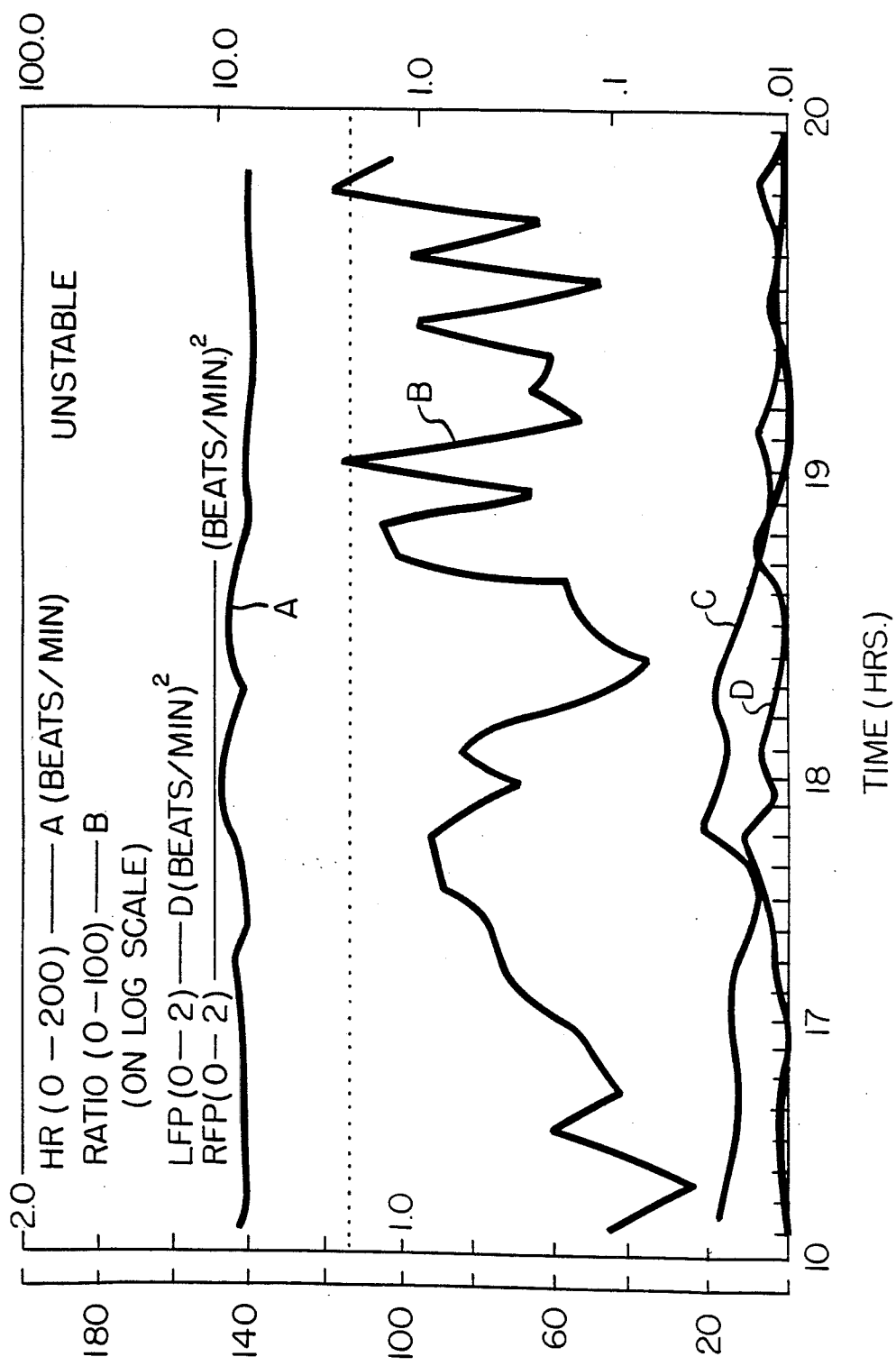

APPARATUS FOR MONITORING CARDIOVASCULAR REGULATION USING HEART RATE POWER SPECTRAL ANALYSIS

BACKGROUND OF THE INVENTION

This application is a continuation of application Ser. No. 742,088, filed June 5, 1985, and now abandoned.

The present invention relates in general to methods and apparatus for monitoring cardiovascular regulation and in particular to methods and apparatus for heart rate spectral analysis.

Changes in cardiovascular regulation associated with congestive heart failure include attenuation of activity in the parasympathetic division of the autonomic nervous system, enhancement of activity in the sympathetic division of the autonomic nervous system, cardiac catecholamine depletion, down regulation of the beta-receptor system, increased renin-angiotensin system activity, and alteration of baroreceptor function. All of these regulatory changes require either specific clinical manipulations, such as a stress test, a Valsalva maneuver, or the like, and/or invasive maneuvers, such as cardiac biopsy, plasma catecholamine measurement, or the like, in order to determine the extent of regulatory dysfunction and its impact upon the clinical state of the patient and upon prognoses for the patient. These procedures are time consuming, and generally do not permit the formation of a clinical judgment and subsequent action within the timeframe of the course of treatment for critically ill patients in an Intensive Care Unit.

Fluctuations from heartbeat to heartbeat in measured properties of the circulatory system reflect both the presence of a variety of naturally occurring physiological disturbances of the circulatory system homeostasis, and the dynamic response of cardiovascular control systems to these disturbances. For example, the cyclic variation in intrathoracic pressure which accompanies breathing mechanically affects the return of venous blood to the heart and also affects blood pressure in pulmonary vessels and in the aorta. The variation in intrathoracic pressure is also coupled to a cyclic variation in heart rate through a neural mechanism mediated by the central nervous system. Furthermore, the resulting cyclic variation in arterial blood pressure impinges on heart rate through a reflex, known as the baroreceptor reflex, which is mediated by the autonomic nervous system. Disturbances in cardiovascular homeostasis also occur with fluctuations in the resistance of peripheral blood vessels as vascular beds regulate local blood flow to match supply with demand. These fluctuations in peripheral resistance may perturb central blood pressure and through the baroreceptor reflex, may also lead to a compensatory variation in heart rate.

Many types of medical instruments exist for studying heart rate variability. The instantaneous rate-meter is perhaps the earliest such instrument. This meter measures each RR interval through analog or digital circuitry and displays the instantaneous heart rate.

An improvement in the rate-meter is achieved by performing first order statistical evaluation on the RR-intervals. With mini- and micro-computer systems histogram displays of RR-interval differences may be generated along with their mean and standard deviations.

Another technique for heart rate variability analysis involves the study of spectral content of the instantaneous heart rate time series. In one approach to spectral analysis in animals, the computations are done on a computer. Akselrod, et al., *Science*, 213, 220-222 (1981) Hyndman, et al., *Automedica*, 1, 239-252 (1975). Such systems analyze data recorded on magnetic or punched tape. However, not only do these systems introduce additional errors during the recording process, they do not perform in real time. Furthermore, these systems are not multichannel in nature.

A Sparse Discrete Fourier Transform algorithm which may be implemented on a personal computer (CBM 2016) and which may perform on-line monitoring of heart rate variability, based on a low pass filtered cardiac event series is disclosed in Rompelman, et al., *IEEE Trans. Biomed. Engineering*, BME-29, 503-510 (1982). A specialized hardware device also exists for low pass filtering the cardiac event series by a stepwise convolution to create the low pass filtered cardiac event series. Coenen, et al., *Medical and Biological Engineering and Computing*, 15, 423-430 (1977). Nevertheless, these instruments posses a limited band width and a limited frequency resolution capability.

There exists a need for an instrument which provides multi-channel spectral analysis of an instantaneous heart rate and of a respiratory activity time series. There also exists a need for an instrument wherein such calculations are performed in real time at the bedside.

SUMMARY OF THE INVENTION

An apparatus according to the present invention corrects artifacts in a series of heartbeats. Means for collecting a series of heartbeat samples are coupled to means for determining a mean interval between heartbeats. Means for identifying a mean variance among the intervals between heartbeats samples are coupled to means for establishing an acceptable of slewing rates as a function of the mean variance. Means for particularizing the absolute value of the slewing rate of a heartbeat sample relative to the mean interval are coupled to the means to determining and means for substituting the mean interval between heartbeats for all heartbeat interval samples having an absolute outside the range of acceptable slewing rates are coupled to the means for particularizing.

A method according to the present invention corrects artifacts in a series of heartbeats. A series of heartbeat interval samples is collected and an appropriate interval between heartbeats is determined. Variances in the intervals between heartbeats are identified and an acceptable range of slewing rates is established as a function of a mean variance. An absolute value of the slewing rate of a heartbeat sample relative to the mean interval was particularized. An appropriate interval is substituted for all heartbeat interval samples having an absolute value outside the range of acceptable slewing rates.

Apparatus according to the present invention calibrates a heart rate power spectrum monitor. Means for supplying a signal simulating a heart rate, means for generating a signal simulating a respiratory frequency fluctuation in heart rate and means for providing a signal simulating a low frequency fluctuation in heart rate are coupled to means for applying signals from these means to a heart rate power spectrum analyzer.

Apparatus according to the present invention performs heart rate fluctuation power spectral analysis. Means for providing an electrocardiogram signal and means for supplying electroplethysmogram signal are coupled to means for obtaining a heart rate fluctuation power spectrum from an electrocardiogram signal and from an electroplethysmogram signal. Real time means for displaying a heart rate fluctuation power spectrum are coupled to the means for obtaining.

Apparatus according to the present invention trends heart rate fluctuation power spectral data. Means for providing an electrocardiogram signal and the means for supplying an electroplethysmogram signal are coupled to means for obtaining a heart rate fluctuation power spectrum from an electrocardiogram signal and from an electroplethysmogram signal. Means for storing heart rate fluctuation power spectral data are coupled to means for obtaining. Addressable means for transmitting stored heart rate fluctuation power spectral data are coupled to the means for storing and means for converting heart rate fluctuation power spectral data into graphic form are coupled to the addressable means for transmitting. Real time means for displaying heart rate fluctuation power spectra are coupled to the means for converting.

A method according to the present invention treats conditions related to malfunctions of the cardiovascular control system. A power spectrum of heart rate fluctuations in the patient are monitored. A level below about 0.1 (beats/min.)$^2$ in the power spectrum of heart rate fluctuations is identified at a frequency between about 0.04 and about 0.10 Hz as indicative of cardiovascular stress. Procedures are applied to treat the condition and thereby to increase the level of heart rate fluctuations at a frequency between about 0.04 and about 0.10 Hz.

A method according to the present invention treats conditions related to malfunctions of the cardiovascular control system in a patient. A power spectrum of heart rate fluctuations is monitored in the patient. A marked increase to above about 10 (beats/min.)$^2$ in heart rate fluctuations at a frequency between about 0.04 to about 0.10 Hz is identified as indicative of cardiovascular instability. Procedures are applied to treat the condition and thereby to decrease the level of heart rate fluctuations between about 0.04 and about 0.10 Hz.

Yet another method according to the present invention treats conditions related to malfunctions of the cardiovascular control system in a patient. A power spectrum of heart rate fluctuations in the patient is monitored. A ratio of the area under a heart rate power spectrum peak at a frequency between about 0.04 and 0.10 Hz to the area under a peak in the respiratory power spectrum centered at the mean respiratory rate about 0.1 Hz is identified as having an absolute value less than 2.0 for longer than or equal to about one hour as indicating of cardiac instability. Procedures are applied to treat the condition and thereby to increase the ratio.

Still another method according to the present invention treats conditions related to malfunctions of the cardiovascular control system in a patient. A power spectrum of heart rate fluctuations in the patient is monitored. A ratio of the area under a heart rate power spectrum peak at a frequency between about 0.04 and 0.10 Hz to the area under a peak in the respiratory power spectrum centered at the mean respiratory rate about 0.1 Hz is identified as having an absolute value greater than or about 50 as indicating of cardiovascular stress. Procedures are applied to treat the condition and thereby to increase the ratio.

BRIEF DESCRIPTION OF THE DRAWINGS

FIG. 10 illustrates a trend for a stable patient according to the present invention;

FIG. 11 illustrates a trend display for an unstable patient according to the present invention;

DETAILED DESCRIPTION

Figure 1:
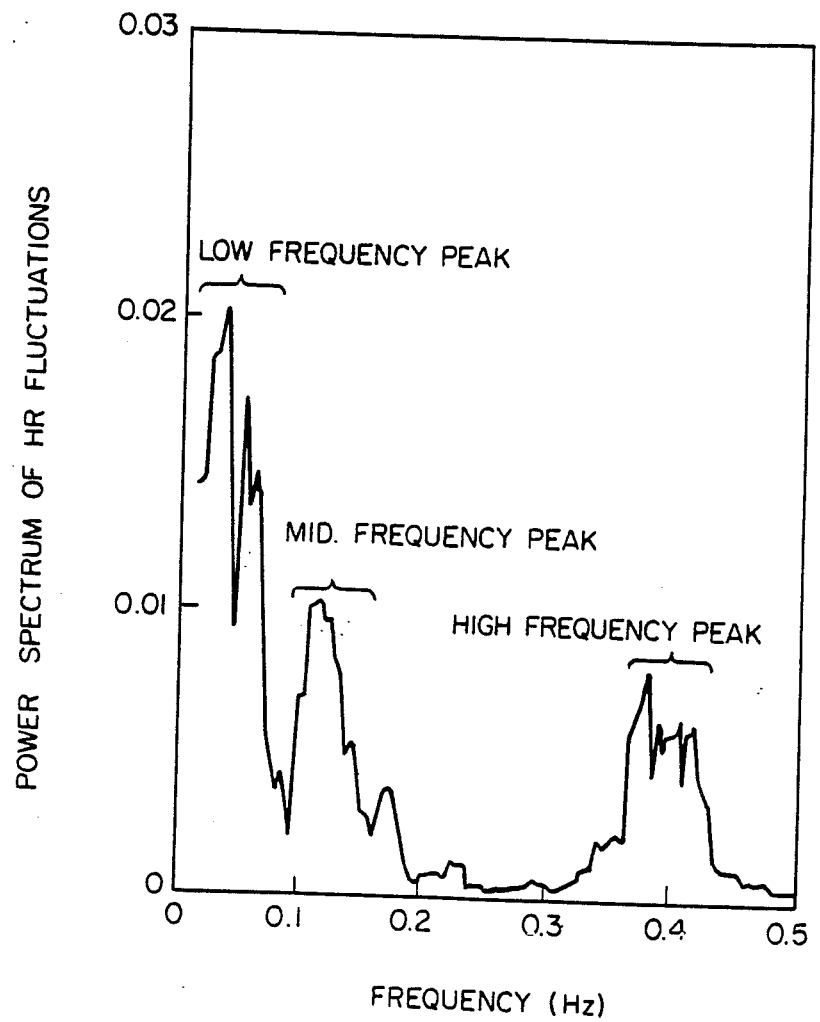
FIG. 1 illustrates low frequency, mid-frequency and high frequency in the power spectrum of heart rate fluctuations in a dog according to the prior art.

Power spectral methods may be used to analyze the frequency content of fluctuations in heart rate and other hemodynamic parameters. Hyndman, et al., *Nature*, 233, 339–341 (1971); Sayers, *Ergonomics*, 16, 17–32 (1973). Short term (i.e., on a time scale of seconds to minutes) fluctuations in these parameters are concentrated in three principal spectral peaks as illustrated for a canine model in FIG. 1. Akselrod, et al., supra. One peak is centered at the respiratory frequency; this peak shifts with changes in the respiratory rate. The second identifiable spectral peak, the mid-frequency peak, occurs typically between 0.1 and 0.15 Hz. The oscillations associated with this second peak occur at 6–9 cycles per minute, a considerably lower frequency than the respiratory frequency, and are related to the frequency response of the baroreceptor reflex. The third peak of the spectrum typically occurs in the frequency band of 0.04 to 0.10 Hz. This low frequency peak is related to thermoregulatory fluctuations in vasomotor tone.

In one approach to the spectral analysis of heart rate, properties of the heart rate fluctuations in the conscious dog may be related to the activity of three cardiovascular control systems—the parasympathetic nervous system, the sympathetic nervous system and the renin-angiotensin system. Akselrod, et al., *Science*, 213, 220-223 (1981). This model is further elaborated in Akselrod, et al., "Hemodynamic Regulation: Investigation by Spectral Analysis" (In Press). Heart rate fluctuations occurring at frequencies above roughly 0.1 Hz are mediated solely by the parasympathetic system. Blockade of the renin-angiotensin system leads to a dramatic increase in the amplitude of the low frequency peak. The effects of an autonomic blockade also exist in humans and changes in body posture alter sympathetic-parasympathetic balance as measured by the heart rate power spectrum. Pomeranz, et al., *Am. J. Physiol.*, 248, H151-H153 (1985).

Figure 2:
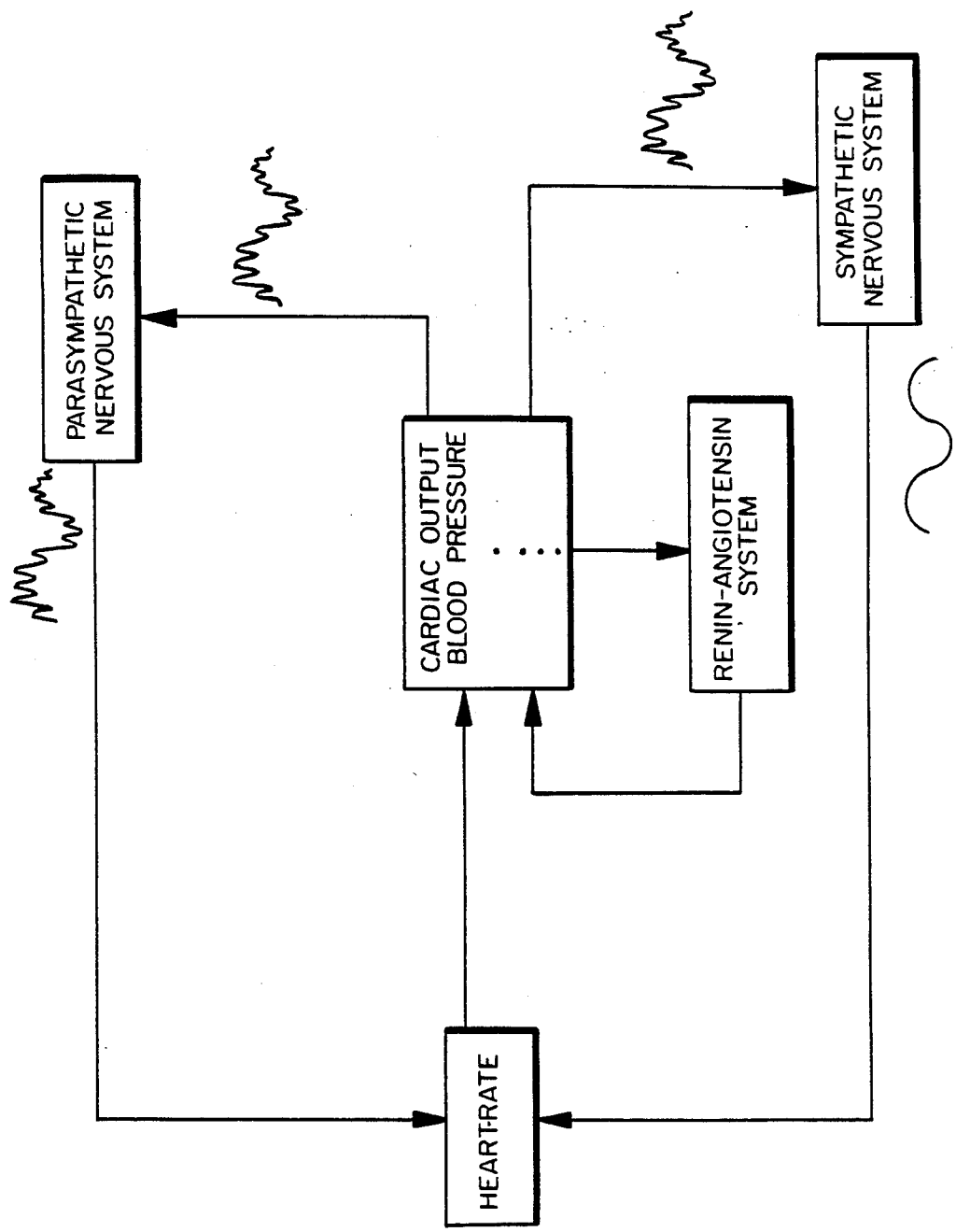
FIG. 2 illustrates aspects of the cardiovascular control system according to the prior art.

A simple model of the short term cardiovascular control system is illustrated in FIG. 2. Akselrod, et al., supra. In this model, heart rate is directly modulated by the sympathetic and parasympathetic nervous systems. Through a variety of receptors both these systems sense, fluctuations in cardiovascular parameters including arterial and venous pressures, vascular volumes, and correlates of blood flow and oxygenation. The parasympathetic system may respond over a wide frequency range while the sympathetic system may only respond at relatively low frequencies below roughly 0.1 Hz.

A hypothesis was proposed in Akselrod, et al., *Science*, 213, 220-223 (1981), that fluctuations in vasomotor tone associated with the low frequency heart rate fluctuations are not solely related to thermoregulation but also reflect local adjustment to resistance in individual beds of blood vessels in order to match local blood flow to local metabolic demand. Such fluctuations in peripheral vasomotor tone lead to fluctuations in central blood pressures which are in turn sensed by pressoreceptors. Stimulation of these pressoreceptors occasions an autonomically mediated baroreceptor reflex, which leads to compensatory fluctuations in heart rate at the corresponding frequency. In addition, the renin-angiotensin hormonal system senses blood pressure fluctuations and, through the elaboration of a substance called angiotensin II, plays the role of the guardian of the overall peripheral vascular resistance. Blockade of the renin-angiotensin system by a converting enzyme inhibitor, may remove this damping influence and may permit increased fluctuations in blood pressure and increased compensatory fluctuations in heart rate in the low frequency regime.

The critically ill infant or child prior to, during, and after cardiac surgery at times exhibits marked changes in heart rate, blood pressure, and peripheral perfusion. These changes may be of no clinical consequence or they may indicate the existence of a major unrecognized pathology whose first outward manifestation may be sudden cardiac arrest. To be able to quantify cardiovascular regulatory reserve permits objective assessment of a patient's cardiovascular stability as well as their response to medical and surgical interventions intended to improve cardiovascular function.

Spectral analysis of tape recorded records of ECG and respiratory activity from patients with complex congenital heart diseases and myocarditis reveals peculiarities in low frequency heart rate fluctuations not seen in studies of healthy children and adults. In particular: (1) low levels of low frequency heart rate fluctuations are noted for critically ill patients in congestive heart failure, which levels revert to normal after surgical or medical treatment and (2) a marked increase in low frequency heart rate fluctuations is observed in patients with otherwise undetected cardiac tamponade.

A transitional microprocessor-based monitoring instrument, which utilized a Z-80 microprocessor and a S-100 bus, was constructed along with a data acquisition system which interfaced the microprocessor with a Hewlett-Packard 78341 patient monitor.

A prototype system is described in Jerome C. Tu, "Microprocessor System for Real-Time Spectral Analysis Physiological Signals," Master of Department of Electrical Engineering and Computer Sciences, Science Thesis, Massachusetts Institute of Technology (1984) which is hereby incorporated by reference herein. An electrocardiogram (ECG) was inputed into a the data acquisition system for this prototype system from a patient monitor.

In the data acquisition system the analog voltage signal of the ECG was applied to the input of a variable frequency voltage controlled oscillator in the data acquisition system. A counter coupled to the output of the VCO provided a digital representation of the voltage associated with the ECG peaks. The largest voltage peak, called the R voltage peak and associated in the ECG with ventricular contraction, was used to trigger a clock. Each R peak load the value of the clock into a holding register and restarted the clock. The value of the clock provided a measure of the heart rate as the inverse of the time between beats. (i.e., as the RR interval)

The regular respiratory signal of a patient on a ventilator employed to obtain a respiratory spectrum was similarly obtained through a VCO The respiratory frequency had to be manually entered to establish a fixed window for computing the power in the heart rate power spectrum in the respiratory peak.

Every 256 seconds the digitized ECG RR intervals were inputed into the microprocessor from the data acquisition system. A smoothed heart rate "tachometer wave form" was created as follows: (1) The instantaneous heart rate time series was computed from the stored RR intervals; (2) A 1024 point time series of the instantaneous heart rate was computed from the stored instantaneous heart rate time series by sampling the latter at 4 Hz; and (3) The mean heart rate computed from the 1024-point time series of instantaneous heart rate was subtracted from the smoothed series resulting in a "tachometer waveform"; The heart rate power spectrum was computed from the heart rate "tachometer waveform" as follows: (1) A 1024-Point Fast Fourier Transform was computed using 1024 points of the tachometer cardiac tachometer waveform; and (2) The heart rate power spectrum was computed by squaring the absolute value of the previously calculated transform.

As new data was inputted into the computer's buffer, the results of the smoothed cardiac tachometer signal, power spectrum and integral of power spectrum were outputted onto a printer. Thus for every 256-second time interval, a spectral representation of the preceding 256 seconds of instantaneous heart rate data was exhibited.

From the above data, the area under the low frequency peak (LFP) between 0.04 and 0.1 Hz and the area under the respiratory frequency peak (RFP) within a peak width window of 0.2 Hz were determined. Trend graphs of LFP, RFP, and LFP/RFP ratio were created. 256 second data segments were rejected if (1) the patient was not in sinus rhythm, (2) transients and/or artifact were present on the cardiac "tachometer wave form", and (3) the LFP/RFP ratios were greater than 2 standard deviations from the mean for the study period.

The practical problems associated with the prototype monitoring instrument included the extremely tedious calculations required for use of the prototype with free-breathing patients and the large amount of data (as much as 50%, in some instances) which had to be discarded due to the presence of motion artifacts. These artifacts resulted from virtually any disturbance of the patient, even one so slight as holding the patient's hand. The prototype system had no capacity to identify or reject artifacts or to examine the data for dropped beats and premature triggers.

Figure 3:
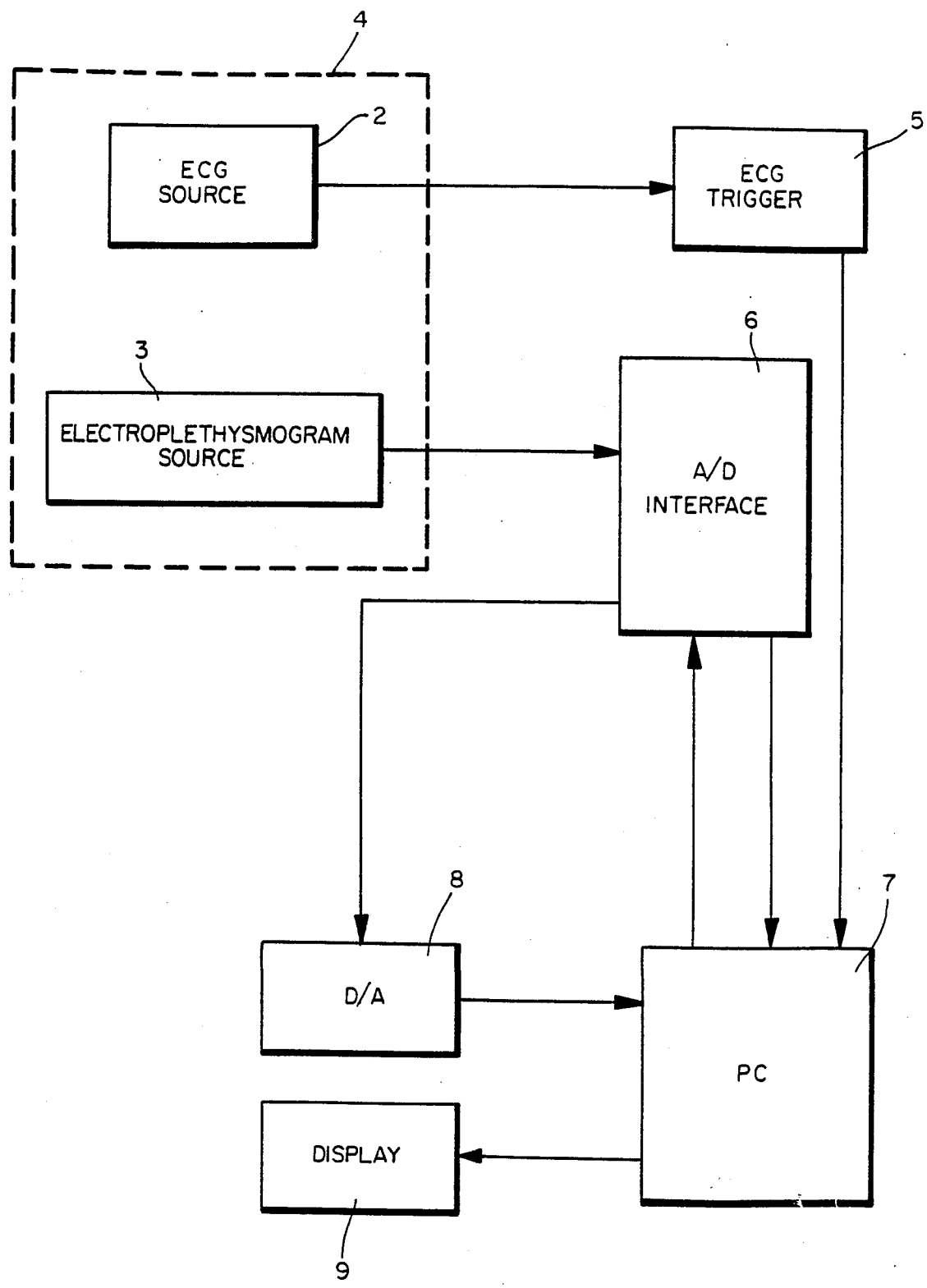
FIG. 3 is a block diagram of apparatus for heart rate fluctuation power spectral analysis according to the present invention.

Upon reviewing clinical studies performed using the prototype, it was discovered that not only were attenuated low frequency heart rate fluctuations associated with a severely compromised regulatory reserve but also that the ratio of the power in the heart rate power spectrum at low frequency to the power at the respiratory frequency provided an even sharper discriminatory index between stable and critically ill patients as illustrated in FIG. 3. In addition it was noted that this ratio was markedly elevated in the setting of moderate to severe congestive heart failure, cardiac tamponade, and prior to the development of malignant ventricular arrthymias.

A low value for LFP/RFP ($<2$) which is sustained for greater than one hour or a value greater than or about 50 is associated with a clinical course characterized by cardiac arrest and/or profound hypotension. At times this ratio may be the only clinical indicator of cardiovascular instability. The LFP/RFP ratio provides a sensitive and specific index of cardiovascular instability and may provide a clinically important continuous non-invasive probe of cardiovascular stability.

In order to further examine the diagnostic value of the power spectrum of heart rate fluctuations and to overcome the difficulties with the prototype, a multipurpose microcomputer based system including data basing, instantaneous heart rate and respiratory activity spectral monitor was developed using a Hewlett Packard Series 200 Computer and Multiprogrammer as available from Hewlett-Packard. Advantages over the original design include: (1) error correcting routines which correct automatically for motion artifact and missed triggerings of the EKG, thus permitting a substantial increase ($>30\%$) in available data; (2) automated trending of spectral densities along with the instanteous heart rate and respiratory activity time series; and (3) a data basing program which permits accurate temporal correlation of spectral densities with virtually every clinical intervention, routine ventilatory changes, hemodynamic, fluid monitoring and laboratory results. Software incorporating these advantages is included herein as Appendix A.

In a further improvement, programs and a data acquisition system and programs were developed for use with an IBM PC or compatible personal computer. This improvement is illustrated in FIGS. 3 through 12.

In FIG. 3, a block diagram of apparatus according to the present invention is illustrated. In FIG. 3, a source of an ECG signal 2 and a source of an electroplythsmogram signal 3 are contained within the patient monitor 4. A patient monitor for use with the present invention may be the system 2 infant monitor available from AR-VEE, Incorporated, Battle Creek, Mich. Source 2 is connected to an ECG trigger 5 which is in turn connected to a personal computer 7. Source 3 is connected to an analog to digital interface 6. Interface 6 is connected to analog converter 8 which is connected in turn to a personal computer 7. Personal computer 7 receives input from and provides output to interface 6. Personal computer 7 is connected to a display 9.

Source 2 receives input from pregelled electrodes adhered to the chest wall and thigh of the patient. Source senses respiratory activity through a pair of electrodes by the impedance method. Personal computer 7 and display 9 are available as an IBM and a compatible display available from IBM, Incorporated, Armonk, N.Y. Elements 5, 6 and 8 are described below.

Figure 4:
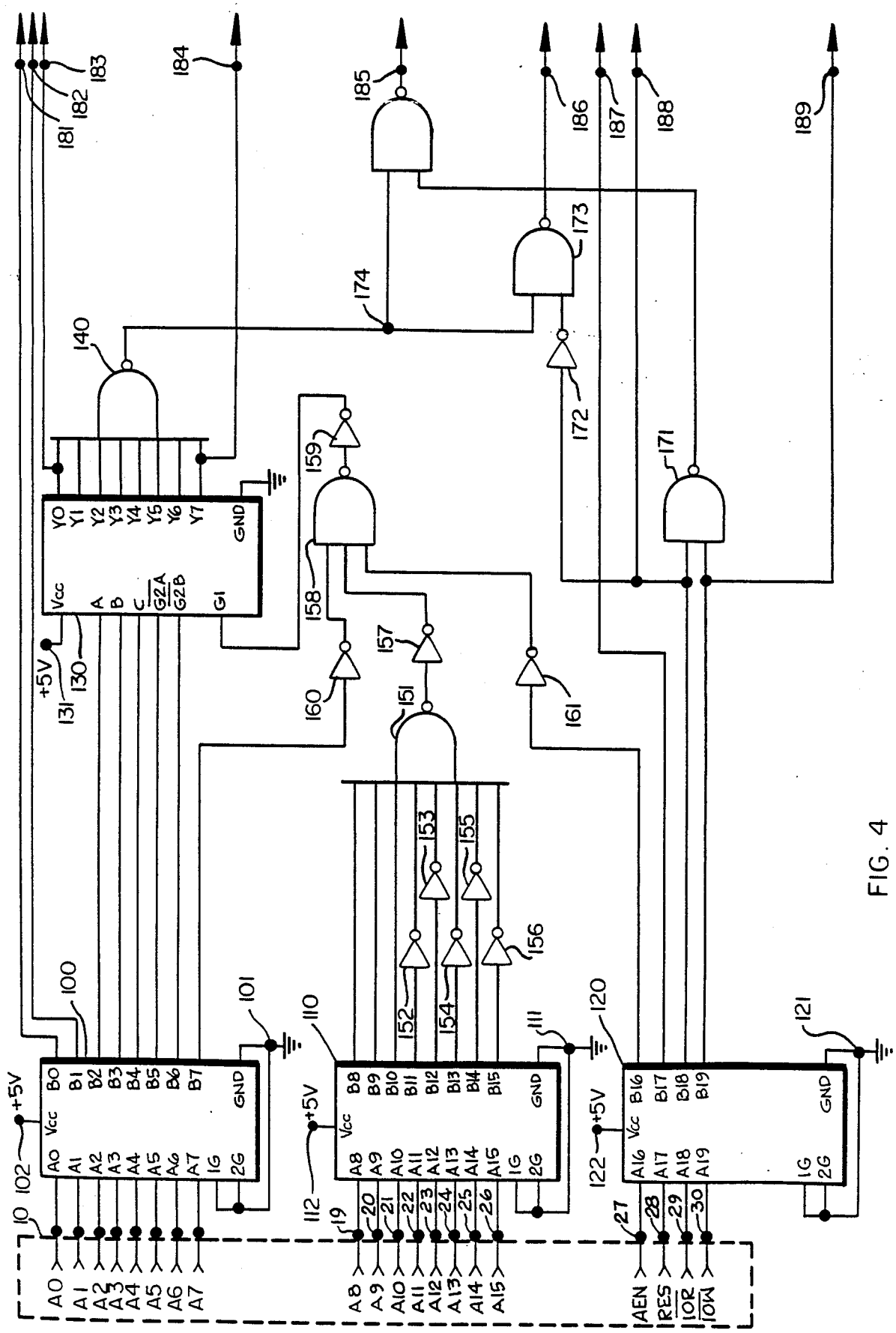
FIG. 4 illustrates address buffers and address decoding in a data acquisition device according to the present invention.

In a data acquisition device according to the present invention, address buffers and address decoding, as illustrated in FIG. 4, receive input from a PC bus 10. Nodes 11, 12, 13, 14, 15, 16, 17, 18, 19, 20, 21, 22, 23, 24, 25 and 26 are respectively connected to address lines A0, A1, A2, A3, A4, A5, A6, A7, A8, A9, A10, A11, A12, A13, A14 and A15 in PC bus 10. A first address buffer 100 has address input A0, A1, A2, A3, A4, A5, A6 and A7 which are respectively connected to nodes 11–18. Buffer 100 also has two gate inputs, 1G and 2G, which are connected to ground along with a ground output GND of buffer 100. A power supply input $V_{CC}$ of buffer 100 is connected to a node 102 at a potential of +5 volts.

A second address buffer 110 has address inputs A8, A9, A10, A11, A12, A13, A14 and A15 which are respectively connected to nodes 19–26. Buffer 110 also has two gate inputs, 1G and 2G, which are connected by way of a node 111 to ground. A ground GND output of buffer 110 is also connected to a common potential. Buffer 110 has a power supply input $V_{CC}$ which is connected to a node 112 at a potential of +5 volts.

A status buffer 120 has address inputs A16, A17, A18 and A19 which are respectively connected to nodes 27, 28, 29 and 30. Nodes 27–30 are respectively connected to an address enable line AEN, a reset line RES, an input/output read line IOR and an input/output write line IOW in PC bus 10. Buffer 120 has two gate inputs, 1G and 2G, which are connected by way of a node 121 to ground. A ground output GND of buffer 120 is also connected to ground by way of node 121. A power supply input $V_{CC}$ of buffer 120 is connected to a node 122 at a potential of +5 volts.

According to the present invention, a data acquisition system board which is both reliable and compatible with a personal computer (PC) bus, preferably adheres to the timing requirements and the loading requirements supplied by the PC bus. This means that all connections to the PC bus should be buffered so that the load provided at any input or output of the bus is equivalent to 1 LS TTL load and high speed CMOS integrated circuits are provided for this purpose.

Because there are multiple devices attached to the address bus, address buffers are provided. This is done by buffers 100 and 110. Parts used for buffers 100, 110 and 120 are normally gated, but the gate enables, 1G and 2G, are tied to ground so that the gates are always enabled. Some of the status lines on the PC bus are buffered by a chip 120, in particular: the reset line RES; the read and write lines IOR and IOW respectively, for the input/output (IO) channels; and the address enable AEN.

An address decoder according to the present invention, as illustrated in FIG. 4, includes a three to eight line decoder 130. Decoder 130 has three line inputs A, B and C which are respectively connected to outputs B2, B3 and B4 of buffer 100. Decoder 130 has gate inputs G2A and G2B which are respectively connected to outputs B5 and B6 of buffer 100. A power supply VCC input of decoder 130 is connected to a node 131 at a potential of +5 volts while a ground GND output of decoder 130 is connected to a common potential. Outputs Y0, Y1, Y2, Y3, Y4, Y5, Y6 and Y7 are connected to inputs of a NAND gate 140.

A NAND gate 151 has an input connected to each of outputs B8, B9 and B10 of buffer 110. An output B10 of buffer 110 is connected to an input of an inverter 152 which has an output connected to an input of NAND gate 151. Similarly, outputs B12, B13, B14 and B15 of buffer 110 are respectively connected to an input of each of inverters 153, 154, 155 and 156, each of which has an output connected to an input of NAND gate 151. NAND gate 151 has an output connected to an input of an inverter 157.

A NAND gate 158 has an input connected to an output of inverter 157 and has an output connected to an input of an inverter 159. An inverter 160 has an input connected to an output B7 of buffer 100 and has an output connected to an input of NAND gate 158. Likewise, an inverter 161 has an input connected to an output B16 of buffer 120 and has an output connected to an input of NAND 158. An output of inverter 159 is connected to a gate input G1 of decoder 130.

So that devices on the board are recognized at a particular IO channel address, address decoding is provided. In this particular case, a fixed address location, location hex 700 to 71F (a total of 32 channels), is used. The decoding of the fixed upper bytes in the address is provided by a combination of nine inverting gates, 152, 153, 154, 155, 156, 157, 159, 160 and 161, and NAND gates 151 and 158. These elements, in combination with decoder 140, provide chip enable signals which can be used to select one or another of the functional chips on our board. Each of the eight chip enable signals correspond to a block of four channels. For example, a chip select #0 from output to of decoder 140 corresponds to channels hex 700, 701, 702 and 703.

A logic network for driving a data buffer, as illustrated in FIG. 4, includes a NAND gate 171, an inverter 172 and a NAND gate 173. An output of inverter 172 is connected to a first input of NAND gate 173 while an output of NAND gate 140 is connected by way of a node 174 to a second input of NAND gate 173 and to a first input of a NAND gate 175. A second input of NAND gate 175 is connected to an output of NAND gate 171.

In addition, a node 181 is connected to an output B0 of buffer 100. A node 182 is connected to an output B1 of buffer 100. Nodes 183 and 184 are respectively connected to output Y0 and output Y7 of decoder 130. Nodes 185 and 186 are respectively connected to an output of NAND gate 175 and an output of NAND gate 173. A node 187 is connected to an output B17 of buffer 120. A node 188 is connected an output B18 of buffer 120, to a first input of NAND gate 171 and to an input of inverter 172. A node 189 is connected to a second input of NAND 171 and to an output B19 of buffer 120.

Additional chips are used to provide logic which drives a data buffer connected to a data bus. The data bus is bidirectional in order to both transmit data to and from devices on the board. In order that this be accomplished, one must determine at any time whether or not data is either being read from or written to the board. This logic is supplied by NAND gate 171, NAND gate 173, AND gate 175 and inverter 172 which translates the read and write signals for the input/output (IO) channel into an output enable and a transmit enable for a data buffer. The apparatus of FIG. 5 may be used to properly interface a device to the PC bus 10.

Figure 5:
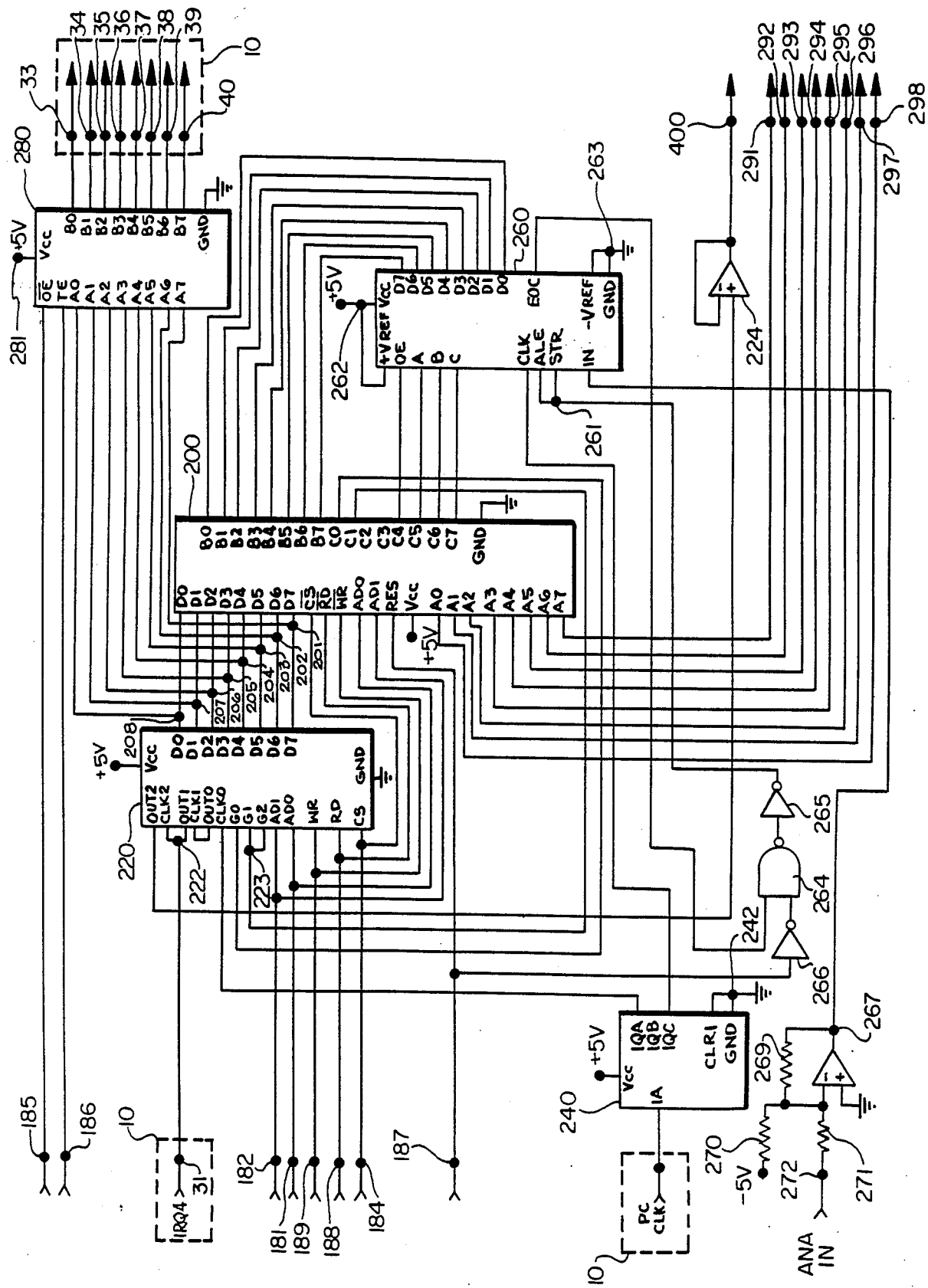
FIG. 5 illustrates components according to the present invention for interfacing an ECG apparatus with a personal computer according to the present invention.

As illustrated in FIG. 5, components according to the present invention for interfacing an ECG apparatus with a personal computer include a port expander 200. Port expander 200 has four sets of 8 nodes each, the four sets correspond to four ports A, B, C and D. The outputs for port A are A0, A1, A2, A3, A4, A5, A6 and A7. The inputs corresponding to port B are B0, B1, B2, B3, B4, B5, B6 and B7. Outputs corresponding to port C are C0, C1, C2, C3, C4, C5, C6 and C7. A set of outputs corresponding to port D includes D0, D1, D2, D3, D4, D5, D6 and D7. Expander 200 has a chip select input CS connected to node 184. Expander 200 also has a read input RD and a write input WR respectively connected to nodes 188 and 189. Expander 200 has two address inputs, AD0 and AD1 which are respectively connected to nodes 181 and 182. A reset RES input of expander 200 is connected to node 187. Inputs A0, A1, A2, A3, A4, A5, A6, A7 are respectively connected to nodes 291, 292, 293, 294, 295, 296, 297 and 298. Outputs D0–D7, are respectively connected to nodes 208, 207, 206, 205, 204, 203, 202 and 201 which defines a data bus. A power supply input $V_{CC}$ of expander 200 is connected to a node 209 at a potential of +5 volts. A ground GND output of expander 200 is connected to a common potential.

Port expander 200 is used to overcome the low speed of the data bus on both A/D converter 260 and a digital analog converter. This permits slowing down the read and write signals inasmuch as they may be provided artificially on port C of expander 200 or as chip select signals from address decoder 130. Port C of expander 200 is a bit addressable register which allows one to individually select or deselect bits without affecting any of the other bits. This is accomplished by sending a one byte command to expander 200. Because expander 200 is given the control function, the address of expander 200 is the highest address in the set of channels. In other words, expander 200 occupies IO channels hex 71C to hex 71F. The ports A, B and C on expander 200 are addresses 71C, 71D and 71E, respectively, and the control register internal for expander is at input/output I/O channel 71F.

A timer 220 according to the present invention has two address inputs, AD0 and AD1 respectively connected to nodes 181 and 182. Timer 220 also has a read input RD connected to node 188, a write input WR connected to node 189 and a chip select input CS connected to node 184. A first gate input G0 is connected to the C0 of expander 200 while a second gate input G1 and a third gate input G2 are both connected by way of a node 223 to output C1 of expander 200. Timer 220 has three clock inputs CLK0, CLK1 and CLK2, of which CLK1 is connected by way of node 222 to an output OUT0 of timer 220 and input CLK2 is connected to an output OUT1 of timer 221 by way of a node 31. An interrupt request line IRQ4 within PC bus 10 is also connected to node 31.

An output OUT2 is connected to a non-inverting input of an operational amplifier 224, an inverting input and a output of which is connected to a node 400.

A power supply input $V_{CC}$ of timer 220 is connected to a node 221 which at a potential of +5 volts.

Timer 221 has seven outputs D0, D1, D2, D3, D4, D5, D6 and D7 which are respectively connected to nodes 208, 207, 206, 205, 204, 203, 202 and 201. A ground output of timer 220 is connected to a common potential.

Timer 220 includes three 16 bit timers which are addressed at hex locations 704, 705, 706, and 707. In other words, they are provided by chip select 1. The three clocks on timer 220 are connected in series which effectively converts it into a 48 bit counter. However, in the operation of the program, some of the bits in this counter are thrown away because the reset values are less than 65,536. The three clock registers are used in the following way. Counter 0, corresponding to input CLK 0, counts an onboard time base to be discussed later and provides an output which gives the minimum resolution of the heart rate counting. In other words, it provides the counter time base for measuring the heart rate. Counter #1, corresponding to input CLK 1, counts the heart rate counter time base and provides as an output an interrupt at IRQ4. This signal drives the sampling of the respiratory signal at a constant frequency, and is also used to measure interbeat intervals. In the standard data collecting mode, where one is interested in measuring the respiratory signal at 4 hertz intervals, this means that the counter 0 is set to generate output pulses at 11 microsec. intervals and that these pulses are in turn counted by counter 1 to generate 4 hertz pulses which are used to drive data acquisition from the respiratory signal. The last counter register, counter #2, corresponding to input CLK2, is used to count the number of respiratory sampling pulses which have been supplied. This functions as an overflow counter and always has the reset value of 65,536. Thus the counter measuring interbeat intervals effectively overflows only every 65,536 respiratory sampling times, which is far in excess of what would be required to recover dropped beats which occur because the heart rate is not adequately detected.

A counter 240 has an input 1A connected to a clock line PC CLK in PC bus 10 by way of a node 32. Counter 240 has a first output 1QA connected to the CLK0 input of timer 220. Counter 240 has a secnd output 1QB and has a third output 1QC. A clear input CLR1 of counter 240 and a ground output GND of timer 240 are connected to a common potential by way of a node 242.

A data output buffer 280 has an output enable input OE connected to node 185 and has a transfer enable input TE connected to a node 186. Eight data inputs, A0, A1, A2, A3, A4, A5, A6 and A7, of buffer 280 are respectively connected to nodes 208, 207, 206, 205, 204, 203, 202 and 201. A power supply $V_{CC}$ input of buffer 280 is connected to a source of potential at +5 volts. A ground GND output of buffer 280 is connected to a common potential. Outputs B0, B1, B2, B3, B4, B5, B6 and B7 of buffer 280 are respectively connected to data lines in PC bus 10 by way of nodes 33, 34, 35, 36, 37, 38, 39 and 40.

The time base for this clock system is provided by counter 240. Timer 220 counts only at a rate of 2.6 MHz megahertz which is exceeded by the IBM PC bus block of 4.77 megahertz. The IBM PC bus clock is divided by 2 using counter 240 and the result used to provide a timer base at 2.38 megahertz for timer 220. The 4.77 megahertz clock is also divided by 8 to provide a 596 kilohertz clock which is used to drive an analog to digital (A/D) converter. A/D converter 260 uses this clock signal in order to properly execute the successive approximation scheme to convert analog inputs into digital outputs.

A/D converter 260 has an output enable input OE connected to output C4 of expander 200. A/D converter 260 also has three inputs A, B and C which are respectively connected to outputs C5, C6 and C7 of expander 200. A clock input CLK of A/D converter 260 is connected to the 1QC output of counter 240. An address latch enable ALE and a start input STR of A/D converter 260 are connected to a node 261. A power supply $V_{CC}$ input and a reference voltage $+V_{REF}$ input of A/D converter 260 are connected to a node 262 at a potential of +5 volts. A reference voltage $-V_{REF}$ output and a ground GND output of A/D. converter 260 are connected to a common potential by way of a node 263. A/D converter 260 has seven outputs D0, D1, D2, D3, D4, D5, D6 and D7 which are respectively connected to inputs B0, B1, B2, B3, B4, B5, B6 and B7 of expander 200. In addition, A/D converter 260 has an end of count EOC output connected to a first input of the NAND gate 264, an output of which is connected to an input of an inverter 265. A second input of NAND gate 264 is connected to an output of an inverter 266 which has an input connected to node 187. An output of inverter 165 is connected to node 261.

A/D converter 260 has a signal input IN connected to a node 267. An output of an operational amplifer 268 is connected to node 267 and to a first lead of a resistor 269. A second lead of resistor 269 is connected to a first lead of resistor 270, a second lead of which is connected to a source of potential at −5 volts. The first end of resistor 270 is also connected to an inverting input of amplifier 268 and to a first end of a resistor 271. A non-inverting input of amplifier 268 is tied to ground. A second end of resistor 271 is connected to a node 272 which provides an analog signal input ANA IN for the apparatus according to the present invention.

A/D converter 260 is connected to port B of port expander 200. This A/D has built into it its own 8 channel analog multiplexer which allows the selection of one of eight analog signals to be converted. The channel select corresponding to inputs A. B and C of converter 260 is connected to port C on bytes 5, 6, and 7.

Because A/D converter 260 operates from 0 to 5 volts, analog input at input IN should be in the range of 0 to 5 volts or an input buffer should be supplied to alter this input range. However, in keeping with general practices for safety and isolation, input IN should always be provided with an analog buffer to provide isolation for both the computer and the instrument being monitored. As illustrated, the input buffer is provided by operational amplifier 268. This amplifier converts a bipolar analog input of plus or minus 5 volts to a single unipolar input of 0 to 5 volts at input IN. This analog input is used to monitor the respiration.

A/D converter 260 is set up in a free running mode such that it continuously does conversions on the analog signal. The end-of-conversion pulse at output EOC is used to generate a start pulse for the A/D so that as soon as an end of conversion occurs it a new conversion is started. This is the reason for the two gates connected between end of conversion output EOC and the start input STR. In order to prevent latchup of the device on power up, the reset line at node 187 is also used to generate a start pulse. This means that the device will always function even after being powered up. Also, in order to update A/D converter 260 as frequently as possible, the address latch enable ALE, which is used to latch in the address value for the channel to be monitored, is re-latched at every start pulse.

Figure 6:
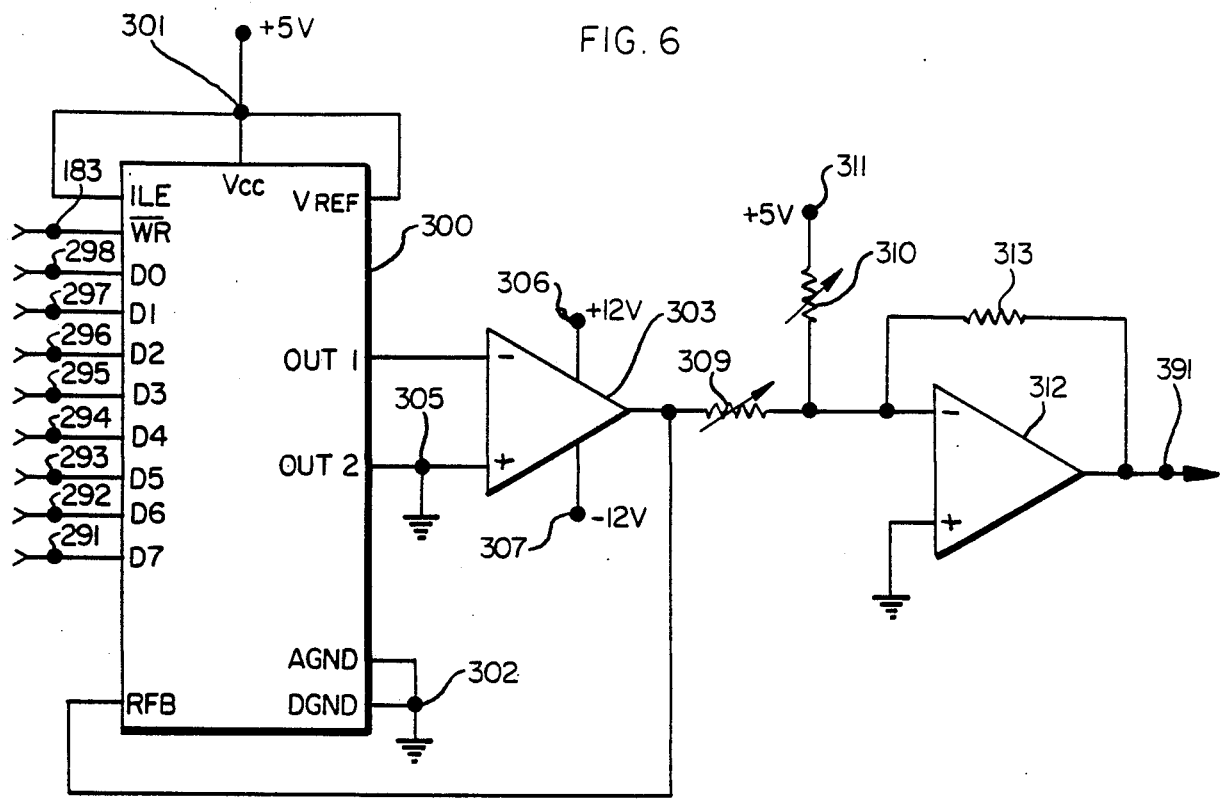
FIG. 6 illustrates a digital 2 analog converter according to the present invention.

As illustrated in FIG. 6, digital analog (D/A) converter 300 has inputs D0, D1, D2, D3, D4, D5, D6 and D7 which are respectively connected to nodes 298, 297, 296, 295, 294, 293, 292 and 291 as illustrated in FIG. 4. Converter 300 has a write WR input connected to node 183 and has a feedback input RFB. Converter 300 also has a power supply $V_{CC}$ input, a reference voltage $V_{REF}$ input and an input latch enable input ILE all of which are connected to a source of potential at +5 volts by way of a node 301. Converter 300 has an analog ground AGND and a digital ground output DGND, both of which are connected by way of a node 302 to a common potential.

Converter 300 has a first output OUT1 and a second output OUT2 which are respectively connected to an inverting and a non-inverting input of an operational amplifier 303. The non-inverting input of amplifier 303 is also connected to a common potential by way of a node 305. Amplifier 303 has an input connected to a node 306 at a potential of +12 volts and an input connected to a node 307 at a potential of <12 volts. An output of amplifier 303 is connected to a node 308 which is connected to the RFB input of converter 300 and to a first end of a variable resistor 309. A second lead of variable resistor 309 is connected to a first lead of a variable resistor 310, a second lead of which is connected to a node 311 at a potential of +5 volts. The second lead of resistor 309 is also connected to an inverting input of operational amplifier 312 and to a first lead of a resistor 313. A non-inverting input of amplifier 312 is connected to ground. A second lead of resistor 313 is connected to an output of amplifier 312 and to a node 391 which serves as an analog output for the apparatus according to the present invention.

Port A of expander which is at location 71C, is attached to a D/A converter data bus which, includes nodes 291-298. The write latch signal for the D/A converter is provided by chip select #0. In other words, any dummy byte written to any of the addresses 700, 701, 702 or 703 hex will cause a write pulse to be sent to D/A converter 300, thereby latching the data on port A of expander 200 into the D/A converter 300 and allowing an analog signal to be generated corresponding to the digital input. The output of D/A converter 300 chip is in the form of differential currents generated at outputs OUT 1 and OUT 2. A system having two operational amplifiers is employed to convert these currents to a voltage. Amplifier 303 is a differential current to voltage converter which provides a signal from 0 to 5 volts. Amplifier 312 converts the signal to a bipolar plus or minus 5 volt signal. Feedback control for the current to voltage converter is provided in D/A converter 300 through input RFB so that in actuality three connections are made from the D/A chip to the first operational amplifier. Because the D/A converter is an 8 bit device, this provides 256 voltage levels which are linearly distributed between plus and minus 5 volts. This D/A output may be used to generate calibrating signals or other control signals.

Figure 7:
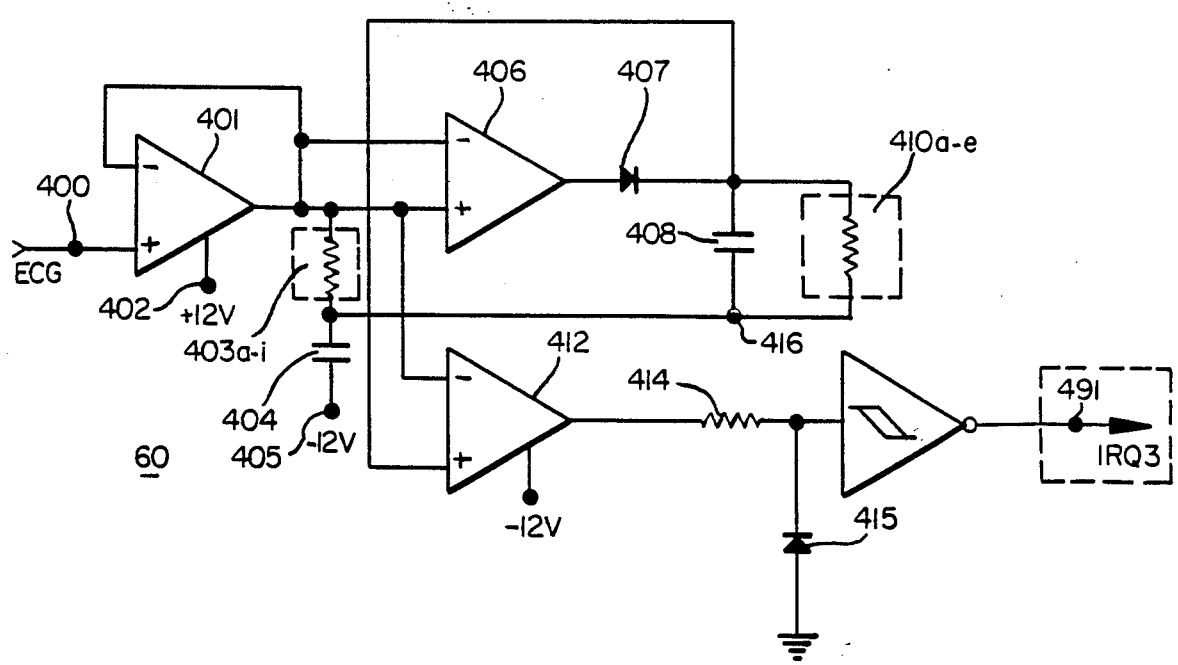
FIG. 7 illustrates a ECG trigger according to the present invention.

As illustrated in FIG. 7, a source of an ECG signal is connected by way of a node 400 to a non-inverting input of an operational amplifier 401 in an ECG trigger 60. An input of amplifier 401 is connected to a node 402 at a potential of plus 12 volts. An inverting input of amplifier 401 is connected to an output of amplifier 401 and to a non-inverting input of an operational amplifier 406. A first lead of each of resistors 403a, 403b, 403c, 403d, 403e, 403f, 403g, 403h and 403i is connected to the output of amplifier 401 while the second lead of resistor 403i is permanently connected and a second lead of one other of resistors 403a through h is connected to a node 410 by a jumper. A first lead of capacitor 404 is connected to node 410 while a second lead of capacitor 404 is connected to a node 405 at a potential of minus 12 volts. An inverting input of amplifier 406 is connected to a cathode of a diode 407, an anode of which is connected to an output of amplifier 406. The cathode of diode 407 is also connected to a first lead of capacitor 408 and a first lead of each of resistors 410a, 410b, 410c, 410d and 410e, the second lead of resistor 410e is permanently connected and the second lead of one other of which is connected to a node 410 by a jumper 411g. A non-inverting input of an operational amplifier 412 is also connected to the cathode of diode 407 while an inverting input of amplifier 412 is connected to the output of amplifier 406. An input of amplifier 412 is connected to a node 413 at a potential of minus 12 volts. A first lead of resistor 414 is connected to the output of amplifier 412 while a second lead of resistor 414 is connected to a cathode of a diode 415 an anode of which is connected to ground. The cathode of diode 415 is also connected to an input of a Schmitt trigger 416 an output of which is connected to a line designated IRQ 3 in PC bus 10 by way of a node 491.

ECG trigger 60 has an input buffer consisting of a non-inverting buffer of an amplifier 401 which isolates the ECG signal from the rest of the board. As illustrated in FIG. 5, the EKG trigger functions in the following manner. The R wave, which is larger than any other signal in the ECG, causes capacitor 408 to charge up to a certain value corresponding to the peak of the R wave. Any values beneath the peak of the R wave will be rejected by amplifier 403 so that no output occurs. Between R waves, the voltage on capacitor 405 decays slowly with a rate given by the RC time constant of capacitor 405 and the resistance across elements 410a-f. The voltage on the capacitor is sent to the inverting input on amplifier 403 and is used as a threshold for the R wave of the EKG. Therefore, as the electrocardiogram is being passed to the non-inverting input of amplifier 406, the only time that the operational amplifier has a positive output is when the EKG signal is larger than the voltage on capacitor 405. Whenever this occurs, capacitor 408 is immediately charged up to the value at the EKG input. In other words, the voltage on capacitor 408 is a sort of envelope on the top of the electrocardiogram, although its decay rate is limited by the RC time constant. Diode 407 insures that the envelope function which is provided by capacitor 408 is the upper envelope and not the lower envelope. The lower envelope is provided by reversing the polarity of diode 407.

The RC network of capacitor 405 and resistors 403a-i provides a low pass filtered ECG. The voltage on capacitor 405 is the baseline for the ECG, which may vary. The array of jumper selected resistors 410a-e allows variation of the time constant of the RC network containing resistors 406a-e and capacitor 408. Thus, this latter network which monitors the ECG envelope is referenced to the ECG baseline present on capacitor 404 permitting accurate tracking of the envelope and therefore better R wave detection. As a further improvement, the jumpers may be replaced within analog switches controlled by the personal computer in order to give the computer control of RC time constant selection.

An output from ECG trigger 60 is generated by connecting amplifier 412 in parallel with peak detector amplifier 406 so that the inputs are reversed. The result is that the output polarity is inverted. Because the amplifiers 401, 406 and 412 are operating from a plus 12 volts to minus 12 volts supply, but the logic levels on the board are only from 0–5 volts, resistor 414 and a diode 415 are used to clamp the output value of the amplifier 412 between 0 and 12 volts. This signal is then passed to a Schmitt trigger 416, which is a single conditioning device. The output of this signal conditioner is finally provided to PC bus 10 in order to drive interrupts at interrupt request 3 (IRQ3) indicating the currents of an R wave. ECG trigger 60 may be modified to allow selection of various decay rates for the envelope and also to provide a floating threshold for the 0 point of the EKG. The ECG triggers if the R wave passes above 0 volts. However, it can be imagined that sometimes the baseline will drift far enough below 0 volts that the R wave does not cross 0 volts and in such a case this trigger would never detect the R wave. This is corrected by connecting the second leads of the charging capacitor 408 and on the selected discharging resistor of 406a-f may be connected to a low pass filter consisting of a capacitor 405 and a selected one of resistors 403a-f (to choose various discharge rates) which low pass filters the electrocardiograms and essentially selects out the baseline. This means that instead of measuring the R wave with respect to 0 volts, the R wave may be measured with respect to the floating baseline of the electrocardiogram. The jumper selected resistor selects an RC time constant much greater than the RR interval. So long as the baseline does not drift faster than one R wave in approximately 10 heart beats, this means that this trigger will successfully detect all R waves. Selecting one of resistors 410a-f allows variation of the RC time constant of elements 408 and 410a-f.

Figure 8:
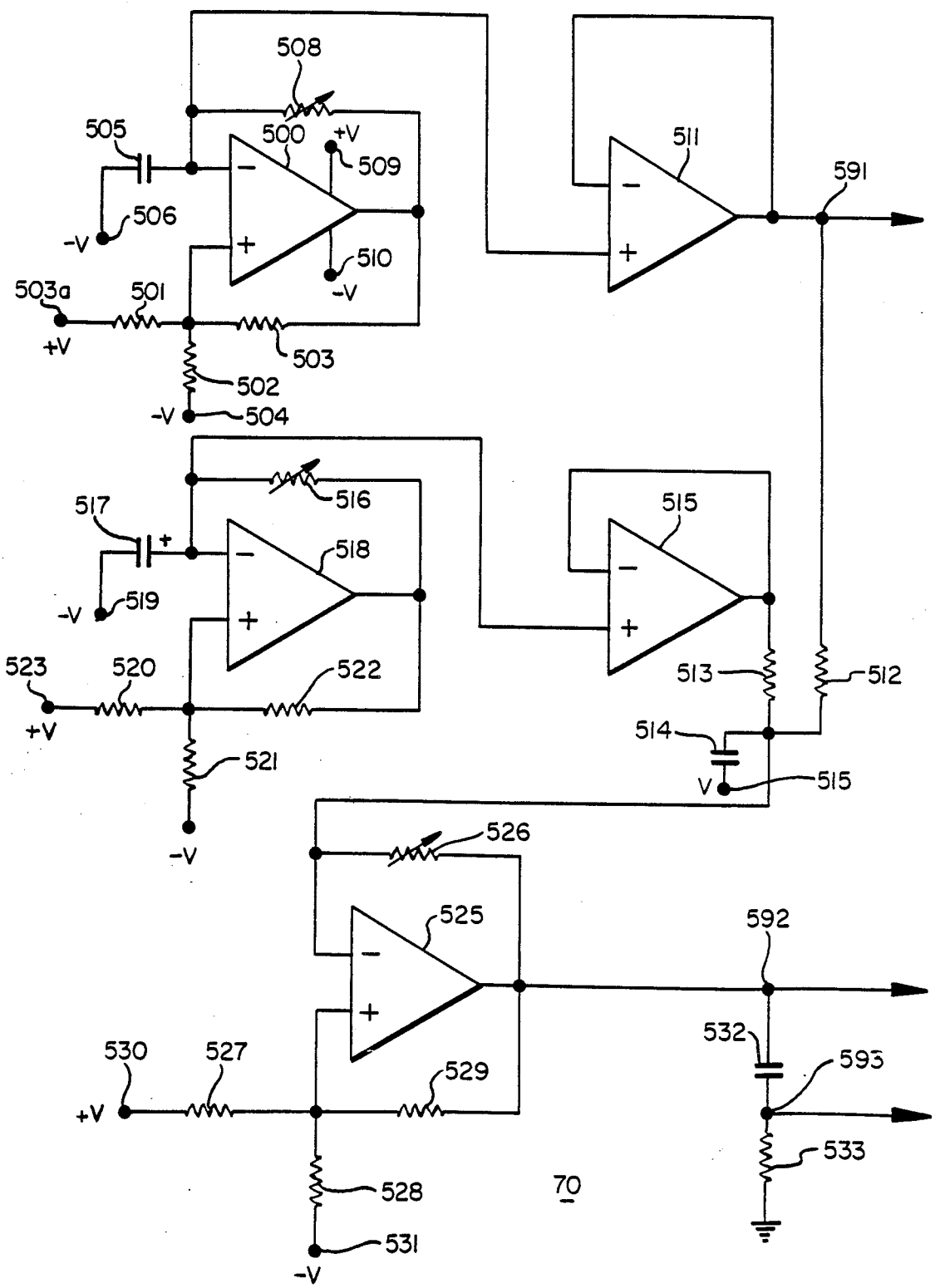
FIG. 8 illustrates a portable calibrater according to the present invention.

As illustrated in FIG. 8, in a portable calibrator 70 according to the present invention, an operational amplifier 500 has a non-inverting input connected to a first lead of each of resistors 501, 502 and 503. A second lead of resistor 501 is connected by way of a node 503a to a positive voltage source while a second lead of resistor 502 is connected by way of a node 504 to a negative voltage source. An inverting input of amplifier 500 is connected to a first lead of a capacitor 505, a second lead of which is connected by way of a node 506 to a negative voltage source. The inverting input of amplifier 505 is also connected to a first lead of a variable resistor 507 and to a first lead of a resistor 508 a second lead of which is connected to an output of amplifier 500. The output of amplifier 500 is also connected to a second lead of resistor 503. Amplifier 500 has an input connected by way of a node 509 to a positive voltage source and by way of a node 510 to a negative voltage source.

A second lead of resistor 507 is connected to a non-inverting input of an amplifier 511, an inverting input of which is connected to an output of amplifier 511 by way of a node 591 which provides an output port for a simulated respiratory frequency.

A first lead of a resistor 512 is connected to node 591 while a second lead of resistor 512 is connected to a first lead of a resistor 513 and to a first lead of a capacitor 514, a second lead of which is connected by way of a node 515 to a negative voltage source. A second lead of resistor 513 is connected to an output of an operational amplifier 514 and to an inverting input of amplifier 515 is connected to a first lead of a resistor 516, to a first lead of a capacitor 517 and to an inverting input of an operational amplifier 518. The second lead of capacitor 517 is connected by way of a node 519 to a negative voltage source. A non-inverting input of amplifier 518 is connected to a first lead of each of resistors 520, 521 and 522. A second lead of resistor 520 is connected by way of a node 523 to a positive voltage source while a second lead of resistor 521 is connected by way of a node 524 to a negative voltage source. A second lead of resistor 522 is connected to an output of amplifer 518 and to a second lead of resistor 516.

An inverting input of an operational amplifier 525 is connected to the first lead of resistor 513 and to a first lead of a variable resistor 526. A non-inverting input of amplifier 525 is connected to a first lead of each of resistors 527, 528 and 529. A second lead of resistor 527 is connected to a node 530 at a positive potential while a second lead of resistor 528 is connected by way of a node 531 to a negative voltage source. A second lead of resistor 529 is connected to a second lead of resistor 526 and to an output of amplifier 525 at a node 592 which provides a square wave output simulating a modulated heart rate pulse. A first lead of a capacitor 532 is connected to node 592 while a second lead of capacitor 532 is connected by way of a node 593 to a first lead of a resistor 533, a second lead of which is connected to ground. Node 593 provides an output port for a spike output simulating the R wave of an EKG.

The source of positive potential for the portable calibrator 70 may be at a voltage between about plus 5 and about plus 18 volts. Similarly, the negative voltage source for portable calibrator 70 may be at a potential of about minus 18 volts to about minus 5 volts.

Portable calibrator 70 provides test signal for the heart rate spectral analysis hardware which, although not of a truly calibrated nature, does allow one to evaluate whether or not the software and hardware is functional. Each of the output signals provided is a triangle wave which represents the respiration and a frequency modulated pulse train representing the heart rate. The modulation of the heart rate is provided at two frequencies which simulate a respiratory modulation and also a low frequency modulation.

The basic circuit of calibrator 70 for providing each pulse train consists of an oscillator having one operational amplifier as typified by the respiratory frequency modulator. A charging capacitor 505 and a variable resistor 507, provide an RC circuit which is charged by the output of the amplifier 500. It is also discharged by the amplifier 500 when the output of the amplifier 500 is low. Progressive cycles of the oscillator consist of charging and discharging the capacitor at the rate prescribed by the RC circuit. The reference level which determines whether or not one is discharging or charging is provided at the non-inverting input of the amplifier 500.

Suppose, for example, that capacitor 505 begins as being completely discharged, then the voltage at the inverting input for the operational amplifier 500 is low. The output of the operational amplifier 500 is therefore high and this means that the input at the non-inverting input is ⅔ the voltage between the negative voltage source V and the positive voltage source V+. Thus the capacitor 505 begins to charge. When the capacitor voltage exceeds the threshold at the non-inverting input of the operational amplifier 500, the output of operational amplifier 500 changes sign and capacitor 505 begins to discharge. However, when the output of the amplifier 500 changes to the negative side, then the threshold voltage at the non-inverting input is changed and now becomes only ⅓ the way from the negative voltage source to the positive voltage source. This means that the voltage on the charging capacitor 505 varies between ⅓ and ⅔ the difference between the negative and the positive voltage source. This determines the range of output on capacitor 505. The voltage at capacitor 505 is buffered by a non-inverting buffer 511 and this provides the respiratory signal at node 591.

An identical oscillator is used to provide low frequency modulation. The difference in the two frequencies is obtained by adjusting the respective variable resistors, 505 and 517, which set the RC time constants. The outputs of these two modulators are fed by resistors 512 and 513 into the charging capacitor 514 for the heart rate.

The heart rate oscillator is similar in design and consists of variable resistor 526 and capacitor 532 which charges and discharges in cycles with the range of voltages on the capacitor ranging between ⅓ the distance from the negative voltage source to the positive voltage source to ⅔ the voltage between the negative voltage source and the positive voltage source. Resistors 512 and 513, which connect the outputs of the low frequency and respiratory frequency modulators to the heart rate modulator, allow a small amount of current flow into charging capacitor 514 of the heart rate modulator. This alters the charging rate of capacitor 514 and thereby affects the rate at which the heart rate oscillator oscillates. For example, on a positive cycle of the respiratory frequency modulator, the heart rate capacitor is charging more rapidly towards the plus side because more current is being supplied on the plus side of the cycle. Finally, the output of the heart rate modulator is sent through an RC filter comprising capacitor 532 and resistor 533 which converts the square wave output of the heart rate modulator into a spike output which may be sent to an R wave detector. Notice that the spike output includes both positive and negative spikes so that an R detector which depends on a high frequency filtering function may be discharging at twice the heart rate, inasmuch as it may trigger on both positive and negative spikes.

Figure 9A:
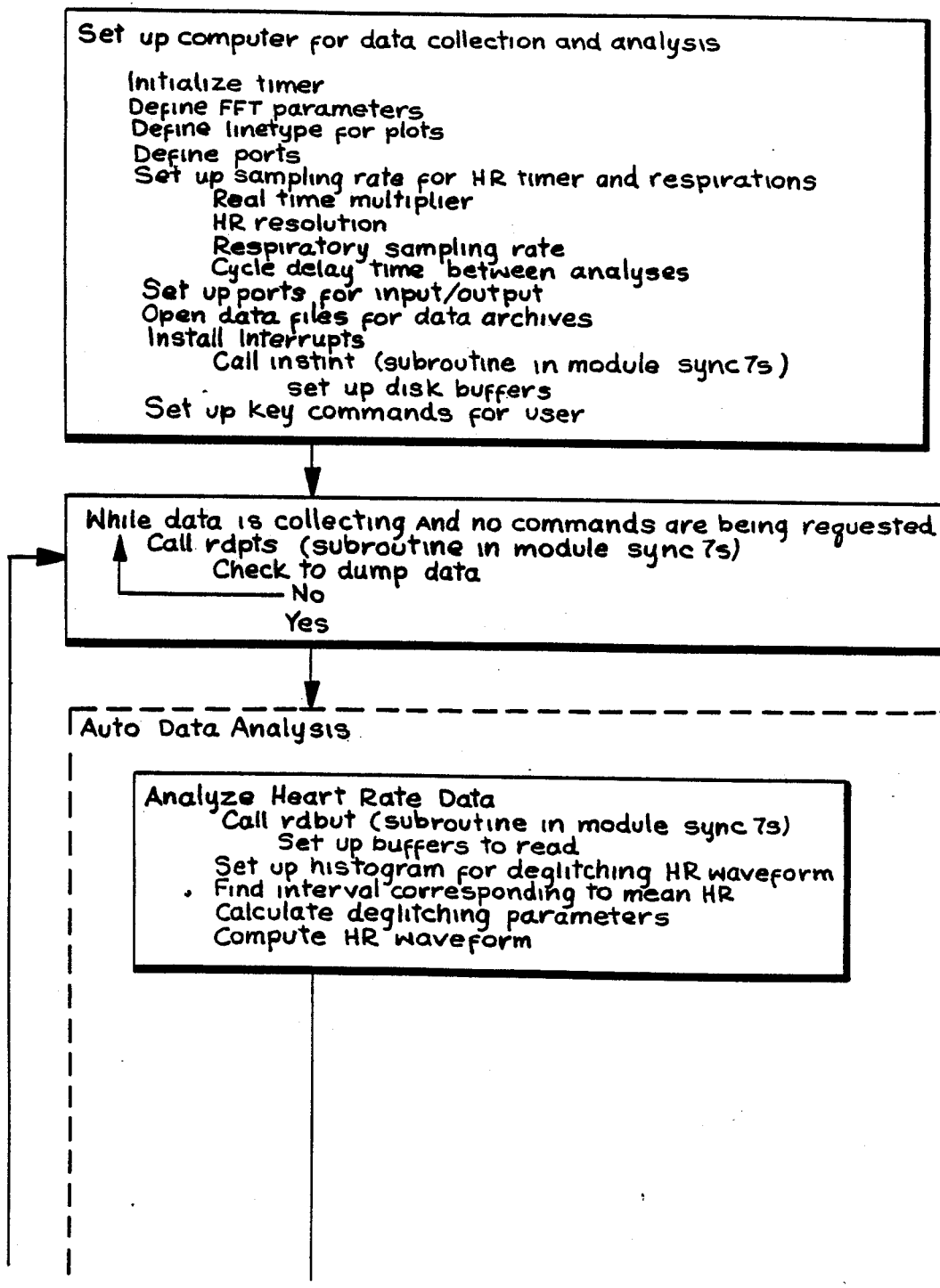
FIGS. 9A and 9B are a flow chart for software applicable to an embodiment of the present invention on a IBM personal computer.
Figure 9B:
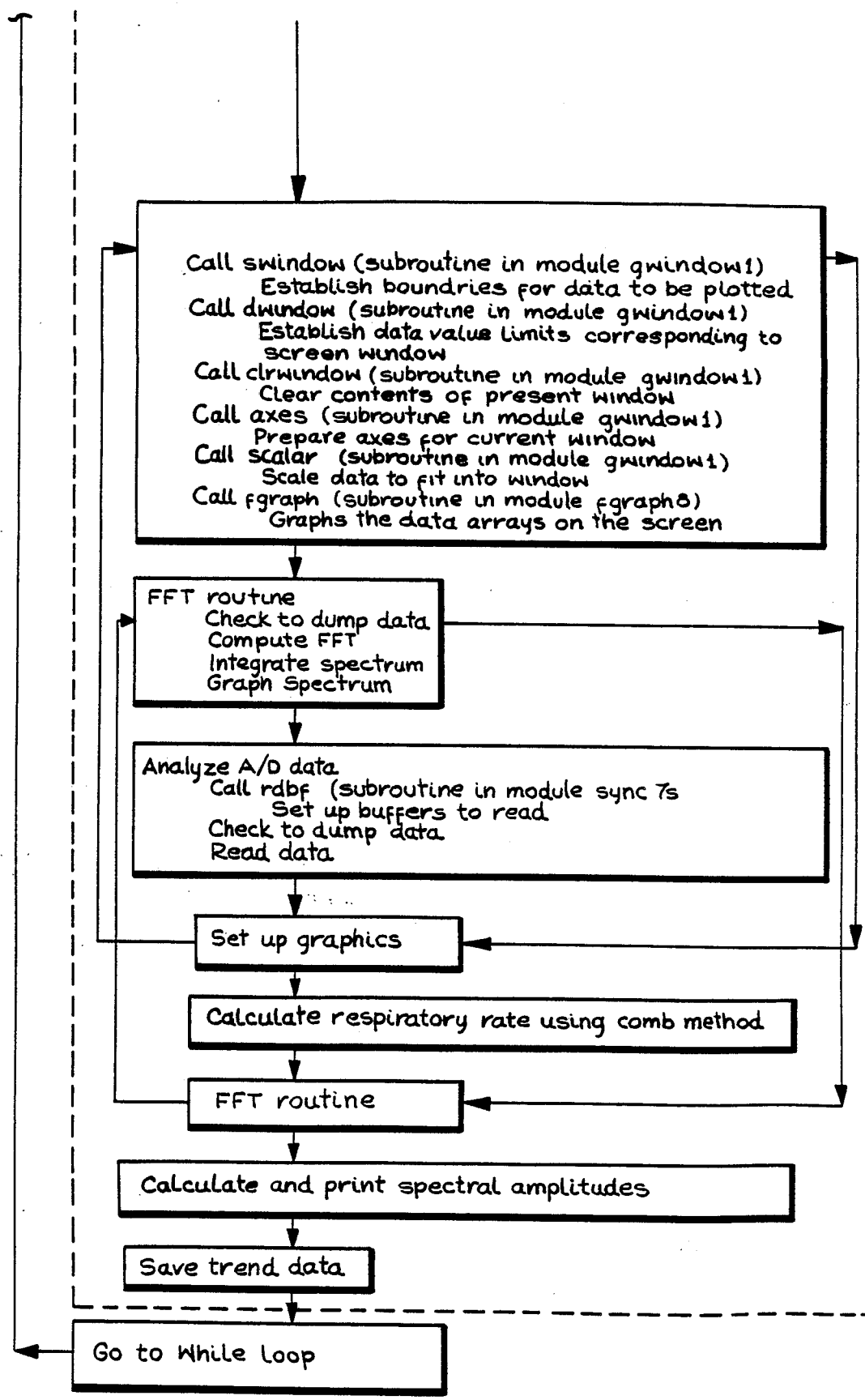

As illustrated by a block diagram in FIGS. 9A and 9B, a block diagram may be constructed for the main program (designated Syncts19) and for sub-routine modules (Sync7s, Gwindow3, and Fgraph8). This block diagram may be used in order to better interpret a complete program for heart rate fluctuation spectral analysis useful on an IBM personal computer, as illustrated in FIG. 11. Although programs are provided for a Hewlett-Packard and an IBM computer herein, the software and other aspects of the present invention may be readily modified for use with other mini- and microcomputers.

In the program of Appendix B, is a routine for removing artifacts from a detected heart rate provided for by an electrocardiograph machine. This program computes histograms from the heart rate data in order to generate a tachometer waveform. The most common rate on the histogram is selected as the correct rate and other rates are interpreted in light of it. Specifically, in order to correct for a spurious extra trigger, where a first and a second beat are close together while a third beat is spaced at an abnormally long interval, the second beat is discarded if the first beat to second beat interval is less than a predetermined value. The resulting interval between the first and the third beats is divided by an integer in order to provide a more normal interbeat interval. Where a trigger has been missed, so that a first and a second beat are separated by an interval which is approximately a multiple of a normal intrabeat interval, the intrabeat interval is divided by that multiple, most commonly two, in order to provide a more correct interval length. If the slewing rate of the heartbeat samples is outside of an acceptable range of slewing rates determined as a function of a mean variance, and the problem cannot be identified as a missed trigger or as a spurious extra trigger, or if the three previous intervals have been corrected, a determined mean interval, against which all other intervals are judged, is substituted for the inappropriate interval.

The slew rate is calculated on a moving average of the heart rate waveform and corrects for triggers that fall within the parameters of 0.05 Hz (3 beats/min.) per beat and five times the maximum slew. This artifact-correcting routine never slews more than 10 percent of the heart rate waveform.

Within the software of Appendix A is a graphic routine for trending heart rate fluctuation spectral data. The parameters of LFP, RFP, LFP/RFP ratio and heart rate are plotted on a graph over time to show trends in the four parameters. These trends may then be studied in order to examine the effects of various clinical interventions. Values for the parameters heart rate, LFP/RFP ratio, LFP and RFP are stored and may be called up at any point in time through a graphing routine in order to provide a graphic depiction of the course of a patient's condition. This sort of graphic depiction is illustrated for a stable patient in FIG. 10 and for an unstable patient in FIG. 11.

Also present in the program of Appendix B, a routine is provided for the segmentation of data and subsequent reanalysis. In this routine, data from the analog to digital converter 260 is collected continuously into a buffer and is dumped to a disk in blocks of 1,024 numbers (2,048 bytes equals 1,024 words and each block is referred to as a record or EPOCH). The time of heartbeat occurrence as measured by the signal provided by outputs OUT1 and OUT2 of timer 220 are collected continuously into two buffers (hb buffer 1 and hb buffer 2). These times are dumped to the disk in blocks of 1,024 pairs of numbers (1,024 from each buffer which equals 2,048 bytes or 1,024 words each). Because the heart rate is less than the sample rate of A/D converter 260 as required by signal processing, there are fewer heartbeat disk dumps.

In order to properly analyze data, the A/D and heartbeat data must correspond to the same time interval for the purpose of doing correlations. The correspondence may be determined from (1) the record number in a A/D file and (2) the absolute of the times stored in the heartbeat file (time differences used for intrabeat intervals). The instantaneous heart rate signal is generated backwards in time from the heartbeat corresponding to the last A/D sample in the record of interest. This means that if the heart rate signal is analyzed on a frequency scale not corresponding to the respiration data (e.g. respiration sample at 16 Hz but a heart rate analysis at 0 to 4 Hz) then the heart rate waveform extends backwards in time beyond the beginning of the present A/D record. This means that the heart rate waveform overlaps the heart rate waveform corresponding to the previous A/D records.

Overlapping permits lower frequency analysis than would be possible if only data corresponding to the present record were used (as in the prototype apparatus). Also, overlapping leads to the smoothing of parameters and to the subsequent reduction of fluctuating artifacts. In addition, it becomes less critical at what point analysis begins.

Figure 12:
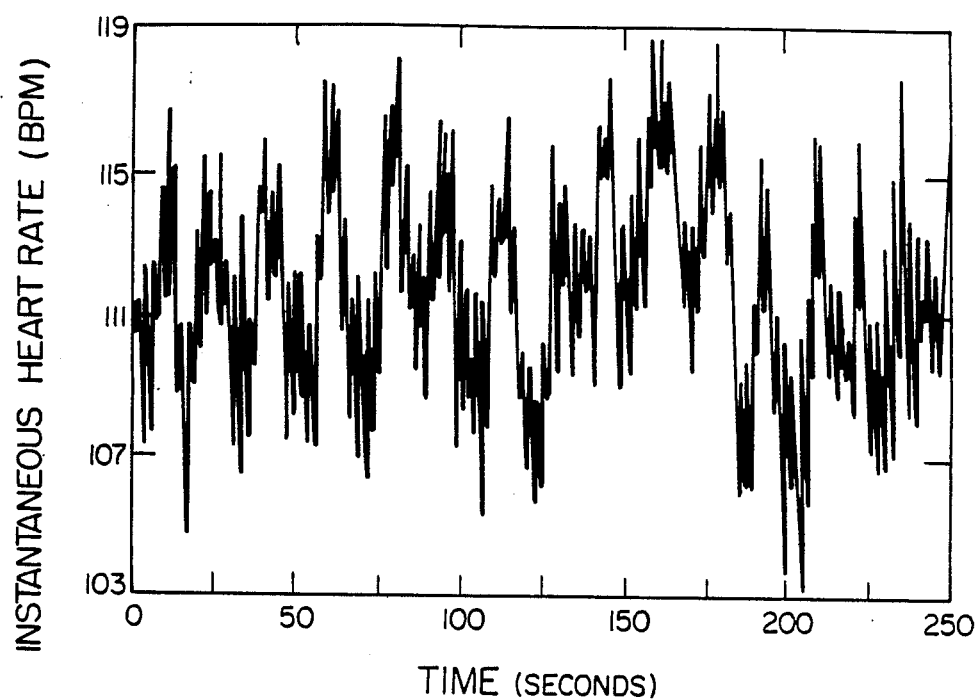
FIG. 12 is an illustration of an instantaneous heart rate according to the present invention.

A calibration program providing a software driven calibrator, which may provide more realistic spectral data than the portable calibrator of FIG. 8, is contained within the program of Appendix A for a Hewlett-Packard micro-computer. FIG. 12 is a program which, although not tested, is believed to provide the same sort of software-driven calibration for an IBM personal computer through the data acquisition system of FIGS. 4 through 7.

In general, outputs OUT0 and OUT1 of timer 220 in FIG. 5 generate a time base used via interrupt request line IRQ4 to clock data from a buffer to D/A converter 300. This buffer contains a respiratory waveform which may be a sign wave or any selected waveform as obtained by changing the contents of the buffer. Output OUT2 of timer 220 generates a heartbeat pulse as its output. In order to work properly, this pulse must be returned to the ECG trigger through node 400 or directly to interrupt request line IRQ3. If the latter course is chosen, however, node 491 must be disconnected from the output of Schmitt trigger 416. By returning the pulse to the ECG trigger, the computer is informed that the timer is through counting the present RR interval and needs a new interval to be loaded into a timer register of timer 220.

Figure 13:
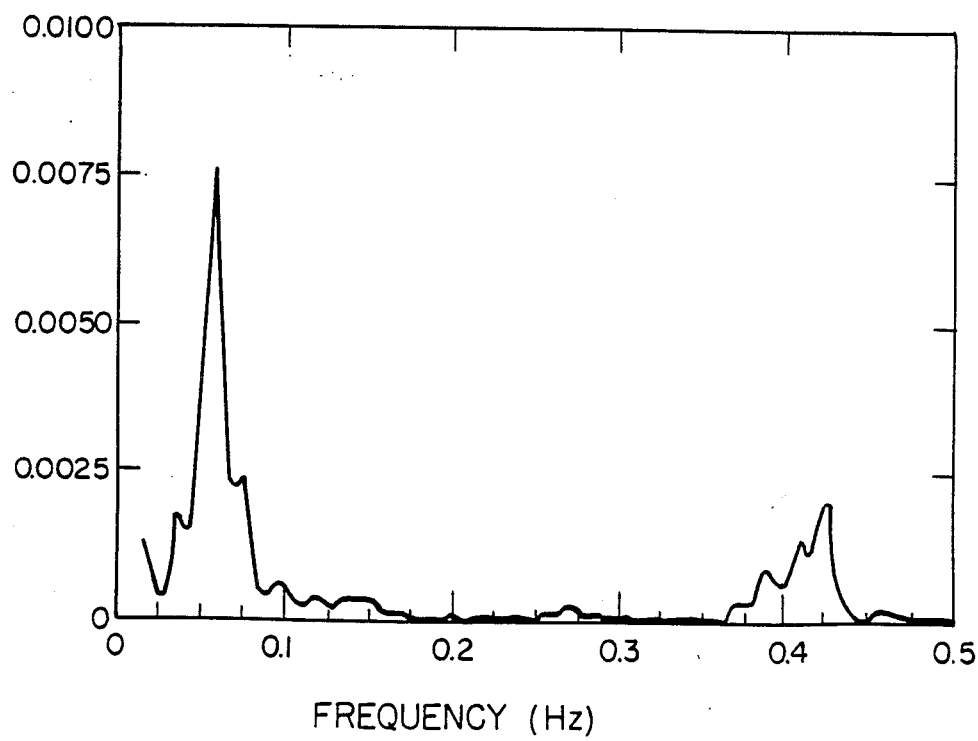
FIG. 13 is an illustration of an instantaneous heart rate fluctuation spectrum of the sort obtainable from apparatus according to the present invention.
Figure 14:
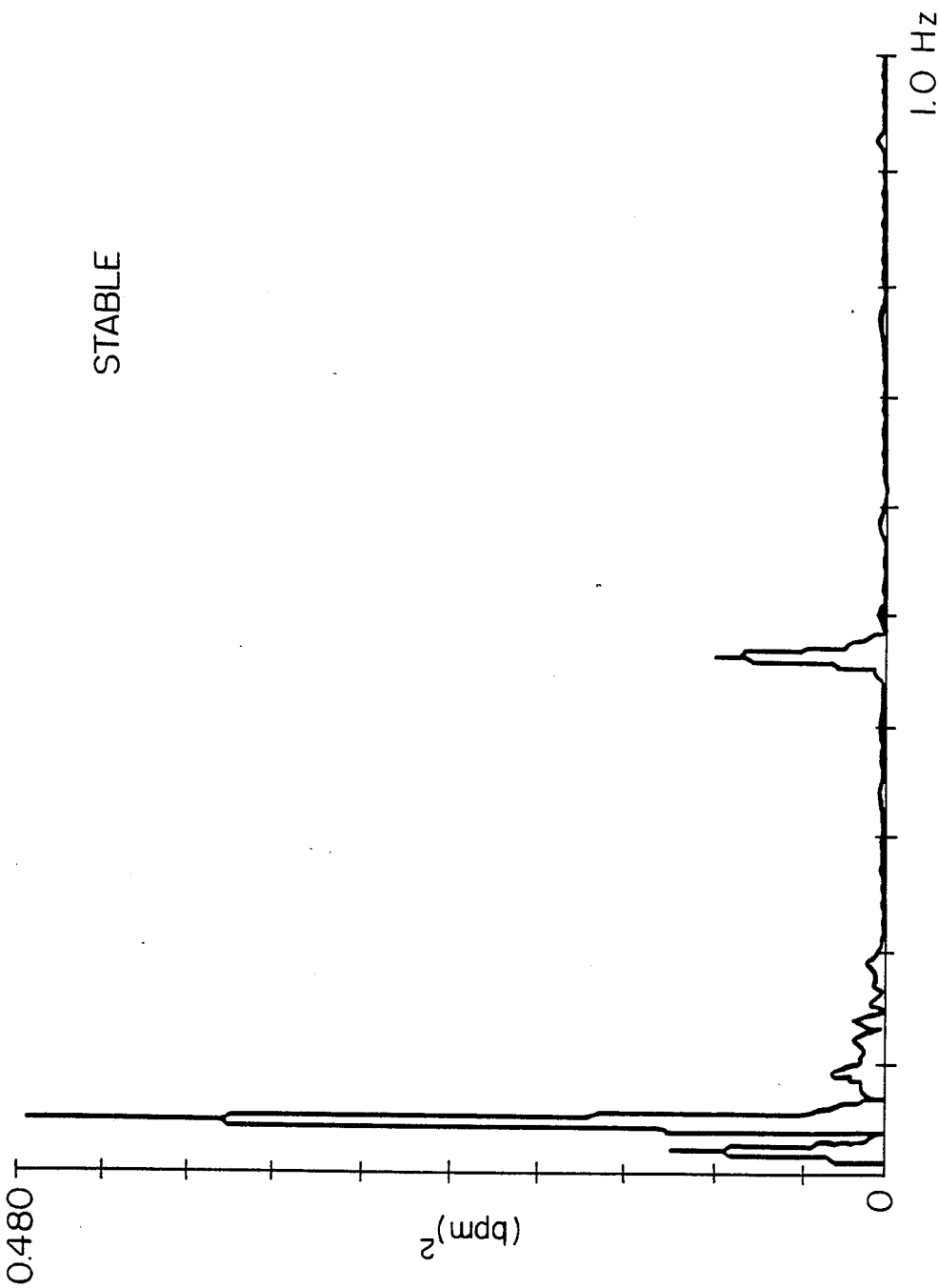
FIG. 14 is a heart rate fluctuation power spectrum according to the present invention of a stable patient.
Figure 15:
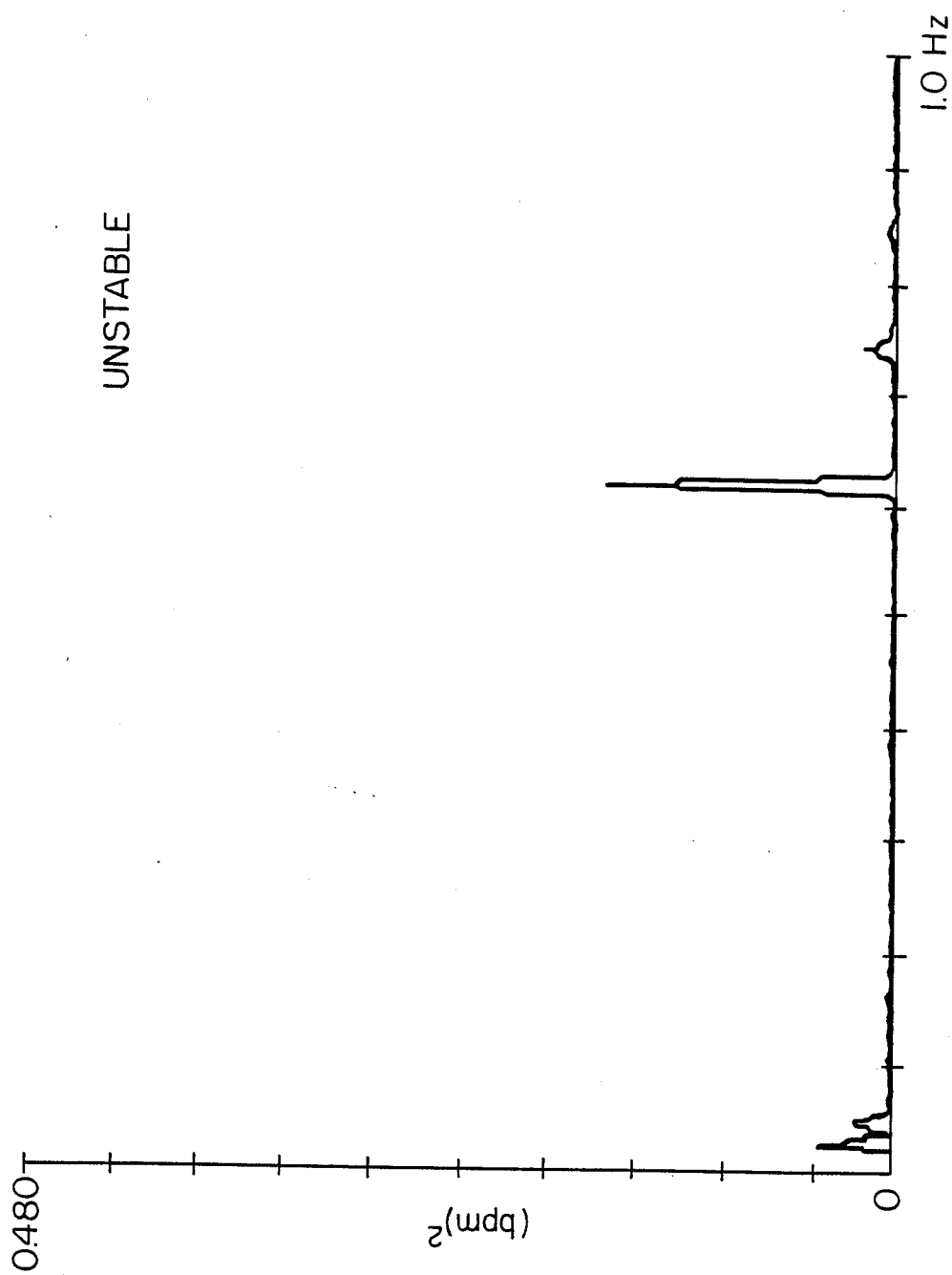
FIG. 15 is a heart rate fluctuation power spectrum according to the present invention of an unstable patient.

Through the use of the apparatus according to the present invention, a display of instantaneous heart rate as provided by an electrocardiograph machine, and as illustrated in FIG. 12, may be converted into an instantaneous heart rate fluctuation spectrum as illustrated in FIG. 13. A typical spectrum for a stable patient is illustrated in FIG. 14 while a typical spectrum for an unstable patient is illustrated in FIG. 15.

Example I and Example II relate respectively to diagnosis and to treatment employing the present invention.

Parts suitable for use in construction of the apparatus as illustrated in FIGS. 3 through 8 may include those as listed in Tables I, II, III and IV.

TABLE I

| Element No. | Part No. | Manufacturer, Location |
| --- | --- | --- |
| 100, 110, 120 | 74HC244 | National Semiconductor Santa Clara, California |
| 130 | 74HC138 | National Semiconductor Santa Clara, California |
| 140, 151, 158 | 74HC30 | National Semiconductor Santa Clara, California |
| 152, 153, 154 155, 156, 157 159, 160, 161 172, 265, 266 | 74HC04 | National Semiconductor Santa Clara, California |
| 171, 173, 185 264 | 74HC00 | National Semiconductor Santa Clara, California |
| 200 | 8255A-5 | Intel Corporation Santa Clara, California |
| 220 | 8253-5 | Intel Corporation Santa Clara, California |

TABLE I-continued

| Element No. | Part No. | Manufacturer, Location |
| --- | --- | --- |
| 224 | | |
| 240 | 74HC393 | National Semiconductor Santa Clara, California |
| 260 | ADC0808 | National Semiconductor Santa Clara, California |
| 268, 303, 312 401, 406, 412 500, 511, 515 518, 525 | LM324AN | National Semiconductor Santa Clara, California |
| 280 | 8286 | Intel Corporation Santa Clara, California |
| 300 | DAC0830 | National Semiconductor Santa Clara, California |
| 416 | 74HC14 | National Semiconductor Santa Clara, California |

TABLE II

| Diodes | |
| --- | --- |
| Element | Part No. |
| 407, 415 | IN4148 |

TABLE III

| Resistors | |
| --- | --- |
| Element No. | Value (in Ohms) |
| 403i, 410 | 2.2k |
| 269 | 5k |
| 270, 271, 409 | 10k |
| 403h | 15k |
| 403g | 27k |
| 403f | 56k |
| 313 | 82k |
| 309, 310, 501, 502, 503, 520, 521, 522, 527, 528, 529, 533, 403e | 100k (variable) |
| 403d, 410d 403c, 410e | 220k 560k |
| 508, 516, 526, 403b, 410b | 1M (variable) |
| 512, 513, 403a, 410a | 2.2M |

TABLE IV

| Capacitors | |
| --- | --- |
| Element No. | Value (in microFarads) |
| 405 | 2.2 |
| 404, 505, 517 | 10 |
| 532 | 0.1 |
| 514 | 1 |

EXAMPLE 1

Heart rate spectral analysis was applied to the study of congestive heart failure in infants and children. Congestive heart failure is characterized by a marked alteration in cardiovascular regulation. However, many cardiovascular functions which are normally monitored in cardiac intensive care units (such as: mean heart rate; arterial blood pressure; arterial blood gases; left arterial pressure and right arterial pressure; right atrial, left atrial and pulmonary artery oxygen saturations; the peripheral pulses; peripheral perfusion; and cardiac output) may not clearly indicate a critically unstable cardiovascular condition. The usually-monitored cardiovascular function parameters may be within a normal range immediately before a major cardiovascular crisis, such as hypotension or cardiac arrest, inasmuch as the cardiovascular regulatory system maintains these parameters within a normal range up to the point of system failure.

Twenty-nine infants and children were studied in a cardiac intensive unit. Of the twenty-nine patients, twenty-six have undergone a cardiac surgical procedure. The patients were studied for a minimum of three hours and a maximum of twenty-seven hours, with a mean study time of eight hours. EKG for cases were recorded and analyzed continuously in real time during the study time.

Data for a particular patient was analyzed only if the patient was in sinus rhythym. The patient's clinical course during the period of study was reviewed and, in particular, major events such as cardiac arrest, hemorrhage and profound hypotension were correlated with spectral analysis data. Administration of medication and the mode of ventilation were noted.

Real time heart rate spectral analysis was performed on a dedicated personal computer using a 6809E Motorola Microprocessor-Based System. A data acquisition system interfaced the computer with a patient monitor, available from Hewlett-Packard, Palo Alto, Calif., as Model No. 78341.

The heart rate power spectrum was calculated in continuous 256 second data epochs. A QRS synchronization pulse from the patient monitor was used to determine an RR interval sequence. An instantaneous heart rate signal was computed from RR interval sequence and the magnitude of the signal was set to the reciprocal of the current interbeat interval. The instantaneous heart rate signal was sampled at 4 Hz and the mean heart rate was substracted from the resulting one thousand twenty-four point time series. A power spectrum was computed by squaring the absolute value of a Fast Fourier Transform of the one thousand twenty-four point time series. Values for low frequency power (LFP) were computed by integrating the spectrum of between 0.04 and 0.1 Hz. Respiratory frequency power (RFP) was computed by integrating the heart rate power spectrum over a 0.2 Hz-wide band centered at the mean respiratory frequency.

Hard copies of the heart rate time series and power spectrum were printed for each 256 second epochs. Trend graphics for the LFP, the RFP, LFP/RFP ratio, mean heart rate and respiratory rate (hereinafter referred to as the study parameters) were constructed by manually entering data in data files and analyzing the entered data by means of a computer.

Mean values for the study parameters were calculated for each period of study. The Mann-Whitney Rank Sum Test was used to determine statistically significant changes in the study parameters in individual patients and to determine differences among groups of patients. When patients were segregated into more than two groups, the Kruskal-Wallis Test, multiple comparison test, and Tukey's HSD were employed to determine statistical significance. P values of less than 0.05 were considered significant.

It was found that during each three to twenty-four hour period of study the study parameters for a given patient, the LFP, the RFP and the LFP/RFP ratio (hereinafter referred to as the spectral parameters) remain fairly stable.

Based upon the results of this study, the patients were retrospectively divided into three groups. Group I included seventeen stable patients whose median age was one month. The patients in Group I were without major post-operative complications and did not need prolonged inotropic support. The eight patients in Group II suffered cardiac arrest and died. The median age for the members of Group II was one month. In Group III, there was a total of four patients each of whom was critically ill at the time of the study but later recovered. Median age of the members of Group III was one month. Of the four members of Group III, one required re-operation, one had intermittent hypotensive episodes, and two had cardiac arrests from which they were successfully resuscitated.

In order to separate all twenty-nine patients into a group of stable patients (Group A) and a group of critical patients (Group B), data from each patient in Group III was divided into the data collected during the stable period (which applied to three patients) and the data collected during the preceding critical period (which applied to four patients). When handled in this way, Group A included data for twenty patients and Group B included data for twelve patients. Typical heartrate fluctuation power spectra for Group A and B are respectively illustrated in FIGS. 19 and 20.

In addition, studies were performed on three patients who had isolated coarctation of the aorta at three points in time: upon admission for congestive heart failure; during treatment; during post-operative period; and prior to discharge from an intensive care unit. An attempt was made to identify changes in cardiovascular regulatory function of each of these stages.

Patient profiles for Groups I, II and III are respectively provided in Tables V, VI and VII. These profiles include age, diagnosis and operation.

TABLE V

| | PATIENT PROFILE: STABLE POST-OP N = 17 | | | |
|---|---|---|---|---|
| AGE | NO. | DIAGNOSIS | (NO.) | OPERATION |
| <30 DAYS | 9 | TGA,IVS | (3) | ARTERIAL SWITCH |
| | | TGA,VSD,PS | (1) | L-BTS |
| | | HLHS | (1) | STAGE 1 REPAIR |
| | | SV | (1) | L-BTS |
| | | SEV. COAO | (3) | SUBCL.FLAP ANGIO. |
| 1–12 MO. | 5 | TGA,IVS | (1) | ARTERIAL SWITCH |
| | | TGA,VSD,PS | (1) | BTS |
| | | MULT.VSD'S | (1) | VSD PATCH REPAIR |
| | | SUPRA-V. PS | (1) | PA PATCH PLASTY |
| | | DCRV,VSD,COAO | (1) | VSD REPAIR, ANOM. B RESECTion |
| 1–10 YRS. | 2 | PS | (1) | PULM. VALVOTOMY |
| | | TOF | (1) | TOF REPAIR |
| >10 YRS. | 1 | AR,MR | | AVR,MVR |

TABLE VI

| | PATIENT PROFILE: | CRITICAL, DIED N = 8 | | |
|---|---|---|---|---|
| AGE | NO. | DIAGNOSIS | (NO.) | OPERATION |
| <30 DAYS | 4 | HLHS | (3) | NORWOOD PROCEDURE |
| | | SV W/IAA | (1) | GORE-TEX GRAFT |
| 1-12 MO. | 3 | HLHS | (1) | Fontan operation |
| | | DORV,TAPVC, | (1) | TAPVC REPAIR, SYS. |
| | | DORV,TAPVC, CCAVC | (1) | TAPVC REPAIR, SYS. PULM. SHUNT |
| | | HLHS | (1) | NON-OPERATIVE |
| 6½ YRS. | 1 | T OF S/P REPAIR W/ CHRONIC SEV. CARDIOMYOPATHY, S/P ARREST | | NON-OPERATIVE |

TABLE VII

| | PATIENT PROFILE: | CRITICAL, RECOVERED N = 4 | | |
|---|---|---|---|---|
| AGE | NO. | DIAGNOSIS | (NO.) | OPERATION |
| <30 DAYS | 3 | HLHS,COAO | (1) | NORWOOD PROCEDURE |
| | | HLHS | (2) | NORWOOD PROCEDURE |
| 14 YRS. | 1 | ACUTE MYOCARDITIS, S/P ARREST | | NON-OPERATIVE |

In Tables V, VI and VII: TGA is Transposition of the Great Arteries; IVS is Ventricular Septal Defect; PS is Pulmonic Stenosis; HLHS is Hypoplastic Left Heart Syndrome; SV is Single Ventricle; SEV. is severe; COAO is Coarctation of the Aorta; MULT is multiple; VSD is Ventricular Septal Defect; Supra-V. is Supravalulvar; DCRV is Double Chamber Right Ventricle; TOF is Tetralogy of Fallot; AR is Aortic Regurgitation; MR is Mitral Regurgitation; W/IAA is with Interrupted Aortic Arch; DORV is Double Outlet Right Ventricle; TAPVC is Total Anomalous Pulmonary Venous Connections; CCAVC is Complete Common Atrial Ventricular Canal; S/P is Status Post; L is Left; BTS is Blailock Taussig Shunt; PA is Pulmonary Artery; ANOM. is Anomalous; B is muscle Bundle; PULM is Pulmonary; and SYS is Systemic.

Statistically significant differences were observed in the heart rates spectral parameters between the groups of patients as well as among the individual patients. However, the mean heart rate alone did not distinguish stable from critically ill patients. Both the LFP and the LFP/RFP ratio discriminated between the Group A (stable) patients and the Group B (critical) patients. The LFP/RFP ratio grew out of a statistically significant (p less than symbol 0.00001) discrimination between stable and critical patients. Table VIII presents means of study parameters.

LFPs was 0.09 to 13.88 (arithmetic mean 1.77). In Group B, the range of LFP/RFP ratios was 0.17 to 1.9 (arithmetic mean 0.83), the ratio of RFPs was 0.02 to 0.32 (arithmetic mean 0.1), and the range of LFPs was 0.01 to 0.1 (arithmetic mean 0.5)

Although the mean value of the LFP/RFP ratio was greater than two for Group I, the ratio for the stable patients fell below two for brief periods. That which distinguishes the stable from the critical patients is the sustained value for greater than or about one hour of the LFP/RFP ratio for the critical group.

Figure 16:
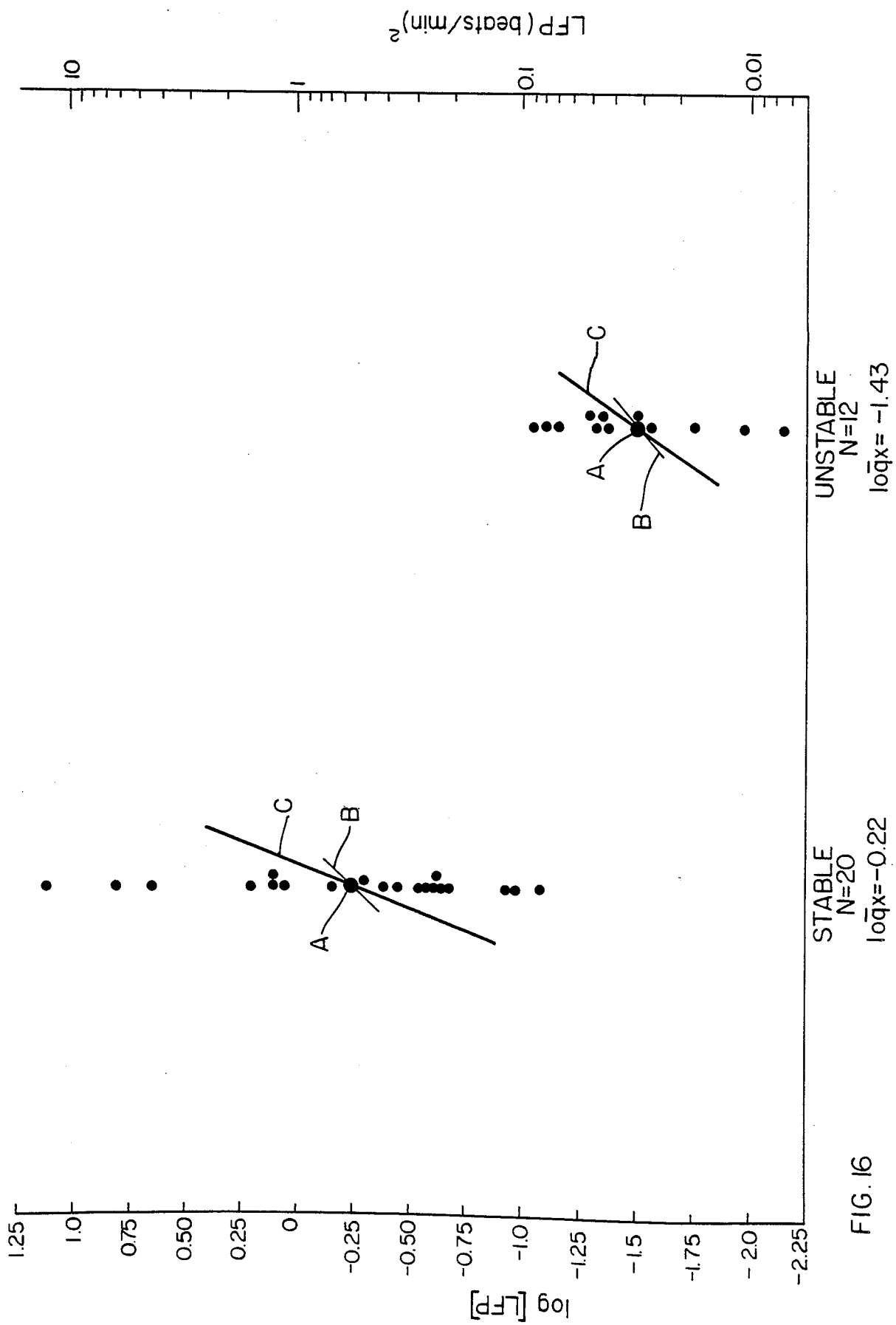
FIG. 16 depicts distributions in LFP data obtained according to the present invention for stable and for unstable patients.
Figure 17:
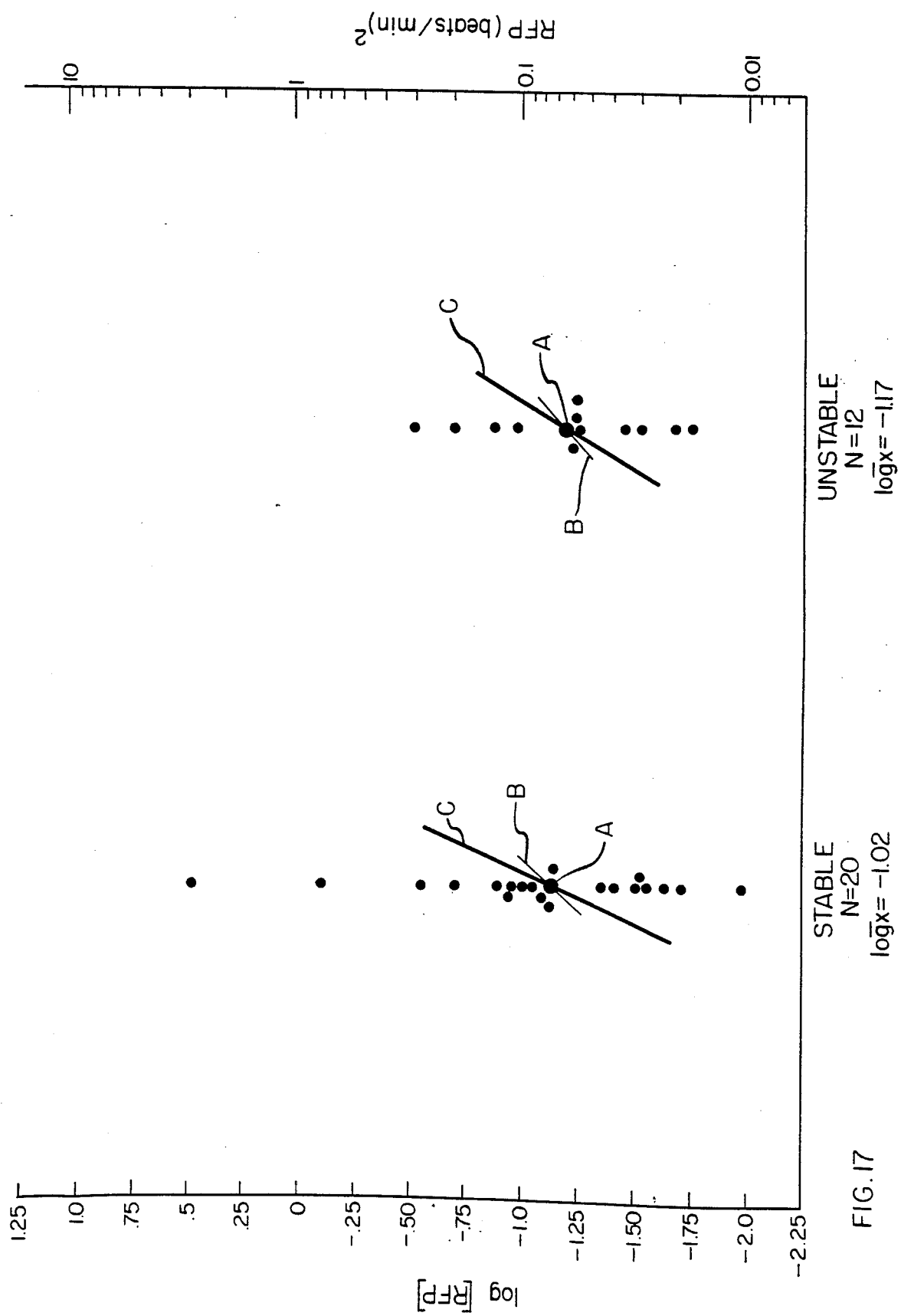
FIG. 17 graphically depicts distributions of RFP data according to the present invention for stable and for unstable patients.
Figure 18:
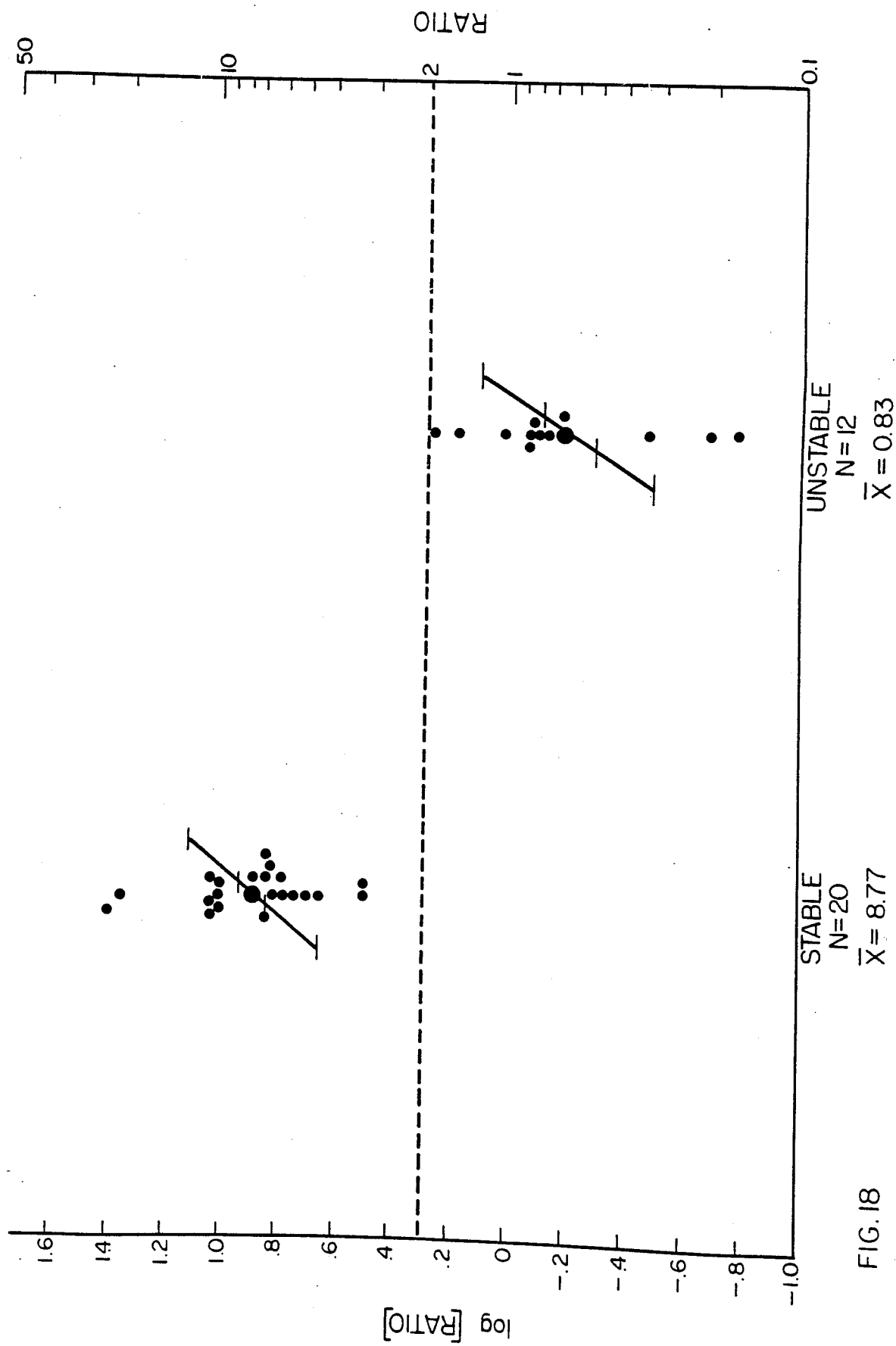
FIG. 18 graphically depicts data for LFP/RFP ratios according to the present invention for stable and for unstable patients.

The results are graphically depicted in FIGS. 16, 17 and 18. In FIGS. 16 and 17, each heavy dot A represents a geometric mean, each light line B indicates the standard error of the geometric mean and each heavy line C represents the standard deviation of the geometric mean. In FIG. 18, each heavy dot A represents an arithmetic mean, each set of slashes B1 and B2 represents the standard error of the arithmetic means and each set of slashes C1 and C2 represents the standard deviation of the arithmetic mean.

The significance of heart rate spectral analysis for diagnosis of cardiovascular stress and the prediction of fatality is highlighted by the fact that patients with a low LFP/RFP ratio underwent a cardiac arrest even in the presence of otherwise normal vital signs. No patient with a LFP/RFP ratio greater than two experienced a

TABLE VIII

| | MEANS OF STUDY PARAMETERS | | | | |
|---|---|---|---|---|---|
| PARAMETER (BEATS/MIN.) | MEAN | STD. DEV. | STD. ERROR OF MEAN | 99% CONFIDENCE LOWER | UPPER |
| GROUP A. STABLE | | | | | |
| LFP | 1.77 | 3.35 | 0.75 | −.37 | 3.91 |
| RFP | 0.28 | 0.70 | 0.16 | −.17 | 0.72 |
| LFP/RFP RATIO | 8.77 | 4.86 | 1.09 | 8.76 | 8.79 |
| HEART RATE | 139 | 19.60 | 4.38 | 139 | 139 |
| GROUP B. CRITICAL | | | | | |
| LFP | .05 | .03 | .01 | .02 | .07 |
| RFP | .10 | .09 | .03 | .01 | .18 |
| LFP/RFP RATIO | .83 | .51 | .15 | .83 | .83 |
| HEART RATE | 142 | 24.32 | 7.02 | 142 | 142 |

The discriminate value for the LFP/RFP ratio was two. In Group A, the range of LFP/RFP ratios was 3 to 22 (arithmetic mean 8.77). The range of RFPs was 0.01 to 3.13 (arithmetic mean 0.28) and the range of cardiac arrest.

Infusion of pressors, alone or in combination with vasodilators, did not induce a low LFP/RFP ratio.

Four patients in Group III had LFP/RFP ratios less than two during their critical periods. For the three of these four patients who were restudied during their recovery periods, all three had LFP/RFP ratios greater than two.

The mean LFP for Group B [0.05 (Beats per minute)$^2$] was less than the mean LFP for Group A [1.77 beats per minute)$^2$], $p < 0.0001$. There was no significant difference between the mean RFP between the groups.

The initial LFP/RFP ratios for the patients with isolated coarctation of the aorta ranged up to 10,000. The LFP/RFP ratios observed for this group immediately after an operation to correct the condition were within the range for Group A patients. Two patients had LFP/RFP ratios greater than 100 before discharge from the intensive care unit. These ratios were correlated with mild to moderate congestive heart failure. One of these patients died suddenly at approximately 2½ after the operation. The other two patients remained alive and well.

Although the LFP/RFP ratio provided the sharpest discrimination between stable and critical patients in these studies, the LFP alone discriminated between Groups A and B, $p < 0.0001$. Neither respiratory frequency peak power nor mean heart rate distinguished between Groups A and B. On the other hand, LFP/RFP ratios and LFP low levels sustained for greater than or about one hour correlate with the course of the conditions of patients who experienced cardiac arrest or severe hypotensive episodes but later recovered.

Although stable patients experienced transient depression of levels of LFP and of the LFP/RFP ratio, depression of these factors for about an hour or more never failed to predict a critical status.

No significant difference was observed between freely ventilating patients and mechanically ventilated patients. Eighteen out the twenty patients in Group A were mechanically ventilated and all twelve of the Group B patients were mechanically ventilated.

All patients in Group B received inotropic support while more than half of the patients in the Group A received at least some inotropic support. The cardiac diagnoses of all of the patients in Group B and for some of the patients in Group A were known to be associated with high mortality. All of the patients in Group B underwent deep hypothermic circulatory arrest during their operations. Of the twenty patients in Group A, nine had extra cardiac surgery (i.e. not involving cardiopulmonary bypass or deep hypothermic circulatory arrest). Three of the patients in Group II did not undergo operations. Therefore, it is not believed that differences in treatment or disease specific pathology alone explained the low values LFP and the low LFP/RFP ratios in Group B patients but that the low values actually reflect a vulnerable circulatory state.

It has also been observed that the value of LFP and of the LFP/RFP ratio increase in moderate to severe heart failure but decreased to subnormal values in end-stage myocardial failure. Thus, these two spectral parameters may indicate cardiovascular regulatory effectiveness (cardiovascular regulatory reserve) during the stress of heart failure.

This analysis is consistent with previous physiological studies which indicated that low frequency heart fluctuations may be mediated by both the beta-sympathetic and parasympathetic mechanisms while respiratory fluctuations are exclusively mediated by parasympathetic mechanisms. It is also consistent with this analysis that LFP has been observed to increase during conditions which elicit enhanced sympathetic activity, such as acute hypoxia, postural changes, hemmorhage and aortic constriction. In this light, the LFP/RFP ratio may represent a measure of the balance between beta adrenergic and parasympathetic modulation of cardiac function.

Thus, the increase in LFP and in the LFP/RFP ratio for patients with isolated coarctation of the aorta and moderate heart failure may result from an increased activity from the sympathetic mechanism and a decreased activity of the parasympathetic mechanism. On the other hand, the decreased level of LFP and of the LFP/RFP ratio found in critical patients may be due to non-responsiveness of the sympathetic mechanism. Sympathetic non-responsiveness may be due to myocardial catechlolamaine depletion alone or in combination with the observed down regulation of beta receptors from cardiac tissue in the end stage of heart failure.

EXAMPLE II

In patients undergoing operations, shifts in body fluid disposition during surgery may lead to changes in intervascular volume (i.e. a shift of fluid out of a circulatory three of blood vessels). Accordingly, the availability of the method of diagnosing cardiovasular stress as described in Example I may be used to choose among various protocols for treatment or to justify a radical change in medical or surgical treatment.

For example, by monitoring a patient with the real time heart rate frequency spectral monitor according to the present invention during administration of anesthesia, an anesthesiologist may non-invasively monitor intravascular volume status. Upon observing an increase in the LFP or in the LFP/RFP ratio, the anesthesiologist may increase the amount of fluids administered by way of intravenous injection or may take steps to reverse effects of a particular anesthetic.

It is a particular advantage of the apparatus according to the present invention that heart rate fluctuation spectral analysis may be done in real time. This capability permits correlation of treatment administered with changes in LFP or LFP/RFP ratios.

Although the present invention has been described in terms of preferred embodiments, it is understood that modifications, variations and improvements will occur to those skilled in the art. For example, it will occur to those skilled in the art to employ the present invention for monitoring cardiovascular instability in the following settings in which significant circulatory stress is commonly observed: Labor and Delivery Room; Operating Room; Cardiac Catheterization Laboratory; Neonatal, Pediatric, Adult Medical, Adult Surgical, Cardiothoracic and Neurosurgical Intensive Care Units; Coronary Care Units; Burn Units; and Emergency Rooms.

The present invention may also be used for monitoring cardiovascular instability in the following patients in which adjustments in cardiovascular regulation may provide a central key to understanding the efficiency and efficacy of treatment. Ambulatory patients with known heart disease in which sudden cardiac death is a common association, one example of which would be a patient with a congestive cardiomyopathy who is being treated with vasodialator drugs and for whom the LFP/RFP ratio has changed from a normal baseline level to decreased levels may then subsequently be either admitted to the hospital for adjustment of medications and/or observed and monitored in the physician's office while his vasodialator drug dose is increased. A patient with renal disease (e.g. one who requires dialysis) may exhibit a marked increase in LFP and LFP/RFP ratio secondary to the onset of incipient moderate congestive heart failure would thus be treated by dialysis to relieve a congested circulatory state; a patient with moderate to severe pulmonary disease resulting in hypoxemia and/or hypercarbia who requires bronchodialator and/or supplementary oxygen and/or mechanical ventilation (e.g. a patient who exhibits a marked decrease in LFP/RFP ratio secondary to myocardial failure due to a profound imbalance between myocardial ventricular output and oxygen demand), may be treated by adjustments in bronchodialator drugs, diuretics, and/or ventilator adjustments.

A premature infant of very low birth weight known to be at risk for intraventricular hemorrhage may, for example, develop a slow intracranial bleed associated with an abrupt increase in LFP, which may alert physicians prior to a brisk bleed thus allowing institution of appropriate changes in medical management to limit substantially known risk factors that may predispose to such an event, or may permit recognition of the presence of unsuspected circumstances that contribute to the bleed. In neurologic disease, such as one in which a patient has sustained a major intracerebral event (e.g. neurosurgical evacuation of a space occupying lesion such as a tumor or blood), a patient may, for example, exhibit a markedly attenuated LFP/RFP ratio, secondary to massively increased parasympathetic activity which would markedly increase RFP, at the expense of LFP, but which may or may not be associated with signs of increased intracranial pressure, and which may be treated by, for example, hyperventillation, rapid diuresis, or burr hole placement.

A patient with severe systemic infection may exhibit shock secondary to the infection process may, for example, exhibit an elevated LFP/RFP ratio which may then be subsequently used by the physician in managing the shock state by means of pressor agents and infusion of significant volumes of fluid, thus providing the physician an indication of how effectively he is treating the shocked state above and beyond the traditional measurements such as systemic blood pressure and cardiac output. A patient with hematologic disease associated with anemia, such as Sickle Cell Anemia, exhibits an oscillation in capillary blood flow when severly anemic at the frequency associated with LFP and may exhibit large values for LFP, and the LFP/RFP ratio may, for example, be treated by blood transfusion which may lead to an expected decrease in LFP, LFP/RFP ratio, and thus enable the physician to monitor by means of heart rate spectral analysis appropriate timing for transfusion therapy. A fetus prior to delivery, may for example, exhibit a marked attenuation in LFP associated with severe fetal distress, and may thus alert the physician to perform an emergency Caesarean section.

One skilled in the art understands that the calibrators according to the present invention may be adjusted to simulate disease states as well as normal conditions. It is also understood that the present invention is not limited to use with patients whose primary disease is of the heart but that modifications may be made for use with such patients.

Lastly, it is clear to one skilled in the art that durations and ranges for levels of LFP and LFP/RFP ratios are conservatively stated herein and that variations from these ranges and durations are contemplated within the scope of the equivalents of the present invention.

Therefore, it is intended that the methods and apparatus according to the present invention to be given the broadest scope allowable for the invention as claimed.

The following appendices are program listings for software useful in implementing the present invention. Specifically: Appendix A illustrates software for an embodiment of the present invention applicable to a Hewlett-Packard microcomputer; Appendix B illustrates software according to the present invention useful for practicing the present invention on an IBM personal computer; and Appendix C is a calibration program designed to implement the software driven calibrator of FIG. 11.

APPENDIX A

```
10  Summary3:!
20      !This program takes data already collected and
        allows the data
30      !to be outputted to a printer
40      !2 MAY 1985
50      !
60      COM /Trends/ Mean_hr_t(60),Lfa_t(60),Rfa_
        t(60),Ratio_t(60),T_ptr,Time_now1,Mean_resp_
        t(60),Trend_dp
70      COM /Multi_param/ Start_chan,Stop_chan,Pacing_
        bits,Pacing_rate,Num_pts,Nu
```

```
            m_xfer,Num_xfer_left,Name_len,Scr_file$[28],Scr_
            file2$[28]
80      COM /Pressure/
        Top1,Top2,Top3,Top4,Bot1,Bot2,Bot3,Bot4
90      COM /Editor/ Edit_msg$[80]
100     COM /Subject/ Sub_name$[25],Hos_num$[15],Id_
        age$[10],Id_wt$[10],Id_ht$[10
        ],Diag$[30],Opera$[45],Halt_pg,In_file$[6]
110-    COM /Io_chart/ Io_time$(8)[10],Iv_intake(8),Fluid_
        in(8),In_tot(8),Urine(8
        ),Chest(8),Out_tot(8),Net(8),Io_ptr
120     COM /Lab_chart/ Lab_
    time$(8)[10],Na(8),K1(8),Cl(8),Hco3(8),Ca(8),Hct(8),G
    luc(8),Dig(8),Pt(8),Ptt(8),Creat(8),Bun(8),Lab_ptr
130     COM /Vent_chart/ Vent_
        time$(8)[15],Rate(8),Fio2(8),Pp(8),Peep(8),Tv(8),
        Ie_ratio$(8)[5],Airp(8),Ph(8),Po2(8),
           Pco2(8),Bgo3(8),Be(8),Vent_ptr
140     COM /Pres_chart/ Pres_time$(20)[15],Ao_s(20),Ao_
        d(20),Ao_m(20),Pa_s(20),P
           a_d(20),Pa_m(20),La_m(20),Ra_m(20),Pres_
           ptr,Pres_in
150     COM /Heart_index/ Heart_
        time$(15)[15],Ci(15),Pvri(15),Svri(15),Heart_ptr
160     COM /Drugs/ Drug_time$(40)[20],Drug_
        name$(40)[40],Drug_dos$(40)[20],Drug_
           ptr
170     DIM Msg_buffer$[6400] BUFFER
180     DIM Pres_p(20),Io_p(8),Lab_p(8),Vent_p(8),Heart_
           p(5),Drug_p(40)
190     INPUT "enter date on which data was collected
        (ddmmyy) e.g. 22AP85",In_file$
200     Disk1$=":HP8290X,700,1"
210     INPUT "is the trend file named 'trnd'(1) or 'temp_
        trend'(2)?",Ans
220     IF Ans=2 THEN
230        ASSIGN @Trend_file TO "temp_
           trend"&Disk1$;FORMAT OFF
```

| | |
|---|---|
| 240 | ASSIGN @Messages TO "messglog"&Disk1$;FORMAT OFF |
| 250 | ASSIGN @Hemo_data TO "hemo_data"&Disk1$;FORMAT OFF |
| 260 | ASSIGN @Io_data TO "io_data"&Disk1$;FORMAT OFF |
| 270 | ASSIGN @Lab_data TO "lab_data"&Disk1$;FORMAT OFF |
| 280 | ASSIGN @Vent_data TO "vent_data"&Disk1$;FORMAT OFF |
| 290 | ASSIGN @Co_data TO "co_data"&Disk1$;FORMAT OFF |
| 300 | ASSIGN @Drug_data TO "drug_data"&Disk1$;FORMAT OFF |
| 310 | ASSIGN @Sub_data TO "sub_data"&Disk1$;FORMAT OFF |
| 320 | ON END @Trend_file GOTO Start |
| 330 | FOR I=0 TO 55 |
| 340 | ENTER @Trend_file;Trans_t(I),Mean_hr_t(I),Lfa_t(I),Rfa_t(I),Ratio_t(I),Mean_resp_t(I) |
| 350 | NEXT I |
| 360 | T_ptr=I |
| 370 | Num_xfer=T_ptr |
| 380 | ELSE |
| 390 | ASSIGN @Trend_file TO "trnd"&In_file$&Disk1$;FORMAT OFF |
| 400 | ASSIGN @Messages TO "msgs"&In_file$&Disk1$;FORMAT OFF |
| 410 | ASSIGN @Hemo_data TO "hemo"&In_file$&Disk1$;FORMAT OFF |
| 420 | ASSIGN @Io_data TO "io__"&In_file$&Disk1$;FORMAT OFF |
| 430 | ASSIGN @Lab_data TO "lab_"&In_file$&Disk1$;FORMAT OFF |
| 440 | ASSIGN @Vent_data TO "vent"&In_file$&Disk1$;FORMAT OFF |
| 450 | ASSIGN @Co_data TO "co__"&In_ |

```
                file$&Disk1$;FORMAT OFF
460         ASSIGN @Drug_data TO "drug"&In_
                file$&Disk1$;FORMAT OFF
470         ASSIGN @Sub_data TO "sub_"&In_
                file$&Disk1$;FORMAT OFF
480         ENTER @Trend_file;Mean_hr_t(*),Lfa_t(*),Rfa_
                t(*),Ratio_t(*),Mean_resp
                _t(*),Trans_time(*),T_ptr
490         Num_xfer=T_ptr
500     END IF
510         ASSIGN @Trend_file TO *
520     ON END @Hemo_data GOTO Hemo1
530     FOR I=0 TO 20
540         ENTER @Hemo_data;Pres_time$(I),Ao_s(I),Ao_
                d(I),Ao_m(I),Pa_s(I),Pa_d(I
                ),Pa_m(I),La_m(I),Ra_m(I),Pres_p(I)
550     NEXT I
560 Hemo1:ASSIGN @Hemo_data TO *
570     Pres_ptr=I-1
580     ON END @Io_data GOTO Io1
590     FOR I=0 TO 8
600         ENTER @Io_data;Io_time$(I),Iv_intake(I),Fluid_
                in(I),In_tot(I),Urine(I
                ),Chest(I),Out_tot(I),Net(I),Io_p(I)
610     NEXT I
620 Io1:ASSIGN @Io_data TO *
630     Io_ptr=I-1
640     ON END @Lab_data GOTO Lab1
650     FOR I=0 TO 8
660         ENTER @Lab_data;Lab_
        time$(I),Na(I),K1(I),Cl(I),Hco3(I),Ca(I),Hct(I),G
        luc(I),Dig(I),Pt(I),Ptt(I),Creat(I),Bun(I),Lab_p(I)
670     NEXT I
680 Lab1:ASSIGN @Lab_data TO *
690     Lab_ptr=I-1
700     ON END @Vent_data GOTO Vent1
710     FOR I=0 TO 8
720         ENTER @Vent_data;Vent_
```

```
            time$(I),Rate(I),Fio2(I),Pp(I),Peep(I),Tv(I),
            Ie_ratio$(I),Airp(I),Ph(I),Po2(I),
              Pco2(I),Bgo3(I),Be(I),Vent_p(I)
730     NEXT I
740 Vent1:ASSIGN @Vent_data TO *
750     Vent_ptr=I-1
760     ON END @Co_data GOTO Co1
770     FOR I=0 TO 5
780         ENTER @Co_data;Heart_
              time$(I),Ci(I),Pvri(I),Svri(I),Heart_p(I)
790     NEXT I
800 Co1:ASSIGN @Co_data TO *
810     Heart_ptr=I-1
820     ON END @Drug_data GOTO Drug1
830     FOR I=0 TO 40
840         ENTER @Drug_data;Drug_time$(I),Drug_
              name$(I),Drug_dos$(I),Drug_p(I)
850     NEXT I
860 Drug1:ASSIGN @Drug_data TO *
870     Drug_ptr=I-1
880         !
890         !
900         !
910     Pacing_rate=250
920     Time_now1=TIMEDATE MOD 86400
930     Out_graph=1
        !....graphics
        dump
940     Trend_dp=2
950     CALL Trend_graph
960     CALL Graph_dump(Out_graph)
970     Trend_dp=1
980     CALL Trend_graph
990     CALL Graph_dump(Out_graph)
1000    !
1010 Chart_dump:!
1020    ENTER @Sub_data;Sub_name$,Hos_num$,Id_age$,Id_
          wt$,Id_ht$,Diag$,Opera$
```

```
1030      ASSIGN @Sub_data TO *
1040      Out_graph=2
1050      FOR I=1 TO 5
1060          CALL Chart(I)
1070      CALL Graph_dump(Out_graph)        !....chart dump
1080      NEXT I
1090      !
1100      !
1110 Msg_dump:  !
1120      IF Ans=1 THEN
1130          ASSIGN @Msg_file TO "msgs"&In_
              file$&Disk1$;FORMAT OFF
1140      ELSE
1150          ASSIGN @Msg_file TO "messglog"&Disk1$;FORMAT
              OFF
1160      END IF
1170      PRINTER IS 701
1180      ASSIGN @Msg_buffer TO BUFFER Msg_buffer$
1190      STATUS @Msg_file,3;Num_rec
1200      STATUS @Msg_file,4;Rec_len
1210      STATUS @Msg_file,7;Eof_rec
1220      STATUS @Msg_file,8;Eof_byte
1230      Num_bytes=(Eof_rec-1)*Rec_len+Eof_byte-1
1240 Read_msg:TRANSFER @Msg_file TO @Msg_buffer;COUNT
     Num_bytes,WAIT
1250      ASSIGN @Msg_file TO *
1260      ASSIGN @Msg_buffer TO *
1270      Cur_ptr=1
1280          PRINT USING Image_wt1;Sub_name$,Hos_num$,In_
              file$
1290 Image_wt1:IMAGE    "Name: ",K,XXXX,"Hosp num:
                         ",K,XXXXX,K
1300          PRINT USING Image_wt2;Id_age$,Id_wt$,Id_
              ht$,Diag$,Opera$
1310 Image_wt2:IMAGE    "Age: ",K,XXXX,"Wt(kg):
              ",K,XXXX,"Ht(cm): ",K,XXXX,"Diag:
              ",K,XXXX,"Op: ",K
1320 Next_msg:!
```

```
1330    Beg_msg=POS(Msg_buffer$[4],"Time")+3
1340    IF Beg_msg=3 THEN GOTO Stopper
1350    PRINT Msg_buffer$[1,Beg_msg-1]
1360    Msg_buffer$=Msg_buffer$[Beg_msg]
1370    GOTO Next_msg
1380 Stopper:!PRINTER IS 1
1390    STOP
1400    END
1410        !
1420    !
1430    !This subroutine prints the graphics
1440    !
1450    !
1460    SUB Trend_graph
1470 !
1480        COM /Trends/ Mean_hr_t(*),Lfa_t(*),Rfa_
              t(*),Ratio_t(*),T_ptr,Time_now
                l,Meas_resp_t(*),Trend_dp,Trans_time(*)
1490        COM /Multi_param/ Start_chan,Stop_chan,Pacing_
              bits,Pacing_rate,Num_pt
                s,Num_xfer,Num_xfer_left,Name_len,Scr_
                  file$[28],Scr_
              file2$[28]
1500        COM /Pressure/
              Top1,Top2,Top3,Top4,Bot1,Bot2,Bot3,Bot4
1510        COM /Pres_chart/ Pres_time$(*),Ao_s(*),Ao_
              d(*),Ao_m(*),Pa_s(*),Pa_d(*
                ),Pa_m(*),La_m(*),Ra_m(*),Pres_ptr,Pres_in
1520        DIM First_line(60),Sec_line(60),Third_
              line(60),Fourth_line(60)
1530        IF Trend_dp=1 THEN
1540            MAT First_line= Ao_m
1550            MAT Sec_line= Pa_m
1560            MAT Third_line= La_m
1570            MAT Fourth_line= Ra_m
1580            G_right=INT((Num_xfer*256/60)/15)
1590            Trend_ptr=Pres_ptr
1600            Top1=150
```

```
1610            Bot1=0
1620            Top2=75
1630            Bot2=0
1640            Top3=50
1650            Bot3=0
1660            Top4=50
1670            Bot4=0
1680        ELSE
1690            MAT First_line= Mean_hr_t
1700            MAT Sec_line= Ratio_t
1710            MAT Third_line= Lfa_t
1720            MAT Fourth_line= Rfa_t
1730            G_right=Num_xfer
1740            Trend_ptr=T_ptr
1750            Top1=200
1760            Bot1=0
1770            Top2=2.5
1780            Bot2=-2.5
1790            Top3=10
1800            Bot3=0
1810            Top4=10
1820            Bot4=0
1830        END IF
1840        Block_time=Pacing_rate*1.024/3600.
1850        GINIT
1860        GCLEAR
1870        PRINT CHR$(12)
1880        GRAPHICS ON
1890        Beg_time=Time_now1/3600-Block_time
1900        End_time=Beg_time+Num_xfer*Block_time
1910        Ibeg_time=INT(Beg_time)
1920        IF Ibeg_time<Beg_time THEN Ibeg_time=Ibeg_time+1
1930    !
1940    ! label the time axes
1950    !
1960        VIEWPORT 0,128,45,50
```

```
1970        WINDOW Beg_time,End_time,0,1
1980        IF INT(End_time)>Beg_time THEN
1990            LDIR 0
2000            FOR T_label=Ibeg_time TO INT(End_time)
2010                MOVE T_label,.5
2020                LORG 5
2030                CSIZE 4
2040                LABEL T_label
2050            NEXT T_label
2060        END IF
2070        VIEWPORT 0,128,40,45
2080        WINDOW 0,1,0,1
2090        MOVE .5,0
2100        LORG 4
2110        LABEL "Time (24 hr)"
2120    !
2130    ! draw the axes
2140    !
2150        VIEWPORT 0,128,50,100
2160        WINDOW Beg_time,End_time,0,1
2170        AXES 1/15.,.1,Beg_time,0
2180        WINDOW 1,0,1,0
2190        AXES 0,.25,0,0
2200    !
2210    ! mean heart rate trends
2220    !
2230        WINDOW -1,G_right,Bot1,Top1
2240        MOVE 0,First_line(0)
2250        FOR I=0 TO Trend_ptr-1
2260            DRAW I,First_line(I)
2270        NEXT I
2280    !
2290    ! ratio trends (with a line at ratio=2)
2300    !
2310        WINDOW -1,G_right,Bot2,Top2
2320        LINE TYPE 8,5
2330        IF Trend_dp=2 THEN
```

```
2340            MOVE 0,LGT(Sec_line(0))
2350        ELSE
2360            MOVE 0,Sec_line(0)
2370        END IF
2380        FOR I=0 TO Trend_ptr-1
2390            IF Trend_dp=2 THEN
2400                DRAW I,LGT(Sec_line(I))
2410            ELSE
2420                DRAW I,Sec_line(I)
2430            END IF
2440        NEXT I
2450        IF Trend_dp=2 THEN
2460            LINE TYPE 3,5!..sparsely dotted line at
                    ratio=2
2470            MOVE 0,LGT(2.)
2480            DRAW Trend_ptr-1,LGT(2.)
2490        END IF
2500    !
2510    ! lfa trends
2520    !
2530        WINDOW -1,G_right,Bot3,Top3
2540        LINE TYPE 4,5
2550        MOVE 0,Third_line(0)
2560        FOR I=0 TO Trend_ptr-1
2570            DRAW I,Third_line(I)
2580        NEXT I
2590    !
2600    ! rfa trends
2610    !
2620        WINDOW -1,G_right,Bot4,Top4
2630        LINE TYPE 5,5
2640        MOVE 0,Fourth_line(0)
2650        FOR I=0 TO Trend_ptr-1
2660            DRAW I,Fourth_line(I)
2670        NEXT I
2680    !
2690    ! draw a key for line types
```

```
2700  !
2710       VIEWPORT 64,128,0,50
2720       WINDOW 0,1,0,13
2730       IF Trend_dp=2 THEN
2740           PRINT TABXY(1,17);"trend graph"
2750           PRINT TABXY(55,15);"mean hr(0-200)"
2760           PRINT TABXY(55,16);"ratio(.01-100)"
2770           PRINT TABXY(55,17);"lfa    (0-10)"
2780           PRINT TABXY(55,18);"rfa    (0-10)"
2790       ELSE
2800           PRINT TABXY(1,17);"mean pressure graphs"
2810           PRINT TABXY(50,15);"ao pressure(0-150)"
2820           PRINT TABXY(50,16);"pa pressure(0-75)"
2830           PRINT TABXY(50,17);"la pressure(0-50)"
2840           PRINT TABXY(50,18);"ra pressure(0-50)"
2850       END IF
2860       LINE TYPE 1,5
2870       MOVE .8,11
2880       DRAW 1.,11
2890       LINE TYPE 8,5
2900       MOVE .8,10
2910       DRAW 1.,10
2920       LINE TYPE 4,5
2930       MOVE .8,9
2940       DRAW 1.,9
2950       LINE TYPE 5,5
2960       MOVE .8,8
2970       DRAW 1.,8
2980    SUBEND
2990  !
3000  !
3010  !This subroutine prints the charts
3020  !
3030  !
3040     SUB Chart(Chart_num)
3050        COM /Subject/ Sub_name$,Hos_num$,Id_age$,Id_wt$,Id_ht$,Diag$,Opera$,H
            alt_pg,In_file$
```

```
3060      COM /Io_chart/ Io_time$(*),Iv_intake(*),Fluid_
          in(*),In_tot(*),Urine(*
          ),Chest(*),Out_tot(*),Net(*),Io_ptr
3070      COM /Lab_chart/ Lab_
    time$(*),Na(*),K1(*),Cl(*),Hco3(*),Ca(*),Hct(*),G
          luc(*),Dig(*),Pt(*),Ptt(*),Creat(*),Bun(*),Lab_
          ptr
3080      COM /Vent_chart/ Vent_
      time$(*),Rate(*),Fio2(*),Pp(*),Peep(*),Tv(*),
      Ie_ratio$(*),Airp(*),Ph(*),Po2(*),Pco2(*),
      Bgo3(*),Be(*),Vent_ptr
3090      COM /Pres_chart/ Pres_time$(*),Ao_s(*),Ao_
          d(*),Ao_m(*),Pa_s(*),Pa_d(*
          ),Pa_m(*),La_m(*),Ra_m(*),Pres_ptr,Pres_in
3100      COM /Pressure/
                  Top1,Top2,Top3,Top4,Bot1,Bot2,Bot3,Bot4
3110      COM /Heart_index/ Heart_
          time$(*),Ci(*),Pvri(*),Svri(*),Heart_ptr
3120      COM /Drugs/ Drug_time$(*),Drug_name$(*),Drug_
          dos$(*),Drug_ptr
3130      Out_graph=2
3140      Pres_stl=0
3150      Lab_stl=0
3160      Io_stl=0
3170      Vent_stl=0
3180      Drug_stl=0
3190      Io_p=Io_ptr
3200      Lab_p=Lab_ptr
3210      Vent_p=Vent_ptr
3220      Pres_p=Pres_ptr
3230      Heart_p=Heart_ptr
3240      Drug_p=Drug_ptr
3250      !
3260      ! set up identifying subject info
3270      !
3280      GRAPHICS OFF
3290      PRINT CHR$(12)
```

```
3300        PRINT TABXY(1,1);
3310        PRINT USING Image_wt1;Sub_name$,Hos_num$,In_
            file$
3320 Image_wt1:IMAGE    "Name: ",K,XXXX,"Hosp num:
            ",K,XXXXX,K
3330        PRINT TABXY(1,2);
3340        PRINT USING Image_wt2;Id_age$,Id_wt$,Id_
            ht$,Diag$,Opera$
3350 Image_wt2:IMAGE    "Age: ",K,XXXX,"Wt(kg):
            ",K,XXXX,"Ht(cm): ",K,XXXX,"Diag:
            ",K,XXXX,"Op: ",K
3360        !
3370        ! go to appropriate chart
3380        !
3390        ON Chart_num GOTO In_out,Lab_val,Vent_
            val,Pres_val,Drug
3400 In_out:!                              ....intake/output
3410        ! IF Io_ptr>3 THEN Io_stl=2
3420        ! IF Io_ptr>5 THEN
3430        !     DISP "do not input more Intake/Output
            !     data; disc full"
3440        !     WAIT 3
3450        !     SUBEXIT
3460        ! END IF
3470        PRINT TABXY(30,3);"INTAKE/OUTPUT CHART"
3480        PRINT TABXY(1,4);"Intake (cc/hr) "
3490        PRINT TABXY(1,5);"Time"
3500        PRINT TABXY(4,6);"Maint. Fluid"
3510        PRINT TABXY(4,7);"Other Fluids"
3520        PRINT TABXY(1,9);"Total "
3530        PRINT TABXY(1,11);"Output (cc/hr)"
3540        PRINT TABXY(4,12);"Urine"
3550        PRINT TABXY(4,13);"Chest"
3560        PRINT TABXY(1,15);"Total"
3570        PRINT TABXY(1,17);"Net I/O"
3580        Start=25
3590        IF Io_ptr>3 THEN Io_p=3
```

```
3600 Io_dp:FOR I=Io_stl TO Io_p
3610        PRINT TABXY(Start,5);Io_time$(I)
3620        PRINT TABXY(Start,6);Iv_intake(I)
3630        PRINT TABXY(Start,7);Fluid_in(I)
3640        PRINT TABXY(Start,9);In_tot(I)
3650        PRINT TABXY(Start,12);Urine(I)
3660        PRINT TABXY(Start,13);Chest(I)
3670        PRINT TABXY(Start,15);Out_tot(I)
3680        PRINT TABXY(Start,17);Net(I)
3690        Start=Start+10
3700      NEXT I
3710      IF Io_ptr>Io_p THEN
3720         INPUT "more data on next page - do you
                    want this dumped to printe
                    r? (Y/N)",Ans$
3730         IF Ans$="Y" OR Ans$="y" THEN CALL Graph_
                    dump(Out_graph)
3740         Io_stl=4
3750         Io_p=Io_ptr
3760         Start=25
3770         FOR J=5 TO 17
3780            PRINT TABXY(Start,J);"         "
3790         NEXT J
3800         GOTO Io_dp
3810      END IF
3820      GOTO Finish
3830 !
3840 !
3850 Lab_val:!                             ...lab values
3860      !IF Lab_ptr>3 THEN Lab_stl=2
3870      !IF Lab_ptr>5 THEN
3880      !    DISP "do not input any more lab values;
              !    disc full"
3890      !    WAIT 3
3900      !    SUBEXIT
3910      !END IF
3920       PRINT TABXY(30,3);"Lab Values"
3930       PRINT TABXY(10,4);"Time"
```

```
3940        PRINT TABXY(1,6);"Na"
3950        PRINT TABXY(1,7);"K"
3960        PRINT TABXY(1,8);"Cl"
3970        PRINT TABXY(1,9);"HCO3"
3980        PRINT TABXY(1,10);"Ca"
3990        PRINT TABXY(1,11);"Hct"
4000        PRINT TABXY(1,12);"Glucose"
4010        PRINT TABXY(1,13);"Dig level"
4020        PRINT TABXY(1,14);"PT"
4030        PRINT TABXY(1,15);"PTT"
4040        PRINT TABXY(1,16);"Creat"
4050        PRINT TABXY(1,17);"Bun"
4060        Start=15
4070        IF Lab_ptr>3 THEN Lab_p=3
4080 Lab_dp:FOR I=Lab_stl TO Lab_p
4090            PRINT TABXY(Start+10,4);Lab_time$(I)
4100            PRINT TABXY(Start+10,6);Na(I)
4110            PRINT TABXY(Start+10,7);Kl(I)
4120            PRINT TABXY(Start+10,8);Cl(I)
4130            PRINT TABXY(Start+10,9);Hco3(I)
4140            PRINT TABXY(Start+10,10);Ca(I)
4150            PRINT TABXY(Start+10,11);Hct(I)
4160            PRINT TABXY(Start+10,12);Gluc(I)
4170            PRINT TABXY(Start+10,13);Dig(I)
4180            PRINT TABXY(Start+10,14);Pt(I)
4190            PRINT TABXY(Start+10,15);Ptt(I)
4200            PRINT TABXY(Start+10,16);Creat(I)
4210            PRINT TABXY(Start+10,17);Bun(I)
4220            Start=Start+10
4230        NEXT I
4240        IF Lab_ptr>Lab_p THEN
4250            INPUT "more data on next page - do you want this dumped to printe
                r? (Y/N)",Ans$
4260            IF Ans$="Y" OR Ans$="y" THEN CALL Graph_dump(Out_graph)
4270            Lab_stl=4
4280            Lab_p=Lab_ptr
```

```
4290        Start=15
4300        FOR J=4 TO 17
4310           PRINT TABXY(Start,J);"          "
4320        NEXT J
4330        GOTO Lab_dp
4340     END IF
4350     GOTO Finish
4360 !
4370 !
4380 Vent_val:!                  ....ventilation values
4390     ! IF Vent_ptr>3 THEN Vent_stl=2
4400     ! IF Vent_ptr>5 THEN Vent_stl=4
4410     ! IF Vent_ptr>7 THEN
4420     !    DISP "do not input any more Vent values; disc full"
4430     !    WAIT 3
4440     !    SUBEXIT
4450     ! END IF
4460     PRINT TABXY(30,3);"VENTILATION"
4470     PRINT TABXY(1,4);"Settings          Hour:"
4480     PRINT TABXY(4,5);"Rate"
4490     PRINT TABXY(4,6);"FIO2"
4500     PRINT TABXY(4,7);"Peak Pres"
4510     PRINT TABXY(4,8);"Peep"
4520     PRINT TABXY(4,9);"TV"
4530     PRINT TABXY(4,10);"I:E ratio"
4540     PRINT TABXY(4,11);"Mean air"
4550     PRINT TABXY(1,12);"Blood Gases"
4560     PRINT TABXY(4,13);"ph"
4570     PRINT TABXY(4,14);"pO2"
4580     PRINT TABXY(4,15);"pCO2"
4590     PRINT TABXY(4,16);"HCO3"
4600     PRINT TABXY(4,17);"BE"
4610     Start=15
4620     IF Vent_ptr>3 THEN Vent_p=3
4630 Vent_dp:FOR I=Vent_stl TO Vent_p
4640        PRINT TABXY(Start+10,4);Vent_time$(I)
4650        PRINT TABXY(Start+10,5);Rate(I)
```

```
4660            PRINT TABXY(Start+10,6);Fio2(I)
4670            PRINT TABXY(Start+10,7);Pp(I)
4680            PRINT TABXY(Start+10,8);Peep(I)
4690            PRINT TABXY(Start+10,9);Tv(I)
4700            PRINT TABXY(Start+10,10);Ie_ratio$(I)
4710            PRINT TABXY(Start+10,11);Airp(I)
4720            PRINT TABXY(Start+10,13);Ph(I)
4730            PRINT TABXY(Start+10,14);Po2(I)
4740            PRINT TABXY(Start+10,15);Pco2(I)
4750            PRINT TABXY(Start+10,16);Bgo3(I)
4760            PRINT TABXY(Start+10,17);Be(I)
4770            Start=Start+10
4780         NEXT I
4790         IF Vent_ptr>Vent_p THEN
4800            INPUT "more data on next page - do you want this dumped to printe
                  r? (Y/N)",Ans$
4810            IF Ans$="Y" OR Ans$="y" THEN CALL Graph_dump(Out_graph)
4820            Vent_stl=4
4830            Vent_p=Vent_ptr
4840            Start=15
4850            FOR J=4 TO 17
4860               PRINT TABXY(Start,J);"          "
4870            NEXT J
4880            GOTO Vent_dp
4890         END IF
4900         GOTO Finish
4910  !
4920  !
4930  Pres_val:!                              ....pressure values
4940         !IF Pres_ptr>12 THEN Pres_stl=5
4950         PRINT TABXY(9,3);"Time:"
4960         PRINT TABXY(1,4);"Systemic"
4970         PRINT TABXY(4,5);"systolic"
4980         PRINT TABXY(4,6);"diastolic"
4990         PRINT TABXY(4,7);"mean"
```

```
5000        PRINT TABXY(1,8);"Pulmonary"
5010        PRINT TABXY(4,9);"systolic"
5020        PRINT TABXY(4,10);"diastolic"
5030        PRINT TABXY(4,11);"mean"
5040        PRINT TABXY(1,12);"LA mean"
5050        PRINT TABXY(1,13);"RA mean"
5060        PRINT TABXY(9,14);"Time: "
5070        PRINT TABXY(1,15);"C.I."
5080        PRINT TABXY(1,16);"PVRI"
5090        PRINT TABXY(1,17);"SVRI"
5100        Start=15
5110        IF Pres_ptr>12 THEN Pres_p=12
5120 Pres_dp:FOR I=Pres_stl TO Pres_p
5130            PRINT TABXY(Start,3);Pres_time$(I)
5140            PRINT TABXY(Start,5);Ao_s(I)
5150            PRINT TABXY(Start,6);Ao_d(I)
5160            PRINT TABXY(Start,7);Ao_m(I)
5170            PRINT TABXY(Start,9);Pa_s(I)
5180            PRINT TABXY(Start,10);Pa_d(I)
5190            PRINT TABXY(Start,11);Pa_m(I)
5200            PRINT TABXY(Start,12);La_m(I)
5210            PRINT TABXY(Start,13);Ra_m(I)
5220            Start=Start+5
5230        NEXT I
5240        Start=15
5250        FOR I=0 TO Heart_ptr
5260            PRINT TABXY(Start,14);Heart_time$(I)
5270            PRINT TABXY(Start,15);Ci(I)
5280            PRINT TABXY(Start,16);Pvri(I)
5290            PRINT TABXY(Start,17);Svri(I)
5300            Start=Start+5
5310        NEXT I
5320        IF Pres_ptr>Pres_p THEN
5330            INPUT "more data on next page - do you want this dumped to printe
                r? (Y/N)",Ans$
5340            IF Ans$="Y" OR Ans$="y" THEN CALL Graph_dump(Out_graph)
```

```
5350          Pres_stl=13
5360          Pres_p=Pres_ptr
5370          Start=15
5380          FOR J=3 TO 13
5390          PRINT TABXY(Start,J);"              "
5400          NEXT J
5410          GOTO Pres_dp
5420       END IF
5430       GOTO Finish
5440 !
5450 !
5460 Drug:!                              ....hey man, drugs
5470     !IF Drug_ptr>9 THEN Drug_stl=4
5480     ! IF Drug_ptr>14 THEN Drug_stl=9
5490     !IF Drug_ptr>19 THEN Drug_stl=14
5500     !IF Drug_ptr>24 THEN Drug_stl=19
5510     !IF Drug_ptr>29 THEN Drug_stl=24
5520     !IF Drug_ptr>34 THEN Drug_stl=29
5530     !IF Drug_ptr>38 THEN
5540     !    DISP "do not enter more drugs; disc full"
5550     !    WAIT 3
5560     !    SUBEXIT
5570     ! END IF
5580       PRINT TABXY(30,4);"Drug Chart"
5590       PRINT TABXY(1,6);"Name"
5600       PRINT TABXY(30,6);"Dosage"
5610       PRINT TABXY(60,6);"Time"
5620       D_line=7
5630       IF Drug_ptr>9 THEN Drug_p=9
5640 Drug_dp:FOR I=Drug_stl TO Drug_p
5650          PRINT TABXY(1,D_line);Drug_name$(I)
5660          PRINT TABXY(30,D_line);Drug_dos$(I)
5670          PRINT TABXY(60,D_line);Drug_time$(I)
5680          D_line=D_line+1
5690       NEXT I
5700       IF Drug_ptr>Drug_p THEN
5710          INPUT "more data on next page - do you
                    want this dumped to printer? (Y/N)",Ans$
```

```
5720            IF Ans$="Y" OR Ans$="y" THEN CALL Graph_
                dump(Out_graph)
5730            Drug_stl=Drug_stl+10
5740            Drug_p=Drug_p+10
5750            D_line=7
5760            FOR J=7 TO 17
5770                PRINT TABXY(1,J);"        "
5780            NEXT J
5790            GOTO Drug_dp
5800         END IF
5810 Finish:  !
5820   SUBEND
5830   !
5840   !
5850   !
5860   SUB Graph_dump(A)
5870 Graph_dump:INPUT "do you want a hard copy?
     <Y/N>",Ans$
5880      IF Ans$="Y" OR Ans$="y" THEN
5890         IF A=1 THEN
5900             DUMP GRAPHICS #701
5910             PRINTER IS 701
5911             PRINT CHR$(12)
5920             GRAPHICS OFF
5930         ELSE
5940             DUMP ALPHA #701
5950             PRINTER IS 701
5960             PRINT CHR$(12)
5970         END IF
5980      END IF
5990      PRINTER IS 1
6000   SUBEND 10 Hrsa3:!THIS IS A PROGRAM TO SET UP THE HIGH SPEED
   A/D        !SYSTEM
20       ! AND CONTINUOUSLY OBTAIN INFORMATION
30       !
40       !
```

```
50      !...........................................
60      !
70      ! LAST REVISION: 30 April 1985
80      !
90      !...........................................

100     !
110     !
120     ! > FULL SET OF DECLARATIONS FOR THE HPIB BUS
          EXTENDED TALK ADDRESSES
130     !
140     !
150 Assignments:   !
160     ASSIGN @Multi TO 723
170     ASSIGN @Input_para TO 72301
180     ASSIGN @Input_intr TO 72302
190     ASSIGN @Input_ext TO 72303
200     ASSIGN @Read_format TO 72304
210     ASSIGN @Memory_input TO 72305
220     ASSIGN @Read_val TO 72306
230     ASSIGN @Read_status TO 72308
240     ASSIGN @Output_intr TO 72309
250     ASSIGN @Hpib_srq_status TO 72310
260     ASSIGN @Err_status_lst TO 72311
270     ASSIGN @Int_addr TO 72312
280     ASSIGN @Busy_instr TO 72313
290     ASSIGN @Read_clock TO 72314
300     !
310     !
320     !...........................................
330     !
340     ! SET UP INTERRUPT/ERROR HANDLERS
350     ! SET UP COMMON STORAGE/ARRAY STORAGE
360     !...........................................

370     !
380     !
390     COM /Intr_7/ Int_flag,Status_bytes(5)
```

```
400    COM /Flags/ Atod_done,Scanner_done,Memory1_
       done,Memory2_done,Timer_done,Counter_done,
          Memory3_done,Memory4_done
410    COM /Io_arrays/ Counters(3),Counters2(3),Time_
       base$[7]
420    COM /Multi_param/ Start_chan,Stop_chan,Pacing_
       bits,Pacing_rate,Num_pts,Nu m_xfer,Num_xfer_
          left,Name_len,Scr_file$[28],Scr_
       file2$[28]
430    COM /Hr_sig/ Num_pulses,Last_pulse,First_blk_
       flg,Last_time,Num_hr_sig,Max_hr_pts,Avg_
          hr,Rollover,Hr_smooth
440    COM /Plot_par/ Plotbox,Boxcar_flg,Log_
          plotflg,Freq_limit,Resp_search,Pct_thresh
450    COM /Graphs/
       Hrdata(512),Hrspec(512),Respspec(512),Bpspec(512)
460    COM /Vitaldata/ Rfa,Lfa,Peakratio,Meas_resp,Next_
       time
470    COM /Messagecom/ Message$(10)[80],@Messages
480    COM /Trends/ Mean_hr_t(60),Lfa_t(60),Rfa_
       t(60),Ratio_t(60),T_ptr,Time_now 1,Meas_resp_
          t(60),Trend_dp
490    COM /Pressure/
       Top1,Top2,Top3,Top4,Bot1,Bot2,Bot3,Bot4
500    COM /Editor/ Edit_msg$[80]
510    COM /Subject/ Sub_name$[25],Hos_num$[15],Id_
       age$[10],Id_wt$[10],Id_ht$[10 ],Diag$[30],
          Opera$[45],Halt_pg
520    COM /Io_chart/ Io_time$(8)[10],Iv_intake(8),Fluid_
       in(8),In_tot(8),Urine(8 ),Chest(8),Out_
          tot(8),Net(8),Io_ptr
530    COM /Lab_chart/ Lab_time$(8)[10],Na(8),Kl(8),
          Cl(8),Hco3(8),Ca(8),Hct(8),G luc(8),
          Dig(8),Pt(8),Ptt(8),Creat(8),Bun(8),Lab_ptr
540    COM /Vent_chart/ Vent_
       time$(8)[15],Rate(8),Fio2(8),Pp(8),Peep(8),Tv(8),
       Ie_ratio$(8)[10],Airp(8),Ph(8),Po2(8),
       Pco2(8),Bgo3(8),Be(8),Vent_ptr
```

```
550   COM /Pres_chart/ Pres_time$(20)[15],Ao_s(20),Ao_
      d(20),Ao_m(20),Pa_s(20),Pa_d(20),Pa_m(20),
      La_m(20),Ra_m(20),Pres_ptr,Pres_in
560   COM /Heart_index/ Heart_
      time$(15)[15],Ci(15),Pvri(15),Svri(15),Heart_ptr
570   COM /Drugs/ Drug_time$(40)[20],Drug_
      name$(40)[40],Drug_dos$(40)[20],Drug_ptr
590   DIM Io$(5,15)[30],Io_msg$(5,15)[80]
600   DIM Msg_pad$(10)[80]
610   DIM Msg_buffer$[80] BUFFER
620   ASSIGN @Msg_buffer TO BUFFER Msg_buffer$
630   Log_plotflg=0
640   Freq_limit=1.
650   Resp_search=.1
660   Pct_thresh=.2
670   Scr_file$="?"
680   Halt_pg=0
690   Message$(0)="messages in "
700   Message$(1)="I/O chart "
710   Message$(2)="lab values"
720   Message$(3)="hemodynamics"
730   Message$(4)="Trends Display"
740   Message$(5)="messages out"
750   Message$(6)="STOP PROGRAM"
760   Message$(7)="ventilation"
770   Message$(8)="drugs"
780   Message$(9)="B.P. Display"
790   Msg_pad_ptr=0
800   P_ptr=0
810   !
820   ! Set up common/array storage for waveform
        analysis
830   !
840   !........................................
850   !
860   ! Set up common/array storage for waveform
        analysis
870   !........................................
```

```
880    !
890    COM /Directory/ Dir$[160],@Printer
900    COM /Wf1/ Printer,Plotter,String$[40]
910    COM /Wf2/ Signal(1089),Number_pnts,Type,Sampling_
           period
920    COM /Wf3/ Segment_size,Overlap,Num_segments,Pnts_
           used,Fft_size
930    COM /Wf5/ Refn(63),Refd(63),Refno,Refdo,Refgain
940    COM /Autoparam/ Up_down,Up_delay,Dn_delay
950    COM /Vars/ Ffthrvar,Fftrespvar
960    !
970    DISP "loading subroutines"
980    LOADSUB ALL FROM "multi_subs"
990    LOADSUB ALL FROM "hr_siggen8"
1000   LOADSUB ALL FROM "automaxsb2"
1010   LOADSUB ALL FROM "fft_anal6"
1020   DISP "load data disks and press CONTINUE"
1030   PAUSE
1040   !
1050   !..........................................
1060   ! The HP 9826/9836 flexible disk (5-1/4") has the
       ! following structure
1070   !  2 sides, 33 tracks/side, 16 sectors/track, 256
       !  bytes/sector
1080   !  1 track =   4096 bytes =   16 sectors
1090   !  1 side  = 135168 bytes =  528 sectors
1100   !  1 disk  = 270336 bytes = 1056 sectors
1110   !  1 disk  = 135168 words =  132K words
1120   !..........................................

1130   !
1140   !
1150   INTEGER Hpib_buffer1(2048) BUFFER
1160   INTEGER Hpib_buffer2(2048) BUFFER
1170   DIM Hr_signal(1024) BUFFER
1180   Read_ptr1=0
1190   Read_ptr2=0
```

```
1200  !
1210  !
1220  !.........................................
1230  ! CLEAR MULTIPROGRAMMER
1240  !.........................................

1250  !
1260  !
1270    ON INTR 7 CALL Hpib_intr
1280  Begin:CALL Multi_clear
1290  !
1300  !
1310  !.........................................
1320  ! LOAD SUPPLEMENTAL INSTRUCTION SET ("MR")
1330  ! usage: "MR,<card addr>,<# words>,<read
      ptr>,<mode>T"
1340  !         <mode= 1-FIFO, 4-recirculating>
1350  !.........................................

1360  !
1370  !
1380    DISP "DOWNLOADING MR INSTRUCTION"
1390    CALL Xfer("MR")
1400  !
1410  !
1420  !.........................................
1430  ! SET UP CARDS FOR DATA COLLECTION
1440  !.........................................

1450  !
1460  !
1470  Selections:DISP "SETUP DATA COLLECTION"
1480    OUTPUT @Multi;"CY,3T"!CYCLE SCAN/PACER CARD TO
        SET DEFINITE STATE
1490  !
1500  !
1510  ! NOW SET UP THE SCAN CARD PARAMETERS (DEFAULT
      ! VALUES)
```

```
1520   !         START CHANNEL (3.0) -  0
1530   !          STOP CHANNEL (3.1) -  1
1540   !                PACING (3.2) - 40 USEC
1550   !           SEQN'L SCAN (3.3) - XXXX XXXX XXX1 (   1)
1560   !         INTN'L PACING (3.3) - XXXX XXXX X1XX (   4)
1570   !         MSEC TIMEBASE (3.3) - XXX1 XXXX XXXX ( 256)
1580   !
1590   CALL Get_param
1600   ASSIGN @Messages TO
       "messglog:HP8290X,700,1";FORMAT OFF
1610   ASSIGN @Temp_trend TO "temp_
       trend:HP8290X,700,1";FORMAT OFF
1620   ASSIGN @Hemo_data TO "hemo_
       data:HP8290X,700,1";FORMAT OFF
1630   ASSIGN @Io_data TO "io_data:HP8290X,700,1";FORMAT
       OFF
1640   ASSIGN @Lab_data TO "lab_
       data:HP8290X,700,1";FORMAT OFF
1650   ASSIGN @Vent_data TO "vent_
data:HP8290X,700,1";FORMAT OFF
1660   ASSIGN @Co_data TO "co_data:HP8290X,700,1";FORMAT
OFF
1670   ASSIGN @Drug_data TO "drug_
data:HP8290X,700,1";FORMAT OFF
1680   IF Num_pts=0 THEN GOTO Begin
1690   Read_ptr1=0
1700   !
1710   !
1720   ! SET FIFO MODE AND CLEAR POINTERS IN MEMORY
1730   !
1740   !
1750 Setup_scan:DISP " NUMBER OF POINTS=";Num_pts
1760   OUTPUT @Multi;"WF,3.0",Start_chan,"3.1",Stop_
       chan,"3.3",Pacing_bits,"3.2"
           ,Pacing_rate,"T"
1770   OUTPUT @Multi;"CC,6T"
1780   OUTPUT @Multi;"WF,5.1,1,T" ! memory set to FIFO
```

```
         input mode
1790     OUTPUT @Multi;"AC,3,5,6T"  ! cards are armed to
         supply interrupts
1800     OUTPUT @Multi;"RV,6.0,6.1,6.2,6.3T" ! checking
         control registers
1810     ENTER @Read_val;Counters(*)
1820     Read_ptr1=0
1830     Read_ptr2=0
1840   !
1850   ! setup the counter card to count
1860   !
1870 Setup_counter:OUTPUT @Multi;"CC,10,11,12,13T"
1880     OUTPUT @Multi;"AC,10,12,13T" !_counter not armed
1890     OUTPUT @Multi;"CY,11T"
1900   !
1910   ! setup the pacer card to generate a clock with
         period 32 Usec
1920   !       (one half period is 16 Usec)
1930   !       (corresponds to 31.25KHz)
1940   !
1950 Setup_clock:OUTPUT @Multi;"WF10.2,1T"
1960     OUTPUT @Multi;"WF10,16U T"
1970     CALL Completer("setup completed")
1980   !
1990   !
2000   ! START THE PACERS BY CYCLING IN PARALLEL
2010   !
2020     OUTPUT @Multi;"GPT"
2030     CALL Init_flags
2040     ENABLE INTR 7;2
2050     OUTPUT @Multi;"CY,3,10T"
2060     OUTPUT @Multi;"GST"
2070     Start_pacing=TIMEDATE
2080     CALL Completer("PACING STARTED")
2090     Block_time=Pacing_rate*1.024
2100     Next_time=TIMEDATE+INT(Block_time)
2110     First_blk_flg=1
```

```
2120    Num_msgs=0
2130    Message_line=0
2140    Msg_dp_request=0
2150    Resp_dpflg=0
2160    Max_hr_pts=1024
2170    Last_time=0
2180    Trend_dp=0
2190    !Hemo_dp=0
2200    Top1=0
2210    Top2=0
2220    Top3=0
2230    Top4=0
2240    Bot1=0
2250    Bot2=0
2260    Bot3=0
2270    Bot4=0
2280    !
2290    Io$(1,1)="Time - hh:mm(hh=1 to 24)"
2300    Io$(1,2)="Maint. fluids"
2310    Io$(1,3)="other fluids"
2320    Io$(1,4)="urine output"
2330    Io$(1,5)="chest output"
2340    Io$(2,1)="Time - hh:mm"
2350    Io$(2,2)="Na"
2360    Io$(2,3)="K"
2370    Io$(2,4)="Cl"
2380    Io$(2,5)="HCO3"
2390    Io$(2,6)="Ca"
2400    Io$(2,7)="Hct"
2410    Io$(2,8)="Glucose"
2420    Io$(2,9)="Dig level"
2430    Io$(2,10)="PT"
2440    Io$(2,11)="PTT"
2450    Io$(2,12)="Creat"
2460    Io$(2,13)="Bun"
2470    Io$(3,1)="Time - hh:mm(hh=1 to 24)"
2480    Io$(3,2)="Resp rate"
2490    Io$(3,3)="FIO2"
```

```
2500    Io$(3,4)="Peak pres"
2510    Io$(3,5)="peep"
2520    Io$(3,6)="TV"
2530    Io$(3,7)="I:E"
2540    Io$(3,8)="mean airway"
2550    Io$(3,9)="ph"
2560    Io$(3,10)="pO2"
2570    Io$(3,11)="pCO2"
2580    Io$(3,12)="HCO3"
2590    Io$(3,13)="BE"
2600    Io$(4,1)="Time - hh:mm(hh=1 to 24)"
2610    Io$(4,2)="ao/s"
2620    Io$(4,3)="ao/d"
2630    Io$(4,4)="ao/m"
2640    Io$(4,5)="pa/s"
2650    Io$(4,6)="pa/d"
2660    Io$(4,7)="pa/m"
2670    Io$(4,8)="la/m"
2680    Io$(4,9)="ra/m"
2690    Io$(4,10)="Time - hh:mm(hh=1 to 24)"
2700    Io$(4,11)="C.I."
2710    Io$(4,12)="pvri"
2720    Io$(4,13)="svri"
2730    Io$(5,1)="name"
2740    Io$(5,2)="dosage"
2750    Io$(5,3)="Time - hh:mm:ss(hh=1 to 24)"
2760    Io_ptr=0
2770    Lab_ptr=0
2780    Vent_ptr=0
2790    Pres_ptr=0
2800    Heart_ptr=0
2810    Drug_ptr=0
2820    Io_in=0
2830    Lab_in=0
2840    Vent_in=0
2850    Pres_in=0
2860    Heart_in=0
```

```
2870    Drug_in=0
2880    Fst=1
2890    Fix_val=0
2900    !
2910    ! Read data continuously and write to the disk
            continuously until enough
2920    ! enough data has been obtained
2930    !
2940    !
2950 Reading:   !
2960    !
2970    ! set up the A/D buffers and disk files
2980    !
2990    ASSIGN @Memory_input TO 72305;FORMAT OFF
3000    ASSIGN @In_buffer TO BUFFER Hpib_buffer1(*)
3010    ASSIGN @Out_buffer TO Scr_file$;FORMAT OFF
3020    !
3030    ! set up the counter memory buffers and files
3040    !
3050    ASSIGN @Memory_input2 TO 72305;FORMAT OFF
3060    ASSIGN @In_buffer2 TO BUFFER Hpib_buffer2(*)
3070    ASSIGN @Out_buffer2 TO Scr_file2$;FORMAT OFF
3080    !
3090    Data_lockout=0
3100  !
3110    Time_now=TIMEDATE
3120    Date_now$=DATE$(TIMEDATE)
3130    Time_now1=Time_now MOD 86400
3140  !
3150 Blk_xfer:!
3160    CONTROL @In_buffer,3;1
        ! Reset fill pointer for buffer
3170    CONTROL @In_buffer,4;0
        ! Reset current number of bytes in buffer
3180    CONTROL @In_buffer,5;1    ! Reset empty pointer
            for buffer
3190    !
```

```
3200  ! write an 8 byte sequence to disk as a header for
      ! the transfer
3210  !
3220  CALL Xfheader(@Out_buffer,Num_pts,"R")
3230  !
3240  ! read A/D buffer into memory (hpib_buffer1) in 32
      segments
3250  ! if possible
3260  !
3270  IF FRACT(Num_pts/32.)=0 THEN
3280      Num_rdseg=32
3290      Num_rdpts=Num_pts/32
3300  ELSE
3310      Num_rdseg=1
3320      Num_rdpts=Num_pts
3330  END IF
3340  !
3350  ! reading segments here. segmenting allows disk
      access between segments
3360  !
3370  FOR Rdseg=1 TO Num_rdseg
3380      OUTPUT @Multi;"MR,5",Num_rdpts,Read_
          ptr1,"1T"! FIFO mode
3390      ON EOT @Memory_input GOTO Next_rdseg
3400      TRANSFER @Memory_input TO @In_buffer;COUNT
          Num_rdpts*2,CONT
3410      PRINT TABXY(1,18);
3420      PRINT USING Image_wt1;Num_xfer-Num_xfer_
          left+1,Num_xfer,TIME$(Next_time),
              Rdseg,Num_rdseg
3430 Image_wt1:IMAGE    "Next xfer(",K,"/",K,"): ",K,"
     seg=",K,"/",K
3440 Waiter1:DISP "Now: ";TIME$(TIMEDATE);"
     ";DATE$(TIMEDATE)
3450      IF Next_time-TIMEDATE<12 THEN
3460          OFF KEY
3470          OFF KBD
3480          OFF KNOB
```

```
3490        GOTO Waiter1
3500      END IF
3510      ON KEY 0 LABEL Message$(0) GOSUB Key0
3520      ON KEY 1 LABEL Message$(1) GOSUB Key1
3530      ON KEY 2 LABEL Message$(2) GOSUB Key2
3540      ON KEY 3 LABEL Message$(3) GOSUB Key3
3550      ON KEY 4 LABEL Message$(4) GOSUB Key4
3560      ON KEY 5 LABEL Message$(5) GOSUB Key5
3570      ON KEY 6 LABEL Message$(6) GOSUB Key6
3580      ON KEY 7 LABEL Message$(7) GOSUB Key7
3590      ON KEY 8 LABEL Message$(8) GOSUB Key8
3600      ON KEY 9 LABEL Message$(9) GOSUB Key9
3610      ON KBD GOTO Control_chars
3620      IF Msg_dp_request=2 THEN
3630          ON KNOB .05 GOSUB Move_msgs
3640      ELSE
3650          OFF KNOB
3660      END IF
3670      STATUS @In_buffer,10;In_xfer_stat
3680      IF In_xfer_stat<64 THEN GOTO Next_rdseg
3690      IF Msg_dp_request=3 THEN
3700          CALL Msg_dump(Message_chart$(*),Message_
                   line,Msg_dp_request)
3710      END IF
3720      GOTO Waiter1
3730 Control_chars:!
3740      Kbd_hold$=KBD$
3741      IF POS(Kbd_hold$,CHR$(6))<>0 THEN
           !..change lfa disp.range
3742          Lfa_top=Lfa_top+2.5
3750      IF POS(Kbd_hold$,CHR$(6))<>0 THEN
           !..change spectra disp.freq.range
3760          IF Freq_limit=1. THEN
3770              Freq_limit=2.
3780          ELSE
3790              Freq_limit=1.
3800          END IF
3810          Resp_search=.1
```

```
              !..reset resp search point each time
3820          DISP "Spectra displayed to";Freq_
                limit;"Hz"
3830          WAIT 2
3840        END IF
3850        IF POS(Kbd_hold$,CHR$(8))<>0 THEN   !..help:
              display commands
3860          CALL Disp_ctrls
3870        END IF
3880        IF POS(Kbd_hold$,CHR$(16))<>0 THEN
     !..change peak search threshold
3890          Pct_thresh=Pct_thresh+.2
3900          IF Pct_thresh>.8 THEN Pct_thresh=.2
3910          DISP "resp peak search threshold=";Pct_
                thresh;"%"
3920          WAIT 1
3930        END IF
3940        IF POS(Kbd_hold$,CHR$(18))<>0 THEN
     !..display respiration time series
3950          IF Resp_dpflg=0 THEN
3960            Resp_dpflg=1
3970            DISP "resp series plot w/hr series"
3980            WAIT 2
3990          ELSE
4000            Resp_dpflg=0
4010            DISP "cancel resp series plot"
4020            WAIT 2
4030          END IF
4040        END IF
4050        IF POS(Kbd_hold$,CHR$(19))<>0 THEN
     !..change respiration peak search
4060          Resp_search=Resp_search+.1
4070          IF Resp_search>Freq_limit-.1 THEN Resp_
                search=.1
4080          DISP "resp peak search starts at";Resp_
                search;"Hz"
4090          WAIT 1
4100        END IF
```

```
4110        GOTO Waiter1
4120 Next_rdseg:!
4130 !
4140 ! storing messages from soft keys if any
4150 !
4160        IF Msg_pad_ptr>0 THEN
4170            Num_msgs=Num_msgs+Msg_pad_ptr
4180            FOR I=0 TO Msg_pad_ptr-1
4190                Msg_buffer$=Msg_pad$(I)
4200                Len_message=LEN(Msg_buffer$)
4210                CONTROL @Msg_buffer,4;Len_
                    message       !....number of bytes
4220                CONTROL @Msg_buffer,5;1
      !..empty pointer to beginning
4230                TRANSFER @Msg_buffer TO
                    @Messages;COUNT Len_message,CONT
4240            NEXT I
4250            IF Msg_dp_request>=2 THEN
4260                DEALLOCATE Message_chart$(*)
4270                Msg_dp_request=0
4280            END IF
4290            OFF KNOB
4300            Msg_pad_ptr=0
4310        END IF
4320        IF Msg_dp_request=1 THEN
4330            Message_line=0
4340            ALLOCATE Message_chart$(17)[640]
4350            CALL Msg_dump(Message_chart$(*),Message_
                    line,Msg_dp_request)
4360            IF Msg_dp_request=0 THEN
      !...no messages
                    yet
4370                DEALLOCATE Message_chart$(*)
4380            END IF
4390        END IF
4400 !
4410 ! get read pointer for next segment
4420 !
```

```
4430        OUTPUT @Multi;"RV,6.0T"
      !    checking current read pointer
4440        ENTER @Read_val;Read_ptr1
4450    NEXT Rdseg
4460    !
4470    ! store A/D buffer on complete data file (also
          save pointers for heart rate)
4480    !
4490    !
4500 Resume1:OFF EOT @Memory_input
4510    OFF KEY
4520    OFF KBD
4530    OFF KNOB
4540    IF Msg_dp_request>=2 THEN
4550        DEALLOCATE Message_chart$(*)
4560        Msg_dp_request=0
4570    END IF
4580    IF Trend_dp=1 OR Trend_dp=2 THEN DEALLOCATE
          Spectra(*)
4590    Next_time=Next_time+INT(Block_time)
4600    ON EOT @Out_buffer GOTO Resume2
4610    OUTPUT @Multi;"RV,13.0,13.1,13.2,13.3T"
      ! checking control registers
4620    ENTER @Read_val;Counters2(*)
4630    Read_ptr2=Counters2(0)
4640    Num_pulses=Counters2(1)
4650    TRANSFER @In_buffer TO @Out_buffer;COUNT Num_
          pts*2,CONT
4660 Waiter2:DISP TIME$(TIMEDATE),DATE$(TIMEDATE)
4670    GOTO Waiter2
4680    !
4690    !
4700    !
4710    !
4720 Resume2:OFF EOT @Out_buffer
4730    Num_xfer_left=Num_xfer_left-1
4740      OUTPUT @Multi;"MR,12",Num_pulses,Read_
          ptr2,"1T"              ! FIFO mode
```

```
4750    CONTROL @In_buffer2,3;1
        ! Reset fill pointer for buffer
4760    CONTROL @In_buffer2,4;0
        ! Reset current number of bytes in buffer
4770    CONTROL @In_buffer2,5;1
        ! Reset empty pointer for buffer
4780    !
4790    ! write an 8 byte sequence to disk as a header for
        ! the transfer
4800    !
4810    CALL Xfheader(@Out_buffer2,Num_pulses,"H")
4820    !
4830    ! read multiprogrammer into computer memory (hpib_
        buffer)
4840    !
4850    ON EOT @Memory_input2 GOTO Resume4
4860    TRANSFER @Memory_input2 TO @In_buffer2;COUNT Num_
        pulses*2,CONT
4870 Waiter4:DISP TIME$(TIMEDATE),DATE$(TIMEDATE)
4880    GOTO Waiter4
4890    !
4900    ! store computer memory on complete data file
4910    !
4920 Resume4:OFF EOT @Memory_input2
4930    ON EOT @Out_buffer2 GOTO Resume5
4940    TRANSFER @In_buffer2 TO @Out_buffer2;COUNT Num_
        pulses*2,CONT
4950 Waiter5:DISP TIME$(TIMEDATE),DATE$(TIMEDATE)
4960    GOTO Waiter5
4970    !
4980 Resume5:OFF EOT @Out_buffer2
4990    CALL Hr_sig_gen(Hpib_buffer2(*),Hr_signal(*))
5000    !

5010    !
5020 Resume6:!
```

```
5030    OUTPUT @Multi;"RV,6.0,6.1,6.2,6.3T"
      ! checking control registers
5040    ENTER @Read_val;Counters(*)
5050    Read_ptr1=Counters(0)
5060    IF Counters(1)=4095 THEN ! Data lockout probably
          occurred
5070       PRINT "DATA LOCKOUT!! TIME RECORD
NOT           CONTINUOUS!!"
5080       PRINT "ABORTING CURRENT DATA COLLECTION."
5090       Data_lockout=1
5100       Num_xfer_left=0
5110    END IF
5120    OUTPUT 2;CHR$(255)&CHR$(75);
      ! Clear CRT of text
5130    GINIT
5140    PLOTTER IS 3,"INTERNAL"
5150    GRAPHICS ON
5160    Xscale=8
5170    Hr_max=MAX(Hr_signal(*))
5180    Hr_min=MIN(Hr_signal(*))
5190    VIEWPORT 0,64,50,100
5200    WINDOW 0,1,0,1
5210    AXES .1,.1,0,0
5220    CSIZE 4
5230    Hr_signal(1024)=0
5240    Hr_sigsum=SUM(Hr_signal)
5250    Mean_hr=INT((Hr_sigsum/1024+Avg_hr))
5260    Hr_bias=Hr_sigsum/1024
5270    LDIR 0
5280    LORG 3
5290    MOVE .2,.9
5300    LABEL "HR data   hr=";Mean_hr
5310    CSIZE 4
5320    MOVE .05,1
5330    LORG 3
5340    LABEL "250 bpm"
5350    WINDOW 1,0,1,0
5360    AXES 0,0,0,0
```

```
5370    IF Hr_dispflg=1 THEN
5380        WINDOW 0,1024,Hr_min,Hr_max
5390    ELSE
5400        Low_window=INT(-Avg_hr)
5410        High_window=Low_window+250.
5420        WINDOW 0,1024,Low_window,High_window
5430    END IF
5440    FOR I=0 TO 1023
5450        PLOT I,Hr_signal(I)
5460    NEXT I
5470    !
5480    ! display respirations time series also
5490    !
5500    IF Resp_dpflg=1 THEN
5510        Max_resp=MAX(Hpib_buffer1(*))
5520        Min_resp=MIN(Hpib_buffer1(*))
5530        IF Mean_hr>100 THEN
5540            VIEWPORT 0,64,50,65
5550        ELSE
5560            VIEWPORT 0,64,75,90
5570        END IF
5580        WINDOW 0,1023,Min_resp,Max_resp
5590        MOVE 0,Hpib_buffer1(0)
5600        FOR I=1 TO 1023
5610            PLOT I,Hpib_buffer1(I)
5620        NEXT I
5630    ELSE
5640        Resp_dpflg=0
5650    END IF
5660    !
5670    ! now process heart rate data with waveform
             analysis package
5680    ! make sure the hr_signal has zero mean
5690    !
5700    FOR I=0 TO 1023
5710        Signal(I)=Hr_signal(I)-Hr_bias
5720    NEXT I
5730    Plotbox=2
```

```
5740    DISP "HR fft in process"
5750    CALL Wf_analyzer(Pacing_rate)
5760    !
5770    ! now process respiration data with waveform
        analysis package
5780    !
5790    MAT Signal= (0)
5800    FOR I=0 TO 1023
5810        Signal(I)=Hpib_buffer1(I)
5820    NEXT I
5830    Signal_avg=SUM(Signal)/1024.
5840    MAT Signal= Signal-(Signal_avg)
5850    Plotbox=4
5860    DISP "RESP fft in process"
5870    CALL Wf_analyzer(Pacing_rate)
5880    Trend_dp=0 !..trend graph not displayed
5890    !
5900    ! waveform analysis completed, compile trends and
        store in temporary file
5910    !
5920    Mean_hr_t(T_ptr)=Mean_hr
5930    Lfa_t(T_ptr)=Lfa
5940    Rfa_t(T_ptr)=Rfa
5950    Ratio_t(T_ptr)=Peakratio
5960    Meas_resp_t(T_ptr)=Meas_resp
5961    Trans_time(T_ptr)=Xfer_time
5970    T_ptr=T_ptr+1
5980    OUTPUT @Temp_trend;T_ptr-1,Mean_
        hr,Lfa,Rfa,Peakratio,Meas_resp,Xfer_time
5990    IF Pres_in=1 THEN
6000        Pr=Pres_ptr-1
6010        OUTPUT @Hemo_data;Pres_time$(Pr),Ao_s(Pr),Ao_
            d(Pr),Ao_m(Pr),Pa_s(Pr),
              Pa_d(Pr),Pa_m(Pr),La_m(Pr),Ra_m(Pr),Pr
6020        Pres_in=0
6030    END IF
6040    IF Io_in=1 THEN
```

```
6050        Io=Io_ptr-1
6060        OUTPUT @Io_data;Io_time$(Io),Iv_
            intake(Io),Fluid_in(Io),In_tot(Io),Ur
             ine(Io),Chest(Io),Out_tot(Io),Net(Io),Io
6070        Io_in=0
6080     END IF
6090     IF Lab_in=1 THEN
6100        L=Lab_ptr-1
6110        OUTPUT @Lab_data;Lab_
time$(L),Na(L),Kl(L),Cl(L),Hco3(L),Ca(L),Hct(L),
Gluc(L),Dig(L),Pt(L),Ptt(L),Creat(L),Bun(L),L
6120        Lab_in=0
6130     END IF
6140     IF Heart_in=1 THEN
6150        H=Heart_ptr-1
6160        OUTPUT @Co_data;Heart_
            time$(H),Ci(H),Pvri(H),Svri(H),H
6170        Heart_in=0
6180     END IF
6190     IF Vent_in=1 THEN
6200        V=Vent_ptr-1
6210        OUTPUT @Vent_data;Vent_
            time$(V),Rate(V),Fio2(V),Pp(V),Peep(V),Tv(V),
            Ie_ratio$(V),Airp(V),Ph(V),Po2(V),Pco2(V),
             Bgo3(V),Be(V),V
6220        Vent_in=0
6230     END IF
6240     IF Drug_in=1 THEN
6250        D=Drug_ptr-1
6260        OUTPUT @Drug_data;Drug_time$(D),Drug_
            name$(D),Drug_dos$(D),D
6270        Drug_in=0
6280     END IF
6290     !
6300     ! continue with data collection
6310     !
6320     IF Num_xfer_left<=0 THEN
6330        Halt_pg=1
```

```
6340        GOTO Eo_blk_xfer
6350    ELSE
6360        DISP Num_xfer_left;"transfers remaining"
6370        WAIT 3
6380        GOTO Blk_xfer
6390    END IF
6400 Eo_blk_xfer:End_time=TIMEDATE
6410    Delta_time=End_time-Start_time
6420    !
6430    OUTPUT @Multi;"WF,3.2,0T"
6440    Stop_pacing=TIMEDATE
6450 !
6460 Aborter:!
6470    ASSIGN @In_buffer TO *
6480    ASSIGN @In_buffer2 TO *
6490    ASSIGN @Out_buffer TO *
6500    ASSIGN @Out_buffer2 TO *
6510    ASSIGN @Messages TO *
6520    ASSIGN @Temp_trend TO *
6530    ASSIGN @Hemo_data TO *
6540    ASSIGN @Io_data TO *
6550    ASSIGN @Lab_data TO *
6560    ASSIGN @Vent_data TO *
6570    ASSIGN @Co_data TO *
6580    ASSIGN @Drug_data TO *
6590    OUTPUT @Multi;"CC,3,5,6,10,11,12,13T"
6600    OUTPUT @Multi;"CC,5T"
6610    CALL Completer("READY TO RESTART")
6620    CALL Pauser
6630    GRAPHICS OFF
6640    CALL Get_param
6650    ASSIGN @Messages TO
            "messglog:HP8290X,700,1";FORMAT OFF
6660    IF Num_pts=0 THEN GOTO Begin
6670    GOTO Setup_scan
6680 Diag:OUTPUT 723;"RV,3.0,3.3T"
6690    ENTER 72306;C,C0
6700    PRINT "CURRENT/START CHANNEL";C,C0
```

```
6710    OUTPUT 723;"RV,6.0,6.1,6.2,6.3T"
        ! checking control registers
6720    ENTER 72306;Counters(*)
6730    PRINT "COUNTERS=";Counters(*)
6740    STOP
6750 Purger:!
6760    GRAPHICS OFF
6770    DELSUB Hpib_intr TO END
6780    PURGE "AOK:HP8290X,700,1"
6790    PURGE "hrAOK:HP8290X,700,1"
6800    PURGE "messglog:HP8290X,700,1"
6810    PURGE "temp_trend:HP8290X,700,1"
6820    PURGE "hemo_data:HP8290X,700,1"
6830    PURGE "co_data:HP8290X,700,1"
6840    PURGE "vent_data:HP8290X,700,1"
6850    PURGE "lab_data:HP8290X,700,1"
6860    PURGE "drug_data:HP8290X,700,1"
6870    PURGE "io_data:HP8290X,700,1"
6871    PURGE "sub_data:HP8290X,700,1"
6880    STOP
6890 !
6900 ! definitions for keys
6910 !
6920 Move_msgs:! knob is processed here
6930    IF Msg_dp_request<>2 THEN RETURN
6940    Message_line=Message_line+KNOBX
6950    IF Message_line>Num_msgs-3 THEN Message_line=Num_msgs-3
6960    IF Message_line<0 THEN Message_line=0
7260        DISP "data in for this xfer; chart displayed"
7270        WAIT 2
7280        Io_ptr=Io_ptr-1
7290        CALL Chart(Chart_num)
7300        Io_ptr=Io_ptr+1
7310        GOTO Keyend
7320    ELSE
7330        INPUT "Input values=1 or display chart=2?",Inp
```

```
7340    IF Inp=1 THEN
7350        IF Io_ptr>5 THEN
7360            DISP "Do not enter more I/O data;
                disc full"
7370            WAIT 3
7380            GOTO Keyend
7390        ELSE
7400            GOTO I_o
7410        END IF
7420    ELSE
7430        CALL Chart(Chart_num)
7440        GOTO Keyend
7450    END IF
7460 END IF
7470 Data1:!
7480    Io_time$(Io_ptr)=Io_msg$(Chart_num,1)
7490    Iv_intake(Io_ptr)=FNLval(Io_msg$(Chart_num,2))
7500    IF Iv_intake(Io_ptr)=9999.999 THEN
7510        Ionum=2
7520        Fix_val=1
7530        GOTO Data_edit
7540    END IF
7550    Fluid_in(Io_ptr)=FNLval(Io_msg$(Chart_num,3))
7560    IF Fluid_in(Io_ptr)=9999.999 THEN
7570        Ionum=3
7580        Fix_val=1
7590        GOTO Data_edit
7600    END IF
7610    Urine(Io_ptr)=FNLval(Io_msg$(Chart_num,4))
7620    IF Urine(Io_ptr)=9999.999 THEN
7630        Ionum=4
7640        Fix_val=1
7650        GOTO Data_edit
7660    END IF
7670    Chest(Io_ptr)=FNLval(Io_msg$(Chart_num,5))
7680    IF Chest(Io_ptr)=9999.999 THEN
7690        Ionum=5
```

```
7700        Fix_val=1
7710        GOTO Data_edit
7720    END IF
7730    In_tot(Io_ptr)=Iv_intake(Io_ptr)+Fluid_in(Io_ptr)
7740    Out_tot(Io_ptr)=Urine(Io_ptr)+Chest(Io_ptr)
7750    Net(Io_ptr)=In_tot(Io_ptr)-Out_tot(Io_ptr)
7760    CALL Chart(Chart_num)
7770    Io_ptr=Io_ptr+1
7780    Io_in=1
7790    Fix_val=0
7800    GOTO Keyend
7810    !
7820    !
7830 Key2:Chart_num=2
        !...ventilation charting
7840    GRAPHICS OFF
7850    PRINT CHR$(12)
7860    IF Next_time-TIMEDATE<45 THEN
7870        DISP "not enough time to enter data; wait for next xfer"
7880        WAIT 2
7890        GOTO Keyend
7900    END IF
7910    Num_var=13
7920    IF Lab_in=1 THEN
7930        DISP "data in for this xfer; chart displayed"
7940        WAIT 2
7950        Lab_ptr=Lab_ptr-1
7960        CALL Chart(Chart_num)
7970        Lab_ptr=Lab_ptr+1
7980        GOTO Keyend
7990    ELSE
8000        INPUT "Input values=1 or display chart=2?",Inp
8010        IF Inp=1 THEN
8020            IF Lab_ptr>7 THEN
8030                DISP "Do not enter more Lab data; disc full"
```

```
8040            WAIT 3
8050            GOTO Keyend
8060         ELSE
8070            GOTO I_o
8080         END IF
8090      ELSE
8100         CALL Chart(Chart_num)
8110         GOTO Keyend
8120      END IF
8130   END IF
8140 Data2:!
8150   Lab_time$(Lab_ptr)=Io_msg$(Chart_num,1)
8160   Na(Lab_ptr)=FNLval(Io_msg$(Chart_num,2))
8170   IF Na(Lab_ptr)=9999.999 THEN
8180      Ionum=2
8190      Fix_val=1
8200      GOTO Data_edit
8210   END IF
8220   Kl(Lab_ptr)=FNLval(Io_msg$(Chart_num,3))
8230   IF Kl(Lab_ptr)=9999.999 THEN
8240      Ionum=3
8250      Fix_val=1
8260      GOTO Data_edit
8270   END IF
8280   Cl(Lab_ptr)=FNLval(Io_msg$(Chart_num,4))
8290   IF Cl(Lab_ptr)=9999.999 THEN
8300      Ionum=4
8310      Fix_val=1
8320      GOTO Data_edit
8330   END IF
8340   Hco3(Lab_ptr)=FNLval(Io_msg$(Chart_num,5))
8350   IF Hco3(Lab_ptr)=9999.999 THEN
8360      Ionum=5
8370      Fix_val=1
8380      GOTO Data_edit
8390   END IF
8400   Ca(Lab_ptr)=FNLval(Io_msg$(Chart_num,6))
8410   IF Ca(Lab_ptr)=9999.999 THEN
```

```
8420        Ionum=6
8430        Fix_val=1
8440        GOTO Data_edit
8450    END IF
8460    Hct(Lab_ptr)=FNLval(Io_msg$(Chart_num,7))
8470    IF Hct(Lab_ptr)=9999.999 THEN
8480        Ionum=7
8490        Fix_val=1
8500        GOTO Data_edit
8510    END IF
8520    Gluc(Lab_ptr)=FNLval(Io_msg$(Chart_num,8))
8530    IF Gluc(Lab_ptr)=9999.999 THEN
8540        Ionum=8
8550        Fix_val=1
8560        GOTO Data_edit
8570    END IF
8580    Dig(Lab_ptr)=FNLval(Io_msg$(Chart_num,9))
8590    IF Dig(Lab_ptr)=9999.999 THEN
8600        Ionum=9
8610        Fix_val=1
8620        GOTO Data_edit
8630    END IF
8640    Pt(Lab_ptr)=FNLval(Io_msg$(Chart_num,10))
8650    IF Pt(Lab_ptr)=9999.999 THEN
8660        Ionum=10
8670        Fix_val=1
8680        GOTO Data_edit
8690    END IF
8700    Ptt(Lab_ptr)=FNLval(Io_msg$(Chart_num,11))
8710    IF Ptt(Lab_ptr)=9999.999 THEN
8720        Ionum=11
8730        Fix_val=1
8740        GOTO Data_edit
8750    END IF
8760    Creat(Lab_ptr)=FNLval(Io_msg$(Chart_num,12))
8770    IF Creat(Lab_ptr)=9999.999 THEN
8780        Ionum=12
8790        Fix_val=1
```

```
8800        GOTO Data_edit
8810     END IF
8820     Bun(Lab_ptr)=FNLval(Io_msg$(Chart_num,13))
8830     IF Bun(Lab_ptr)=9999.999 THEN
8840        Ionum=13
8850        Fix_val=1
8860        GOTO Data_edit
8870     END IF
8880     CALL Chart(Chart_num)
8890     Lab_ptr=Lab_ptr+1
8900     Lab_in=1
8910     Fix_val=0
8920     GOTO Keyend
8930     !
8940     !
8950 Key3:Chart_num=4
         !...hemodynamic graphics
8960     IF Next_time-TIMEDATE<45 THEN
8970        DISP "not enough time to enter data; wait for next xfer"
8980        WAIT 2
8990        GOTO Keyend
9000     END IF 9010     GRAPHICS OFF
9020     PRINT CHR$(12)
9030     INPUT "Blood pressures(1) or cardiac indices(2)?",Bp
9040     IF Bp=1 THEN
9050        Num_var=9
9060     ELSE
9070        Fst=10
9080        Num_var=13
9090     END IF
9100     IF Pres_in=1 AND Bp=1 THEN
9110        DISP "data in for this xfer; chart displayed"
9120        WAIT 2
```

```
9130        Pres_ptr=Pres_ptr-1
9140        IF Heart_in=1 THEN Heart_ptr=Heart_ptr-1
9150        CALL Chart(Chart_num)
9160        IF Heart_in=1 THEN Heart_ptr=Heart_ptr+1
9170        Pres_ptr=Pres_ptr+1
9180        GOTO Keyend
9190     ELSE
9200        IF Heart_in=1 AND Bp=2 THEN
9210           DISP "data in for this xfer; chart
                displayed"
9220           WAIT 2
9230           IF Pres_in=1 THEN Pres_ptr=Pres_ptr-1
9240           Heart_ptr=Heart_ptr-1
9250           CALL Chart(Chart_num)
9260           Heart_ptr=Heart_ptr+1
9270           IF Pres_in=1 THEN Pres_ptr=Pres_ptr-1
9280           GOTO Keyend
9290        ELSE
9300           INPUT "Input values=1 or display
                chart=2?",Inp
9310           IF Inp=1 THEN
9320              IF Bp=1 AND Pres_ptr>17 THEN
9330                 DISP "Do not enter more Pressure
                     data; disc full"
9340                 WAIT 3
9350                 GOTO Keyend
9360              ELSE
9370                 GOTO I_o
9380              END IF
9390           ELSE
9400              IF Heart_in=1 THEN Heart_ptr=Heart_
                   ptr-1
9410              IF Pres_in=1 THEN Pres_ptr=Pres_ptr-1
9420              CALL Chart(Chart_num)
9430              IF Heart_in=1 THEN Heart_ptr=Heart_
                   ptr+1
9440              IF Pres_in=1 THEN Pres_ptr=Pres_ptr+1
9450              GOTO Keyend
```

```
9460            END IF
9470          END IF
9480      END IF
9490 Data4:!
9500    IF Bp=1 THEN
9510        Pres_time$(Pres_ptr)=Io_msg$(Chart_num,1)
9520        Ao_s(Pres_ptr)=FNLval(Io_msg$(Chart_num,2))
9530        IF Ao_s(Pres_ptr)=9999.999 THEN
9540            Ionum=2
9550            Fix_val=1
9560            GOTO Data_edit
9570        END IF
9580        Ao_d(Pres_ptr)=FNLval(Io_msg$(Chart_num,3))
9590        IF Ao_d(Pres_ptr)=9999.999 THEN
9600            Ionum=3
9610            Fix_val=1
9620            GOTO Data_edit
9630        END IF
9640        Ao_m(Pres_ptr)=FNLval(Io_msg$(Chart_num,4))
9650        IF Ao_m(Pres_ptr)=9999.999 THEN
9660            Ionum=4
9670            Fix_val=1
9680            GOTO Data_edit
9690        END IF
9700        Pa_s(Pres_ptr)=FNLval(Io_msg$(Chart_num,5))
9710        IF Pa_s(Pres_ptr)=9999.999 THEN
9720            Ionum=5
9730            Fix_val=1
9740            GOTO Data_edit
9750        END IF
9760        Pa_d(Pres_ptr)=FNLval(Io_msg$(Chart_num,6))
9770        IF Pa_d(Pres_ptr)=9999.999 THEN
9780            Ionum=6
9790            Fix_val=1
9800            GOTO Data_edit
9810        END IF
9820        Pa_m(Pres_ptr)=FNLval(Io_msg$(Chart_num,7))
9830        IF Pa_m(Pres_ptr)=9999.999 THEN
```

```
9840            Ionum=7
9850            Fix_val=1
9860            GOTO Data_edit
9870        END IF
9880        La_m(Pres_ptr)=FNLval(Io_msg$(Chart_num,8))
9890        IF La_m(Pres_ptr)=9999.999 THEN
9900            Ionum=8
9910            Fix_val=1
9920            GOTO Data_edit
9930        END IF
9940        Ra_m(Pres_ptr)=FNLval(Io_msg$(Chart_num,9))
9950        IF Ra_m(Pres_ptr)=9999.999 THEN
9960            Ionum=9
9970            Fix_val=1
9980            GOTO Data_edit
9990        END IF
10000       IF Heart_in=1 THEN Heart_ptr=Heart_ptr-1
10010       CALL Chart(Chart_num)
10020       IF Heart_in=1 THEN Heart_ptr=Heart_ptr+1
10030       Pres_ptr=Pres_ptr+1
10040       Pres_in=1
10050       Fix_val=0
10060       GOTO Keyend
10070   ELSE
10080       Heart_time$(Heart_ptr)=Io_msg$(Chart_num,10)
10090       Ci(Heart_ptr)=FNLval(Io_msg$(Chart_num,11))
10100       IF Ci(Heart_ptr)=9999.999 THEN
10110           Ionum=11
10120           Fix_val=1
10130           GOTO Data_edit
10140       END IF
10150       Pvri(Heart_ptr)=FNLval(Io_msg$(Chart_num,12))
10160       IF Pvri(Heart_ptr)=9999.999 THEN
10170           Ionum=12
10180           Fix_val=1
10190           GOTO Data_edit
10200       END IF
10210       Svri(Heart_ptr)=FNLval(Io_msg$(Chart_num,13))
```

```
10220      IF Svri(Heart_ptr)=9999.999 THEN
10230           Ionum=13
10240           Fix_val=1
10250           GOTO Data_edit
10260      END IF
10270      IF Pres_in=1 THEN Pres_ptr=Pres_ptr-1
10280      CALL Chart(Chart_num)
10290      IF Pres_in=1 THEN Pres_ptr=Pres_ptr+1
10300      Heart_ptr=Heart_ptr+1
10310      Heart_in=1
10320      Fst=1
10330      Fix_val=0
10340 END IF
10350 GOTO Keyend
10360 !
10370 !
10380 Key4:Key_id=4
10390 IF Trend_dp=0 THEN
10400      ALLOCATE INTEGER Spectra(7499)
10410      GSTORE Spectra(*)
10420      Trend_dp=2
10430      Top1=200
10440      Top2=2.5
10450      Bot2=-2.5
10460      Top3=10
10470      Top4=10
10480      CALL Trend_graph
10490 ELSE
10500      IF Trend_dp=2 THEN
10510           GRAPHICS ON
10520           GLOAD Spectra(*)
10530           DEALLOCATE Spectra(*)
10540           CALL Offgraph
10550           Trend_dp=0
10560      ELSE
10570           Trend_dp=2
10580           Top1=200
```

```
10590            Top2=2.5
10600            Bot2=-2.5
10610            Top3=10
10620            Top4=10
10630            CALL Trend_graph
10640        END IF
10650    END IF
10660    GOTO Keyend
10670    !
10680    !
10690 Key5:Key_id=5
         !...display message file
10700    IF Msg_dp_request<2 THEN
10710        DISP "messages will be recalled soon"
10720        Msg_dp_request=1
10730        WAIT 1
10740    ELSE
10750        Msg_dp_request=3
10760    END IF
10770    GOTO Keyend
10780    !
10790    !
10800 Key6:Key_id=6              !..premature program
                                    termination
10810    DISP "To halt program hit KEY 6 again (within 10
         sec)"
10820    ON TIME (TIMEDATE+10) MOD 86400,4 GOTO Keyend
10830    ON KEY 6,3 GOTO Halter
10840 Cancel_wait:GOTO Cancel_wait
10850 Halter:Num_xfer_left=1
10860    Halt_pg=1
10870    GOTO Key_msg
10880    !
10890    !
10900 Key7:Chart_num=3
10910    IF Next_time-TIMEDATE<45 THEN
10920        DISP "not enough time to enter data; wait for
             next xfer"
```

```
10930      WAIT 2
10940      GOTO Keyend
10950  END IF
10960  GRAPHICS OFF
10970  PRINT CHR$(12)
10980  Num_var=13
10990  IF Vent_in=1 THEN
11000      DISP "data in for this xfer; chart displayed"
11010      WAIT 2
11020      Vent_ptr=Vent_ptr-1
11030      CALL Chart(Chart_num)
11040      Vent_ptr=Vent_ptr+1
11050      GOTO Keyend
11060  ELSE
11070      INPUT "Input values=1 or display chart=2?",Inp
11080      IF Inp=1 THEN
11090          IF Vent_ptr>7 THEN
11100              DISP "Do not enter more Vent data; disc full"
11110              WAIT 3
11120              GOTO Keyend
11130          ELSE
11140              GOTO I_o
11150          END IF
11160      ELSE
11170          CALL Chart(Chart_num)
11180          GOTO Keyend
11190      END IF
11200  END IF
11210  Data3:!
11220  Vent_time$(Vent_ptr)=Io_msg$(Chart_num,1)
11230  Rate(Vent_ptr)=FNLval(Io_msg$(Chart_num,2))
11240  IF Rate(Vent_ptr)=9999.999 THEN
11250      Ionum=2
11260      Fix_val=1
11270      GOTO Data_edit
11280  END IF
```

```
11290   Fio2(Vent_ptr)=FNLval(Io_msg$(Chart_num,3))
11300   IF Fio2(Vent_ptr)=9999.999 THEN
11310       Ionum=3
11320       Fix_val=1
11330       GOTO Data_edit
11340   END IF
11350   Pp(Vent_ptr)=FNLval(Io_msg$(Chart_num,4))
11360   IF Pp(Vent_ptr)=9999.999 THEN
11370       Ionum=4
11380       Fix_val=1
11390       GOTO Data_edit
11400   END IF
11410   Peep(Vent_ptr)=FNLval(Io_msg$(Chart_num,5))
11420   IF Peep(Vent_ptr)=9999.999 THEN
11430       Ionum=5
11440       Fix_val=1
11450       GOTO Data_edit
11460   END IF
11470   Tv(Vent_ptr)=FNLval(Io_msg$(Chart_num,6))
11480   IF Tv(Vent_ptr)=9999.999 THEN
11490       Ionum=6
11500       Fix_val=1
11510       GOTO Data_edit
11520   END IF
11530   Ie_ratio$(Vent_ptr)=Io_msg$(Chart_num,7)
11540   Airp(Vent_ptr)=FNLval(Io_msg$(Chart_num,8))
11550   IF Airp(Vent_ptr)=9999.999 THEN
11560       Ionum=8
11570       Fix_val=1
11580       GOTO Data_edit
11590   END IF
11600   Ph(Vent_ptr)=FNLval(Io_msg$(Chart_num,9))
11610   IF Ph(Vent_ptr)=9999.999 THEN
11620       Ionum=9
11630       Fix_val=1
11640       GOTO Data_edit
11650   END IF
11660   Po2(Vent_ptr)=FNLval(Io_msg$(Chart_num,10))
```

```
11670    IF Po2(Vent_ptr)=9999.999 THEN
11680        Ionum=10
11690        Fix_val=1
11700        GOTO Data_edit
11710    END IF
11720    Pco2(Vent_ptr)=FNLval(Io_msg$(Chart_num,11))
11730    IF Pco2(Vent_ptr)=9999.999 THEN
11740        Ionum=11
11750        Fix_val=1
11760        GOTO Data_edit
11770    END IF
11780    Bgo3(Vent_ptr)=FNLval(Io_msg$(Chart_num,12))
11790    IF Bgo3(Vent_ptr)=9999.999 THEN
11800        Ionum=12
11810        Fix_val=1
11820        GOTO Data_edit
11830    END IF
11840    Be(Vent_ptr)=FNLval(Io_msg$(Chart_num,13))
11850    IF Be(Vent_ptr)=9999.999 THEN
11860        Ionum=13
11870        Fix_val=1
11880        GOTO Data_edit
11890    END IF
11900    CALL Chart(Chart_num)
11910    Vent_ptr=Vent_ptr+1
11920    Vent_in=1
11930    Fix_val=0
11940    GOTO Keyend
11950  !
11960  !
11970  Key8:Chart_num=5
11980    IF Next_time-TIMEDATE<45 THEN
11990        DISP "not enough time to enter data; wait for next xfer"
12000        WAIT 2
12010        GOTO Keyend
12020    END IF
12030    GRAPHICS OFF
```

```
12040   PRINT CHR$(12)
12050   Num_var=3
12060   IF Drug_in=1 THEN
12070      DISP "data in for this xfer; chart displayed"
12080      WAIT 2
12090      Drug_ptr=Drug_ptr-1
12100      CALL Chart(Chart_num)
12110      Drug_ptr=Drug_ptr+1
12120      GOTO Keyend
12130   ELSE
12140      INPUT "Input values=1 or display chart=2?",Inp
12150      IF Inp=1 THEN
12160         IF Drug_ptr>38 THEN
12170            DISP "Do not enter more Drug data; disc full"
12180            WAIT 3
12190            GOTO Keyend
12200         ELSE
12210            GOTO I_o
12220         END IF
12230      ELSE
12240         CALL Chart(Chart_num)
12250         GOTO Keyend
12260      END IF
12270   END IF
12280 Data5:!
12290   Drug_time$(Drug_ptr)=Io_msg$(Chart_num,3)
12300   Drug_name$(Drug_ptr)=Io_msg$(Chart_num,1)
12310   Drug_dos$(Drug_ptr)=Io_msg$(Chart_num,2)
12320   CALL Chart(Chart_num)
12330   Drug_ptr=Drug_ptr+1
12340   Drug_in=1
12350   GOTO Keyend
12360   !
12370   !
12380 Key9:Key_id=9
```

```
12390 Bp_graph: !
12400 IF Next_time-TIMEDATE<12 THEN GOTO Waiter1
12410 IF Trend_dp=0 THEN
12420     Trend_dp=1
12430     Top1=150
12440     Top2=75
12450     Bot2=0
12460     Top3=50
12470     Top4=50
12480     ALLOCATE INTEGER Spectra(7499)
12490     GSTORE Spectra(*)
12500     CALL Trend_graph
12510 ELSE
12520     IF Trend_dp=1 THEN
12530         GRAPHICS ON
12540         GLOAD Spectra(*)
12550         DEALLOCATE Spectra(*)
12560         CALL Offgraph
12570         Trend_dp=0
12580     ELSE
12590         Trend_dp=1
12600         Top1=150
12610         Top2=75
12620         Bot2=0
12630         Top3=50
12640         Top4=50
12650         CALL Trend_graph
12660     END IF
12670 END IF
12680 GOTO Keyend
12690 !
12700 !
12710 I_o:!
12720 IF TIMEDATE>Next_time-20 THEN
12730     DISP "not enough time to enter data; wait for next xfer"
12740     WAIT 2
12750     GOTO Keyend
```

```
12760    END IF
12770    PRINT TABXY(1,1);"enter values"
12780    FOR I=Fst TO Num_var
12790        PRINT TABXY(1,17);"                "
12800        PRINT TABXY(1,17);Io$(Chart_num,I)
12810        Edit_msg$=""
12820        CALL Editor
12830        Io_msg$(Chart_num,I)=Edit_msg$
12840        PRINT TABXY(1,I+2);Io$(Chart_num,I);"=";Io_msg$(Chart_num,I)
12850    NEXT I
12860    PRINT TABXY(1,17);"                "
12870    PRINT TABXY(1,18);"                "
12880 !
12890 !....editting the data
12900 !
12910 Io_fix:DISP "Do you want to edit I/O values?                    (Y/N)"
12920    ENTER 2;Ans$
12930    DISP "                     "
12940    IF Ans$="Y" OR Ans$="y" THEN
12950        IF TIMEDATE>Next_time-15 THEN
12960            DISP "not enough time; data not stored; retry next xfer"
12970            GOTO Keyend
12980        END IF
12990        ON Chart_num GOTO Value,Lab,Vent,Pres,Drug
13000 Value:DISP "which value? 1=time, 2=maint. fluid, 3=other fluids, 4=urine, 5=chest"
13010        ENTER 2;Ionum
13020        IF Ionum<1 OR Ionum>5 THEN GOTO Value
13030        GOTO Data_edit
13040 Lab: DISP "which value? 1=time,2=Na,3=K,4=Cl,5=HCO3,6=Ca,7=Hct,8=Gluc,9=Dig,10=PT,11=PTT,12=Creat,13=Bun"
13050        ENTER 2;Ionum
13060        IF Ionum<1 OR Ionum>13 THEN GOTO Lab
13070        GOTO Data_edit
```

```
13080 Vent:PRINT TABXY(1,17);"which value?
              1=time,2=rate,3=FIO2,4=PP,5=peep,6=TV,
              7=I:E,8=airway"
13090         PRINT TABXY(1,18);
              "9=ph,10=pO2,11=pCO2,12=HCO3,13=Be"
13100         ENTER 2;Ionum
13110         IF Ionum<1 OR Ionum>13 THEN GOTO Vent
13120         GOTO Data_edit
13130 Pres:IF Bp=1 THEN
13140         PRINT TABXY(1,17);"which value? 1=pres
                      time,2=ao/s,3=ao/d,4=ao/m,
                      5=pa/s,6=pa/d,7=pa/m,8=la,9=ra"
13150      ELSE
13160         PRINT TABXY(1,18);"which value? 10=heart
                      time,11=c.i.,12=pvri,13=svri"
13170      END IF
13180      ENTER 2;Ionum
13190      IF Ionum<1 OR Ionum>13 THEN GOTO Pres
13200      GOTO Data_edit
13210 Drug:DISP "which value? 1=name,2=dosage,3=time"
13220      ENTER 2;Ionum
13230      IF Ionum<1 OR Ionum>10 THEN GOTO Drug
13240      GOTO Data_edit
13250 Data_edit:!
13260      IF TIMEDATE>Next_time-15 THEN
13270          DISP "not enough time; data not stored;
                    retry next xfer"
13280          WAIT 2
13290          GOTO Keyend
13300      END IF
13310      C_num=Chart_num
13320      R_num=2
13330      IF Fix_val=1 THEN
13340          PRINT TABXY(1,17);"Error on input; enter
                    value again"
13350          PRINT TABXY(1,18);Io$(C_num,Ionum)
13360      END IF
13370      PRINT TABXY(1,18);Io_msg$(C_num,Ionum)
```

```
13380      Edit_msg$=Io_msg$(C_num,Ionum)
13390      CALL Editor
13400      Io_msg$(C_num,Ionum)=Edit_msg$
13410      PRINT TABXY(1,Ionum+R_num);"          "
13420      PRINT TABXY(1,Ionum+R_num);Io$(C_num,Ionum);"=";Edit_msg$
13430      PRINT TABXY(1,17);"          "
13440      PRINT TABXY(1,18);"          "
13460      GOTO Io_fix
13470    ELSE
13480      ON Chart_num GOTO Data1,Data2,Data3,Data4,Data5
13490    END IF
13500 Keyend:OFF TIME
13510    OFF KBD
13520    RETURN
13530    END
13540  !
13550  !
13560  !
13570  !
13580  !
13590  SUB Pauser
13600      DISP "press CONTINUE to continue"
13610      PAUSE
13620      DISP
13630  SUBEND
13640  !
13650  !
13660  !
13670  !
13680  !
13690  SUB Get_param
13700      COM /Multi_param/ Start_chan,Stop_chan,Pacing_bits,Pacing_rate,Num_pts,Num_xfer,Num_xfer_left,Name_len,Scr_file$[28],Scr_file2$[28]
```

```
13710        COM /Messagecom/ Message$(10)[80],@Messages
13720        COM /Trends/ Mean_hr_t(*),Lfa_t(*),Rfa_
             t(*),Ratio_t(*),T_ptr,Time_now
             1,Meas_resp_t(*),Trend_dp
13730        COM /Vitaldata/ Rfa,Lfa,Peakratio,Meas_
             resp,Next_time
13740        COM /Pressure/
             Top1,Top2,Top3,Top4,Bot1,Bot2,Bot3,Bot4
13750        COM /Pres_chart/ Pres_time$(*),Ao_s(*),Ao_
             d(*),Ao_m(*),Pa_s(*),Pa_d(*
             ),Pa_m(*),La_m(*),Ra_m(*),Pres_ptr,Pres_in
13760        COM /Subject/ Sub_name$[25],Hos_num$[15],Id_
             age$[10],Id_wt$[10],Id_ht
             $[10],Diag$[30],Opera$[45],Halt_pg
13770        COM /Io_chart/ Io_time$(*),Iv_intake(*),Fluid_
             in(*),In_tot(*),Urine(*
             ),Chest(*),Out_tot(*),Net(*),Io_ptr
13780        COM /Lab_chart/ Lab_
             time$(*),Na(*),Kl(*),Cl(*),Hco3(*),
                Ca(*),Hct(*),Gluc(*),Dig(*),Pt(*),
                Ptt(*),Creat(*),Bun(*),Lab_ptr
13790        COM /Vent_chart/ Vent_
             time$(*),Rate(*),Fio2(*),Pp(*),Peep(*),Tv(*),Ie
             _ratio$(*),Airp(*),Ph(*),Po2(*),Pco2(*),
             Bgo3(*),Be(*),Vent_ptr
13800        COM /Heart_index/ Heart_
             time$(*),Ci(*),Pvri(*),Svri(*),Heart_ptr
13810        COM /Drugs/ Drug_time$(*),Drug_name$(*),Drug_
             dos$(*),Drug_ptr
13820        DIM Mo$[24]
13830        Mo$="JAFBMRAPMYJNJLAUSPOCNODC"
13840 !      INTEGER Id_buffer(255) BUFFER
13850        Disk_name$=":HP8290X,700,1"
13860        IF Halt_pg=1 THEN GOTO Purger_get!.....quit
             program
13870 !
13880 ! change soft key messages
13890 !
```

```
13900 Oldmsg:PRINT CHR$(12)
13910     PRINT "These are the current soft key
          messages:"
13920     FOR I=0 TO 9
13930         PRINT "KEY";I;":";Message$(I)
13940     NEXT I
14100     DISP "Press cont when ready to continue"
14110     PAUSE
14120 !
14130     INPUT "Enter subject name, 10 chars (Doe if
          unknown)",Sub_name$
14140     Sub_name$=Sub_name$[1,10]
14150     INPUT "Enter hospital number, 8 chars (00 if
          unknown):",Hos_num$
14160     Hos_num$=Hos_num$[1,8]
14170     INPUT "Enter subject age(00 if unknown):",Id_
          age$
14180     INPUT "Enter subject weight,kg (00 if
          unknown):",Id_wt$
14190     INPUT "Enter subject height,cm (00 if
          unknown):",Id_ht$
14200     INPUT "Enter diagnosis, 10 chars (Unk if
          unknown):",Diag$
14210     Diag$=Diag$[1,10]
14220     INPUT "Enter operation, 15 chars (Unk if
          unknown):",Opera$
14230     Opera$=Opera$[1,15]
14240 !
14250 Ch_sel:!
14260     Start_chan=0
14270     Stop_chan=0
14280 !
14290     Pacing_bits=0
14300 Pacing_sel:!
14310     Base$="M"
14320     Pacing_bits=261
14330 !
14340     Base$=Base$&"SEC"
```

```
14350 !
14360 !
14370 ! FINDOUT BLOCKSIZE FOR DATA TRANSFER
14380 !
14390     Num_xfer=55
14400 !
14410 ! since new data is to be taken, zero the trend
      graphs (120 pts=8hrs)
14420 !
14430     MAT Mean_hr_t= (0)
14440     MAT Rfa_t= (0)
14450     MAT Lla_t= (0)
14460     MAT Ratio_t= (0)
14470     MAT Meas_resp_t= (0)
14471     MAT Trans_time= (0)
14480     T_ptr=0
14490     MAT Pres_time$= ("")
14500     MAT Ao_s= (0)
14510     MAT Ao_d= (0)
14520     MAT Ao_m= (0)
14530     MAT Pa_s= (0)
14540     MAT Pa_d= (0)
14550     MAT Pa_m= (0)
14560     MAT La_m= (0)
14570     MAT Ra_m= (0)
14580     MAT Io_time$= ("")
14590     MAT Iv_intake= (0)
14600     MAT Fluid_in= (0)
14610     MAT In_tot= (0)
14620     MAT Urine= (0)
14630     MAT Chest= (0)
14640     MAT Out_tot= (0)
14650     MAT Net= (0)
14660     MAT Lab_time$= ("")
14670     MAT Na= (0)
14680     MAT K1= (0)
14690     MAT Cl= (0)
14700     MAT Hco3= (0)
```

```
14710      MAT Ca= (0)
14720      MAT Hct= (0)
14730      MAT Gluc= (0)
14740      MAT Dig= (0)
14750      MAT Pt= (0)
14760      MAT Ptt= (0)
14770      MAT Creat= (0)
14780      MAT Bun= (0)
14790      MAT Vent_time$= ("")
14800      MAT Rate= (0)
14810      MAT Fio2= (0)
14820      MAT Pp= (0)
14830      MAT Peep= (0)
14840      MAT Tv= (0)
14850      MAT Ie_ratio$= ("")
14860      MAT Airp= (0)
14870      MAT Ph= (0)
14880      MAT Po2= (0)
14890      MAT Pco2= (0)
14900      MAT Bgo3= (0)
14910      MAT Be= (0)
14920      MAT Heart_time$= ("")
14930      MAT Ci= (0)
14940      MAT Pvri= (0)
14950      MAT Svri= (0)
14960      MAT Drug_time$= ("")
14970      MAT Drug_name$= ("")
14980      MAT Drug_dos$= ("")
14990      Pres_ptr=0
15000      Trend_ptr=0

15010      Ratio_t(0)=1 !..prevent trend graph errors on
           startup
15020      Rfa=0
15030      Lfa=0
15040      Meas_resp=0
15050      Peakratio=1
```

```
15060   !
15070   !
15080       Pacing_rate=250
15090       Num_pts=1024*Num_xfer
15100       Num_header=256+8*Num_xfer
15110       IF Scr_file$="?" THEN GOTO Skip1
15120 Purger_get:DISP "PURGE FILE?"
15130       ENTER 2;Resp$
15140       IF Resp$="Y" OR Resp$="YES" THEN
15150           PURGE Scr_file$
15160           PURGE Scr_file2$
15170           PURGE "messglog:HP8290X,700,1"
15180           PURGE "temp_trend:HP8290X,700,1"
15190           PURGE "hemo_data:HP8290X,700,1"
15200           PURGE "io_data:HP8290X,700,1"
15210           PURGE "drug_data:HP8290X,700,1"
15220           PURGE "lab_data:HP8290X,700,1"
15230           PURGE "co_data:HP8290X,700,1"
15231           PURGE "sub_data:HP8290X,700,1"
15240       ELSE
15250 !
15260 ! the data files are named according to the date
15270 ! in the following format:
15280 !     xxxxmmddyy
15290 ! where
15300 !     xxxx - resp,hr__,msgs,errs,trnd
15310 !     dd   - day
15320 !     mm   - month
                     (JA,FB,MR,AP,MY,JN,JL,AU,SP,OC,NO,DC)
15330 !     yy   - year
15340           Date_now$=DATE$(TIMEDATE)
15350           Month_now=FNMonth(Date_now$)*2-1
15360           Mm$=Mo$[Month_now;2]
15370           Id_field$=Date_now$[1;2]&Mm$&Date_
                now$[10;2]
15380 ! new name for respiratory file: respddmmyy
15390           RENAME Scr_file$ TO "resp"&Id_field$&Disk_
                name$
```

```
15400! new name for heart rate file: hr__ddmmyy
15410        RENAME Scr_file2$ TO "hr__"&Id_
             field$&Disk_name$
15420! new name for message log: msgsddmmyy
15430        RENAME "messglog:HP8290X,700,1" TO
             "msgs"&Id_field$&Disk_name$
15440! new name for hemo data: dataddmmyy
15450        RENAME "hemo_data:HP8290X,700,1" TO
             "hemo"&Id_field$&Disk_name$
15460! new name for io data
15470        RENAME "io_data:HP8290X,700,1" TO "io__
             "&Id_field$&Disk_name$
15480! new name for lab data
15490        RENAME "lab_data:HP8290X,700,1" TO "lab_
             "&Id_field$&Disk_name$
15500! new name for vent data
15510        RENAME "vent_data:HP8290X,700,1" TO
             "vent"&Id_field$&Disk_name$
15520! new name for co data
15530        RENAME "co_data:HP8290X,700,1" TO "co__
             "&Id_field$&Disk_name$
15540! new name for drug data
15550        RENAME "drug_data:HP8290X,700,1" TO
             "drug"&Id_field$&Disk_name$
15551! new name for subject data
15552        RENAME "sub_data:HP8290X,700,1" TO "sub_
             "&Id_field$&Disk_name$
15560! name for trend summary file: trndddmmyy
15570        PURGE "temp_trend:HP8290X,700,1"
15580        CREATE BDAT "trnd"&Id_field$&Disk_
             name$,19,256
15590        ASSIGN @Trend_file TO "trnd"&Id_
             field$&Disk_name$;FORMAT OFF
15600        OUTPUT @Trend_file;Mean_hr_t(*),Lfa_
             t(*),Rfa_t(*),Ratio_t(*),Meas
             _resp_t(*),Trans_time(*),T_ptr
15610        ASSIGN @Trend_file TO *
15620    END IF
```

```
15630        IF Halt_pg=1 THEN        !..terminate program
15640            DISP "PROGRAM COMPLETED"
15650            STOP
15660        END IF
15670 Skip1:DISP
15680        Scr_file$="AOK"&Disk_name$
15690        Num_rec=-INT(-(Num_pts+Num_header)/128.)
15700        Scr_file2$="hr"&Scr_file$
15710        CREATE BDAT Scr_file$,Num_rec,256
15720        CREATE BDAT Scr_file2$,Num_rec,256
15730        CREATE BDAT "messglog:HP8290X,700,1",20,640
15740        CREATE BDAT "temp_trend"&Disk_name$,19,256
15750        CREATE BDAT "hemo_data"&Disk_name$,10,256
15760        CREATE BDAT "io_data"&Disk_name$,10,256
15770        CREATE BDAT "lab_data"&Disk_name$,10,256
15780        CREATE BDAT "vent_data"&Disk_name$,10,256
15790        CREATE BDAT "co_data"&Disk_name$,10,256
15800        CREATE BDAT "drug_data"&Disk_name$,10,256
15801        CREATE BDAT "sub_data"&Disk_name$,1,256
15802        ASSIGN @Sub_data TO "sub_data"&Disk_name$;FORMAT OFF
15803        OUTPUT @Sub_data;Sub_name$,Hos_num$,Id_age$,Id_wt$,Id_ht$,Diag$,Opera$
15804        ASSIGN @Sub_data TO *
15810        Halt_pg=0
15820        Num_pts=1024
15830        PRINT Num_pts*Num_xfer;"points will be transferred in";Num_xfer;"blocks of";Num_pts;"points"
15840   !
15850        Num_xfer_left=Num_xfer
15860   SUBEND
15870   !
15880   !
15890   !
15900   !
15910   DEF FNMonth(Date_now$)
15920        Month$=Date_now$[4;3]
```

```
15930      Month=0
15940      IF Month$="Jan" THEN Month=1
15950      IF Month$="Feb" THEN Month=2
15960      IF Month$="Mar" THEN Month=3
15970      IF Month$="Apr" THEN Month=4
15980      IF Month$="May" THEN Month=5
15990      IF Month$="Jun" THEN Month=6
16000      IF Month$="Jul" THEN Month=7
16010      IF Month$="Aug" THEN Month=8
16020      IF Month$="Sep" THEN Month=9
16030      IF Month$="Oct" THEN Month=10
16040      IF Month$="Nov" THEN Month=11
16050      IF Month$="Dec" THEN Month=12
16060      RETURN Month
16070 FNEND
16080 !
16090 !
16100 !
16110 !
16120 !
16130 SUB Xfheader(@Disk,Num_bytes,File_id$)
16140      INTEGER Xheader(7) BUFFER
16150      Xheader(0)=(TIMEDATE MOD 86400)/60
16160      Xheader(1)=Num_bytes
16170      Xheader(2)=NUM(File_id$[1;1])
16180      Xheader(3)=0
16190      Xheader(4)=0
16200      Xheader(5)=0
16210      Xheader(6)=0
16220      Xheader(7)=0
16230      ASSIGN @Xheader TO BUFFER Xheader(*)
16240      CONTROL @Xheader,5;1    ! Reset empty pointer
                                   for buffer
16250      CONTROL @Xheader,4;16   ! Reset current number
                                   of bytes in buffer
16260      TRANSFER @Xheader TO @Disk;COUNT 16,WAIT
16270      ASSIGN @Xheader TO *
```

```
16280   SUBEND
16290!
16300!
16310!
16320!
16330!
16340!
16350   SUB Trend_graph
16360!
16370       COM /Trends/ Mean_hr_t(*),Lfa_t(*),Rfa_
            t(*),Ratio_t(*),T_ptr,Time_now
            1,Meas_resp_t(*),Trend_dp,Trans_time(*),Lfa_
              top,Rfa_top
16380       COM /Multi_param/ Start_chan,Stop_chan,Pacing_
            bits,Pacing_rate,Num_pt
            s,Num_xfer,Num_xfer_left,Name_len,Scr_
              file$[28],Scr_
            file2$[28]
16390       COM /Pressure/
            Top1,Top2,Top3,Top4,Bot1,Bot2,Bot3,Bot4
16400       COM /Pres_chart/ Pres_time$(*),Ao_s(*),Ao_
            d(*),Ao_m(*),Pa_s(*),Pa_d(*
            ),Pa_m(*),La_m(*),Ra_m(*),Pres_ptr,Pres_in
16410       DIM First_line(60),Sec_line(60),Third_
            line(60),Fourth_line(60)
16420       IF Trend_dp=1 THEN
16430           MAT First_line= Ao_m
16440           MAT Sec_line= Pa_m
16450           MAT Third_line= La_m
16460           MAT Fourth_line= Ra_m
16470           G_right=INT((Num_xfer*256/60)/15)
16480       !   IF Pres_in=0 THEN !   Trend_ptr=Pres_
                ptr+1
16490       !       Trend_ptr=Pres_ptr+1
16500       !   ELSE
16510           Trend_ptr=Pres_ptr
16520       !   END IF
16530       ELSE
```

```
16540          MAT First_line= Mean_hr_t
16550          MAT Sec_line= Ratio_t
16560          MAT Third_line= Lfa_t
16570          MAT Fourth_line= Rfa_t
16580          G_right=Num_xfer
16590          Trend_ptr=T_ptr
16600       END IF
16610       Block_time=Pacing_rate*1.024/3600.
16620       GINIT
16630       GCLEAR
16640       PRINT CHR$(12)
16650       GRAPHICS ON
16660       Beg_time=Time_now1/3600-Block_time
16670       End_time=Beg_time+Num_xfer*Block_time
16680       Ibeg_time=INT(Beg_time)
16690       IF Ibeg_time<Beg_time THEN Ibeg_time=Ibeg_time+1
16700 !
16710 ! label the time axes
16720 !
16730       VIEWPORT 0,128,45,50
16740       WINDOW Beg_time,End_time,0,1
16750       IF INT(End_time)>Beg_time THEN
16760          LDIR 0
16770          FOR T_label=Ibeg_time TO INT(End_time)
16780             MOVE T_label,.5
16790             LORG 5
16800             CSIZE 4
16810             LABEL T_label
16820          NEXT T_label
16830       END IF
16840       VIEWPORT 0,128,40,45
16850       WINDOW 0,1,0,1
16860       MOVE .5,0
16870       LORG 4
16880       LABEL "Time (24 hr)"
16890 !
16900 ! draw the axes
```

```
16910!
16920      VIEWPORT 0,128,50,100
16930      WINDOW Beg_time,End_time,0,1
16940      AXES 1/15.,.1,Beg_time,0
16950      WINDOW 1,0,1,0
16960      AXES 0,.25,0,0
16970!
16980! mean heart rate trends
16990!
17000      WINDOW -1,G_right,Bot1,Top1
17010      MOVE 0,First_line(0)
17020      FOR I=0 TO Trend_ptr-1
17030          DRAW I,First_line(I)
17040      NEXT I
17050!
17060! ratio trends (with a line at ratio=2)
17070!
17080      WINDOW -1,G_right,Bot2,Top2
17090      LINE TYPE 8,5
17100      IF Trend_dp=2 THEN
17110          MOVE 0,LGT(Sec_line(0))
17120      ELSE
17130          MOVE 0,Sec_line(0)
17140      END IF
17150      FOR I=0 TO Trend_ptr-1
17160          IF Trend_dp=2 THEN
17170              DRAW I,LGT(Sec_line(I))
17180          ELSE
17190              DRAW I,Sec_line(I)
17200          END IF
17210      NEXT I
17220      IF Trend_dp=2 THEN
17230          LINE TYPE 3,5!..sparsely dotted line at ratio=2
17240          MOVE 0,LGT(2.)
17250          DRAW Trend_ptr-1,LGT(2.)
17260      END IF
17270!
```

```
17280! lfa trends
17290!
17300      WINDOW -1,G_right,Bot3,Top3
17310      LINE TYPE 4,5
17320      MOVE 0,Third_line(0)
17330      FOR I=0 TO Trend_ptr-1
17340          DRAW I,Third_line(I)
17350      NEXT I
17360!
17370! rfa trends
17380!
17390      WINDOW -1,G_right,Bot4,Top4
17400      LINE TYPE 5,5
17410      MOVE 0,Fourth_line(0)
17420      FOR I=0 TO Trend_ptr-1
17430          DRAW I,Fourth_line(I)
17440      NEXT I
17450!
17460! draw a key for line types
17470!
17480      VIEWPORT 64,128,0,50
17490      WINDOW 0,1,0,13
17500      IF Trend_dp=2 THEN
17510          PRINT TABXY(1,17);"trend graph"
17520          PRINT TABXY(55,15);"mean hr(0-200)"
17530          PRINT TABXY(55,16);"ratio(.01-100)"
17540          PRINT TABXY(55,17);"lfa    (0-10)"
17550          PRINT TABXY(55,18);"rfa    (0-10)"
17560      ELSE
17570          PRINT TABXY(1,17);"mean pressure graphs"
17580          PRINT TABXY(50,15);"ao pressure(0-150)"
17590          PRINT TABXY(50,16);"pa pressure(0-75)"
17600          PRINT TABXY(50,17);"la pressure(0-50)"
17610          PRINT TABXY(50,18);"ra pressure(0-50)"
17620      END IF
17630      LINE TYPE 1,5
17640      MOVE .8,11
17650      DRAW 1.,11
```

```
17660      LINE TYPE 8,5
17670      MOVE .8,10
17680      DRAW 1.,10
17690      LINE TYPE 4,5
17700      MOVE .8,9
17710      DRAW 1.,9
17720      LINE TYPE 5,5
17730      MOVE .8,8
17740      DRAW 1.,8
17750  SUBEND
17760!
17770!
17780!
17790!
17800!
17810  SUB Msg_dump(Message_chart$(*),Message_line,Flg)
17820      COM /Messagecom/ Message$(10)[80],@Messages
17830      DIM Msg_buffer$[1280] BUFFER
17840      IF Flg>=2 THEN GOTO Chart_filled
17850      ASSIGN @Msg_buffer TO BUFFER Msg_buffer$;FORMAT OFF
17860      STATUS @Messages,3;Num_rec
17870      STATUS @Messages,4;Rec_len
17880      STATUS @Messages,5;Cur_rec
17890      STATUS @Messages,6;Cur_byte
17900      IF Cur_rec<=1 AND Cur_byte<=1 THEN !.. no messages yet
17910          Flg=0
17920          DISP "no messages yet"
17930          WAIT 2
17940          SUBEXIT
17950      END IF
17960      Flg=2
17970      CONTROL @Messages,5;1
17980      CONTROL @Messages,6;1
17990      FOR Rec=1 TO Cur_rec-1
18000 Read_msg:TRANSFER @Messages TO @Msg_buffer;COUNT Rec_len,WAIT
```

```
18010           Message_chart$(Rec-1)=Msg_buffer$[1;Rec_
                len]
18020           CONTROL @Msg_buffer,4;0
18030           CONTROL @Msg_buffer,5;1
18040       NEXT Rec
18050       IF Cur_byte>1 THEN
18060           TRANSFER @Messages TO @Msg_buffer;COUNT
                Cur_byte-1,WAIT
18070           Message_chart$(Cur_rec-1)=Msg_
                buffer$[1;Cur_byte-1]
18080       END IF
18090       ASSIGN @Msg_buffer TO *
18100 Reset_msg_file:!
18110       CONTROL @Messages,5;Cur_rec
18120       CONTROL @Messages,6;Cur_byte
18130 Chart_filled:!
18140       STATUS @Messages,5;Cur_rec
18150       STATUS @Messages,6;Cur_byte
18160       Flg=2
18170       Cur_msg_ptr=0
18180       Chart_line=1
18190       Msg_buffer$=Message_chart$(0)
18200       Last_msg=Message_line+17
18210       Clear$=CHR$(255)&CHR$(75)
18220       OUTPUT 2;Clear$
18230       GRAPHICS OFF
18240 Next_msg:!
18250       Beg_msg=POS(Msg_buffer$[4],"Time")+3
18260       IF Beg_msg=3 THEN GOTO Next_chart_line
18270       Cur_msg_ptr=Cur_msg_ptr+1
18280       IF Cur_msg_ptr>Message_line THEN
18290           Tab_line=Cur_msg_ptr-Message_line
18300           PRINT TABXY(1,Tab_line);"           "
18310           PRINT TABXY(1,Tab_line);Msg_buffer$[1,Beg_
                msg-1]
18320       END IF
18330       Msg_buffer$=Msg_buffer$[Beg_msg]
18340       IF Cur_msg_ptr=Last_msg THEN Subend_msg
```

```
18350           GOTO Next_msg
18360 Next_chart_line:IF Chart_line<Cur_rec THEN
18370              Msg_buffer$=Msg_buffer$&Message_
                        chart$(Chart_line)
18380              Chart_line=Chart_line+1
18390              GOTO Next_msg
18400           END IF
18410 Stopper:PRINT Msg_buffer$
18420 Subend_msg:PRINT
18430    SUBEND
18440 !
18450 !
18460 !
18470 !
18480 !
18490    SUB Disp_ctrls
18500        DISP "f̂ - freq range adjust (1 or 2 Hz)"
18510        WAIT 2
18520        DISP "ĥ - help: display these controls"
18530        WAIT 2
18540        DISP "p̂ - peak threshold adjust (+20%)"
18550        WAIT 2
18560        DISP "r̂ - resp time series display"
18570        WAIT 2
18580        DISP "ŝ - search for resp peak (+.1 Hz)"
18590        WAIT 2
18600    SUBEND
18610 !
18620 !
18630 !
18640    SUB Offgraph
18650        COM /Vitaldata/ Rfa,Lfa,Peakratio,Meas_
                    resp,Next_time
18660        PRINT CHR$(12)
18670        PRINT TABXY(1,14);"RR=";PROUND(Meas_resp,-
                    2);"Hz"
18680        PRINT TABXY(1,15);"lfa=";Lfa
18690        PRINT TABXY(1,16);"rfa=";Rfa
```

```
18700        PRINT TABXY(1,17);"ratio=";Peakratio
18710        PRINT TABXY(1,18);"next transfer:
             ";TIME$(Next_time)
18720  SUBEND
18730     !
18740     !
18750     ! This subroutine edits the data
18760     !
18770     !
18780  SUB Editor
18790        COM /Editor/ Edit_msg$[80]
18800        COM /Vitaldata/ Rfa,Lfa,Peakratio,Meas_
             resp,Next_time
18810 Key_in:!
18820        PRINT TABXY(1,18);"                    "
18830        PRINT TABXY(1,18);Edit_msg$
18840        IF TIMEDATE>Next_time-15 THEN GOTO Keyend
18850        ON TIME (TIMEDATE+10) MOD 86400,3 GOTO Keyend
18860        DISP "type message"
18870        GRAPHICS OFF
18880        ON KBD,2 GOTO Next_char
18890 Key_wait:GOTO Key_wait
18900 Next_char:Key$=KBD$
18910        ON TIME (TIMEDATE+10) MOD 86400,3 GOTO Keyend
18920        IF NUM(Key$)=255 THEN
18930           IF NUM(Key$[2])=69 THEN GOTO End_key
18940           IF NUM(Key$[2])=66 THEN !..backspacing
18950              New_msg_len=LEN(Edit_msg$)-1
18960              IF New_msg_len<=0 THEN New_msg_len=0
18970              Edit_msg$=Edit_msg$[1;New_msg_len]
18980           END IF
18990           IF NUM(Key$[2])=35 THEN !..clear line
19000              Edit_msg$=""
19010           END IF
19020        ELSE
19030           IF LEN(Edit_msg$)<66 THEN !..can add
             ! characters
```

```
19040              Edit_msg$=Edit_msg$&Key$
19050          ELSE
19060             BEEP
19070          END IF
19080       END IF
19090       PRINT TABXY(1,18);"                    "
19100       PRINT TABXY(1,18);Edit_msg$
19110       GOTO Key_wait
19120 Keyend: !
19130 End_key:OFF KBD
19140       OFF TIME
19150   SUBEND
19160 !
19170 !
19180 !
19190   SUB Chart(Chart_num)
19200       COM /Subject/ Sub_name$,Hos_num$,Id_age$,Id_
            wt$,Id_ht$,Diag$,Opera$,Halt_pg
19210       COM /Io_chart/ Io_time$(*),Iv_intake(*),Fluid_
            in(*),In_tot(*),Urine(*),Chest(*),Out_
              tot(*),Net(*),Io_ptr
19220       COM /Lab_chart/ Lab_
       time$(*),Na(*),Kl(*),Cl(*),Hco3(*),Ca(*),Hct(*),G
         luc(*),Dig(*),Pt(*),Ptt(*),Creat(*),Bun(*),Lab_
         ptr
19230       COM /Vent_chart/ Vent_
            time$(*),Rate(*),Fio2(*),Pp(*),Peep(*),Tv(*),
            Ie_ratio$(*),Airp(*),Ph(*),Po2(*),Pco2(*),
            Bgo3(*),Be(*),Vent_ptr
19240       COM /Pres_chart/ Pres_time$(*),Ao_s(*),Ao_
            d(*),Ao_m(*),Pa_s(*),Pa_d(*
              ),Pa_m(*),La_m(*),Ra_m(*),Pres_ptr,Pres_in
19250       COM /Pressure/
            Top1,Top2,Top3,Top4,Bot1,Bot2,Bot3,Bot4
19260       COM /Heart_index/ Heart_
            time$(*),Ci(*),Pvri(*),Svri(*),Heart_ptr
19270       COM /Drugs/ Drug_time$(*),Drug_name$(*),Drug_
            dos$(*),Drug_ptr
```

```
19280      Pres_stl=0
19290      Lab_stl=0
19300      Io_stl=0
19310      Vent_stl=0
19320      Drug_stl=0
19330      !
19340      ! set up identifying subject info
19350      !
19360      PRINT CHR$(12)
19370      PRINT TABXY(1,1);
19380      PRINT USING Image_wt1;Sub_name$,Hos_
           num$,TIME$(TIMEDATE),DATE$(TIMEDATE)
19390 Image_wt1:IMAGE   "Name: ",K,XXXX,"Hosp num:
           ",K,XXXXX,K,XXXXX,K
19400      PRINT TABXY(1,2);
19410      PRINT USING Image_wt2;Id_age$,Id_wt$,Id_
           ht$,Diag$,Opera$
19420 Image_wt2:IMAGE   "Age: ",K,XXXX,"Wt(kg):
           ",K,XXXX,"Ht(cm): ",K,XXXX,"Diag
             : ",K,XXXX,"Op: ",K
19430      !
19440      ! go to appropriate chart
19450      !
19460      ON Chart_num GOTO In_out,Lab_val,Vent_
           val,Pres_val,Drug
19470 In_out:!                           ....intake/output
19480      IF Io_ptr>3 THEN Io_stl=2
19490      IF Io_ptr>5 THEN
19500         DISP "do not input more Intake/Output
              data; disc full"
19510         WAIT 3
19520         SUBEXIT
19530      END IF
19540      PRINT TABXY(30,3);"INTAKE/OUTPUT CHART"
19550      PRINT TABXY(1,4);"Intake (cc/hr) "
19560      PRINT TABXY(1,5);"Time"
19570      PRINT TABXY(4,6);"Maint. Fluid"
```

```
19580       PRINT TABXY(4,7);"Other Fluids"
19590       PRINT TABXY(1,9);"Total "
19600       PRINT TABXY(1,11);"Output (cc/hr)"
19610       PRINT TABXY(4,12);"Urine"
19620       PRINT TABXY(4,13);"Chest"
19630       PRINT TABXY(1,15);"Total"
19640       PRINT TABXY(1,17);"Net I/O"
19650       Start=25
19660       FOR I=Io_stl TO Io_ptr
19670           PRINT TABXY(Start,5);Io_time$(I)
19680           PRINT TABXY(Start,6);Iv_intake(I)
19690           PRINT TABXY(Start,7);Fluid_in(I)
19700           PRINT TABXY(Start,9);In_tot(I)
19710           PRINT TABXY(Start,12);Urine(I)
19720           PRINT TABXY(Start,13);Chest(I)
19730           PRINT TABXY(Start,15);Out_tot(I)
19740           PRINT TABXY(Start,17);Net(I)
19750           Start=Start+10
19760       NEXT I
19770       GOTO Finish
19780 !
19790 !
19800 Lab_val:!         ...lab values
19810       IF Lab_ptr>3 THEN Lab_stl=2
19820       IF Lab_ptr>7 THEN
19830           DISP "do not input any more lab values;
                    disc full"
19840           WAIT 3
19850           SUBEXIT
19860       END IF
19870       PRINT TABXY(30,3);"Lab Values"
19880       PRINT TABXY(10,4);"Time"
19890       PRINT TABXY(1,6);"Na"
19900       PRINT TABXY(1,7);"K"
19910       PRINT TABXY(1,8);"Cl"
19920       PRINT TABXY(1,9);"HCO3"
19930       PRINT TABXY(1,10);"Ca"
19940       PRINT TABXY(1,11);"Hct"
```

```
19950        PRINT TABXY(1,12);"Glucose"
19960        PRINT TABXY(1,13);"Dig level"
19970        PRINT TABXY(1,14);"PT"
19980        PRINT TABXY(1,15);"PTT"
19990        PRINT TABXY(1,16);"Creat"
20000        PRINT TABXY(1,17);"Bun"

20010        Start=15
20020        FOR I=Lab_stl TO Lab_ptr
20030            PRINT TABXY(Start+10,4);Lab_time$(I)
20040            PRINT TABXY(Start+10,6);Na(I)
20050            PRINT TABXY(Start+10,7);Kl(I)
20060            PRINT TABXY(Start+10,8);Cl(I)
20070            PRINT TABXY(Start+10,9);Hco3(I)
20080            PRINT TABXY(Start+10,10);Ca(I)
20090            PRINT TABXY(Start+10,11);Hct(I)
20100            PRINT TABXY(Start+10,12);Gluc(I)
20110            PRINT TABXY(Start+10,13);Dig(I)
20120            PRINT TABXY(Start+10,14);Pt(I)
20130            PRINT TABXY(Start+10,15);Ptt(I)
20140            PRINT TABXY(Start+10,16);Creat(I)
20150            PRINT TABXY(Start+10,17);Bun(I)
20160            Start=Start+10
20170        NEXT I
20180        GOTO Finish
20190 !
20200 !
20210 Vent_val:!                    ....ventilation values
20220        IF Vent_ptr>3 THEN Vent_stl=2
20230        IF Vent_ptr>5 THEN Vent_stl=4
20240        IF Vent_ptr>7 THEN
20250            DISP "do not input any more Vent values; disc full"
20260            WAIT 3
20270            SUBEXIT
20280        END IF
20290        PRINT TABXY(30,3);"VENTILATION"
```

```
20300        PRINT TABXY(1,4);"Settings            Hour:"
20310        PRINT TABXY(4,5);"Rate"
20320        PRINT TABXY(4,6);"FIO2"
20330        PRINT TABXY(4,7);"Peak Pres"
20340        PRINT TABXY(4,8);"Peep"
20350        PRINT TABXY(4,9);"TV"
20360        PRINT TABXY(4,10);"I:E ratio"
20370        PRINT TABXY(4,11);"Mean air"
20380        PRINT TABXY(1,12);"Blood Gases"
20390        PRINT TABXY(4,13);"ph"
20400        PRINT TABXY(4,14);"pO2"
20410        PRINT TABXY(4,15);"pCO2"
20420        PRINT TABXY(4,16);"HCO3"
20430        PRINT TABXY(4,17);"BE"
20440        Start=15
20450        FOR I=Vent_stl TO Vent_ptr
20460             PRINT TABXY(Start+10,4);Vent_time$(I)
20470             PRINT TABXY(Start+10,5);Rate(I)
20480             PRINT TABXY(Start+10,6);Fio2(I)
20490             PRINT TABXY(Start+10,7);Pp(I)
20500             PRINT TABXY(Start+10,8);Peep(I)
20510             PRINT TABXY(Start+10,9);Tv(I)
20520             PRINT TABXY(Start+10,10);Ie_ratio$(I)
20530             PRINT TABXY(Start+10,11);Airp(I)
20540             PRINT TABXY(Start+10,13);Ph(I)
20550             PRINT TABXY(Start+10,14);Po2(I)
20560             PRINT TABXY(Start+10,15);Pco2(I)
20570             PRINT TABXY(Start+10,16);Bgo3(I)
20580             PRINT TABXY(Start+10,17);Be(I)
20590             Start=Start+10
20600        NEXT I
20610        GOTO Finish
20620 !
20630 !
20640 Pres_val:!                    ....pressure values
20650        IF Pres_ptr>12 THEN Pres_stl=5
20660        IF Pres_ptr>17 THEN
20670             DISP "Do not input any more pressures;
```

```
                    disc full"
20680           WAIT 3
20690           SUBEXIT
20700       END IF
20710       PRINT TABXY(9,3);"Time:"
20720       PRINT TABXY(1,4);"Systemic"
20730       PRINT TABXY(4,5);"systolic"
20740       PRINT TABXY(4,6);"diastolic"
20750       PRINT TABXY(4,7);"mean"
20760       PRINT TABXY(1,8);"Pulmonary"
20770       PRINT TABXY(4,9);"systolic"
20780       PRINT TABXY(4,10);"diastolic"
20790       PRINT TABXY(4,11);"mean"
20800       PRINT TABXY(1,12);"LA mean"
20810       PRINT TABXY(1,13);"RA mean"
20820       PRINT TABXY(9,14);"Time: "
20830       PRINT TABXY(1,15);"C.I."
20840       PRINT TABXY(1,16);"PVRI"
20850       PRINT TABXY(1,17);"SVRI"
20860       Start=15
20870       FOR I=Pres_stl TO Pres_ptr
20880           PRINT TABXY(Start,3);Pres_time$(I)
20890           PRINT TABXY(Start,5);Ao_s(I)
20900           PRINT TABXY(Start,6);Ao_d(I)
20910           PRINT TABXY(Start,7);Ao_m(I)
20920           PRINT TABXY(Start,9);Pa_s(I)
20930           PRINT TABXY(Start,10);Pa_d(I)
20940           PRINT TABXY(Start,11);Pa_m(I)
20950           PRINT TABXY(Start,12);La_m(I)
20960           PRINT TABXY(Start,13);Ra_m(I)
20970           Start=Start+5
20980       NEXT I
20990       Start=15
21000       FOR I=0 TO Heart_ptr
21010           PRINT TABXY(Start,14);Heart_time$(I)
21020           PRINT TABXY(Start,15);Ci(I)
21030           PRINT TABXY(Start,16);Pvri(I)
21040           PRINT TABXY(Start,17);Svri(I)
```

```
21050        Start=Start+5
21060     NEXT I
21070     GOTO Finish
21080 !
21090 !
21100 Drug:!                              ....hey man, drugs
21110     IF Drug_ptr>9 THEN Drug_stl=4
21120     IF Drug_ptr>14 THEN Drug_stl=9
21130     IF Drug_ptr>19 THEN Drug_stl=14
21140     IF Drug_ptr>24 THEN Drug_stl=19
21150     IF Drug_ptr>29 THEN Drug_stl=24
21160     IF Drug_ptr>34 THEN Drug_stl=29
21170     IF Drug_ptr>38 THEN
21180        DISP "do not enter more drugs; disc full"
21190        WAIT 3
21200        SUBEXIT
21210     END IF
21220     PRINT TABXY(30,4);"Drug Chart"
21230     PRINT TABXY(1,6);"Name"
21240     PRINT TABXY(30,6);"Dosage"
21250     PRINT TABXY(60,6);"Time"
21260     D_line=7
21270     FOR I=Drug_stl TO Drug_ptr
21280        PRINT TABXY(1,D_line);Drug_name$(I)
21290        PRINT TABXY(30,D_line);Drug_dos$(I)
21300        PRINT TABXY(60,D_line);Drug_time$(I)
21310        D_line=D_line+1
21320     NEXT I
21330 Finish: !
21340   SUBEND
21350 !
21360 !
21370   DEF FNLval(Lnum$)
21380     Numval=VAL("9"&Lnum$)
21390     If Num val=9 THEN
21400     Rval=9999.999
21410     RETURN Rval
21420     ELSE
```

```
21430      Numval=VAL(Lnum$)
21440.     RETURN Numval
21450      END IF
21460      FNEND 10 Teaser7:!This program reviews data taken by sgrape
20      ! and allows all the graphs to be printed (when
30      ! its done)
40      !
50      !..............................................
60      !
70      ! LAST REVISION: 1 May. 1985
80      !..............................................

90      !
100     !
110     !..............................................
120     !
130     ! SET UP ERROR HANDLERS
140     ! SET UP COMMON STORAGE/ARRAY STORAGE
150     !..............................................

160     !
170     !
171     COM /Vars/ Ffthrvar,Fftrespvar
180     COM /Intr_7/ Int_flag,Status_bytes(5)
190     COM /Flags/ Atod_done,Scanner_done,Memory1_
            done,Memory2_done,Timer_done,Counter_done,
              Memory3_done,Memory4_done
200     COM /Io_arrays/ Counters(3),Counters2(3),Time_
            base$[7]
210     COM /Multi_param/ Start_chan,Stop_chan,Pacing_
            bits,Pacing_rate,Num_pts,Num_xfer,
              Num_xfer_left,Name_len,Scr_file$[28],Scr_
                file2$[28]
220     COM /Hr_sig/ Num_pulses,Last_pulse,First_blk_
            flg,Last_time,Num_hr_sig,Max
              _hr_pts,Avg_hr,Rollover,Hr_smooth
```

```
230   COM /Hr_stats/ Hr_histo(128),Histo_min,Histo_
      max,Num_fudge,Num_histo_pnts
      ,@Err_log
240   COM /Plot_par/ Plotbox,Boxcar_flg,Log_
      plotflg,Freq_limit,Resp_search,Pct_thresh
250   COM /Graphs/
      Hrdata(512),Hrspec(512),Respspec(512),Bpspec(512)
260   COM /Vitaldata/ Rfa,Lfa,Peakratio,Meas_resp,Next_
      time
270   COM /Idfield/ Id_field$[18]
280   COM /Messagecom/ Message$(10)[80],@Messages
290   COM /Trends/ Mean_hr_t(60),Lfa_t(60),Rfa_
      t(60),Ratio_t(60),T_ptr,Time_now
          1,Meas_resp_t(60)
300   DIM Msg_pad$(20)[80],Edit_msg$[80]
310   DIM Msg_buffer$[80] BUFFER
320   ASSIGN @Msg_buffer TO BUFFER Msg_buffer$
330   Log_plotflg=0
340   Freq_limit=1.
350   Resp_search=.1
360   Pct_thresh=.2
370   Scr_file$="?"
380   !
390   ! Set up common/array storage for waveform
        analysis
400   !
410   !.........................................
420   !
430   ! Set up common/array storage for waveform
      ! analysis
440   !.........................................

450   !
460   COM /Directory/ Dir$[160],@Printer
470   COM /Wf1/ Printer,Plotter,String$[40]
480   COM /Wf2/ Signal(8257),Number_pnts,Type,Sampling_
      period
```

```
490    COM /Wf3/ Segment_size,Overlap,Num_segments,Pnts_
       used,Fft_size
500    COM /Wf5/ Refn(63),Refd(63),Refno,Refdo,Refgain
510    COM /Autoparam/ Up_down,Up_delay,Dn_delay
520    COM /Fftcom/ INTEGER Bitrev(512),Sincos(512)
530    !
540    DISP "loading subroutines"
550    LOADSUB ALL FROM "hr_siggen8"
560    LOADSUB ALL FROM "automaxsb2"
570    LOADSUB ALL FROM "fft_anal6"
580    DISP "load data disks and press CONTINUE"
590    PAUSE
600    !
610    !................................................
620    ! The HP 9826/9836 flexible disk (5-1/4") has the
       following structure
630    ! 2 sides, 33 tracks/side, 16 sectors/track, 256
       bytes/sector
640    !  1 track =   4096 bytes =   16 sectors
650    !  1 side  = 135168 bytes =  528 sectors
660    !  1 disk  = 270336 bytes = 1056 sectors
670    !  1 disk  = 135168 words =  132K words
680    !................................................
690    !
700    !
710    INTEGER Hpib_buffer1(2048) BUFFER
720    INTEGER Hpib_buffer2(2048) BUFFER
730    DIM Hr_signal(1024) BUFFER
740    Read_ptr1=0
750    Read_ptr2=0
760 Begin: !
770 Selections: !
780    !
790    !
800    ! NOW SET UP THE SCAN CARD PARAMETERS (DEFAULT
       ! VALUES)
810    !    START CHANNEL (3.0) - 0
```

```
820   !         STOP CHANNEL (3.1) - 1
830   !               PACING (3.2) - 40 USEC
840   !         SEQN'L SCAN (3.3) - XXXX XXXX XXX1 (  1)
850   !      INTN'L PACING (3.3) - XXXX XXXX X1XX (  4)
860   !      MSEC TIMEBASE (3.3) - XXX1 XXXX XXXX (256)
870   !
880     CALL Get_param
890   !
900   ! set up the bit reverse index
910   !
920     Npair=Num_pts/2
930     K=0
940     FOR J=1 TO Npair-1
950        I=2
960        Ndivi=Npair/I
970        IF K<Ndivi THEN 1010
980        K=K-Ndivi
990        I=I+I
1000       GOTO 960
1010       K=K+Ndivi
1020       Bitrev(J+1)=K+1
1030    NEXT J
1040  !
1050  ! set up the sin/cosine table
1060  !
1070    Angl=ATN(1)*8/Npair
1080    FOR J=0 TO Npair-1
1090       Sincos(J)=SIN(Angl*J)
1100    NEXT J
1110  !
1120  ! set up other data  paths
1130  !
1140  ! ASSIGN @Err_log TO "errs"&Id_
            field$&":HP8290X,700,1";FORMAT OFF
1150  ! ASSIGN @Messages TO "msgs"&Id_
            field$&":HP8290X,700,1";FORMAT OFF
1160  ! ASSIGN @Temp_trend TO "trnd"&Id_
            field$&":HP8290X,700,1";FORMAT OFF
```

```
1170    IF Num_pts=0 THEN GOTO Begin
1180    Read_ptr1=0
1190 Setup_scan:DISP " NUMBER OF POINTS=";Num_pts
1200    Read_ptr1=0
1210    Read_ptr2=0
1220 Setup_counter:!
1230 Setup_clock:!
1240    Block_time=Pacing_rate*1.024
1250    First_blk_flg=1
1260    Num_msgs=0
1270    Message_line=0
1280    Msg_dp_request=0
1290    Resp_dpflg=0
1300    Max_hr_pts=1024
1310    Last_time=0
1320 !
1330 ! setup control parameters
1340 !
1350 Defaultset:!
1360    INPUT "use default settings?",Resp$
1370    IF Resp$="N" THEN Frqlimset
1380    Freq_limit=2.
1390    Pct_thresh=.2
1400    Resp_dpflg=1
1410    Resp_search=.2
1420    Hcdopyflg=0
1430    PRINT "Spectra displayed to";Freq_limit;"Hz"
1440    PRINT "resp peak search threshold=";Pct_thresh
1450    PRINT "resp series plot w/hr series"
1460    PRINT "resp peak search starts at";Resp_search;"Hz"
1470    PRINT "no hard copy will be printed"
1480    INPUT "is this ok?",Resp$
1490    IF Resp$<>"Y" THEN Defaultset
1500    GOTO Skipset
1510 Frqlimset:!
1520    INPUT "frequency limit?",Freq_limit   !..change spectra disp.freq.range
```

```
1530    IF Freq_limit<>1. THEN Freq_limit=2.
1540    PRINT "Spectra displayed to";Freq_limit;"Hz"
1550    INPUT "is this ok?",Resp$
1560    IF Resp$<>"Y" THEN Frqlimset
1570 Searchset:!
1580    INPUT "resp peak threshold?",Pct_thresh !..change
        peak search threshold
1590    IF Pct_thresh>.8 THEN Pct_thresh=.2
1600    PRINT "resp peak search threshold=";Pct_thresh
1610    INPUT "is this ok?",Resp$
1620    IF Resp$<>"Y" THEN Searchset
1630 Respdpset:!
1640    INPUT "display resp time series?",Resp$
            !..display respiration time series
1650    IF Resp$<>"N" THEN
1660        Resp_dpflg=1
1670        PRINT "resp series plot w/hr series"
1680    ELSE
1690        Resp_dpflg=0
1700        PRINT "cancel resp series plot"
1710    END IF
1720    INPUT "is this ok?",Resp$
1730    IF Resp$<>"Y" THEN Respdpset
1740 Resppkset: !
1750    INPUT "start for resp peak search?",Resp_
        search   !..change respiration
                    peak search
1760    IF Resp_search>Freq_limit-.1 THEN Resp_search=.1
1770    PRINT "resp peak search starts at";Resp_
        search;"Hz"
1780    INPUT "is this ok?",Resp$
1790    IF Resp$<>"Y" THEN Resppkset
1800 Hdcopyset: !
1810    INPUT "print hardcopy?",Resp$
1820    IF Resp$="N" THEN
1830        Hdcopyflg=0
1840        PRINT "no hard copy will be printed"
1850    ELSE
```

```
1860        Hdcopyflg=1
1870        PRINT "hard copy will be printed"
1880     END IF
1890     INPUT "is this ok?",Resp$
1900     IF Resp$<>"Y" THEN Hdcopyset
1910 Skipset:  !
1920  !
1930  ! Read data continuously
1940  !
1950  ! Set up the memory buffers and disk files
1960  !
1970 Reading:  !
1980     ASSIGN @In_buffer TO BUFFER Hpib_buffer1(*)
1990     ASSIGN @Diskbuffer TO Scr_file$;FORMAT OFF
2000     ASSIGN @In_buffer2 TO BUFFER Hpib_buffer2(*)
2010     ASSIGN @Diskbuffer2 TO Scr_file2$;FORMAT OFF
2020  !
2030     Data_lockout=0
2040  !
2050  ! generate id fields to identify data files
2060  !........................................
2070  ! the first 256 bytes of the file are reserved for
      !   identification
2080  !
2090  ! the reserved data are:
2100  !    byte    1 - 72 ("H") or 82 ("R"): hr or resp_
      !    file
2110  !    byte    2 - year (at beginnig of expt.)
2120  !    byte    3 - month
2130  !    byte    4 - day
2140  !    byte    5 - hour
2150  !    byte    6 - minute
2160  !    byte    7 - collecting program date (0-365)
2170  !    byte    8 - collecting program year (1984-?)
2180  !    byte    9-16: unused
2190  !    byte   17 - pacing rate (0-32768)
2200  !    byte   18 - pacing rate units(77 ="M" or 85
      !    ="U")
```

```
2210 !    byte  19 - number of transfers
2220 !    byte  20 - number of point/transfer (=1024)
2230 !    byte  21 - number of A/D channels used (=1)
2240 !    byte  22-256 : unassigned
2250 !
2260 !    the remainder of the file is data
2270 !    each transfer is preceded by an identifying
     !    string of 8 bytes
2280 !    byte 1 - time of day (timedate mod 86400)/60
2290 !    byte 2 - number of points in next transfer
2300 !    byte 3 - H/R (check to make sure this is the
     !    right file)
2310 !............................................
2320 !
2330 ! INTEGER Id_buffer(255) BUFFER
2340   Time_now=TIMEDATE
2350 ! Id_buffer(0)=72                      !..Heart rate file
2360   Date_now$=DATE$(TIMEDATE)
2370 ! Day_now=VAL(Date_now$)
2380 ! Year_now=VAL(Date_now$[8;4])
2390 ! Month_now=FNMonth(Date_now$)
2400 ! Id_buffer(1)=Year_now                !..year
2410 ! Id_buffer(2)=Month_now               !..month
2420 ! Id_buffer(3)=Day_now                 !..day
2430   Time_now1=Time_now MOD 86400
2440 ! Id_buffer(4)=Time_now1/3600          !..hour
2450 ! Id_buffer(5)=(Time_now1 MOD 3600)/60 !..min
2460 ! Id_buffer(6)=348                     !..pgm date
2470 ! Id_buffer(7)=1984                    !..pgm year
2480 ! Id_buffer(16)=Pacing_rate
2490 ! Id_buffer(17)=77                     !..MSEC
2500 ! Id_buffer(18)=Num_xfer
2510 ! Id_buffer(19)=1024                   !..num_pts
2520 ! Id_buffer(20)=1                      !..# channels
2530 !
2540 !
2550 ! read id field for heart rate file
2560 !
```

```
2570 ! ASSIGN @Id_buffer TO BUFFER Id_buffer(*)
2580 ! TRANSFER @Diskbuffer2 TO @Id_buffer;COUNT
     ! 256,WAIT
2590 ! ASSIGN @Id_buffer TO *
2600 !
2610 ! read id field for respiratory file
2620 !
2630 ! Id_buffer(0)=82                    !..Resp file
2640 ! ASSIGN @Id_buffer TO BUFFER Id_buffer(*)
2650 ! TRANSFER @Diskbuffer TO @Id_buffer;COUNT 256,WAIT
2660 ! ASSIGN @Id_buffer TO *
2670 !
2680 !
2690 !
2700 ! begin transferring data from the A/D buffer
2710 !
2720 Blk_xfer:!
2730   CONTROL @In_buffer,3;1
     ! Reset fill pointer for buffer
2740   CONTROL @In_buffer,4;0
     ! Reset current number of bytes in buffer
2750   CONTROL @In_buffer,5;1
     ! Reset empty pointer for buffer
2760 !
2770 ! read an 8 byte sequence to disk as a header for
     ! the transfer
2780 !
2790   CALL Rdheader(@Diskbuffer,Num_pts,"R")
2800 !
2810   Num_rdpts=Num_pts
2820   TRANSFER @Diskbuffer TO @In_buffer;COUNT Num_rdpts*2,CONT
2830   PRINT TABXY(1,18);
2840   PRINT USING Image_wt1;Num_xfer-Num_xfer_left+1,Num_xfer,TIME$(Next_time),
Rdseg,Num_rdseg
2850 Image_wt1:IMAGE    "Next xfer(",K,"/",K,"): ",K,"
                        seg=",K,"/",K
```

```
2860  !
2870  ! store A/D buffer on complete data file (also
      !   save pointers for heart rate)
2880  !
2890  !
2900 Resume1:!
2910   Next_time=Next_time+INT(Block_time)
2920  !
2930  !
2940  !
2950 Resume2:!
2960   Num_xfer_left=Num_xfer_left-1
2970   CONTROL @In_buffer2,3;1
      ! Reset fill pointer for buffer
2980   CONTROL @In_buffer2,4;0
      ! Reset current number of bytes in buffer
2990   CONTROL @In_buffer2,5;1
      ! Reset empty pointer for buffer
3000  !
3010  ! read an 8 byte sequence to disk as a header for
      ! the transfer
3020  !
3030   CALL Rdheader(@Diskbuffer2,Num_pulses,"H")
3040   TRANSFER @Diskbuffer2 TO @In_buffer2;COUNT Num_
         pulses*2,WAIT
3050  !
3060 Resume5:!
3070   Histo_max=8000
3080   Histo_min=-8000
3090   CALL Hr_sig_gen(Hpib_buffer2(*),Hr_signal(*))
3100  !
3110  !
3120 Resume6:!
3130   OUTPUT 2;CHR$(255)&CHR$(75);
      ! Clear CRT of text
3140   GINIT
3150   PLOTTER IS 3,"INTERNAL"
```

```
3160    GRAPHICS ON
3170    Xscale=8
3180    Hr_max=MAX(Hr_signal(*))
3190    Hr_min=MIN(Hr_signal(*))
3200    VIEWPORT 0,64,50,100
3210    WINDOW 0,1,0,1
3220    AXES .1,.1,0,0
3230    CSIZE 4
3240    Hr_signal(1024)=0
3250    Hr_sigsum=SUM(Hr_signal)
3260    Mean_hr=INT((Hr_sigsum/1024+Avg_hr))
3270    LDIR 0
3280    LORG 3
3290    MOVE .2,.9
3300    LABEL "HR data   hr=";Mean_hr
3310    CSIZE 4
3320    MOVE .05,1
3330    LORG 3
3340    LABEL "250 bpm"
3350    WINDOW 1,0,1,0
3360    AXES 0,0,0,0
3370    IF Hr_dispflg=1 THEN
3380        WINDOW 0,1024,Hr_min,Hr_max
3390    ELSE
3400        Low_window=INT(-Avg_hr)
3410        High_window=Low_window+250.
3420        WINDOW 0,1024,Low_window,High_window
3430    END IF
3440    FOR I=0 TO 1023
3450        PLOT I,Hr_signal(I)
3460    NEXT I
3470    !CALL Pauser
3480    IF Fftskpflg=1 THEN GOTO Skip_fft
3490    !
3500    ! display respirations time series also
3510    !
3520    IF Resp_dpflg=1 THEN
3530        Max_resp=MAX(Hpib_buffer1(*))
```

```
3540        Min_resp=MIN(Hpib_buffer1(*))
3550        IF Mean_hr>100 THEN
3560            VIEWPORT 0,64,50,65
3570        ELSE
3580            VIEWPORT 0,64,75,90
3590        END IF
3600        WINDOW 0,1023,Min_resp,Max_resp
3610        MOVE 0,Hpib_buffer1(0)
3620        FOR I=1 TO 1023
3630            PLOT I,Hpib_buffer1(I)
3640        NEXT I
3650    ELSE
3660        Resp_dpflg=0
3670    END IF
3680    !
3690    ! now process heart rate data with waveform
            analysis package
3700    ! make sure the hr_signal has zero mean
3710    !
3711    MAT Signal= (0)
3720    Hr_bias=Hr_sigsum/1024
3730    FOR I=0 TO 1023
3740        Signal(I)=Hr_signal(I)-Hr_bias
3750    NEXT I
3751    Hr_var=DOT(Signal,Signal)/1024
3760    Plotbox=2
3770    DISP "HR fft in process"
3780    CALL Wf_analyzer(Pacing_rate)
3790    !
3800    ! now process respiration data with waveform
            analysis package
3810    !
3820    MAT Signal= (0)
3830    FOR I=0 TO 1023
3840        Signal(I)=Hpib_buffer1(I)
3850    NEXT I
3860    Signal_avg=SUM(Signal)/1024.
3870    MAT Signal= Signal-(Signal_avg)
```

```
3880    Plotbox=4
3881    Respvar=DOT(Signal,Signal)/1024
3890    DISP "RESP fft in process"
3900    CALL Wf_analyzer(Pacing_rate)
3901    PRINT "hr_var,respvar";Hr_var;Respvar
3902    PRINT "fft vars: ";Ffthrvar,Fftrespvar
3910    Trend_dp=0 !..trend graph not displayed
3920    !
3930    ! waveform analysis completed, compile trends and
            store in temporary file
3940    !
3950    Mean_hr_t(T_ptr)=Mean_hr
3960    Lfa_t(T_ptr)=Lfa
3970    Rfa_t(T_ptr)=Rfa
3980    Ratio_t(T_ptr)=Peakratio
3990    Meas_resp_t(T_ptr)=Meas_resp
4000    T_ptr=T_ptr+1
4010    IF Hdcopyflg=1 THEN
4011        DUMP DEVICE IS 701
4020        DUMP GRAPHICS
4030        PRINTER IS 701
4040        PRINT "hr=";Mean_hr
4050        PRINT "lfa=";Lfa
4060        PRINT "rfa=";Rfa
4070        PRINT "ratio";Peakratio
4080        PRINT "RR";Meas_resp
4090        PRINT "transfer#";T_ptr
4091        PRINT "hr_var,respvar";Hr_var;Respvar
4092        PRINT "fft vars: ";Ffthrvar,Fftrespvar
4100        PRINTER IS 1
4110    END IF
4120    !
4130    ! continue with data collection
4140    !
4150 Skip_fft: !
4160    IF Num_xfer_left<=0 THEN
4170        GOTO Eo_blk_xfer
4180    ELSE
```

```
4190        DISP Num_xfer_left;"transfers remaining"
4200        WAIT 3
4210        GOTO Blk_xfer
4220     END IF
4230 Eo_blk_xfer:End_time=TIMEDATE
4240     Delta_time=End_time-Start_time
4250     !
4260     Stop_pacing=TIMEDATE
4270 !
4280 Aborter:!
4290     ASSIGN @In_buffer TO *
4300     ASSIGN @In_buffer2 TO *
4310     ASSIGN @Diskbuffer TO *
4320     ASSIGN @Diskbuffer2 TO *
4330 !   ASSIGN @Err_log TO *
4340 !   ASSIGN @Messages TO *
4350 !   ASSIGN @Temp_trend TO *
4360     CALL Pauser
4370     GRAPHICS OFF
4380     CALL Get_param
4390 !   ASSIGN @Err_log TO "errs"&Id_field$&":HP8290X,700,1";FORMAT OFF
4400 !   ASSIGN @Messages TO "msgs"&Id_field$&":HP8290X,700,1";FORMAT OFF
4410     IF Num_pts=0 THEN GOTO Begin
4420     GOTO Setup_scan
4430     END
4440     !
4450     !
4460     !
4470     !
4480     !
4490     SUB Pauser
4500        DISP "press CONTINUE to continue"
4510        PAUSE
4520        DISP
4530     SUBEND
4540     !
```

```
4550    !
4560    !
4570    !
4580    !
4590    SUB Get_param
4600        COM /Multi_param/ Start_chan,Stop_chan,Pacing_
            bits,Pacing_rate,Num_pt
            s,Num_xfer,Num_xfer_left,Name_len,Scr_
            file$[28],Scr_
            file2$[28]
4610        COM /Trends/ Mean_hr_t(*),Lfa_t(*),Rfa_
            t(*),Ratio_t(*),T_ptr,Time_now
              1,Meas_resp_t(*)
4620        COM /Vitaldata/ Rfa,Lfa,Peakratio,Meas_
            resp,Next_time
4630        COM /Idfield/ Id_field$
4640        DIM Mo$[24]
4650        Mo$="JAFBMRAPMYJNJLAUSPOCNODC"
4660        INTEGER Id_buffer(255) BUFFER
4670        Disk_name$=":HP8290X,700,1"
4680 Oldmsg:PRINT CHR$(12)
4690    !
4700    !
4710 Ch_sel:!
4720        Start_chan=0
4730        Stop_chan=0
4740    !
4750        Pacing_bits=0
4760 Pacing_sel:!
4770        Base$="M"
4780        Pacing_bits=261
4790    !
4800        Base$=Base$&"SEC"
4810    !
4820    !
4830    ! FINDOUT BLOCKSIZE FOR DATA TRANSFER
4840    !
```

```
4850 Get_xfer:DISP "Enter number of transfers: (0 -
       change scan, <0 - quit)"
4860       OUTPUT 2;55;
4870       ENTER 2;Num_xfer
4880       IF Num_xfer<0 THEN    !..terminate program
4890           INPUT "to lose trend data type
               'lose'",Response$
4900           IF Response$<>"lose" THEN
4910               CREATE BDAT
                   "teasertrnd:HP8290X,700,1",19,256
4920               ASSIGN @Trndfile TO
                   "teasertrnd:HP8290X,700,1";FORMAT OFF
4930               OUTPUT @Trndfile;Mean_hr_t(*),Lfa_
                   t(*),Rfa_t(*),Ratio_t(*),Me
                      as_resp_t(*),T_ptr
4940               ASSIGN @Trndfile TO *
4950           END IF
4960           DISP "PROGRAM COMPLETED"
4970           STOP
4980       END IF
4990       IF Num_xfer=0 THEN
5000           Num_pts=0
5010           SUBEXIT
5020       END IF
5030 !
5040 ! since new data is to be taken, zero the trend
     graphs (120 pts=8hrs)
5050 !
5060       MAT Mean_hr_t= (0)
5070       MAT Rfa_t= (0)
5080       MAT Lfa_t= (0)
5090       MAT Ratio_t= (0)
5100       MAT Meas_resp_t= (0)
5110       T_ptr=0
5120       Ratio_t(0)=1 !..prevent trend graph errors on
           startup
5130       Rfa=0
5140       Lfa=0
```

```
5150        Meas_resp=0
5160        Peakratio=1
5170  !
5180  Intvl_sel:DISP "ENTER PACING RATE (IN
      ";Base$[1,4];"):"
5190        OUTPUT 2;250;
5200        ENTER 2;Pacing_rate
5210        IF Pacing_rate<0 OR Pacing_rate>65535 THEN
            GOTO Intvl_sel
5220  !
5230        Num_pts=1024*Num_xfer
5240        Num_header=256+8*Num_xfer
5250        INPUT "type in date on which data was
            taken",Datdate$
5251        INPUT "is trend file named 'trnd' (1) or
            'temp_trend' (2)?",File_nm
5260        Datdate$=DATE$(DATE(Datdate$))
5270  !
5280  ! the data files are named according to the date
5290  ! in the following format:
5300  !     xxxxmmddyy
5310  ! where
5320  !     xxxx - resp,hr__,msgs,errs,trnd
5330  !     dd   - day
5340  !     mm   - month
              (JA,FB,MR,AP,MY,JN,JL,AU,SP,OC,NO,DC)
5350  !     yy   - year
5360        Month_now=FNMonth(Datdate$)*2-1
5370        Mm$=Mo$[Month_now;2]
5380        Id_field$=Datdate$[1;2]&Mm$&Datdate$[10;2]
5390  ! new name for respiratory file: respddmmyy
5391  IF File_nm=1 THEN
5400        Scr_file$="resp"&Id_field$&Disk_name$
5410  ! new name for heart rate file: hr__ddmmyy
5420        Scr_file2$="hr__"&Id_field$&Disk_name$
5421        ELSE
5422            Scr_file$="AOK"&Disk_name$
```

```
5423            Scr_file2$="hrAOK"&Disk_name$
5424          END IF
5430 ! new name for errorlog: errsddmmyy
5440 ! new name for message log: msgsddmmyy
5450 ! name for trend summary file: trndddmmyy
5460       Num_rec=-INT(-(Num_pts+Num_header)/128.)
5470       Num_pts=1024
5480       PRINT Num_pts*Num_xfer;"points were transferred in";Num_xfer;"blocks of";Num_pts;"points"
5490    !
5500       Num_xfer_left=Num_xfer
5510    SUBEND
5520    !
5530    !
5540    !
5550    !
5560    DEF FNMonth(Date_now$)
5570       Month$=Date_now$[4;3]
5580       Month=0
5590       IF Month$="Jan" THEN Month=1
5600       IF Month$="Feb" THEN Month=2
5610       IF Month$="Mar" THEN Month=3
5620       IF Month$="Apr" THEN Month=4
5630       IF Month$="May" THEN Month=5
5640       IF Month$="Jun" THEN Month=6
5650       IF Month$="Jul" THEN Month=7
5660       IF Month$="Aug" THEN Month=8
5670       IF Month$="Sep" THEN Month=9
5680       IF Month$="Oct" THEN Month=10
5690       IF Month$="Nov" THEN Month=11
5700       IF Month$="Dec" THEN Month=12
5710       RETURN Month
5720    FNEND
5730 !
5740 !
5750 !
5760 !
```

```
5770  !
5780   SUB Rdheader(@Disk,Num_bytes,File_id$)
5790       INTEGER Xheader(7) BUFFER
5800       ASSIGN @Xheader TO BUFFER Xheader(*)
5810       TRANSFER @Disk TO @Xheader;COUNT 16,WAIT
5820       ASSIGN @Xheader TO *
5830       Num_bytes=Xheader(1)
5840       File_id$=CHR$(Xheader(2))
5850   SUBEND
5860  !
5870  !
5880  !
5890  !
5900  !
5910  !
5920   SUB Trend_graph
5930  !
5940       COM /Trends/ Mean_hr_t(*),Lfa_t(*),Rfa_
           t(*),Ratio_t(*),T_ptr,Time_now
             1,Meas_resp_t(*)
5950       COM /Multi_param/ Start_chan,Stop_chan,Pacing_
           bits,Pacing_rate,Num_pt
           s,Num_xfer,Num_xfer_left,Name_len,Scr_
            file$[28],Scr_
           file2$[28]
5960       Block_time=Pacing_rate*1.024/3600.
5970       GINIT
5980       GCLEAR
5990       PRINT CHR$(12)
6000       GRAPHICS ON
6010       PRINT TABXY(1,18);"trend graph"
6020       Beg_time=Time_now1/3600-Block_time
6030       End_time=Beg_time+Num_xfer*Block_time
6040       Ibeg_time=INT(Beg_time)
6050       IF Ibeg_time<Beg_time THEN Ibeg_time=Ibeg_
           time+1
6060  !
6070  ! label the time axes
```

```
6080  !
6090        VIEWPORT 0,128,45,50
6100        WINDOW Beg_time,End_time,0,1
6110        IF INT(End_time)>Beg_time THEN
6120            LDIR 0
6130            FOR T_label=Ibeg_time TO INT(End_time)
6140                MOVE T_label,.5
6150                LORG 5
6160                CSIZE 4
6170                LABEL T_label
6180            NEXT T_label
6190        END IF
6200        VIEWPORT 0,128,40,45
6210        WINDOW 0,1,0,1
6220        MOVE .5,0
6230        LORG 4
6240        LABEL "Time (24 hr)"
6250  !
6260  ! draw the axes
6270  !
6280        VIEWPORT 0,128,50,100
6290        WINDOW Beg_time,End_time,0,1
6300        AXES 1/15.,.1,Beg_time,0
6310        WINDOW 1,0,1,0
6320        AXES 0,.25,0,0
6330  !
6340  ! mean heart rate trends
6350  !
6360        WINDOW -1,Num_xfer,0,200.
6370        MOVE 0,Mean_hr_t(0)
6380        FOR I=0 TO T_ptr-1
6390            DRAW I,Mean_hr_t(I)
6400        NEXT I
6410  !
6420  ! lfa trends
6430  !
6440        WINDOW -1,Num_xfer,0,10.
6450        LINE TYPE 4,5
```

```
6460        MOVE 0,Lfa_t(0)
6470        FOR I=0 TO T_ptr-1
6480            DRAW I,Lfa_t(I)
6490        NEXT I
6500 !
6510 ! rfa trends
6520 !
6530        WINDOW -1,Num_xfer,0,10.
6540        LINE TYPE 5,5
6550        MOVE 0,Rfa_t(0)
6560        FOR I=0 TO T_ptr-1
6570            DRAW I,Rfa_t(I)
6580        NEXT I
6590 !
6600 ! ratio trends (with a line at ratio=2)
6610 !
6620        WINDOW -1,Num_xfer,-2.5,2.5
6630        LINE TYPE 8,5
6640        MOVE 0,LGT(Ratio_t(0))
6650        FOR I=0 TO T_ptr-1
6660            DRAW I,LGT(Ratio_t(I))
6670        NEXT I
6680        LINE TYPE 3,5 !..sparsely dotted line at
                 ratio=2
6690        MOVE 0,LGT(2.)
6700        DRAW T_ptr-1,LGT(2.)
6710 !
6720 ! respiration trends
6730 !
6740        WINDOW -1,Num_xfer,0,200
6750        LINE TYPE 5,10
6760        MOVE 0,Meas_resp_t(0)
6770        FOR I=0 TO T_ptr-1
6780            DRAW I,Meas_resp_t(I)
6790        NEXT I
6800 !
6810 ! draw a key for line types
6820 !
```

```
6830        VIEWPORT 64,128,0,50
6840        WINDOW 0,1,0,13
6850        PRINT TABXY(55,15);"mean hr(0-200)"
6860        PRINT TABXY(55,16);"lfa    (0-10)"
6870        PRINT TABXY(55,17);"rfa    (0-10)"
6880        PRINT TABXY(55,18);"ratio(.01-100)"
6890        LINE TYPE 1,5
6900        MOVE .8,11
6910        DRAW 1.,11
6920        LINE TYPE 4,5
6930        MOVE .8,10
6940        DRAW 1.,10
6950        LINE TYPE 5,5
6960        MOVE .8,9
6970        DRAW 1.,9
6980        LINE TYPE 8,5
6990        MOVE .8,8
7000        DRAW 1.,8
7010        LINE TYPE 1,5
7020    SUBEND
```

' CALIB - program to calibrate instruments using board#1

' last revision: 4 April 1985

```
defint a-y          ' only z denotes a real number
dim buffer(12800)
hrbpm=0
zfqlow=0.
zfqres=0.
zlfa=0.
zrfa=0.
cls 'define ports on 8253
timer0=&h720
```

```
        timer1=&h721
        timer2=&h722
        con8253=&h723

' set timer modes to 16 bit square wave rate
            generators
        out con8253,&h36
        out con8253,&h76
        out con8253,&hB6

'for testing set timer 0 to 100Hz timebase
'2.38MHz/23864: 23864=93*256+56
'set timer 0 to 1280Hz timebase
'(2.38MHz/1864) (1864=7*256+72)
'set timer 1 as a 1Hz clock at startup
'(gives a heart rate signal at
'60bpm) 'set timer 2 as a flip flop
        out timer0,56
        out timer0,93
        out timer0,72
        out timer0,7
        out timer1,0
        out timer1,5
        hrbpm=60
        out timer2,2
        out timer2,0

' turn the gates on using the 8255 at bits 0,1,2
on portc
        porta=&H700
        portb=&H708
        portc=&H710
        con8255=&H718

' first set all 8255 ports to output, then set
portc to 0FFH
```

```
        out con8255,128
        out portc,&H0FF

' first print out the present value of the
interrupt vectors
        locate 4,1
        gosub 10000

' install the interrupt with a dummy buffer and
            print vectors
        reseter=256
        call wrbuffer(reseter)

reseter=128
        call wrbuffer(reseter)
        call instint
        locate 5,1
        gosub 10000

' now go through required startup subroutines
        gosub 90                ' set up breathing
signal
        gosub 70                ' set up heart rate
variations
        gosub 50                ' put some information
on screen
        gosub 80                ' turn D/A on
        locate 1,1
        print "commands: h(rvar),i(nt
on),q(uit),r(beats),b(reath),c(ounts)"

' wait until user hits a key
        savekey$=""
40.     while
```

```
        len(savekey$)=0:savekey$=savekey$+inkey$:wend
        if savekey$="r" then gosub 50     'print heart
beats
        if savekey$="q" then goto 9996    'quit
        if savekey$="c" then gosub 60     'print timers
        if savekey$="h" then gosub 70     'set up heart
rate
        ' variations
        if savekey$="i" then gosub 80     'unmask
interrupts
        if savekey$="b" then gosub 90     'set up
breathing signal
        savekey$=""
        goto 40

'print present value of heartbeats 50      locate 7,1
        call rdbeat(n)
        print "present heart beats are: ";n;time$
        return ' print present value of counters
60      out control,0               'latch timer0
        tlow0=inp(timer0)
        thigh0=inp(timer0)
        out control,&h40            'latch timer1
        tlow1=inp(timer1)
        thigh1=inp(timer1)
        out control,&h80            'latch timer2
        tlow2=inp(timer2)
        thigh2=inp(timer2)
        locate 8,1
        print "timer0: ";tlow0+thigh0*16;tab(20);"
timer1:
            ";tlow1+thigh1*16;
        print tab(40);"timer2: ";tlow2+thigh2*16
        return
```

```
         ' set up the heart rate variations
         '       respiratory frequency is given by
1280Hz/buffer
         '         length
         '         low frequency is 1280Hz/low frequency
divider
         '
         '————————————

70       if numval<=0 then beep:print "setup analog
buffer
         first":return
71       locate 17,1
         print "present lfa,rfa(bpm)= ";zlfa,zrfa,"at
freqs(Hz):
         ";zfqlow,zfqres
         input "lfa,rfa,low freq: ",zlfan,zrfan,zfqlown
         if zlfan>30. then beep:goto 71 else zlfa=zlfan
         if zrfan>30. then beep:goto 71 else zrfa=zrfan
         if zfqlown<.02 or zfrlown>zfqres then beep:goto
71 else
         zfqlow=zfqlown
         locate 21,1
         print "mean heart rate(bpm)= ";hrbpm
72       locate 22,1
         input "new mean heart rate(bpm): ",newhrbpm
         if newhrbpm>150 or newhrbpm<30 then beep:goto 72
else
         hrbpm=newhrbpm
                 'clear screen after input
         locate 17,1
         print space$(72)
         print space$(72)
         print space$(72)
         print space$(72)
         print space$(72)

' now compute values for hrsetup subroutine
         meandiv=76800#/hrbpm    '1280*60 ticks/min gives
           ticks/beat
```

```
rfascal=76800#/(hrbpm-zrfa)-76800#/(hrbpm+zrfa)
                    ' rfascal is the total excursion of
                    ' respiration
lfascal=76800#/(hrbpm-zlfa)-76800#/(hrbpm+zlfa)
                    ' lfascal is the total excursion
                              of low frequency
lowdiv=meandiv-(rfascal+lfascal)/2# tbaserst=1280#/zfqlow
locate 17,1
print "tbaserst,rfascal,lfascal,lowdiv:
       ";tbaserst;rfascal;lfascal;
print lowdiv
call hrsetup(tbaserst,rfascal,lfascal,lowdiv)

return

' print out interrupt controller parameters
80         locate 10,1
           mask=inp(&h21)
           if (mask mod 16)<8 then mask=mask+8 else
mask=mask-8
           out &h21,mask
           mask=inp(&h21)
           print "8259 IMR(interrupt mask regsiter)=
";mask;"
                 =";hex$(mask)
           return ' this subroutine will change the analog buffer
90         locate 12,1
           input "enter breathing rate (bpm): ",brate
           if brate>75 or brate<7 then beep:goto 90
```

```
        zfqres=brate/60#
        numval=76800#/brate
        ztincr=8*ATN(1#)/numval
        locate 12,40
        color 31:print "calculating respiratory
signal...":color 7
        call exstint      ' turn off interrupts
                                    while resetting buffer
        reseter=256
        call wrbuffer(reseter)
        for itime=0 to numval
            ztnow=ztnow+ztincr
            analogval=127*(1#+SIN(ztnow))
            call wrbuffer(analogval)
        next itime
        call instint
        locate 12,40
        print "respiratory signal active now     "
        return ' exstall the interrupt and print vector
9996    cls
        locate 4,1
        gosub 10000
        call exstint
        locate 5,1
        gosub 10000
        locate 21,1
9999    stop ' subroutine to print out the interrupt vectors 10000   def seg=0
        print "IRQ3 @0B*4H: ";hex$(peek(&h2C));"
               ";hex$(peek(&h2D));" ";
```

```
        print hex$(peek(&h2E));" ";hex$(peek(&h2F));tab(40);
        print "IRQ4 @0C*4H: ";hex$(peek(&h30));" ";hex$(peek(&h31));" ";
        print hex$(peek(&h32));" ";hex$(peek(&h33))
    return end
```

```
                    page    66,80
; bdzint.asm - an assembler routine to handle interrupts
;               from IRQ3
; Last revision:  1 April 1985
;
;

;----------------------------------;
                ;   8088 interrupt location        ;
                ;----------------------------------;

abs0            segment at 0     ;absolute memory segment
                                 ;allows placement of
                                 ;interrupt address
                                 ;future timebase
                                 ;   interrupt handler
                                 ;   resides at int 0B
IRQ3_int        dw      2 dup(?);offset value is a word org     0CH*4    ;heart beat interrupt
                                 ;handler resides at int
                                 ; 0C
IRQ4_int        dw      2 dup(?);offset value is a w...

abs0            ends             ;

;----------------------------------;
                ; int_buffer: area to save DOS     ;
                ;        dummy interrupt ptr      ;
                ;----------------------------------;
```

```
int_buffer      segment             ;data segment containing
                                    ;user interrupt buffer
save_int        dw      4 dup(?)    ;offset for two DOS
                                    ;interrupts saved
                                    ;to be restored using
                                    ;exstint int_buffer      ends                ;
```

```
;----------------------------------;
; working storage for              ;
; time base interrupts             ;
;----------------------------------;
```

```
dseg_tbase      segment             ;data segment for timebase
                                    ; interrupt
heartbeats      dw      ?           ;keep track of heart beats
                                    ; here (for debugging)
base_rate       dw      ?           ;lowest divisor for heart
                                    ; rate
lfa_scal        db      ?           ;lo  frequency modulation
rfa_scal        db      ?           ;high frequency modulation
tbase_ctr       dw      ?           ;counter for timebase
                                    ; interrupt
                                    ;(use for low frequency
                                    ;  generation)
tbase_rst       dw      ?           ;reset value for tbase_ctr
                                    ; used to set low frequency
tbase_ptr       dw      ?           ;pointer to present analog
                                    ; value
tbase_len       dw      ?           ;length of analog data buffer
tbase_buffer    db      2800dup(?)  ;buffer for A/D values
dseg_tbase      ends                ;
```

```
;------------------------------------;
; setup structures to allow access to;
; arguments pased by BASIC           ;
;------------------------------------;

; subroutine rdbeat(BASIC_beats)
frame_rd        struc           ;define the stack
                                ;structure for passing
                                ;arguments to BASIC
savebp1         dw      ?       ;caller's base pointer
saveret1        dd      ?       ;return offset and
                                ;segment pushed by BASIC
BASIC_beats     dw      ?       ;place to return heart
                                ;beats to BASIC
frame_rd        ends ;subroutine wrbuffer (analog)
frame_wr        struc   ;define the stack structure
                        ;  for passing
                        ;arguments from BASIC to
                        ;  analog buffer
savebp2         dw      ?       ;caller's base pointer
saveret2        dd      ?       ;return offset and segment
                                ;  pushed by BASIC
analog          dw      ?       ;place to receive analog value
                                ;  from BASIC
frame_wr        ends ;subroutine hrsetup(B_lreset;
                ;   Brfa_scal,Blfa_scal,Bbase_
                ;   rate)
frame_hr        struc   ;define the stack structure for
                        ;   passing
                        ;arguments from BASIC to heart
                        ;   rate controls
savebp3         dw      ?       ;caller's base pointer
saveret3        dd      ?       ;return offset and segment pushed
                                ;   by BASIC
```

```
Bbase_rate  dw      ?       ;BASIC's lowest divider for heart
                            ;  rate Blfa_scal   dw      ?       ;BASIC's low frequency scaler
                            ;  (amplitude)

Brfa_scal   dw      ?       ;BASIC's high frequency scaler
                            ;  (amplitude)

B_lreset    dw      ?       ;BASIC's low frequency timer
                            ;  reset value frame_hr    ends ;..........code segment begins here cseg_calibs         segment 'code'
basic_dgroup        group   data,stack,const,heap,memory
                            ;defining link to BASIC
porta               equ     0700H   ;port definitions for
                                    ;8255 port expander
portb               equ     0708H   ;these addresses are
                                    ;decoded on the homemade
portc               equ     0710H   ;board
control             equ     0718H   ;control word in the
                                    ;8255
timer0              equ     0720H   ;8253 timer0 register
timer1              equ     0721H   ;8253 timer1 register
timer2              equ     0722H   ;8253 timer2 register
con8253             equ     0723H   ;8253 control register ;-----------------------------------------------;
; timebase interrupt handler (not accessible to ;
; BASIC)                                        ;
;-----------------------------------------------;
            ;this routine reads the A/D every timer0
            ;tick
            ;with the next point in the analog
            ;buffer
```

```
tbase_int   proc    far         ;this procedure is not
                                ;made public
            assume  cs:cseg_sync,ds:dseg_
                base,es:nothing,ss:nothing
            push    ax          ;save registers used
                                ;during interrupt
            push    bx          ;
            push    dx          ;
            push    ds          ;

mov     ax,dseg_base ;set up segment
                                ;register for data area
            mov     ds,ax       ;

;..........increment counter used for
                    ;low frequency generation
            dec     tbase_ctr   ;decrement
                                ;interrupt counter
            jnz     ctr_ok      ;if not zero then
                                ;continue
            mov     ax,tbase_rst ;else reload reset
                                ;value
            mov     tbase_ctr,ax ;
ctr_ok:
                    ;..........get analog value from
                    ;buffer and send to DAC mov     bx,tbase_ptr ;get pointer to
                                ;analog data
            dec     bx          ;
            mov     al,tbase_buffer[bx]  ;get analog
                                ;value mov     dx,porta    ;send analog value
                                ;to DAC
```

```
                out     dx,al               ;

mov     dx,control          ;toggle the write
                                            ;latch for the DAC
                mov     al,6                ;by using direct
                                            ;bit reset
                out     dx,al               ;and
                inc     al                  ;reset commands
                out     dx,al               ;

dec     tbase_ptr           ;point to next
                                            ;value
                jnz     tbase_eoi           ;if zero, reset
                                            ;pointer
                mov     ax,tbase_len        ;reset with buffer
                                            ;length
                mov     tbase_ptr,ax        ;

;..........acknowledge interrupt to
                ;          8259A
tbase_eoi:      mov     al,20H              ;send EOI to 8259A
                out     20H,al              ;

pop     ds                  ;restore registers which
                                            ;were used
                pop     dx                  ;
                pop     bx                  ;
                pop     ax                  ;
                iret                        ;return to place where
                                            ;interrupt occurred debugmsg1       db      'this is the end of the time
                        base interrupt' tbase_int       endp
```

```
;----------------------------------------;
; heart beat interrupt handler (not accessible ;
; to BASIC)                               ;
;----------------------------------------;

;this routine updates the timer1 rate generator
;every heart beat with the divider necessary to
;generate the next heart beat
;
;the respiratory modulation is given by a scaler
;     (0-255)
;times the present value of the respiratory
;     signal.
;the low frequency modulation is given by scaler
;     (0-255)
;times a value selected from the respiratory
;     buffer.
;the value selected is the
;     (tbase_ctr/tbase_rst)*buffer_length
;element hbeat_int       proc    far     ;this procedure is not
                                ;made public
                assume  cs:cseg_calibs,ds:dseg_tbase
                assume  es:nothing,ss:nothing
                push    ax      ;save registers during
                                ;interrupt
                push    bx      ;
                push    cx      ;
                push    dx      ;
                push    ds      ;

mov     ax,dseg_tbase   ;set up segment
                                        ;register for data area
                mov     ds,ax           ;

inc     heartbeats      ;increment heart
                                        ; beat counter
```

```
;........calculate low frequency modulation
;       (the tbase buffer is used as a trig
;           table here)
mov     ax,tbase_ctr    ;get number of 1280Hz
                        ;pulses
dec     ax              ;
mul     tbase_len       ;scale by length of
                        ; respiratory
                        ; buffer
div     tbase_rst       ;divided by reset
                        ;value to get
                        ; pointer
mov     bx,ax           ;to low frequency
                        ; modulation
mov     al,tbase_buffer[bx]  ;get sinusoidal
                        ;       modulation
mul     lfa_scal        ;and scale
                        ;   appropriately
mov     cx,ax           ;cx accumulate
                        ;divider for 1280Hz
                        ; clock
;........calculate respiratory modulation
mov     bx,tbase_ptr    ;get present
                        ;respiration signal
mov     al,tbase_buffer[bx]  ;from buffer
mul     rfa_scal        ;scale with rfa scaler
add     cx,ax           ;and add to cx add     cx,base_rate    ;finally add base rate
                        ;to get
                        ; value for
                        ;timer1 (heart rate
                        ;generator on
                        ;  8253)

;........send new divider to 8253 timer
mov     al,76H          ;set timer 1 to square
                        ; wave
```

```
                                      ; generator
        mov     dx,con8253      ;
        out     dx,al           ;

mov     dx,timer1       ;send divider to
                                ;time1
        mov     al,cl           ;low byte first
        out     dx,al           ;
        mov.    al,ch           ;high byte next
        out     dx,al           ;

;..........acknowledge interrupt to
        ;            8259A
        mov     al,20H          ;send EOI to 8259A
        out     20H,al          ;

pop     ds              ;restore registers and
        pop     dx              ;
        pop     cx              ;
        pop     bx              ;
        pop     ax              ;
        iret                    ;return to place where
                                ;interrupt occurred debugmsg2       db      'this is the end of the heart
                        beat interrupt' hbeat_int       endp

;------------------------------------------------;
; subroutine instint (install_interrupts)        ;
;------------------------------------------------;

instint         proc    far
                public  instint
```

```
;public symbol allows external references
;es,ds used to access interrupt and must
;  be restored movsw
;uses (ds:si)(es:di) addr
 assume  cs:cseg_calibs,ss:basic_
     dgroup,ds:basic_dgroup
 assume  es:int_buffer ;..........save registers
 push    ds          ;save ds register on the
                     ;   stack
 push    es          ;save es register on the
                     ;   stack push    bp          ;save BASIC base pointer
                     ;    for return to BASIC
 mov     bp,sp       ;point stack pointer at
                     ;frame reference to
                     ;address of BASIC analog
                     ;data buffer push    ax          ;save additional
                     ;registers
 push    si          ;
 push    di          ;

;set up the segment registers as assumed mov     ax,int_buffer  ;
;es points to buffer area to save
;DOS dummy interrupt vector
 mov     es,ax          ;
 mov     ax,0           ;ds points to
                        ;abs0 (interrupt table)
 mov     ds,ax          ;
 assume  ds:abs0        ;

;setup access to interrupt vectors
```

```
        lea     di,save_int     ;load offset of
                                ;save_int in es,di
        lea     si,IRQ3_int     ;load offset of
                                ;IRQ3_int in ds,si
        movsw                   ;save DOS dummy
                                ;interrupt vectors to be
        movsw                   ;restored later
        movsw                   ;now saving IRQ4
        movsw                   ;

;install the DAC timebase (IRQ3)
        mov     IRQ3_int+2,cseg_calibs
        mov     IRQ3_int,offset tbase_int;
                                ;interrupt handler now
;install the heart beat (IRQ4) interrupt handler now
        mov     IRQ4_int+2,cseg_calibs;
        mov     IRQ4_int,offset hbeat_int;

;..........return to BASIC pop     di      ;restore additional
                        ;  registers
        pop     si      ;
        pop     ax      ;

pop     bp      ;restore BASIC's base
                        ;pointer and
        pop     es      ;segment registers
                        ;  before returning
        pop     ds      ;
        ret     0       ;delete 0 parameters (0
                        ;bytes) from the stack
                        ;and return to the
                        ;calling routine debugmsg3       db      'this is the end of the
``` interrupt installation'

```
instint        endp

;---------------------------------;
               ; subroutine exstint (exstall_    ;
               ; interrupts)                     ;
               ;---------------------------------;
exstint        proc    far
               public  exstint    ;public symbol allows
                                  ;external references
               assume  cs:cseg_calibs,ss:basic_dgroup
               assume  ds:int_buffer,es:abs0
               ;es,ds used to access interrupt
               ;vectors and must be restored
               ;movsw uses (ds:si)(es:di) addr ;..........save registers push    ds         ;save ds register on the
                                  ;  stack
               push    es         ;save es register on the
                                  ;  stack
               push    bp         ;save BASIC base pointer
                                  ;    for return to BASIC
               mov     bp,sp      ;point stack pointer at
                                  ;    frame reference to
                                  ;access arguments passed
                                  ;   by BASIC (none here)

push    ax         ;save additional
                                  ;registers
               push    si         ;
               push    di         ;
                                  ;set up the segment
```

```
                                    ;   registers as assumed
                mov     ax,0         ;es points to
                                    ;abs0 (interrupt table)
                mov     es,ax        ;
                mov     ax,int_buffer ;ds points to
                                    ;buffer area to save
                mov     ds,ax        ;DOS dummy
                                    ;interrupt vector
            ;setup access to interrupt vectors
                lea     di,IRQ3_int  ;load offset of
                                    ;IRQ3_int in es,di
                lea     si,save_int  ;load offset of
                                    ;save_int in ds,si
                movsw                ;restore DOS
                                    ;dummy interrupt vectors
                movsw                ;for IRQ3
                movsw                ;and IRQ4
                movsw                ;
            ;..........return to BASIC pop     di           ;restore additional
                                    ;   registers
                pop     si           ;
                pop     ax           ;

pop     bp           ;restore BASIC's base
                pop     es           ;pointer and segment
                pop     ds           ;registers before
                                    ;returning
                ret     0            ;delete 0 parameters (0
                                    ;bytes) from the stack
                                    ;and return to the
                                    ;calling routine debugmsg4       db      'this is the end of the
                        interrupt exstallation' exstint         endp
```

```
;----------------------------------------;
; subroutine rdbeat (read_heart_beats    ;
;----------------------------------------;

rdbeat      proc    far
            public  rdbeat      ;public symbol allows
                                ;external references
            assume  cs:cseg_calibs,es:dseg_tbase
            assume  ds:basic_dgroup,ss:basic_dgroup ;..........save registers push    bp          ;save BASIC base pointer
                                ;for return to BASIC
            mov     bp,sp       ;point stack pointer at
                                ;frame reference to
                                ;access arguments passed
                                ;by BASIC (one here)

push    ax          ;save additional
                                ;registers
            push    es          ;
            push    di          ;

mov     ax,dseg_tbase   ;set up segment
                                    ;register for data area
            mov     es,ax           ;

mov     ax,heartbeats           ;get
                                            ;beats from local memory
            mov     di,[bp].BASIC_beats     ;
            mov     [di],ax                 ;send
                                            ;beats to BASIC
```

;..........return to BASIC

```
        pop     di          ;restore additional
                            ; registers
        pop     es          ;
        pop     ax          ;

pop     bp          ;restore BASIC's base
                            ;pointer,
        ret     2           ;delete 2 parameters (4
                            ;bytes) from the stack
                            ;and return to the
                            ;calling routine debugmsg5   db  'this is the end of the heart
                 beat read routine' rdbeat  endp

;----------------------------------------;
; subroutine wrbuffer(analog)            ;
;----------------------------------------;

wrbuffer    proc    far
            public wrbuffer     ;public symbol allows
                                ;external references
            assume cs:cseg_calibs,es:dseg_tbase
            assume ds:basic_dgroup,ss:basic_dgroup ;..........save registers
        push    bp          ;save BASIC base pointer
                            ;for return to BASIC
        mov     bp,sp       ;point stack pointer at
                            ;frame reference to
                            ;access arguments passed
                            ;by BASIC (one here)
```

```
        push    ax              ;save additional
                                ;registers
        push    bx              ;
        push    es              ;
        push    si              ;
        mov     ax,dseg_tbase   ;set up segment
                                ;register for data area
        mov     es,ax mov     si,[bp].analog  ;get analog value
                                ;from BASIC
        mov     ax,[si]         ;
        test    ah,0FFH         ;if upper byte is
                                ;zero
        jz      new_buff        ;then install a
                                ; new point in
                                ;  the buffer
        mov     tbase_len,0     ;otherwise reset
                                ;the buffer
        mov     tbase_ptr,1     ;
        jmp     wr_ret          ;

mov     bx,tbase_len    ;get present
                                ;pointer and
                                ;use it
        mov     tbase_buffer[bx],al    ;to store
                                ;   buffer value
        inc     tbase_len       ;point to next
                                ;buffer value
;..........return to BASIC pop     si              ;restore additional
                                ;registers
wr_ret: pop     es              ;wr_ret:
        pop     bx              ;
        pop     ax              ;

pop     bp              ;restore BASIC's base
```

```
                            ret     2           ;pointer,
                                                ;delete 1 parameters (2
                                                ;bytes) from the stack
                                                ;and return to the
                                                ;calling routine debugmsg6       db      'this is the end of the buffer
                        write routine' wrbuffer        endp

;----------------------------------------------------------------;
; subroutine hrsetup(B_lreset,Brfa_scal,Blfa_scal,               ;
; Bbase_rate)                                                    ;
;----------------------------------------------------------------;

proc    far
                public  hrsetup     ;public symbol allows
                                        external references
                assume cs:cseg_calibs,es:dseg_tbase
                assume ds:basic_dgroup,ss:basic_dgroup ;...........save registers
                push    bp          ;save BASIC base
                                    ;pointer for return
                                    ;to BASIC
                mov     bp,sp       ;point stack pointer
                                    ;at frame
                                    ;reference to
                                    ;access arguments
                                    ;passed by BASIC
                                    ;(one here)

push    ax          ;save additional
                                    ;registers
                push    es          ;
```

```
        push    si              ;

mov     ax,dseg_tbase   ;set up segment
                                ;register for
                                ;data area
        mov     es,ax           ;

mov     si,[bp].Bbase_rate ;get lowest
                                ;divisor for heart
        mov     ax,[si]         ;rate from BASIC
        mov     base_rate,ax    ;and save in local
                                ;    data
                                ;    segment mov     si,[bp],Blfa_sacl  ;get low freq
                                ;        modulation
                                ;        scale
        mov     ax,[si]         ;        from BASIC
        mov     lfa_scal,al ;and save LSbyte in
                                ;local data
                                ;  segment mov     si,[bp].Brfa_scal  ;get high freq
                                ;    modulation scale
        mov     ax,[si]         ;from BASIC
        mov     rfa_scal,al     ;and save
                                ;LSbyte in local data
                                ;segment
        mov     si,[bp].B_lreset   ;get low freq
                                ;   timer reset value
        mov     ax,[si]         ;from BASIC
        mov     tbase_rst,ax    ;and save in
                                ; local data segment ;......  ..return to BASIC pop                     ;restore additional
                                ;registers
        pop     es              ;
```

```
            pop     ax      ;

pop     bp      ;restore BASIC's base
                            ;pointer,
            ret     8       ;delete 4 parameters (8
                            ; bytes) from the stack
                            ;and return to the
                            ; calling routine debugmsg 7      db      'this is the end of the heart rate
                        setup routine' hrsetup         endp cseg_calibs     ends end
```

APPENDIX B

1985 - Makoto R. Arai
Laura E. McAlpine, and
Daivd Gordon

```
' SYNCTS19 - program to test synchrounous data
'                   acquisition and also
'                   test asynchronous processing using
'                   board#2
'                   addition: asynchronous data
'                   archiving (poll driven)
'                   reviewing old data
' last revision:  15 May 1985
'
' REQUIRED SUBROUTINES: <MODULE>
'
'       instint(fdbuf1ptr,fdbuf2ptr,fdbuf3ptr)
'         <SYNC7S>
'       exstint                              <SYNC7S>
'       rdbeat(heart,sync)                   <SYNC7S>
```

```
'       rdbuf(dataptr,bufferno)          <SYNC7S>
'       rdptrs(adrd,hbrd,adflag,hbflag) <SYNC7S>
'
'       swindow(xmins,xmaxs,ymins,ymaxs)
'         <GWINDOW3>
'       dwindow(xmind,xmaxd,ymind,ymaxd)
'         <GWINDOW3>
'       clrwindw                         <GWINDOW3>
'       axes                             <GWINDOW3>
'       scaler(dataptr,gdataptr,numval)
'         <GWINDOW3>
'
'       fgraph(dataptr,numval,xnow,linemask)
'         <FGRAPH8>
'              [for scaled graphs, use
'              xnow=xmins,
'              numval=numvalg=xmaxs-xmins+1,
'              and gdataptr]
'       dumpgr   [to dump graphics]      <DUMPGR>
' defint a-y       ' only z denotes a real number
defdbl z
dim zreal(514),zrimag(514),zdata(1025)
dim ydata(1025),ydatag(1025)
dim hb1(1025),hb2(1025),zhr(1025)
dim zspec.hb.real(512),zspec.hb.imag(512)
dim sresetval(5),resprstval(5)
dim linetype(3),histogram(100)
def fnzmag(z1,z2)=z1*z1+z2*z2
def fnzcoher(zr1,zi1,zr2,zi2)=fnzmag
  (zr1*zr2+zi1*zi2,zi1*zr2-zr1*zi2)

' initialize timer reset values
1    sval=27 : for i=1 to 5 : sresetval(i)=sval :
     sval=sval+sval : next i
```

2  sval=1381 : for i=0 to 3 : resprstval(i)=sval :
      sval=sval+sval : next i
3  resprstval(4)=sval ' define fft parameters
4  fftsize=1024 : npair=fftsize/2 :
      znpair=cdbl(npair) : lpower=9

5  for i=0 to 514 : zreal(i)=0# : zrimag(i)=0# :
      next i datacycle=0
            ' flag for automatic fft: when non-zero,
            '   marks stage of data
            '   processing.(semi asynchronous)
cyclewait=0
        ' define linetype for plots
        linetype(0)=&HFFFF
        linetype(1)=&HAAAA
        linetype(2)=&HCCCC
        linetype(3)=&HFAFA
        req.cls=0
        sounder=1

'define ports on 8253
        timer0=&h704
        timer1=&h705
        timer2=&h706
        con8253=&h707

'define ports on 8255
        porta=&H71C
        portb=&H71D
        portc=&H71E
        con8255=&H71F

```
' set up sampling rate for heart rate timer and
'   respirations
gosub 100

' first set 8255 ports A,C to output, port B to
'   input
' turn the gates on using the 8255 at bits 0,1,2
'   on portc
' by setting portc to 1FH
' this also selects channel 0 for the A/D
out con8255,130
out portc,&H1F ' now go through required startup subroutines to
'   set up data archives
    open "R",1,"resp.dat",2048
    open "R",2,"hb1.dat",2048
    open "R",3,"hb2.dat",2048
    open "R",10,"trends.dat",128
```

31      `field #1,2048 as analog$`
        `field #2,2048 as fdhb1$`
        `field #3,2048 as fdhb2$`
        `field #10,128 as trends$`

```
fdflag=0
fdrecord=1
record1no=0 : record2no=0 : record3no=0 :
   record10no=0
adflag1st=0 : hbflag1st=0
fdbuf1ptr=varptr(#1)+188        ' set up
    'pointers to disk buffers
fdbuf2ptr=varptr(#2)+188
fdbuf3ptr=varptr(#3)+188
```

```
'..........field definitions for
'            trend data file
field #10,8 as hr$,8 as rr$,8 as rcf$,8
   as lfa$,8 as rfa$,8 as coher$
field #10,48 as dummy1$,8 as ratio$,8
   as cratio$,8 as hrintegral$
field #10,72 as dummy2$,8 as respintegral$,8
   as timestamp$
field #10,120 as dummy3$,2 as hbrecord$,2
   as adrecord$
field #10,124 as dummy4$,2 as hbeat$,2
   as samplrate$ ' first print out the present value of the
'    interrupt vectors
locate 23,1 : gosub 20000
gosub 19000

' make sure interrupts are off before installing
'    handlers
mask=inp(&h21) : mask=mask or 24 : out &h21,mask ' install the interrupts
call instint(fdbuf1ptr,fdbuf2ptr,fdbuf3ptr)
locate 24,1 : gosub 20000
gosub 19000

' turn interrupts back on
mask=inp(&h21) : mask=mask and &h0e7 : out
   &h21,mask 40      locate 1,1 : gosub 20000
        print "commands: c(ounts), f(ft), g(raph),
           i(in on), q(uit), r(beats)";
```

```
              print "s(tore), x(cls), #(samples);

' wait until user hits a key
41            savekey$=""
              while len(savekey$)=0 and datacycle<=0
                 savekey$=savekey$+inkey$:gosub 30000:locate
                    24,70:print time$;:wend while datacycle=1
                 fdrecord=record1no : fdflag=1
                                  'set up future A/D analysis
                 analrec.ad=record1no : analrec.hr=record2no+1
                 if req.cls=1 then cls : req.cls=0
                    'clear screen if needed gosub 950   '......analyze heart rate
42              hrspecsum#=zspectsum*2# gosub 900   '..........analyze A/D data (from floppy
43              respspecsum#=zspectsum*2# gosub 15000
                 '                calculate spectral amplitudes
                 gosub 16000
                                              save trend data datacycle=cyclewait : wend
              'end auto data analysis cycle 49
              if savekey$="c" then gosub 60
              ' print timer counts
              if savekey$="f" then gosub 900
              ' fft A/D buffer contents
              if savekey$="F" then gosub 950
```

```
' fft heart rate buffer contents
if savekey$="g" then gosub 12700
' graph current A/D buffer
if savekey$="G" then gosub 12710
' graph current heart rate buffer
if savekey$="h" then gosub 90
' (no) plot histogram
if savekey$="p" then gosub 91
' (no) print trends
if savekey$="i" then gosub 80
' unmask interrupt 3
if savekey$="I" then gosub 81
'unmask interrupt 4
if savekey$="q" then goto 9996
' quit
if savekey$="r" then gosub 50
' print heart beats
if savekey$="S" then gosub 800
' analyze data in disk file (set fdflag)
if savekey$="t" then gosub 16500
' print out the trends
if savekey$="x" then cls        'clear screen
if savekey$="#" then gosub 100
' reset sampling rate
if savekey$="?" then gosub 700   'help
savekey$=""

goto 41

'print present value of heartbeats 50      locate 24,1 : gosub 20000
        call rdbeat(heart,sync)
        print "heart beats: ";heart,"sync pulses:
            ";sync;time$;
        return
```

```
                  ' print present value of counters
60         out con8253,0            'latch timer0
           tlow0=inp(timer0)
           thigh0=inp(timer0)
           out con8253,&h40         'latch timer1
           tlow1=inp(timer1)
           thigh1=inp(timer1)
           out con8253,&h80         'latch timer2
           tlow2=inp(timer2)
           thigh2=inp(timer2)
           locate 24,1 : gosub 20000
           print "timer0: ";tlow0+thigh0*256;tab(20);"
              timer1: ";tlow1+thigh1*256;
61         print tab(40);"timer2: ";tlow2+thigh2*256#;
           return ' print out interrupt controller parameters:
           ' entry point for IRQ3
80         mask=inp(&h21) : mask=mask xor 8 : out &h21,mask
           goto 82
           ' entry point for IRQ4
81         mask=inp(&h21) : mask=mask xor 16 : out
              &h21,mask
82         mask=inp(&h21)
           locate 24,1 : gosub 20000
           print "8259 IMR(interrupt mask regsiter)=
              ";mask;" =";hex$(mask);
           return ' (re)set sampling rates
           ' set timer0 to 16 bit square wave rate
           ' generator mode
           ' set timers 1,2 to 16 bit rate generator mode
100        out con8253,&h36
```

```
            out con8253,&h74
            out con8253,&hB4

'..........set real time multiplier
105         locate 23,1 : gosub 20000
            input "real time multiplier: ",rt.mult
            rt.multqual=0
            if rt.mult=1 then rt.multqual=1
            if rt.mult=2 then rt.multqual=2
            if rt.mult=4 then rt.multqual=3
            if rt.mult=8 then rt.multqual=4
            if rt.multqual<>0 then goto 110
            beep : goto 105

' get heart rate resolution desired to reset
            ' timer0 reset value
110         locate 1,1 : gosub 20000
            input "heart rate resolution: (11,23,45,91,181
               usec) ",hrresol ' check heart rate resolution validity
            hrqual=0
            if hrresol=11 then hrqual=1
            if hrresol=23 then hrqual=2
            if hrresol=45 then hrqual=3
            if hrresol=91 then hrqual=4
            if hrresol=181 then hrqual=5
            if hrqual<>0 then sreset=sresetval(hrqual) :
               goto 120
            beep : goto 110
            ' invalid heart rate resolution
                                        'set timer 0 to 88384Hz
                                        'timebase (11.3 usec res
'           sreset=27                   '(2.38MHz/27)(max resp
                                        'samples then 64Hz)

'set timer 0 to 44192Hz
```

```
'                              'timebase (22.6 usec res
     sreset=54                 '(2.38MHz/54)(max resp
                               'samples then 32Hz)

'set timer 0 to 22096Hz
                               'timebase (45.3 usec res
     sreset=108                '(2.38MHz/108)(max resp
                               'samples then 16Hz)

'set timer 0 to 11048Hz
                               'timebase (90.5 usec res
     sreset=216                '(2.38MHz/216)(max resp
                               'samples then 8Hz)

'set timer 0 to 5524Hz
                                timebase (181 usec res
     sreset=432              ' (2.38MHz/432)(max resp
                                samples then 4Hz)

'..........set respiratory sampling rate
120  locate 2,1 : gosub 20000
     print "respiratory sampling rate: ( 4";
     twopwr=4 : for i=hrqual+rt.multqual to 5 :
     twopwr=twopwr+twopwr
         print using ",##";twopwr; : next i : print "
           Hz) ";
     input respsampl ' check respiratory sampling rate validity
     respqual=0 : respsampl.eff=respsampl*rt.mult
     if respsampl=4 then respqual=1
     if respsampl=8 then respqual=2
     if respsampl=16 then respqual=3
     if respsampl=32 then respqual=4
     if respsampl=64 then respqual=5
     if respqual=0 or respqual+hrqual+rt.multqual>7
         then beep : goto 120
``` resprst=resprstval(7-hrqual-respqual-
   rt.multqual)

```
                '..........set cycle delay time between
                '              analyses
130    locate 3,1 : gosub 20000
       input "waiting time between cycles: ",dropcycle
       if dropcycle<0 or dropcycle>5 then beep : goto
          130
       cyclewait=0-dropcycle out timer0,(sreset mod 256)
       ' system timebase generated here out
       '    timer0,(sreset\256)

out timer1,(resprst mod 256)
       ' timer 1 counts timebase and outputs out
       '    timer1,(resprst\256)
       ' the respiratory sampling rate out timer2,0
       ' set timer 2 as an overflow counter for the
       '    out timer2,0
       ' number of overflows (65536 counts)
200    timer2over#=65536#
       ' overflow value for timer2
201    zlover=resprst              ' reset count for timer1
202    zlfreq=14318180#/6#/sreset
       ' timer1 input clock frequency
203    zhrsampler=zlover/zlfreq
       ' timer1 output=sampling interval
204    segment.time=fftsize*zhrsampler
205    zlfreq.real=zlfreq/rt.mult
       ' real time used to calculate HR
206    zhrsampler.real=zlover/zlfreq.real '..........respiratory peak search
                '              parameters
```

```
210     minrespfrq#=.2#
        ' start at frequency (in pixels)
211     minresp=minrespfrq#/respsampl*1024
212     combwidth#=.032#
        use comb tooth width (in pixels)
213     combpix=combwidth#/respsampl*1024
214     if combpix<=0 then combp' .-0

'..........low frequency
                        peak/integration parameters
220     pixel.04=cint(40.96#/fftsampl)+1
        ' pixel for .04Hz
221     pixel.10=cint(102.4#/fftsampl)+1
        ' pixel for .10Hz
222     fft.expansion=respsampl/fftsampl if datacycle=0 then datacycle=-1
        if recordlno=0 then return
        ' on startup don't delay
        ' exclude the current data segment
        ' from analysis since changes in
        ' sampling rate will introduce glitches
        return ' set floppy disk flag (fdflag) to analyze data
        ' stored on floppy (resp)
800     fdflag=1
        locate 23,1 : gosub 20000 : input "record
            number: ",fdrecord
        if fdrecord>=1 and fdrecord<=recordlno then
            gosub 12700 : return
        locate 24,1 : gosub 20000 : beep : print
            "invalid record number";
        return
```

```
                ' set up data for fft here
                ' get analog data from the A/D
900             gosub 12700       ' get analog data and plot
901             for i=1 to fftsize : zdata(i)=ydata(i) : next i
902             locate 23,1 : gosub 20000 : print "A/D buffer is
                   transformed";

xmins=330 : xmaxs=630 : ymins=102 : ymaxs=167
                call swindow(xmins,xmaxs,ymins,ymaxs)

glabel=3          ' plot label is "resp spect"
                gosub 10000       ' fft
                return ' get heart rate data for fft
950             locate 23,1 : gosub 20000 : print "heart rate is
                   transformed";
951             gosub 12710       ' get hr function and plot it
952             for i=1 to fftsize : zdata(i)=zhr(i) : next i 953             xmins=330 : xmaxs=630 : ymins=28 : ymaxs=93
954             call swindow(xmins,xmaxs,ymins,ymaxs)

955             glabel=4          ' plot label is "hr spect"
956             gosub 10000       ' fft ' save spectrum in spec.hr buffers
960             for i=0 to 512
961                zspec.hb.real(i)= zreal(i) :
                      zspec.hb.imag(i)=zrimag(i)
962             next i return
                ' exstall the interrupt and print vecto
9996            cls
                      ' make sure interrupts are off before
                         removing handlers
                mask=inp(&h21) : mask=mask or 24 : out &h21,mask
```

```
                ' remove interrupt handlers
        screen 0 locate 4,1
        gosub 19000
        call exstint
        locate 5,1
        gosub 19000
        locate 21,1
        ' close files after storing last bit of data
        bufferno=0
        call rdbuf(fdbuf1ptr,bufferno)
        put #1,record1no+1
        bufferno=1
        call rdbuf(fdbuf2ptr,bufferno)
        put #2,record2no+1
        bufferno=2
        call rdbuf(fdbuf3ptr,bufferno)
        put #3,record3no+1 close #1,#2,#3,#10

' and quit
9999    stop

' FFT ROUTINE
        '
        ' set up the data
        '
10000   zreal(0)=0#
10001   zrimag(0)=0#
10002   zreal(npair+1)=0#
10003   zrimag(npair+1)=0#
```

```
                ' compute mean value of array
10004   zmean=0#
10005   for i=1 to fftsize : zmean=zmean+zdata(i)
            : next i
10006   zmean=zmean/1024#
10007   for k=1 to npair : j=k+k-1 : zreal(k)=zdata
            (j)-zmean
10008   zrimag(k)=zdata(j+1)-zmean : next k 10009   ' locate 24,1 : gosub 20000
10010   ' print "arrays initialized at
        ' ";time$;space$(20);

'
        ' fft routine <fftandift> begins here
        '
10011   ' locate 24,1 : print "entering fft routine at
        ' ";time$;space$(20);
10012   k=0
10013   for j=1 to npair-1 : i=2
10014     ndivi=npair/i
10015     if k<ndivi then 10017
10016        k=k-ndivi : i=i+i : goto 10014
10017     k=k+ndivi
10018     if k<=j then 10025
10019        za=zreal(j+1)
10020        zreal(j+1)=zreal(k+1)
10021        zreal(k+1)=za
10022        za=zrimag(j+1)
10023        zrimag(j+1)=zrimag(k+1)
10024        zrimag(k+1)=za
10025     next j
10026   ' locate 24,1:print "bit reversal completed at
        ' ";time$;space$(20);

10030   q=1 : zp=1#
10031   for i=1 to lpower : gosub 30000
        'check if disk requires service
```

```
10032   'locate 24,1:print "entering stage ";g;" at
         '   time ";time$;space$(20);
10033      if i=1 then zsign=-1# else zsign=1#
10034      zc=1# : ze=0#
10035      zq2=(1#-zp)/2# : if zq2<=0# then zq=0# : else
              zq=sqr(zq2)
10036      zp2=(1#+zp)/2# : if zp2<=0# then zp=0# : else
              zp=zsign*sqr(zp2)
10037      itwog=g+g 10040      for r=1 to g
10041         for j=r to npair step itwog
                 k=j+g : if k>npair then print "kjg
                    over>> ";k;j;g
10042            za=zc*zreal(k)+ze*zrimag(k)
10043            zb=ze*zreal(k)-zc*zrimag(k)
10044            zreal(k) =zreal(j) -za
10045            zrimag(k)=zrimag(j)+zb
10046            zreal(j) =zreal(j) +za
10047            zrimag(j)=zrimag(j)-zb
10048         next j
10049         za=ze*zp+zc*zq
10050         zc=zc*zp-ze*zq
10051         ze=za
10052      next r
10053      g=itwog
10054   next i
10055   'locate 24,1:print "entering final stage at
           ";time$;space$(20);
10056   gosub 30000
         ' check if disk requires service 10060   za=4#*atn(1#)/znpair
10061   zp=cos(za)
10062   zq=sin(za)
10063   za=zreal(1)
10064   zreal(1)=za+zrimag(1)
```

```
10065    zrimag(1)=za-zrimag(1)
10066    zreal(1)=zreal(1)/2#
10067    zrimag(1)=zrimag(1)/2#
10068    zc=1# : ze=0#

10070    j=2
10071    while j<npair/2
10072       za=ze*zp+zc*zq
10073       zc=zc*zp-ze*zq
10074       ze=za
10075       k=npair-j+2
10076       za=zreal(j)+zreal(k)
10077       zb=(zrimag(j)+zrimag(k))*zc-(zreal(j)-
                zreal(k))*ze
10078       zu=zrimag(j)-zrimag(k)
10079       zv=(zrimag(j)+zrimag(k))*ze+(zreal(j)-
                zreal(k))*zc
10080       zreal(j)=(za+zb)/2#
10081       zrimag(j)=(zu-zv)/2#
10082       zreal(k)=(za-zb)/2#
10083       zrimag(k)=(zu+zv)/2#
10084    j=j+1 : wend
10085    zrimag(npair/2+1)=-zrimag(npair/2+1)

10090    for j=2 to npair
10091       zreal(j)=zreal(j)/znpair/2#
10092       zrimag(j)=zrimag(j)/znpair/2#
10093    next j
10094    zreal(1)=zreal(1)/znpair
10095    zrimag(1)=zrimag(1)/znpair '
         ' fft routine now completed
         '
10100    locate 24,1:print "fft completed
             ";time$;space$(20);
         '...integrate spectrum
         '     sum up the spectrum noting that only the
```

```
                  '     first npair elements of
                  '     the fft are valid
                  '     (npair+1 to fftsize are complex conjugates
                  '     of 1 to npair and are
                  '        not calculated)
10101    zspectsum=0#
10102    zsummax=0#
10103    ipeak=-1
10104    for i=1 to npair
10105       zadd=fnzmag(zreal(i),zrimag(i))
10106       zspectsum=zspectsum+zadd
10107       if zadd<=zsummax then 10110
10108           zsummax=zadd
10109           ipeak=i
10110    next i '
         ' graphing routine for fft spectra
         '
10111    'locate 1,1 : gosub 20000
10113    'print "total spectral weight
         '     <variance>:";zspectsum*2#;
10114    'locate 2,1 : gosub 20000
10115    'print "peak weight : ";zsummax;" peak
         '     frequency= ";
10116    'print (ipeak-1#)/fftsize*respsampl;

10117    gosub 12730
         ' fgraph of spectrum
10118    return
         '_____'
         ' UTILITIY ROUTINES HERE          '
         '_____'

' graphing routine: gets data from A/D buffer
         '  and displays graph
12700    glabel=1
```

```
      numpts=fftsize
      indata=0
' local flag
'    indicating data is read while indata=0 and
'    fdflag=0
      dataptr=varptr(ydata(1))
      bufferno=0              'read A/D buffer
      call rdbuf(dataptr,bufferno)
      indata=1
      wend while indata=0 and fdflag=
   gosub 30000
' check file buffer to see if service is
'   required
   get #1,fdrecord
   for i=1 to 1024 :
   ydata(i)=cvi(mid$(analog$,i+i-1,2)) : next i
   indata=1
   wend xmins=10 : xmaxs=310 : ymins=102 : ymaxs=167
call swindow(xmins,xmaxs,ymins,ymaxs)

xmind=0 : xmaxd=300 : ymind=0 : ymaxd=255
call dwindow(xmind,xmaxd,ymind,ymaxd)
' max A/D value is 255
call clrwindw
call axes
goto 12770

' entry point for plot of heart rate function
12710  screen 2           ' get heart rate function
12711  glabel=2
12712  numpts=fftsize
12713  gosub 13000
```

```
12714    ibeg=adrd+2
12715    for i=1 to fftsize : if ibeg=i then
            ibeg=ibeg+fftsize
12716       ydata(i)=cint(zhr(ibeg-i)) : next i xmins=10 : xmaxs=310 : ymins=28 : ymaxs=93
         call swindow(xmins,xmaxs,ymins,ymaxs)

xmind=0 : xmaxd=300 : ymind=0 : ymaxd=250
         call dwindow(xmind,xmaxd,ymind,ymaxd)
         ' max hr is 250 bpm goto 12770

' entry point for plotting spectra (screen
         '    windows already setup)
12730    zgain=250#/zsummax
12731    for i=1 to npair
12732       ydata(i)=cint(zgain*fnzmag
            (zreal(i),zrimag(i))) +1
12733    next i
12734    numpts=npair ' max spectral element (scaled to 250)
         xmind=0 : xmaxd=300 : ymind=0 : ymaxd=255
         call dwindow(xmind,xmaxd,ymind,ymaxd)

12770    call clrwindw
         call axes 12780    dataptr=varptr(ydata(1))
         gdataptr=varptr(ydatag(1))
         call scaler(dataptr,gdataptr,numpts)
         'correctly selects screen width ' entry point for plot of ydatag(i)
12790    x=xmins
```

```
           numvalg=xmaxs-xmins+1
           linemask=&hffff
           gdataptr=varptr(ydatag(1))
           call fgraph(gdataptr,numvalg,x,linemask)

' graph labels printed here
           on glabel goto 12800,12810,12820,12830
           return   'invalid label ' respirations in time domain
12800      if fdflag=1 then locate 14,30 : print
               "rec#";fdrecord : fdflag=0
           return ' heart rate in time domain
12810      locate 5,3
           print using "HR= ### bpm";cint(zavghr)
           return ' respiratory spectrum
12820      locate 14,63 :        print " Resp Spect ";
           locate 15,63 : print using " (0-
               ##Hz)";respsampl\2
           gosub 14000
           ' respiratory rate from spectrum by comb method
           locate 14,3
           ' print respiratory rate with time tracing
           print using "RR=### bpm
              (rcf=#.###)";cint(respfreq#*60),respcombfrac#
           return ' heart rate spectrum
12830      locate 4,63 :        print " HR Spect ";
           locate 5,63 : print using " (0-##Hz)";fftsampl\2
           return 'heart rate functions:
           '    read times from memory
```

```
                ' convert to heart rate function
                ' FFT resulting buffer
                ' display the spectral amplitudes 13000   call rdptrs(adrd,hbrd,adflag,hbflag)
13002   if record2no=0 then startup=1 else startup=0 '
            startup is special 13003   hbptr1=varptr(hb1(1))
13004   bufferno=1
            'read heart beat buffer 1 (least sig. cts
13005   call rdbuf(hbptr1,bufferno)
13006   locate 24,1 : gosub 20000
13007   print "hbrd= ";hbrd; : anal.beat=hbrd 13008   hbptr2=varptr(hb2(1))
13009   bufferno=2
            'read heart beat buffer 2 (most sig. cts
13010   call rdbuf(hbptr2,bufferno)
13011   for i=0 to 100 : histogram(i)=0 : next i
            'initialize histogram for deglitching (.4-40Hz)
13012   histomax#=zlfreq.real*2.5#
13013   histoscal#=zlfreq.real/40#

' compute time differences for entire hb array
        ' and save in zdata
        ' from the top down
        ' zdata will contain the latest hr intervals,
        ' with the latest in
        ' (hbrd) and older intervals for decreasing
        ' array index
        ' since the timers are decrementing,
        ' lstbeat<thisbeat
        ' (lstbeat is later, therefore smaller)
        ' this relation fails whenever there is a carry
        ' over (timer overflow)
        ' note: timer1 overflows exactly fftsize times
        ' during one data segment
```

```
13020   lstbeat#=hbl(hbrd) : lstover#=hb2(hbrd)
13022   hbnow=hbrd-1
13023   if hbnow<=0 then hbnow=fftsize
13024   if startup=1 and hbnow=fftsize then return ' no
            data yet 13025   numint=1
                ' valid intervals only (1 less than
                ' buffer size
13026   while numint<fftsize
13027       thisbeat#=hbl(hbnow)
                ' check for overflow of overflow counter
13028       thisover#=hb2(hbnow)
13029       if hb2(hbnow)<cint(lstover#) then
                lstover#=lstover#-timer2over#
13030       hbnow=hbnow-1
13031       if hbnow=0 then hbnow=fftsize
13032       if hbnow=fftsize and startup=1 then goto
                13048
13033       zdatnow=thisbeat#-lstbeat#+overdif#*zlover
13034       if zdatnow>=0 then goto 13047 '?error 13040       if zdatnow>histomax# then goto 13044
13041       index=cint(zdatnow/histoscal#)
13042       histogram(index=histogram(index)+1
13043       goto 13045
            'keep histogram of intervals (.2-20Hz:
            '   give 10% resolution @2Hz) extended
            '       data lapses
13044           histogram(100)=histogram(100)+1
                ' extended data lapses 13045       zdata(numint)=zdatnow : numint=numint+1
13046       lstbeat#=thisbeat# : lstover#=thisover#
13047       wend
13048   numint=numint-1

'..........find the interval
```

```
                                    corresponding to mean heart rate
                              '     1) find largest peak in
                              '        .5-4Hz (2 pixels wide)
                              '     2) calculate corrected
                              '        mean interval
                              '     3) calculate corrected
                              '        interval variance
                              '     4) set slewing
                                       parameters for HR
                                       generation 13050   lstint=histogram(4) : hpeak=0 : hpeak.ht=0
13051   for i=3 to 40 : thisint=histogram(i)
13052       if (thisint+lstint)>hpeak.ht then
                hpeak.ht=thisint+lstint : hpeak=i
13053       lstint=thisint : next i
13054   approx.avg#=(hpeak-0.5#)*histoscal#

13060   zhistsum=0# : zhistsum2=0#
13061   for i=1 to numint :
            index=cint(zdata(i)/approx.avg#)
13062       if index<=0 then index=1
13063       zhistsum=zhistsum+zdata(i)/index : next i
13064   avgint#=zhistsum/numint 13070   for i=1 to numint : index=cint(zdata(i)/avgint#)
13071       if index<=0 then index=1
13072       zdif=zdata(i)/index-avgint# :
                zhistsum2=zhistsum2+zdif*zdif
13073       next i
13074   histvar#=zhistsum2/numint ' calculate deglitching parameters
13081   varslew#=31.4#*sqr(histvar#)/respsampl
        '5x max slew (1Hz rfa) slew = least .05Hz
        '   (3bpm)/beat infslew has infimum of slew
        '         maxima
13082   min.maxslew#=.05
```

```
13083    infslew#=1#/(1#/avgint#-
             min.maxslew#/zlfreq.real)-avgint#
13084    if maxslew#<infslew# then maxslew#=infslew#
13085    supslew#=avgint#/5#
         'never slew more than 20% HR
13086    if maxslew#>supslew# then maxslew#=supslew#
13087    locate 1,1 : gosub 20000 ': print "maxslew:
             ";maxslew#

' compute heart rate waveform next
13100    ztime=0#
         ' time for present heart rate signal
         ' pointer in zdata to present beat number
         ' of beats accepted
13101    intnow=1
13102    beatno=1 :
13103    while zdata(intnow)<=0
13104        intnow=intnow+1 : if intnow>numint then goto
                 13140 : wend
13105    zintlst=avgint# : zdropper=avgint# :
             zintnow=zdata(intnow)
13106    znext=zintnow/zlfreq.real
         ' time of previous heart beat deglitch first
         '   beat present heart rate keep statistics for
         '      deglitching sampling rate determined by
         '         timers
13107    avgnow#=avgint# : gosub 13500
13108    zhrnow=60#*zlfreq.real/zintnow
13109    zsum=zhrnow
13110    zsum2=zhrnow*zhrnow
13111    zincr=zhrsampler.real
13120    numsig=1
         ' point to heart rate function 13121    while numsig<=fftsize and ztime<=znext
13122        zhr(numsig)=zhrnow : numsig=numsig+1 :
                 ztime=ztime+zincr
13123        wend:zintlst=zintnow
```

```
13124   if numsig=fftsize+1 then goto 13142
13125       intnow=intnow+1 : if intnow>numint then goto
                13140
13126       zintnow=zdata(intnow) : if zintnow<=0 then
                goto 13125
13127       znext=znext+zintnow/zlfreq.real : gosub
                13500        ' deglitcher
13128       zhrnow=60#*zlfreq.real/zintnow
13129       zsum=zsum+zhrnow : zsum2=zsum2+zhrnow*zhrnow
                : beatno=beatno+1
13130       goto 13121

13140   zavghr=zsum/beatno
        ' averaged over number of beats
13141   while numsig<=fftsize : zhr(numsig)=zavghr :
            numsig=numsig+1 : wend
13142   zavghr=zsum/beatno 13400   locate 24,13 : print "  avg hr(bpm): ";zavghr;

' zhr now has heart rate function
13401   print " ...heart rate function computed";

return

' deglitching of three types employed here:
        '       correction of premature triggers (not
        '       yet)
        '       correction of dropped beats (not yet)
        '       slew rate limiting of final output '_
        '       crude bandlimiter)
13500   if abs(zintnow-zintlst)<maxslew# then return
        'check for dropped beats
13501   numdrop=cint(zintnow/avgnow#) : if numdrop<=0
            then goto 13510
13502   if abs(zintlst-zintnow/numdrop)>maxslew# then
            1350#
```

```
13503   zintnow=zintnow/numdrop : sound 1200,sounder :
            return                          'dropped beat
13504   if numdrop>1 then goto 13520 else goto 13510

' check for premature trigger (note:
            '       premature trigger assump-
            '       -tion remains in effect
            '       only for glitched time
            '       (if added portion is an
            '       acceptable beat,
            '       (that's how it's used;
            '       otherwise slew rate
            '       (limiter extends '             assumption to added portion
13510       if abs(zintnow+zdata(intnow+1)_
                zintlst)>maxslew# then 13520
13511       zintnow=zintnow+zdata(intnow+1)
            ' assume premature trigger here
13512       sound 1400,sounder : return ' slew rate limiter
13520   sound 600,sounder : zintnow=zintlstr return ' calculating the respiratory rate using the
'     comb method
' [spectrum in ydata(*)]
'       start at frequency :    minrespfrq#
'       (in pixels):            minresp
'       use comb tooth width:   combwidth#
'       (in pixels):            combpix 14000   maxcomb#=0# : respcomb=0 : combstep=combpix\2+1
```

```
                ' for loop shifts comb beginning to different
                ' frequencies
14001   for comb=minresp to npair step combstep
14002       curcomb#=0# : harmbeg=comb-combstep+2
14003       lastbeg=harmbeg+9*comb : if lastbeg>npair
                then lastbeg=npair ' while loop adds up 10 teeth
            ' (harmonics) in the comb
14004       while harmbeg<=lastbeg
14005           toothptr=harmbeg
14006           lstooth=harmbeg+combpix : if
                    lstooth>npair then lstooth=npair ' this while loop adds one tooth's
                ' contribution to comb
14007           while toothptr<=lstooth
14008               curcomb#=curcomb#+ydata(toothptr)
14009               toothptr=toothptr+1
14010           wend
14011           harmbeg=harmbeg+comb
14012       wend
14013       if curcomb#>maxcomb# then maxcomb#=curcomb# :
                respcomb=comb
14014   next comb 14050   locate 3,1 : gosub 20000 : print "respiratory
            comb fraction: ";
14051   curcomb#=0# : for i=1 to npair :
            curcomb#=curcomb#+ydata(i) : next i
14052   respcombfrac#=maxcomb#/curcomb# : print using
            "#.###";respcombfrac#;

' respcomb now has respiratory frequency or a
        ' subharmonic
        ' to decide which is the first harmonic look at
        ' weight in each tooth
        ' of the comb; a higher harmonic comb must
```

```
                    ' contribute at least double
                    ' amplitude to be designated as the fundamental
                    ' (4xspectral weight)

14100   maxtooth#=0 : resptooth=0 : harmbeg=respcomb+1-
            combpix
14101   lastbeg=harmbeg+9*respcomb : if lastbeg>npair
            then lastbeg=npair 14102       while harmbeg<=lastbeg
14103           toothptr=harmbeg : curtooth#=0#
14104           lstooth=harmbeg+combpix+combpix
14105           if lstooth>npair then lstooth=npair ' add up one widened tooth
14110           while toothptr<=lstooth
14111               curtooth#=curtooth#+ydata(toothptr)
                        : toothptr=toothptr+1
14112           wend
                    ' compare to previous teeth
14120           if curtooth#<4*maxtooth# then goto 14130
14121               maxtooth#=curtooth# :
                        resptooth=harmbeg 14130           harmbeg=harmbeg+respcomb
14131       wend ' compute respiratory frequency as peak
                    ' average
14200   toothptr=resptooth : respfreq#=0#
14201   lstooth=toothptr+combpix+combpix
14202   if lstooth>npair then lstooth=npair ' average frequency over fundamental
                    ' peak
14210   while toothptr<=lstooth
14211       respfreq#=respfreq#+ydata(toothptr)
                *cdbl(toothptr-1)
```

```
14212           toothptr=toothptr+1
14213         wend
14214   respfreq#=respfreq#/maxtooth#/1024#*respsampl 14220   resp.lopixel=cint((respfreq#-
            .06#)/respsampl*1024#)+1
        ' integration limits
14221   resp.hipixel=cint((respfreq#+.06#)
            /respsampl*1024#)+1 return

' spectral amplitude calculations
15000   lfa#=0# : rfa#=0# : coherence#=0#
15001   for i=pixel.04 to pixel.10
15002       lfa#=lfa#+fnzmag(zspec.hb.real(i),
                zspec.hb.imag(i))
15003   next i
15004   lfa#=lfa#+lfa#

15010   for i=resp.lopixel to resp.hipixel
15011       rfa#=rfa#+fnzmag(zspec.hb.real(i),
                zspec.hb.imag(i))
15012   next i
15013   rfa#=rfa#+rfa#

15020   for i=1 to 512
15021       coherence#=coherence#+fnzcoher
            (zreal(i),zrimag(i),_
                      zspec.hb.real(i),
                      zspec.hb.imag(i))
15022   next i
15023   coherence#=coherence#/zspectsum 15030   ratio#=lfa#/rfa#
15031   cratio#=lfa#/coherence#

15040   locate 6,60 : print using    "lfa: ##.###";lfa#;
```

```
15041   locate 7,60 : print using    "rfa: ##.###
                                      (##.###)";rfa#,coherence#;
15042   locate 8,58 : print using "ratio: ##.###
                                      (##.###)";ratio#,cratio#;
        return ' storing trend data on floppy disk (file #10)
16000   lset hr$=mkd$(zavghr)
16001   lset rr$=mkd$(respfreq#)
16002   lset rcf$=mkd$(respcombfrac#)
16003   lset lfa$=mkd$(lfa#)
16004   lset rfa$=mkd$(rfa#)
16005   lset coher$=mkd$(coherence#)
16006   lset ratio$=mkd$(ratio#)
16007   lset cratio$=mkd$(cratio#)
16008   lset hrintegral$=mkd$(hrspecsum#)
16009   lset respintegral$=mkd$(respspecsum#)
16010   lset timestamp$=time$
16011   lset hbrecord$=mki$(analrec.hr)
16012   lset adrecord$=mki$(analrec.ad)
16013   lset hbeat$=mki$(anal.beat)
16014   lset samplrate$=mki$(respsampl)

record10no=record10no+1 : put #10,record10no return

' reading trend data from floppy disk (file #10)
16500   if record10no<=1 then return
16501   cls 16510   xmins=10 : xmaxs=310 : ymins=2: ymaxs=197 :
           numvalg=xmaxs-xmins+1
16511   call swindow(xmins,xmaxs,ymins,ymaxs)
```

```
16512    call clrwindw
16513    call axes 16520    numpts=record10no
16521    lfa.beg=record10no
16522    rfa.beg=2*record10no
16523    ratio.beg=3*record10no
16524    lastydata=4*record10no
16525    ln10#=log(10#)
16526    xscale#=numvalg/record10no ' get trend information from the disk file
16530    for temprec=1 to record10no
16531       get #10,temprec
16532       ydata(temprec)=197-.78#*cvd(hr$)
16533       ydata(temprec+lfa.beg)=197-19.5*cvd(lfa$)
16534       ydata(temprec+rfa.beg)=197-19.5*cvd(rfa$)
16535       ydata(temprec+ratio.beg)=100-
                log(cvd(ratio$))/ln10#*45#
16536    next temprec 16537    for i=1 to lastydata : if ydata(i)<ymins then
             ydata(i)=ymins
16538        if ydata(i)>ymaxs then ydata(i)=ymaxs :
                 next i ' plot trends here
16540    for trend=0 to 3 : trendoff=trend*record10no
16542       gctr=1 : ydatalst=ydata(1) :
                ydatag(1)=ydatalst
16543       for temprec=2 to record10no :
                gctrmax=temprec*xscale#
16544          gdif=gctrmax-gctr : if gdif<=0 then goto
                   16550
16545          ydatadif=ydata(temprec+trendoff)-
                   ydatalst : part=0
16546          while gctr<gctrmax : gctr=gctr+1 :
                   part=part+1
```

```
16547            ydatag(gctr)=ydatalst+
                  (part/gdif)*ydatadif : wend
16548        ydatalst=ydata(temprec+trendoff)
16550        next temprec
16551     linemask=linetype(trend) : x=xmins
16552     gdataptr=varptr(ydatag(1)) : numvalg=xmaxs-
              xmins+1
16553     call fgraph(gdataptr,numvalg,x,linemask)
16554     next trend 16560   locate 2,42 : print "HR (0-250 bpm)";
16561   locate 3,42 : print "lfa (0-10 bpm^2)";
16562   locate 4,42 : print "rfa (0-10 bpm^2)";
16563   locate 5,42 : print "ratio (.01-100)";

16600   req.cls=1 return

' subroutine to print out the interrupt vectors 19000   def seg=0
        print "IRQ3 @0B*4H: ";hex$(peek(&h2C));
        '   "";hex$(peek(&h2D));" ";
        print hex$(peek(&h2E));
        '   "";hex$(peek(&h2F));tab(40);
        print "IRQ4 @0C*4H: ";hex$(peek(&h30));
        '   "";hex$(peek(&h31));" ";
        print hex$(peek(&h32));" ";hex$(peek(&h33));
        return ' routine to clear the present line
20000   csnow=csrlin:locate csnow,1:print
        return
```

```
       ' check pointers to see if any disk files need
       ' to be written
30000  call rdptrs(adwr,hbwr,adflag,hbflag)
30001  if adflag=adflaglst and hbflag=hbflaglst then
                 return 30010  while adflag>record1no+1 : beep : locate 23,1 :
             print "data #1 loss";
30011          record1no=adflag-1 : wend
30020  while hbflag>record2no+1 : beep : locate 23,1 :
             print "data #2 loss";
30021          record2no=hbflag-1 : wend
30030  while hbflag>record3no+1 : beep : locate 23,1 :
             print "data #3 loss";
30031          record3no=hbflag-1 : wend 30040  if adflag<record1no+1 then goto 30050
30041      record1no=adflag : put #1,adflag
30042      if datacycle<=0 then datacycle=datacycle+1
           'if not processing, begin
30050  if hbflag=record2no+1 then record2no=hbflag :
             put #2,hbflag
30060  if hbflag=record3no+1 then record3no=hbflag :
             put #3,hbflag locate 3,1 : gosub 20000 : print "current file
       records: ";adflag; print " (#1) ";hbflag;"
          (#2)";
       adflaglst=adflag : hbflaglst=hbflag return end
           page    66,80
; sync7s.asm - an assembler routine to handle interrupts
;              from IRQ4 and collect
;              synchronous data from the A/D (board 2
;              configuration assumed)
```

```
;                       The routine checks A/D readings for
;                       output validity
;                       Data is loaded by interrupts into both a
;                       processing buffer and
;                       a disk file I/O buffer to allow quick
;                       archival; an overflow
;                       flag signals when a disk file buffer
;                       should be stored and
;                       also indicates whether the disk buffer
;                       was corrupted.
;                       To acknowledge storage of a disk buffer
;                       one must reset the
;                       overflow flag using <ackfdio>
; Last revision:  3 May 1985
;
;

;--------------------------------;
                        ; 8088 interrupt location        ;
                        ;--------------------------------;

abs0            segment at 0      ;absolute memory segment
                                  ;allows placement of
                                  ;interrupt address
                org     0BH*4     ;future heart beat
                                  interrupt handler resides
IRQ3_int        dw      2 dup(?); at int 0B org     0CH*4     ;8253 timebase interrupt
                                  ;handler resides
IRQ4_int        dw      2 dup(?); at int 0C
abs0            ends            ;

;--------------------------------;
                        ; int_buffer: area to save DOS   ;
                        ;        dummy interrupt ptrs    ;
                        ;--------------------------------;
```

```
int_buffer      segment         ;data segment containing
                                ;user interrupt buffer save_int        dw      4 dup(?);offset for two DOS
                                ;interrupts saved
                                ;to be restored using
                                ;exstint int_buffer      ends            ;
```

```
;----------------------------;
; working storage for        ;
; interrupts                 ;
;----------------------------;

dseg_sync       segment         ;data segment for
                                ;interrupts ;..........declare all variables public
        ;           for use by other
        ;           assembly level routines
        public ad_buffer,ad_rd,ad_wr,sync_ctr
        public hb_buffer1,hb_buffer2,hb_rd,hb_wr,heartbeats ;..........timebase local storage and
                    buffer ad_buffer       db      1024 dup(?) ;buffer for A/D
                                    values
ad_rd           dw      ?       ;read indicator for A/D
                                ;disk buffer
ad_wr           dw      ?       ;write pointer for A/D
                                ;buffer (incrementing)
sync_ctr        dw      ?       ;counter for timebase
                                ;interrupt (overflows)
```

```
;..........heart beat local storage and
;                buffer
;          note:for main clock
;                14.318 180 MHz (osc)
;          system clock
;                4.772 ?? MHz (clock)
;          8253 clock
;                2.386 363 MHz (ck8253)
;                     (ck8253 /   432)
;                5.524 KHz     (hb.clk)
;               (ck8253 /596592)  4 Hz
;                              (respck)
;          hb.clk = 1381*respck
;          sync.ctr overflow =
;                16384 sec (4:33:04)

hb_buffer1    dw      1024 dup(?) ;heart beat time
                                   stamps for previous 1024
hb_buffer2    dw      1024 dup(?) ;beats (2 words:
                                   hb.clk,sync.ctr)
hb_rd         dw      ?           ;read indicator for
                                  ;heart beat disk buffers
hb_wr         dw      ?           ;write pointer
                                  ;(incrementing) for hb_buffer heartbeats    dw      ?           ;keep track of number of
                                  ;beats processed ;..........pointers to disk file buffers fd1ptr        label   dword       ;pointer to floppy disk
                                   file #1 buffer
fd1ptroff     dw      ?           ; (offset)
fd1ptrseg     dw      ?           ; (segment)

fd2ptr        label   dword       ;pointer to floppy disk
                                   file #2 buffer
fd2ptroff     dw      ?           ; (offset)
```

```
fd2ptrseg       dw      ?       ; (segment)

fd3ptr          label   dword   ;pointer to floppy disk
                                  file #3 buffer
fd3ptroff       dw      ?       ; (offset)
fd3ptrseg       dw      ?       ; (segment)

dseg_sync       ends            ;

;------------------------------------;
; setup structures to allow access to;
; arguments pased by BASIC           ;
;------------------------------------;

; subroutine
; instint(fil1ptr,fil2ptr,fil3ptr)
frame_rd        struc           ;define the stack
                                ;structure for passing
                                ;arguments to BASIC
savebp0         dw      ?       ;caller's base pointer
saveret0        dd      ?       ;return offset and
                                ;segment pushed by BASIC
B_fil3ptr       dw      ?       ;offset of file #3 disk
                                ;buffer
B_fil2ptr       dw      ?       ;offset of file #2 disk
                                ;buffer
B_fil1ptr       dw      ?       ;offset of file #1 disk
                                  buffer
frame_rd        ends ; subroutine rdbeat(BASIC_beats,BASIC_
; syncs)
frame_rd        struc           ;define the stack
                                ;structure for passing
                                ;arguments to BASIC
```

| | | | |
|---|---|---|---|
| savebp1 | dw | ? | ;caller's base pointer |
| saveret1 | dd | ? | ;return offset and |
| | | | ;segment pushed by BASIC |
| BASIC_syncs | dw | ? | ;place to return sync |
| | | | ;pulses to BASIC |
| BASIC_beats | dw | ? | ;place to return heart |
| | | | ;beats to BASIC |
| frame_rd | ends | | |

```
              ; subroutine rdbuf (BASIC_ptr,whichbuff)
frame_rdbuf    struc           ;define the stack
                               ;structure for passing
                               ;arguments to BASIC
savebp2        dw     ?        ;caller's base pointer
saveret2       dd     ?        ;return offset and
                               ;segment pushed by BASIC
whichbuff      dw     ?        ;place to select which
                               ;buffer to read
BASIC_ptr      dw     ?        ;place to get pointer to
                               ;BASIC data array
frame_rdbuf    ends ; subroutine rdptrs
               ;(adwr,hbwr,adflag,hbflag)
frame_rdptrs   struc           ;define the stack
                               ;structure for passing
                               ;arguments to BASIC
savebp3        dw     ?        ;caller's base pointer
saveret3       dd     ?        ;return offset and
                               ;segment pushed by BASIC
hbflag         dw     ?        ;flag indicating disk
                               ;file #1,#2 buffers full
adflag         dw     ?        ;flag indicating disk
                               ;file #1 buffer is full
BASIC_hbwr     dw     ?        ;write pointer for heart
                               ;beat buffer
BASIC_adwr     dw     ?        ;write pointer for ad
                               ;buffer
```

```
frame_rdptrs    ends

;..........code segment begins here cseg_sync       segment 'code'
basic_dgroup    group   data,stack,const,heap,memory
                                ;defining link to BASIC
porta           equ     071CH   ;port definitions for
                                ;8255 port expander
portb           equ     071DH   ;these addresses are
                                ;decoded on the homemade
portc           equ     071EH   ;board
control         equ     071FH   ;control word in the
                                ;8255
timer0          equ     0704H   ;8253 timer0 register
timer1          equ     0705H   ;8253 timer1 register
timer2          equ     0706H   ;8253 timer2 register
con8253         equ     0707H   ;8253 control register ;----------------------------------------;
; timebase interrupt handler (not accessible to;
; BASIC)                                  ;
;----------------------------------------;
                ;this routine reads the A/D every timer1
                ;tick
                ;and stores the point in the analog
                ;buffer tbase_int       proc    far     ;this procedure is not
                                ;made public
                assume  cs:cseg_sync,ds:dseg_
                sync,es:nothing,ss:nothing
                push    ax      ;save registers used
                                ;during interrupt
```

```
            push    bx      ;
            push    cx      ;
            push    dx      ;
            push    si      ;
            push    di      ;
            push    ds      ;
            push    es      ;

mov     ax,dseg_sync    ;set up segment
                                    ;register for data area
            mov     ds,ax           ;
;..........increment counters/ decrement
;          pointers
            inc     sync_ctr        ;increment
                                    ;interrupt counter
            mov     cx,20           ;allow up to 20
                                    ;rereads of A/D ;..........get analog value from A/D and
;          send to buffer
            mov     dx,portb        ;get analog
                                    ;value from A/D
            in      al,dx           ;

mov     bx,ad_wr        ;and put analog
                                    ;data pointer in bx
retry:      mov     ad_buffer[bx],al
;save analog value in ad_buffer chk_adc:    in      al,dx           ;reread adc and
                                    ;check if previous
            cmp     ad_buffer[bx],al ;value agrees
            je      adc_ok          ;if value is the
                                    ;same we're done
            loop    retry           ;retry if retry
                                    ;counter is not depleted
                                    ;failure returns
                                    ;last value read
```

```
adc_ok:         inc     ad_wr           ;increment write
                                        ;pointer
                cmp     ad_wr,1023      ;see if write
                                            pointer<=1023
                jle     tbase_eoi       ;if pointer is
int                                     ;in range then finish ;..........reset local ptr and load disk
                ;          buffer for file #1 xor     ah,ah           ;zero ah as
                                        ;upper byte of A/D reading
                mov     cx,1024         ;load counter
                                        ;for 1024 repetitions
                lea     si,ad_buffer    ;load local
                                        ;buffer address
                les     di,fd1ptr       ;load pointer to
                                        ;disk file #1 buffer
fd1lp:          lodsb                   ;repeat moves
                                        ;1024 times (ds:si->es:di)
                stosw                   ;converting
                                        ;bytes to words
                loop    fd1lp           ;
                mov     ad_wr,cx        ;reset write
                                        ;pointer (wrap around)
                inc     ad_rd           ;increment read
                                        ;reques_ for disk ;..........acknowledge interrupt to
                ;          8259A
tbase_eoi:      mov     al,20H          ;send EOI to 8259A
                out     20H,al          ;

pop     es              ;restore registers which
                                        ;were used
                pop     ds              ;
                pop     di              ;
```

```
                pop     si      ;
                pop     dx      ;
                pop     cx      ;
                pop     bx      ;
                pop     ax      ;
                iret            ;return to place where
                                ;interrupt occurred debugmsg1       db      'this is the end of the time
                        base interrupt' tbase_int       endp

;----------------------------------------------;
; heart beat interrupt handler (not accessible ;
; to BASIC)                                    ;
;----------------------------------------------;
                ;this routine reads the local system
                ;timers
                ;every heart beat and stores the time in
                ;the heart beat buffer for use in
                ;spectral analysis
                ;

hbeat_int       proc    far     ;this procedure is not
                                ;made public
                assume  cs:cseg_sync,ds:dseg_sync
                assume  es:nothing,ss:nothing push    ax      ;save registers during
                                ;interrupt
                push    bx      ;
                push    cx      ;
                push    dx      ;
```

```
        push    si        ;
        push    di        ;
        push    ds        ;
        push    es        ;        | mov     ax,dseg_sync    ;set up segment
                                ;register for data area
        mov     ds,ax           ;

inc     heartbeats      ;increment heart
                                ;   beat counter ;..........read counters and store
;          result in hb_buffer
        mov     dx,con8253      ;prepare to read
                                ;hb1.clk from timer1
        mov     al,40H          ;by latching
                                ;counts in timer1
        out     dx,al           ;

mov     dx,timer1       ;prepare to read
                                ;the latched value
        in      al,dx           ;from the timer
                                ;(low byte first)
        mov     ah,al           ;save low byte
                                ;in ah
        in      al,dx           ;(high byte
                                ;last)
        xchg    al,ah           ;get the bytes'
                                ;order right mov     bx,hb_wr        ;get write
                                ;pointer for hb_buffer
        add     bx,bx           ;double to
                                ;point to a word
        mov     hb_buffer1[bx],ax  ;and store
                                ;hb1.clk counts
;........read overflow counter from
```

```
;         timer2
    mov     dx,con8253          ;prepare to read
                                ;hb2.clk from timer2
    mov     al,80H              ;by latching ;counts in timer2
    out     dx,al               ;

mov     dx,timer2           ;prepare to read
                                ;the latched value
    in      al,dx               ;from the timer
                                ;(low byte first)
    mov     ah,al               ;save low byte
                                ;in ah
    in      al,dx               ;(high byte
                                ;last)
    xchg    al,ah               ;get the bytes'
                                ;order right in ax mov     hb_buffer2[bx],ax   ;store
                    result i... hb2.clk buffer ;........increment write pointer and
;          check for buffer overflow
    inc     hb_wr               ;increment write
                                ;pointer
    cmp     hb_wr,1023          ;if hb_wr<=1023
    jle     hb_eoi              ;then finish up ;..........reset local ptr/load disk
;           buffers for files #2,#3
;           (routine takes about 15-20
;           msec to fill disk buffer)
    mov     cx,1024             ;load counter
                                ;for 1024 repetitions
    lea     si,hb_buffer1       ;load local
                                ;buffer address
    les     di,fd2ptr           ;load pointer to
```

```
                                                ;disk file #2 buffer
fd2lp:      movsw                   ;repeat moves
                                    ;1024 times (ds:si->es:di)
            loop    fd2lp           ;
            mov     cx,1024         ;load counter
                                    ;for 1024 repetitions
            lea     si,hb_buffer2   ;load local
                                    ;buffer address
            les     di,fd3ptr       ;load pointer to
                                    ;disk file #3 buffer
fd3lp:      movsw                   ;repeat moves
                                    ;1024 times (ds:si->es:di)
            loop    fd3lp           ;
            mov     hb_wr,cx        ;reset write
                                    ;pointer (wrap around)
            inc     hb_rd           ;increment read
                                    ;request ;.........acknowledge interrupt to
            ;         8259A
hb_eoi:     mov     al,20H          ;send EOI to 8259A
            out     20H,al          ;

pop     es              ;restore registers and
            pop     ds              ;
            pop     di              ;
            pop     si              ;
            pop     dx              ;
            pop     cx              ;
            pop     bx              ;
            pop     ax              ;
            iret                    ;return to place where
                                    ;interrupt occurred debugmsg2   db      'this is the end of the heart
                    beat interrupt' hbeat_int   endp
```

```
;---------------------------------------;
; subroutine instint [install_interrupts]   ;
; (fil1ptr,fil2ptr,fil3ptr)                 ;
;---------------------------------------;

instint         proc    far
                public  instint
                ;public symbol allows external references
                ;es,ds vectors and must be restored movsw
                ;uses (ds:si)(es:di) addr
                assume  cs:cseg_sync,ss:basic_
                    dgroup,ds:basic_dgroup
                assume  es:basic_dgroup
                used to access interrupt ;..........save registers push    bp      ;save BASIC base pointer
                                ;   for return to BASIC
                mov     bp,sp   ;point stack pointer at
                                ;frame reference to
                                ;address of BASIC analog
                                ;data buffer push    ax      ;save additional
                                ;registers
                push    si      ;
                push    di      ;
                push    ds      ;
                push    es      ;
                pushf           ;and flags ;set up the segment
                                ;registers
                mov     ax,dseg_sync    ;set up access
                                        ;to floopy disk data ptrs
                mov     es,ax           ;
                assume  es:dseg_sync    ;
```

```
;..........put disk file pointers into
;          local memory
        mov     di,[bp].B_fil1ptr       ;get
                        pointers from BASIC
        mov     ax,[di]                 ;and
;                  save in dseg_sync areas
        mov     fd1ptroff,ax            ;

mov     di,[bp].B_fil2ptr       ;
        mov     ax,[di]                 ;
        mov     fd2ptroff,ax            ;

mov     di,[bp].B_fil3ptr       ;
        mov     ax,[di]                 ;
        mov     fd3ptroff,ax            ;

mov     ax,ds           ;put segment
                                ;registers into
        mov     fd1ptrseg,ax    ;pointers
        mov     fd2ptrseg,ax    ;
        mov     fd3ptrseg,ax    ;

;set up the segment
                        ;registers
        mov     ax,int_buffer
;es points to buffer area to save
        mov     es,ax           ;DOS dummy
                                ;interrupt vector
        assume  es:int_buffer   ;
        mov     ax,0            ;ds points to
                                ;abs0 (interrupt table)
        mov     ds,ax           ;
        assume  ds:abs0         ;

;setup access to
                        ;interrupt vectors
        lea     di,save_int     ;load offset of
```

```
            lea     si,IRQ3_int     ;save_int in es,di
                                    ;load offset of
                                    ;IRQ3_int in ds,si
            cld                     ;clear direction
                                    ;flag to increment ptrs
            movsw                   ;save DOS dummy
                                    ;interrupt vectors to be
            movsw                   ;restored later
            movsw                   ;now saving IRQ4
            movsw                   ;

mov     IRQ3_int+2,cseg_sync    ;install
                                    ;the heart beat (IRQ3)
            mov     IRQ3_int,offset hbeat_int
                                    ;interrupt handler now
            mov     IRQ4_int+2,cseg_sync    ;install
                                    ;the DAC timebase (IRQ4
            mov     IRQ4_int,offset tbase_int
                                    ;interrupt handler now
;..........initialization of buffer
            control variables mov     ax,dseg_sync    ;setup data
                                    ;segment for initialization
            mov     ds,ax           ;
            assume  ds:dseg_sync    ;ds segment
                                    ;register now redefined xor     ax,ax           ;zero ax
                                    ;register to initialize
            mov     heartbeats,ax   ;counters
            mov     sync_ctr,ax     ;
            mov     ad_wr,ax        ;initialize
                                    ;read/write pointers to top
            mov     hb_wr,ax        ;of buffer
            mov     ad_rd,ax        ;
```

```
                mov     hb_rd,ax        ;

;..........return to BASIC popf                    ;restore flags
                pop     es              ;restore additional
                                         registers
                pop     ds              ;
                pop     di              ;
                pop     si              ;
                pop     ax              ;

pop     bp              ;restore BASIC's base
                                        ;pointer and
                ret     6               ;delete 3 parameters (6
                                        ;bytes) from the stack
                                        ;and return to the
                                        ;calling routine debugmsg3       db      'this is the end of the
                        interrupt installation' instint         endp

;----------------------------------------;
; subroutine exstint (exstall_           ;
; interrupts)                            ;
;----------------------------------------;

exstint         proc    far
                public  exstint ;public symbol allows
                                ;external references
                assume  cs:cseg_sync,ss:basic_dgroup
```

```
        assume  ds:int_buffer,~ abs0
        ;es,ds used to access interrupt
        ;vectors and must be restored
        ;movsw uses (ds:si)(es:di) addr ;..........save registers push    bp          ;save BASIC base pointer
                    ;   for return to BASIC
mov     bp,sp       ;point stack pointer at
                    ;   frame reference to
                    ;access arguments passed
                    ;   by BASIC (none here)

push    ax          ;save additional
                    ;registers
push    si          ;
push    di          ;
push    ds          ;
push    es          ;
pushf               ;and flags ;set up the segment
                    ;registers as assumed
mov     ax,0        ;es points to
                    ;abs0 (interrupt table)
mov     es,ax       ;
mov     ax,int_buffer  ;ds points to
                    ;buffer area to save
mov     ds,ax       ;DOS dummy
                    ;interrupt vector ;setup access to
                    ;   interrupt vectors
lea     di,IRQ3_int ;load offset of
                    ;IRQ3_int in es,di
lea     si,save_int ;load offset of
                    ;save_int in ds,si
```

```
        cld                     ;clear direction
                                ;flag to increment ptrs
        movsw                   ;restore DOS
                                ;dummy interrupt vectors
        movsw                   ;for IRQ3
        movsw                   ;and IRQ4
        movsw                   ;

;..........return to BASIC popf            ;restore flags
        pop     es      ;restore additional
                        ;registers
        pop     ds      ;
        pop     di      ;
        pop     si      ;
        pop     ax      ;

pop     bp      ;restore BASIC's base
                        ;pointer and
        ret     0       ;delete 0 parameters (0
                        ;bytes) from the stack
                        ;and return to the
                        ;calling routine debugmsg4       db      'this is the end of the
                        interrupt exstallation' exstint         endp

;---------------------------------------;
        ; subroutine rdbeat (heartbeats,sync_   ;
        ; pulses)                               ;
```

```
;----------------------------------------;

rdbeat          proc    far
                public rdbeat   ;public symbol allows
                external references
                assume cs:cseg_sync,es:dseg_sync
                assume ds:basic_dgroup,ss:basic_dgroup ;..........save registers push    bp          ;save BASIC base poin
                                    ;ter for return to BASIC
                mov     bp,sp       ;point stack pointer at
                                    ;frame reference to
                                    ;access arguments passed
                                    ;by BASIC (one here)

push    ax          ;save additional
                                        registers
                push    di          ;
                push    es          ;

mov     ax,dseg_sync    ;set up segment
                                        register for data area
                mov     es,ax           ;

mov     ax,heartbeats           ;get
                                        ;beats from local memory
                mov     di,[bp].BASIC_beats     ;
                mov     [di],ax                 ;send
                                        ;beats to BASIC mov     ax,sync_ctr             ;get
                                        ;sync pulses from local
                mov     di,[bp].BASIC_syncs     ;memory
                mov     [di],ax                 ;send
```

;sync pulses to BASIC

;..........return to BASIC

```
        pop     es      ;restore additional
                        registers
        pop     di      ;
        pop     ax      ;
        pop     bp      ;restore BASIC's base
                        ;pointer,
        ret     4       ;delete 2 parameters (4
                        ;bytes) from the stack
                        ;and return to the
                        ;calling routine debugmsg5       db      'this is the end of the heart
                        beat read routine' rdbeat  endp
```

```
;-------------------------------------;
; subroutine rdbuf (BASIC_             ;
; ptr,whichbuff)                       ;
;-------------------------------------;
                ;this routine dumps a buffer
                ;from the
                ;assembly routine data area to a
                ;BASIC array
                ;pointed to by BASIC_ptr;
                ;whichbuff selects
                ;the assembler buffer to be
                ;dumped.
                ;choices of buffer are:
                ;   0 - ad_buffer       (bytes)
                ;   1 - hb_buffer1      (words)
                ;   2 - hb_buffer2      (words)
```

```
rdbuf   proc    far
        public rdbuf        ;public symbol allows
                            ;external references
        assume cs:cseg_sync,es:basic_dgroup
        assume ds:basic_dgroup,ss:basic_dgroup
;..........save registers push    bp          ;save BASIC base pointer
                            ;for return to BASIC
        mov     bp,sp       ;point stack pointer at
                            ;frame reference to
                            ;access arguments passed
                            ;by BASIC (one here)

push    ax          ;save additional
                            ;registers
        push    cx          ;
        push    si          ;
        push    di          ;
        push    ds          ;
        push    es          ;
        pushf               ;and flags ;..........get pointers from BASIC
        mov     di,[bp].whichbuff       ;get
                            ;buffer choice from BASIC
        mov     ax,[di]                 ;

mov     di,[bp].BASIC_ptr
;get pointer to BASIC's data area
        mov     di,[di]     ;and put pointer
                            ;into di ;..........set up extra segment register
;              and counter
```

```
        mov     cx,dseg_sync    ;set up segment
                                    register for data area
        mov     ds,cx           ;
        assume  ds:dseg_sync
        mov     cx,1024         ;load counter
                                ;with number of objects ;..........select buffer here and place
;           pointer in si
        or      ax,ax           ;compare
                                ;selector with 0
        jz      rd_adbuf
;if zero (select =0) read ad_buffer
        dec     ax              ;decrement to
                                ;see if select was 1
        jz      rd_hbbuf1
;if zero (select =1) read hb_buffer1
        dec     ax              ;decrement to
                                ;see if select was 2
        jz      rd_hbbuf2
;if zero (select =2) read hb_buffer2
        jmp     rdbuf_end
;not a valid buffer, so return to BASIC rd_adbuf:       lea     si,ad_buffer    ;point source
                                        ;index to ad_buffer
                jmp     move_dta_byte   ;

rd_hbbuf1:      lea     si,hb_buffer1   ;point source
                                        ;index to hb_buffer1
                jmp     move_dta_word   ;

rd_hbbuf2:      lea     si,hb_buffer2   ;point source
                                        ;index to hb_buffer2
                jmp     move_dta_word   ;
;..........move byte data from local
;           storage to BASIC array
```

```
move_dta_byte:  xor     ah,ah       ;zero upper byte of ax cld                 ;clear direction flag to
                                    ;increment si,di by 2
byt_lp:         lodsb               ;move data bytes from
                                    ;local storage (ds:si)
                stosw               ;and store as a word in
                                    ;BASIC's area (es:di)
                loop    byt_lp  ;
                jmp     rdbuf_end ;finished ;..........move word data from local
;          storage to BASIC array
move_dta_word:  cld                 ;clear direction flag to
                                    ;increment si,di by 2
wd_lp:          movsw               ;get data word from
                                    ;local storage (ds:si)
                loop    wd_lp   ;and store as a word in
                                    ;BASIC's area (es:di)

;..........return to BASIC rdbuf_end:      popf                ;restore flags
                pop     es          ;restore additional
                                    ;registers
                pop     ds          ;
                pop     di          ;
                pop     si          ;
                pop     cx          ;
                pop     ax          ;

pop     bp          ;restore BASIC's base
                                    ;pointer,
                ret     4           ;delete 2 parameters (4
                                    ;bytes) from the stack
                                    ;and return to the
```

;calling routine

```
debugmsg6        db      'this is the end of the buffer
                          read routine' rdbuf    endp
```

;----------------------------------------;
; subroutine rdptrs (BASIC_adwr,BASIC_    ;
; hbwr,adflag,hbflag)                     ;
;----------------------------------------;

```
                 ;this routine returns pointers
                 ;appropriate
                 ;arrays returned to BASIC through rdbuf
                 ;this means the pointers are subtracted
                 ;from 1025
                 ;since the buffers have decrementing
                 ;pointers
                 ;whereas the BASIC data has incrementing
                 ;pointers
                 ;the flags indicate whether or not the
                 ;respective
                 ;disk file buffers have been filled and
                 ;therefore require
                 ;service (eg, a BASIC PUT command to
                 ;store the buffer on disk)

rdptrs           proc    far
                 public rdptrs    ;public symbol allows
                                  ;external references
                 assume cs:cseg_sync,es:dseg_sync
                 assume ds:basic_dgroup,ss:basic_dgroup ;..........save registers push    bp       ;save BASIC base pointer
```

```
           mov    bp,sp           ;for return to BASIC
                                  ;point stack pointer at
                                  ;frame reference to
                                  ;access arguments passed
                                  ;by BASIC (one here)

push   ax              ;save additional
                                  ;registers
           push   di              ;
           push   es              ;

mov    ax,dseg_sync    ;set up segment
                                  ;register for data area
           mov    es,ax           ;

mov    ax,ad_wr        ;get write
                                  ;pointer for A/D buffer
           mov    di,[bp].BASIC_adwr   ;and send
                                       ;to BASIC
           mov    [di],ax         ;

mov    ax,hb_wr        ;get
                                  ;write pointer for heart
           mov    di,[bp].BASIC_hbwr   ;beat
                                       ;buffer and send to BASIC
           mov    [di],ax         ;

mov    ax,ad_rd        ;get
                                  ;disk file flag for A/D
           mov    di,[bp].adflag  ;buffer
                                  ;and send to BASIC
           mov    [di],ax         ;

mov    ax,hb_rd        ;get
                                  ;disk file flag for heart
           mov    di,[bp].hbflag  ;beat
                                  ;buffers and send to BASIC
```

```
            mov     [di],ax             ;

;..........return to BASIC pop     es          ;restore additional
                                ;registers
            pop     di          ;
            pop     ax          ;

pop     bp          ;restore BASIC's base
                                ;pointer,
            ret     8           ;delete 4 parameters (8
                                ;bytes) from the stack
                                ;and return to the
                                ;calling routine debugmsg7   db      'this is the end of the pointer
                    read routine' rdptrs  endp cseg_sync       ends
                end
; module gwindowl.asm - a collection of routines useful
;                       for preparing data
;                       for the fast graphics routine.
;
;       subroutines:
;
;           dwindow(xmin,xmax,ymin,ymax) - establish
;           data value limits corresponding to
;               screen window.
;
;           swindow(xmin,xmax,ymin,ymax) - establish
;             screen boundaries for data to be
;             plotted.
;
```

```
;                   clrwindw - clear contents of present
;                        window
;
;                   axes - prepare axes for current window
;                                     (no tick marks yet)
;                            (first version: only draws a box
;                               around window)
;
;                   scaler(indata_ptr,outdata_ptr,numval) -
;                       scale data to fit into window requires
;                                  correct initializati
;                                       using dwindow
;                                       and swindow
;                            (first version: only scales y-
;                                coordinate with dwindow)
;                            (            x coordinate
;                                scaled by numval)
;                            (            maximum y-value
;                                is plotted)
;
;
;------------------------------------------------------------
;
;                    arguments passed by BASIC
;
;
;       indata_ptr     - offset of BASIC array
;                          containing y-coordinates of
;                              points to be plotted
;       outdata_ptr    - offset of BASIC array
;                          containing scaled y-coordinates
;       numval         - number of values to plot
;
;------------------------------------------------------------

;..........screen memory definition
```

```
screen_memory    segment at 0B800H
even_pixels      db       8000 dup(?)      ;pixels with
                                           ;even y-coordinates
                 org      2000H            ;beginning of
                                           ;high screen memory
odd_pixels       db       8000 dup(?)      ;pixels with odd
                                           ;y-coordinates
screen_memory    ends ;..........local memory definitions dseg_wind        segment                   ;valid default values
                                           ;present at startup xmin_s           dw       0                ;minimum screen ordinate
                                           ;for window
xmax_s           dw       639              ;maximum screen ordinate
                                           ;for window
ymin_s           dw       0                ;minimum screen abscissa
                                           ;for window
ymax_s           dw       199              ;maximum screen abscissa
                                           ;for window
xmin_d           dw       0                ;minimum data ordinate
                                           ;for window
xmax_d           dw       16384            ;maximum data ordinate
                                           ;for window
ymin_d           dw       0                ;minimum data abscissa
                                           ;for window
ymax_d           dw       16384            ;maximum data abscissa
                                           ;for window ulh_cor          dw       0                ;offset for upper left
                                           ;hand corner of screen
urh_cor          dw       79               ;offset for upper right
                                           ;hand corner of screen
llh_cor          dw       3EF0H            ;offset for lower left
                                           ;hand corner of screen
```

```
lrh_cor         dw        3F3FH      ;offset for lower right
                                     ;hand corner of screen outptr          dw        ?          ;pointer to output array
                                     ;in BASIC (must be
                                     ;at least as large as
                                     ;input array)
rndoff          dw        ?          ;roundoff correction (if
                                     ;fraction>.5 round up)
numvalt         dw        ?          ;save number of points
                                     ;in input array for xpass
bx_last         dw        ?          ;save pointer during x-
                                     ;scaling to allow
                                     ;use of largest y per x
                                     ;pixel
dseg_wind       ends ;----------------------------------------------;
; define structures for passing arguments from ;
; BASIC                                        ;
;----------------------------------------------;

; subroutines
                        dwindow/swindow(xmin,xmax,ymin,ymax)
frame_lim       struc                ;define structure
savebpl         dw        ?          ;caller's base pointer
saveretl        dd        ?          ;return offset and
                                     ;segment pushed by BASIC
ymax            dw        ?          ;maximum abscissa
                                     ;(screen or data coordinate)
ymin            dw        ?          ;minimum abscissa
                                     ;(screen or data coordinate)
xmax            dw        ?          ;maximum ordinate
                                     ;(screen or data coordinate)
xmin            dw        ?          ;minimum ordinate
                                     ;(screen or data coordinate)
frame_lim       ends
```

```
                        ; subroutine scaler(indata_ptr,outdata_
                        ; ptr,numval)
frame_scl       struc               ;define structure
savebp2         dw      ?           ;caller's base pointer
saveret2        dd      ?           ;return offset and
                                    ;segment pushed by BASIC
numval          dw      ?           ;number of values in
                                    ;BASIC's data array
outdata_ptr     dw      ?           ;scaled values are
                                    ;passed to a BASIC
                                    ;array pointed to by
                                    ;this pointer(for fgraph)
indata_ptr      dw      ?           ;values to be graphed
                                    ;are passed from a BASIC
                                    ;array pointed to by
                                    ;this pointer.
frame_scl       ends ;..........subroutines' code begins here cseg_gr segment 'code'
dgroup  group   data,stack,const,heap,memory
        ;defining link to BASIC ;--------------------------------------------------;
        ; subroutine dwindow(xmin,xmax,ymin,ymax)          ;
        ;--------------------------------------------------;
                ;subroutine to establish data value
                ;limits
                ;corresponding to screen window.

dwindow         proc    far
```

```
        public  dwindow
       ;public symbols allow external references
        assume  cs:cseg_gr,ds:dgroup
       ;BASIC defines regs
        assume  ss:dgroup,es:dseg_wind push    bp              ;save base pointer for the
                        ;return to BASIC
mov     bp,sp           ;point stack pointer at frame
                        ;structure
                ;..........save additional registers and
                ;          set up extra data seg
push    ax              ;
push    di              ;
push    es              ;

mov     ax,dseg_wind    ;set up extra data
                        ;segment as assumed
mov     es,ax           ;

;....get specifications for window from
                ;     BASIC and store locally mov     di,[bp].ymax    ;
mov     ax,[di]         ;
mov     ymax_d,ax       ;

mov     di,[bp].ymin    ;
mov     ax,[di]         ;
mov     ymin_d,ax       ;

mov     di,[bp].xmax    ;
mov     ax,[di]         ;
mov     xmax_d,ax       ;

mov     di,[bp].xmin    ;
```

```
        mov     ax,[di]         ;
        mov     xmin_d,ax       ;

;..........restore all registers which
                ;          were corrupted
        pop     es              ;
        pop     di              ;
        pop     ax              ;
        pop     bp              ;restore BASIC base
                                ;pointer before returning
        ret     8               ;delete 4 parameter
                                ;addresses (8 bytes) from
                                ;stack and return to
                                ;calling routine
dwindow endp ;-----------------------------------------------;
; subroutine swindow(xmin,xmax,ymin,ymax)       ;
;-----------------------------------------------;
                ;subroutine to establish absolute screen
                ;coordinate limits
                ;corresponding to screen window.

swindow         proc    far
                public  swindow ;public symbols allow
                external references
                assume  cs:cseg_gr,ss:dgroup
                ;BASIC defines regs
                assume  ds:dseg_wind,es:dgroup push    bp              ;save base pointer for the
                                ;return to BASIC
        mov     bp,sp           ;point stack pointer at frame
                                ;structure
```

```
                    ;..........save additional registers and
                    ;          set up extra data seg
        push    ax      ;
        push    cx      ;
        push    dx      ;
        push    di      ;
        push    ds      ;

mov     ax,dseg_wind    ;set up extra data
                                ;segment as assumed
        mov     ds,ax           ;

;....get specifications for window from
                    ;    BASIC and store locally
                    ;........first y coordinate ranges
        mov     di,es:[bp].ymax ;
        mov     ax,es:[di]              ;
        cmp     ax,199          ;make sure ymax_s <=199
        jg      y_bad           ;use default value if
                                ;value sent is bad
        mov     ymax_s,ax       ;

mov     di,es:[bp].ymin ;
        mov     ax,es:[di]              ;
        mov     ymin_s,ax       ;

;..........y range limits examined
        add     ax,8            ;make sure that ymax
                                ;exceeds ymin by at least 8
        cmp     ax,ymax_s       ;
        jng     y_ok            ;if ymax_s <= ymin_s+8
y_bad:  mov     ax,199          ;then set ymax_s,ymin_s
                                ;to default values
        mov     ymax_s,ax       ;ymax_s default=199
        xor     ax,ax           ;ymin_s default=0
        mov     ymin_s,ax       ;
                    ;..........x coordinate ranges set up
```

```
y_ok:      mov    di,es:[bp].xmax    ;
           mov    ax,es:[di]         ;
           cmp    ax,639             ;make sure xmax_s <=639
           jg     x_bad              ;use default value if
                                     ;value sent is bad
           mov    xmax_s,ax          ;

mov    di,es:[bp].xmin    ;
           mov    ax,es:[di]         ;
           mov    xmin_s,ax          ;

;..........x range limits examined
           cmp    ax,xmax_s          ;make sure that xmax
                                     ;exceeds xmin
           jnge   x_ok               ;if xmax_s < xmin_s
x_bad:     mov    ax,639             ;then set xmax_s,xmin_s
                                     ;to default values
           mov    xmax_s,ax          ;xmax_s default=199
           xor    ax,ax              ;xmin_s default=0
           mov    xmin_s,ax          ;

;..........set up the pointers to the
           ;          four screen corners

; --ymin
x_ok:      xor    dx,dx              ;put lowest screen
                                     ;memory location (=0) into dx
           mov    ax,ymin_s          ;first calculate y
                                     ;contribution to offset of
           shr    ax,1               ;upper corners by
                                     multiplying (ymin/2) by 80.
           jnc    y0_even            ;if ymin was not even
           mov    dx,2000H           ;then the upper corners
                                     ;are odd pixels (2000H)
y0_even:   mov    cl,80              ;[promised
                                     ;multiplication by 80]
```

```
            mul     cl              ;
            add     dx,ax           ;y contribution to
                                    ;offset is here
            mov     ulh_cor,dx      ;save partial result
            mov     urh_cor,dx      ;

;  --ymax
            xor     dx,dx           ;put lowest screen
                                    ;memory location (=0) into dx
            mov     ax,ymax_s       ;first calculate y
                                    ;contribution to offset of
            shr     ax,1            ;lower corners by
                                    ;multiplying (ymax/2) by 80.
            jnc     yl_even         ;if ymax was not even
            mov     dx,2000H        ;then the upper corners
                                    ;are odd pixels (2000H)
yl_even:    mov     cl,80           ;[promised
                                    ;multiplication by 80]
            mul     cl              ;
            add     dx,ax           ;y contribution to
                                    ;offset is here
            mov     llh_cor,dx      ;save partial result
            mov     lrh_cor,dx      ;

mov     ax,xmin_s       ;x contribution is
                                    ;xmin/8
            mov     cl,3            ;calculated by shifting
                                    ;right 3 bits
            shr     ax,cl           ;and
            add     ulh_cor,ax      ;adding the result to
                                    ;the stored partial result
            add     llh_cor,ax      ;

mov     ax,xmax_s       ;x contribution is
                                    xmin/8
        mov     cl,3                ;calculated by shifting
                                    ;right 3 bits
        shr     ax,cl               ;and
```

```
        add     urh_cor,ax      ;adding the result to
                                ;the stored partial result
        add     lrh_cor,ax      ;

;..........restore all registers which
                ;          were corrupted
        pop     ds              ;
        pop     di              ;
        pop     dx              ;
        pop     cx              ;
        pop     ax              ;

pop     bp              ;restore BASIC base
                                ;pointer before returning
        ret     8               ;delete 4 parameter
                                ;addresses (8 bytes) from
                                ;stack and return to
                                ;calling routine
swindow endp ;----------------------------------------;
                ; subroutine clrwindw                    ;
                ;----------------------------------------;
                ;subroutine to clear
                ;the screen window.

clrwindw        proc    far
                public  clrwindw ;public symbols allow
                                 ;external references
                assume  cs:cseg_gr,ss:dgroup
                ;BASIC defines regs
                assume  ds:dseg_wind,es:screen_memory push    bp              ;save base pointer for the
```

```
                        ;return to BASIC
        mov     bp,sp   ;point stack pointer at frame
                        ;structure ;..........save additional registers and
                ;          set up data segments
        push    ax      ;
        push    bx      ;
        push    cx      ;
        push    dx      ;
        push    si      ;
        push    di      ;
        push    ds      ;
        push    es      ;

;..........set up data segments as
                ;          assumed
        mov     ax,dseg_wind    ;
        mov     ds,ax           ;
        mov     ax,screen_memory;
        mov     es,ax           ;

;..........clear screen by zeroing out
                ;          graphics memory
                ;             register usage:
                ;             ax - marker for
                ;                rightmost column
                ;             bh - # x bytes
                ;             bl - pixel mask
                ;             cx - y
                ;                coordinate counter
                ;             dx - # y lines
                ;             si - offset of
                ;                top of column
                ;             di - offset of
```

```
                   ;               present byte
                   ;....first clear leftmost part of window
        mov    dx,ymax_s       ;compute number of
                               ;vertical lines
        sub    dx,ymin_s       ;
        inc    dx              ;and save in dx mov    ax,urh_cor      ;compute number of
                               ;horizontal bytes
        sub    ax,ulh_cor      ;(a number 1-79)
        mov    bh,al           ;and save in bh
        xor    ax,ax           ;clear ax register to
                               ;indicate clearing of all
                               ;columns except one
                               ;rightmost one ;..........set up to blank leftmost
                   ;            column
        mov    cx,xmin_s       ;compute mask for
                               ;blanking leftmost column
        call   mask0           ;

lea    di,even_pixels  ;get offset of
        add    di,ulh_cor      ;upper left hand corner
                                of window
        mov    si,di           ;save location in si
                   ;..........blank all columns except
                   ;            rightmost
nxt_col:call   clr_col         ;
        xor    bl,bl           ;subsequent columns
                       ;blank all bits (bl mask=0)
        inc    si              ;compute offset of
                               ;present column
        mov    di,si           ;and load into di
        dec    bh              ;see if there are any
                               ;columns left
        jnz    nxt_col         ;
```

```
                ;..........blank rightmost column
        mov     cx,xmax_s       ;compute mask for
                                ;rightmost column
        inc     cx              ;include rightmost pixel
        and     cl,7            ;using cx mod 8
        mov     bl,0FFH         ;put mask in bl
        jz      mask_r          ;if cx mod 8 <>0 then
        shr     bl,cl           ;shift mask
                                ;appropriately
        jmp     1st_clr         ;
mask_r: xor     bl,bl           ;set bl mask to blank
                                ;all bits
1st_clr:call   clr_col          ;clear rightmost column ;..........restore all registers which
                ;              were corrupted
        pop     es              ;
        pop     ds              ;
        pop     di              ;
        pop     si              ;
        pop     dx              ;
        pop     cx              ;
        pop     bx              ;
        pop     ax              ;

pop     bp              ;restore BASIC base
                                ;pointer before returning
        ret     0               ;delete 0 parameter
                                ;addresses (0 bytes) from
                                ;stack and return to
                                ;calling routine
clrwindw endp
```

;----------------------------------------;

; subroutine axes
;----------------------------------;
                ;subroutine to draw a box
                ;enclosing the screen window.

axes            proc    far
                public  axes        ;public symbols allow
                                    ;external references
                assume  cs:cseg_gr,ss:dgroup
                ;BASIC defines regs
                assume  ds:dseg_wind,es:screen_memory push    bp          ;save base pointer for the
                            ;return to BASIC
        mov     bp,sp       ;point stack pointer at frame
                            ;structure ;..........save additional registers and
                ;          set up data segments
        push    ax      ;
        push    bx      ;
        push    cx      ;
        push    dx      ;
        push    si      ;
        push    di      ;
        push    ds      ;
        push    es      ;

;..........set up data segments as
                ;          assumed
        mov     ax,dseg_wind    ;
        mov     ds,ax           ;
        mov     ax,screen_memory;
        mov     es,ax           ;

```
                ;..........draw box screen by setting
                ;          appropriate bits
                ;               register usage
                ;               ax - marker for
                ;                 rightmost column
                ;               bh - # x bytes
                ;               bl - pixel mask
                ;               cx - y
                ;                 coordinate counter
                ;               dx - # y lines
                ;               si - offset of
                ;                 top of column
                ;               di - offset of
                ;                 present byte
                ;....first calculate number of
                ;     vertical,horizontal counts
        mov     dx,ymax_s       ;compute number of
                                ;vertical lines
        sub     dx,ymin_s       ;
        inc     dx              ;and save in dx mov     ax,urh_cor      ;compute number of
                                ;horizontal bytes
        sub     ax,ulh_cor      ;(a number 1-79)
        mov     bh,al           ;and save in bh ;..........left edge of box
        lea     di,even_pixels  ;get offset of
        add     di,ulh_cor      ;upper left hand corner
                                ;of window mov     cx,xmin_s       ;compute mask to draw
                                ;left end of top line
        call    mask0           ;[mask0 gives pixels to
                                ;left of x coordinate]
        xor     bl,0FFH         ;[requiring
                                ;complementation here]
```

```
        or      es:[di],bl          ;

mov     cx,xmin_s           ;compute mask for
                                    ;setting leftmost box edge
        call    mask1               ;
        call    drw_ln              ;draw the left most
                                    ;border of the box lea     di,even_pixels      ;get offset of
        add     di,llh_cor          ;lower left hand corner
                                    ; of window
        mov     cx,xmin_s           ;compute mask to draw
                                    ;left end of bottom line
        call    mask0               ;[mask0 gives pixels to
                                    ;left of x coordinate]
        xor     bl,0FFH             ;[requiring
                                    ;complementation here]
        or      es:[di],bl          ;

;..........bottom edge of box
        mov     bl,bh               ;save number of
                                    ;horizontal bytes in bl
        call    hbar                ;draw horizontal bar ;..........top edge of box
        mov     bh,bl               ;get number of
                                    ;horizontal bytes from bl
        lea     di,even_pixels      ;get offset of
        add     di,ulh_cor          ;upper left hand corner
                                    ;of window
        call    hbar                ;draw horizontal bar ;..........right edge of box
        lea     di,even_pixels      ;get offset of
        add     di,urh_cor          ;upper left hand corner
                                    ;of window
```

```
        mov     cx,xmax_s       ;compute mask to draw
                                ;right end of top line
        call    mask0           ;
        or      es:[di],bl      ;

mov     cx,xmax_s       ;compute mask for
                                ;setting rightmost box edge
        call    mask1           ;
        call    drw_ln          ;set rightmost box edge lea     di,even_pixels  ;get offset of
        add     di,lrh_cor      ;lower right hand corner
                                ;of window
        mov     cx,xmax_s       ;compute mask to draw
                                ;right end of bottom line
        call    mask0           ;
        or      es:[di],bl      ;

;..........restore all registers which
        ;              were corrupted
        pop     es              ;
        pop     ds              ;
        pop     di              ;
        pop     si              ;
        pop     dx              ;
        pop     cx              ;
        pop     bx              ;
        pop     ax              ;

pop     bp              ;restore BASIC base
                                ;pointer before returning
        ret     0               ;delete 0 parameter
                                ;addresses (0 bytes) from
                                ;stack and return to
                                ;calling routine
axes endp
```

```
;----------------------------------------;
; subroutine scaler(indata_ptr,outdata_   ;
; ptr,numval)                             ;
;----------------------------------------;
                ;subroutine to scale data values within
                ;limits
                ;corresponding to data window. As a
                ;convenience,
                ;the data is inverted so ymax_d is at
                ;top of
                ;the window (screen values increase
                ;towards
                ;bottom of the screen)
                ;
                ;scaling occurs in two passes: first y
                ;is scaled, then x
scaler          proc    far
                public  scaler   ;public symbols allow
                                         external references
                assume  cs:cseg_gr,es:dgroup
                ;BASIC defines regs
                assume  ss:dgroup,ds:dseg_wind push    bp      ;save base pointer for the
                        ;return to BASIC
        mov     bp,sp   ;point stack pointer at frame
                        ;structure ;..........save additional registers and
                ;         set up extra data seg
        push    ax      ;
        push    bx      ;
        push    cx      ;
        push    dx      ;
        push    si      ;
        push    di      ;
```

```
        push    ds              ;

mov     ax,dseg_wind    ;set up extra data
                                ;segment as assumed
        mov     ds,ax           ;
        ;....get data from BASIC point by point
        ;            and scale according to
        ;       data window. (use di,bx as
        ;       holding registers)

mov     si,es:[bp].outdata_ptr
                ;get pointer for scaled data output
        mov     si,es:[si]      ;pointer is now in si
        mov     outptr,si       ;save output pointer mov     si,es:[bp].numval
                ;get number of points to scale into cx
        mov     cx,es:[si]      ;
        mov     numvalt,cx      ;save value for second
                                ;pass mov     si,es:[bp].indata_ptr
                ;get pointer to BASIC's array of data
        mov     si,es:[si]              ;pointer for
                                ;input is now in si
        mov     di,outptr               ;pointer for
                                ;output is now in di mov     bx,ymax_s       ;put screen scale into
                                ;bx
        sub     bx,ymin_s       ;

mov     ax,bx           ;use half screen scale
                                ;as a roundoff correction
        shr     ax,1            ;
        mov     rndoff,ax       ;

mov     bp,ymax_d       ;put data scale into bp
```

```
        sub     bp,ymin_d       ;
getval: mov     ax,es:[si]      ;get data value from
                                ;BASIC cmp     ax,ymin_d       ;if less than ymin_d
        jle     minval          ;then use minimum value
        sub     ax,ymax_d       ;if greater than ymax_d
        jge     maxval          ;then use maximum value
        neg     ax              ;ax now has distance
                                ;from full scale mul     bx              ;multiply by screen
                                ;scale (corrupts dx)
        add     ax,rndoff       ;add roundoff correction
        jnc     div_d           ;if no carry (ax,dx)
                                ;pair is correct
        inc     dx              ;otherwise increment dx
                                ;(carry from add)
div_d:  div     bp              ;and divide by data
                                ;scale
        add     ax,ymin_s       ;add screen offset value
                                ;to get final scaled
        jmp     nextval         ;value maxval: mov     ax,ymax_s       ;insert maximum value
        jmp     nextval         ;

minval: mov     ax,ymin_s       ;insert minimum value
        jmp     nextval         ;

nextval:mov     es:[di],ax      ;store y-scaled result
                                ;in BASIC output array
        inc     si              ;point to next data
                                ;value (integer is 2 bytes)
        inc     si              ;
        inc     di              ;point to next output
                                ;point for y-scaled data
        inc     di              ;
```

```
        loop     getval           ;if cx shows points
                                  ;remain, scale them ;..........scale x-axis
        mov      di,outptr        ;point di to beginning
                                  ;of output array
        mov      cx,numvalt       ;restore counter for
                                  ;number of points mov      bp,xmax_s        ;put screen scale into
                                  ;bp
        sub      bp,xmin_s        ;

mov      bx,639           ;initialize bx_last to
                                  ;rightmost pixel
        mov      bx_last,bx       ;

xor      ax,ax            ;zero ax,bx to start
        xor      bx,bx            ;bx points to x-unscaled
                                  ;source get_ysc: mov     si,es:[di][bx]   ;get current value y
                                  ;scaled value into si mov      ax,bx            ;calculate twice x-
                                  ;coordinate plus 1
        inc      ax               ;(gives proper roundoff)

mul      bp               ;multiply by screen
                                  ;scale (corrupts dx)
div_x:  div      numvalt          ;scale by number of
                                  ;input points
        and      ax,0FFFEH        ;trim off lsb for
                                  ;aligned access to words
        xchg     ax,bx            ;save source ptr in ax,
                                  ;using bx to point to
                                  ;offset of destination
```

```
                cmp     bx,bx_last          ;(which is a word)
                                            ;see if we are on the
                                            ;same x-coordinate
                jne     y_save              ;if not put a valid
                                            ;abcissa at this coordinate
                cmp     es:[di][bx],si      ;compare yscaled value
                                            ;to last yscaled value
                jle     y_more              ;stored. if y was
                                            ;greater or equal then keep it
y_save:         mov     es:[di][bx],si      ;else store yscaled
                                            ;value in output array
                mov     bx_last,bx          ;save current
                                            ;destination pointer y_more:         xchg    bx,ax               ;restore bx register inc     bx                  ;point to ne   input
                                            ;point
                inc     bx                  ;
                loop    get_ysc             ;continue scaling x
                                            ;until counter cx is zero ;..........restore all registers which
                ;          were corrupted
                pop     ds                  ;
                pop     di                  ;
                pop     si                  ;
                pop     dx                  ;
                pop     cx                  ;
                pop     bx                  ;
                pop     ax                  ;

pop     bp                  ;restore BASIC base
                                            ;pointer before returning
                ret     6                   ;delete 3 parameter
                                            ;addresses (6 bytes) from
```

```
                                        ;stack and return to
                                        ;calling routine
scaler   endp ;----------------------------------;
         ; utility routines local to the window ;
         ; module                               ;
         ;----------------------------------;

;..........utility procedure for fast
         ;          clearing of vertical cols
clr_col  proc    near mov     cx,dx           ;set up counter for
                                 ;clearing first column
clr_lp:  and     es:[di],bl      ;clear a graphics byte
                                 ;using mask
         xor     di,2000H        ;switch even/odd pixel
         test    di,2000H        ;if odd pixel go to
loop                             ;     statement
         jnz     go_clr          ;
         add     di,80           ;go to next even/odd
                                 ;pair
go_clr:  loop    clr_lp          ;continue clearing this
                                 ;column
         ret                     ;

clr_col  endp

;..........utility procedure for fast
         ;          drawing of vertical lines
drw_ln   proc    near mov     cx,dx           ;set up counter for
                                 ;clearing first column
drw_lp:  or      es:[di],bl      ;set a graphics bit
                                 ;using mask
```

```
            xor     di,2000H            ;switch even/odd pixel
            test    di,2000H            ;if odd pixel go to loop
                                        ;statement
            jnz     go_drw              ;
            add     di,80               ;go to next even/odd
                                        ;pair
go_drw:     loop    drw_lp              ;continue clearing this
                                        ;column
            ret                         ;

drw_ln      endp

;..........utility for fast drawing of
            ;          horizontal lines
hbar        proc    near    ;requires di to have byte before
                            ;first byte of line
                            ;bh is used as a decrementing
                            ;byte counter for number
                            ;of bytes drawn dec     bh                  ;check to make sure at
                                        ;least one byte to plot
            jz      hbar_ok             ;if bh=0 then done
hbar_lp:    inc     di                  ;go to next byte
            mov     byte ptr es:[di],0FFH    ;set byte
            dec     bh                  ;decrement number of
                                        ;bytes remaining
            jnz     hbar_lp             ;continue if more bytes
                                        ;need to be drawn hbar_ok:    ret                         ;

hbar        endp

;..........utility procedure for
            ;          computing bit mask for clears
```

```
mask0   proc    near        ;uses value in cx to compute bit
                            ;mask in bl and     cl,7        ;using cx mod 8
        mov     bl,0FFH     ;put mask in bl
        jz      mask0_ok    ;if .. mod 8 <>0 then
        shr     bl,cl       ;shift mask
                            ;appropriately
mask0_ok:xor    bl,0FFH     ;complement mask to set
                            ;bits to be retained
        ret mask0   endp ;..........utility procedure for
        ;          computing bit mask for drawing
mask1   proc    near        ;uses value in cx to compute bit
                            ;mask in bl
        and     cl,7        ;using cx mod 8
        mov     bl,80H      ;put mask in bl
        jz      mask1_ok    ;if cx mod 8 <>0 then
        shr     bl,cl       ;shift mask
                            ;appropriately
mask1_ok:ret mask1   endp cseg_gr ends
        end ; subroutine fgraph (data_ptr,numval,x_coord,line_type)
;       called from BASIC this routine graphs an array
;       on the screen
;       this routine is designed to allow rapid access
```

```
;               to the screen to allow
;               real time graph generation.
;
;---------------------------------------------------------------
;
;                 arguments passed by BASIC
;
;
;         data_ptr          - offset of BASIC array
;                             containing y-coordinates of
;                             points to be plotted
;         numval            - number of values to plot
;         x_coord           - absolute (screen) x coordinate
;                             of first point
;                             succeeding values are plotted
;                             at succeeding pixels
;         line_type         - if 0 then just plot points
;                             if not zero this byte value
;                             gives the line mask for
;                             plotting various lines
;                             (eg. 55H interpolates a line
;                             between adjacent
;                             points with every other point
;                             on the interpolation
;                             line; in other words, a fine
;                             dotted line)
;
;---------------------------------------------------------------

;..........screen memory definition screen_memory   segment at 0B800H
even_pixels     db      8000 dup(?)     ;pixels with
                                        ;even y-coordinates
                org     2000H           ;beginning of
                                        ;high screen memory
```

```
odd_pixels      db      8000 dup(?)         ;pixels with odd
                                            ;y-coordinates
screen_memory   ends frame   struc                       ;define structure
savebp          dw      ?           ;caller's base pointer
save_es         dw      ?           ;save es on stack for
                                    ;return to BASIC
saveret         dd      ?           ;return offset and
                                    ;segment pushed by BASIC
line_type       dw      ?           ;mask for plotting
                                    ;various line types
x_coord         dw      ?           ;x_coordinate of first
                                    ;point to be plotted
numval          dw      ?           ;number of values in
                                    ;graph_data(*) array
data_ptr        dw      ?           ;values to be graphed
                                    ;are passed in an array
                                    ;graph_data(*) pointed
                                    ;to by this pointer.
frame   ends cseg    segment 'code'
dgroup  group   data,stack,const,heap,memory
        ;defining link to BASIC
        assume  cs:cseg,ds:dgroup,ss:dgroup
        ;BASIC defines regs
        assume  es:screen_memory            ;use extra data
                                            ;segment to access the
                                            ;screen memory fgraph  proc    far
        public  fgraph                      ;public symbols allow
                                            ;external references
```

```
        push    es              ;save BASIC's es
                                ;register
        push    bp              ;save base pointer for
                                ;the return to BASIC
        mov     bp,sp           ;point stack pointer at
                                ;frame structure ;..........save additional registers
        push    ax              ;
        push    bx              ;
        push    cx              ;
        push    dx              ;
        push    si              ;
        push    di              ;

;this routine assumes that the proper
                ;graphics
                ;mode has been established (eg., <SCREEN
                ;2>)

mov     si,[bp].numval  ;get number of points
                                ;remaining to be graphed.
        mov     ax,[si]         ;
        or      ax,ax           ;if number of
                        ;repetitions is zero we're done.
        jnz     setup           ;otherwise there is work
                                ;remaining.
        jmp     finish          ;done ;..........temporary storage area
                ;           (aligned on word boundary)

even
numval_t        dw      ?       ;number of points left
                                ;to plot
```

```
x_now       dw      ?       ;byte offset in screen
                            ;memory for x-coordinate
last_x      dw      ?       ;last x-coord (saved for
                            ;return to BASIC)
last_y      dw      ?       ;last y-coord (used only
                            ;for line plots)
last_di     dw      ?       ;last screen offset
                            ;(used only for line plots)
line_mask   db      ?       ;line mask is the
                            ;rotating buffer which is
                            ;to generate various
                            ;dotted/dashed lines
pixel_mask  db      ?       ;pixel mask is used to
                            ;set one pixel in the
                            ;screen memory (using an
                            ;OR instruction)

setup:  mov     last_di,0ffffH      ;initialize last_di to
                                    ;ffff
        mov     numval_t,ax         ;save number of points
                                    ;to plot
        mov     si,[bp].line_type   ;get line type mask
                                    ;from BASIC
        mov     ax,[si]             ;
        mov     line_mask,al        ;and store lower byte in
                                    ;local storage mov     si,[bp].x_coord     ;get x coordinate of
                                    ;first point from BASIC
        mov     ax,[si]             ;
        mov     bx,numval_t         ;get number of points in
                                    ;order
        dec     bx                  ;to compute
        add     bx,ax               ;the last x-coordinate
        cmp     bx,640              ;x-coordinate is modulo
                                    ;640
        jle     lst_x               ;if less than 640 store
```

```
                                        ;value
        sub     bx,640                  ;else make less than 640
lst_x:  mov     last_x,bx               ;store last_x value for
                                        ;return to BASIC mov     bx,seg even_pixels      ;set up screen
                                        ;memory as extra segment
        mov     es,bx                   ; (note: cannot move an
                                        ;immediate direct to es)

mov     cl,al                   ;get low byte of x_
                                        ;coordinate
        and     cl,7                    ;modulo 8
        mov     pixel_mask,80H          ;initialize pixel mask
                                        ;to first bit
        jz      mask_ok                 ;if x_coord mod 8 is
                                        ;zero, the mask is ok
        shr     pixel_mask,cl           ;rotate mask bit to
                                        ;correct position mask_ok:mov     cl,3                    ;x_coord/8 is byte
                                        ;offset for pixel
        shr     ax,cl                   ;this result is termed x_
                                        ;now
        mov     x_now,ax                ;

mov     di,[bp].data_ptr
        ;use [si] with offset in bx to access y
        mov     si,[di]                 ;coordinates in BASIC
                                        ;data(*) array
        mov     bx,0                    ;initialize to first
                                        ;element of array
        mov     dx,[si][bx]             ;get first y-coordinate
                                        ;from BASIC
        mov     last_y,dx               ;and initialize last_y get_y:  mov     dx,[si][bx]             ;get y-coordinate from
                                        ;BASIC
```

```
        mov     ax,dx               ;ax is used to calculate
                                    ;screen memory offset
        shr     ax,1                ;divide by two to get
                                    ;rid of lsb
        mov     cl,80               ;80 bytes per line (lsb
                                    ;gives interlace)
        mul     cl                  ;ax is offset for y-
                                    ;coord in screen memory
        add     ax,x_now            ;add offset for x-
                                    ;coordinate to y offset in ax
        mov     di,ax               ;and put x,y offset into
                                    ;di
        test    dx,1                ;if y_coordinate was
                                    ;even
        jz      ln_beg              ;then we are ready to
                                    ;plot a point or a line
        add     di,2000H            ;odd pixels require the
                                    ;interlace offset ln_beg: cmp     last_di,0ffffH      ;if last_di is not ffff
                                    ;(first point)
        jne     1st_di              ;then go to set next
                                    ;pixel
        mov     last_di,di          ;else initialize di
                                    ;properly
1st_di: cmp     line_mask,0         ;if line mask is not 0
        jne     draw_line           ;then draw the
                                    ;approrpiate line
set_px: mov     al,pixel_mask       ;else set pixel using OR
                                    ;with mask
        or      even_pixels[di],al
        jmp     more                ;and go to next point ;..........drawing the required line draw_line:xchg  di,last_di          ;get old screen memory
                                    ;location to start
```

```
            mov     cx,last_y           ;cx will be the y
                                        ;distance to current pixel
            sub     cx,dx               ;dx still has current y-
                                        ;coord.
            jcxz    ln_done             ;if cx is zero then plot
                                        ;only one point
            jg      nxt_pxu             ;if last_y>y-coord then
                                        ;draw up on screen
                                        ;since lowest y is at
                                        ;top of screen ;..........draw a line down on screen
            ;          (increasing y)

neg     cx                  ;cx was negative
            jmp     nxt_pix             ;only plot one point per
                                        ;y-coord if possible
dn_lp:      shl     line_mask,1         ;set up line mask for
                                        ;next pixel
            jnc     nxt_pix             ;if no bits are shifted
                                        ;out then no pixel here
            or      line_mask,1         ;is msb was shifted out,
                                        ;now set lsb
            mov     al,pixel_mask       ;load pixel mask and
            or      even_pixels[di],al  ;set pixel using
                                        ;OR with mask ;..........now find next pixel position
            ;          for line
nxt_pix:xor di,2000H             ;change from high to low
                                        ;memory (or vice versa)
            test    di,2000H            ;if in high screen
                                        ;memory
            jnz     dn_di               ;then di points to next
                                        ;pixel
            add     di,80               ;else go to next line in
                                        ;lower memory
```

```
dn_di:  loop    dn_lp           ;do another pixel in
                                ;this line
        jmp     ln_done         ;plot last pixel when
                                ;done ;..........draw a line up on screen
                ;              (decreasing y)

up_lp:  shl     line_mask,1     ;set up line mask for
                                ;next pixel
        jnc     nxt_pxu         ;if no bits are shifted
                                ;out then no pixel here
        or      line_mask,1     ;is msb was shifted out,
                                ;now set lsb
        mov     al,pixel_mask   ;load pixel mask and
        or      even_pixels[di],al    ;set pixel using
                                      ;OR with mask ;..........now find next pixel position
                ;              for line
nxt_pxu:xor     di,2000H        ;change from high to low
                                ;memory (or vice versa)
        test    di,2000H        ;f in low screen memory
        jz      up_di           ;then di points to next
                                ;pixel
        sub     di,80           ;else go to next line in
                                ;upper memory
up_di:  loop    up_lp           ;do another pixel in
                                ;this line
;       jmp     ln_done         ;plot last pixel when
                                ;done(statement not needed
;                                here)

;..........finish up with line by
                ;              storing current data
ln_done:shl     line_mask,1     ;set up line mask for
```

```
                                ;next pixel
        jnc     end_pix         ;if no bits are shifted
                                ;out then no pixel here
        or      line_mask,1     ;is msb was shifted out,
                                ;now set lsb
        mov     al,pixel_mask   ;load pixel mask and
        or      even_pixels[di],al   ;set pixel using
                                     ;OR with mask
end_pix:mov     last_y,dx       ;save present y-
                                ;coordinate
        mov     last_di,di      ;save present
                                ;pixel byte pointer ;..........prepare for next point if
        ;          there is one more:   dec     numval_t        ;one less point left now
        jz      finish          ;finished if none left
        inc     bx              ;if not done increment
                                ;base index by 2 to point
        inc     bx              ;to next y-coord in
                                ;BASIC array
        shr     pixel_mask,1    ;move pixel mask to next
                                ;x-coord
        jnz     go_gety         ;if mask points to some
                                ;pixel get the y-coord
        mov     pixel_mask,80H  ;otherwise set up mask
                                ;for next 8 x-coordinates
        inc     x_now           ;x_now points to next
                                ;byte (for next 8 pts)
        inc     last_di         ;fix last di to point to
                                ;present column
        cmp     x_now,80        ;there are only 80 bytes
                                ;per line, so
        jl      go_gety         ;if x_now<80 then x_now
                                ;is ok to get next y
        mov     x_now,0         ;otherwise wrap around
```

```
                                        ;to x_now=0
         sub       last_di,80           ;also reset di to first
                                        ;column
go_gety: jmp       get_y                ;

;..........finish up and send present
                   ;          pointers,mask to BASIC finish:  mov       al,line_mask         ;get present line mask
         xor       ah,ah                ;zero upper byte
         mov       si,[bp].line_type    ;and
         mov       [si],ax              ;send to BASIC
         mov       ax,last_x            ;get last x-coordinate
         mov       si,[bp].x_coord      ;and send to BASIC
         mov       [si],ax              ;

;..........restore all registers which
                   ;          were corrupted
         pop       di                   ;
         pop       si                   ;
         pop       dx                   ;
         pop       cx                   ;
         pop       bx                   ;
         pop       ax                   ;

pop       es                   ;restore the es register
                                        ;and
         pop       bp                   ;restore BASIC base
                                        ;pointer before returning
         ret       8                    ;delete 4 parameter
                                        ;addresses (8 bytes) from
                                        ;stack and return to
                                        ;calling routine
fgraph   endp
cseg     ends
         end
```

APPENDIX C

```
' CALIB - program to calibrate instruments using
'    board#1
' last revision:  1985 defint a-y
    ' only z denotes a real number
    dim buffer(12800)
    hrbpm=0
    zfqlow=0.
    zfqres=0.
    zlfa=0.
    zrfa=0.
    cls 'define ports on 8253
    timer0=&h704
    timer1=&h705
    timer2=&h706
    con8253=&h707

' set timer modes to 16 bit square wave rate
    '    generators
    out con8253,&h36
    out con8253,&h76
    out con8253,&hB6

'for testing set timer 0 to 100Hz timebase
    out timer1,164
    out timer1,3
```

```
out timer2,0
'set timer 0 to 1280Hz timebase
out timer2,5
' (2.38MHz/1864) (1864=2*256+104)
                              'set timer 2 as a 1Hz
                              ' clock at
                              'startup
hrbpm=60                      '(gives a heart rate
                              ' signal at
                              '60bpm)
out timer0,1                  'set timer 0 as a flip
                              ' flop
out timer0,0                  '

' turn the gates on using the 8255 at bits 0,1,2
'    on portc
porta=&H70C
portb=&H70D
portc=&H71E
con8255=&H71F
' port A output port B input port C output
' first set all 8255 ports to output, then set
'   portc to
' 0FFH
out con8255,130
out portc,&H0FF ' first print out the present value of the
'    interrupt
' vectors
locate 4,1
gosub 10000

' install the interrupt with a dummy buffer and
```

```
'   print
'   vectors
reseter=256
call wrbuffer(reseter)
reseter=128
call wrbuffer(reseter)
call instint
locate 5,1
gosub 10000

' now go through required startup subroutines
gosub 90
' set up breathing signal
gosub 70
' set up heart rate variations
gosub 50
' put some information on s--en
gosub 80                     ' turn D/A on
locate 1,1
print "commands: h(rvar),i(nt
        on),q(uit),r(beats),b(reath),c(ounts)"

' wait until user hits a key
savekey$=""
```
40      while len(savekey$)=0:savekey$=savekey$+inkey$:wend
```
        if savekey$="r" then gosub 50
        'print heart beats
        if savekey$="q" then goto 9996   'quit
        if savekey$="c" then gosub 60    'print timers
        if savekey$="h" then gosub 70
        'set up heart rate variations unmask interrupts
        if savekey$="i" then gosub 80
        if savekey$="b" then gosub 90
        'set up breathing signal
        savekey$=""
```

```
           goto 40

'print present value of heartbeats 50    locate 7,1
      call rdbeat(n)
      print "present heart beats are: ";n;time$
      return ' print present value of counters
60    out control,0            'latch timer0
      tlow0=inp(timer0)
      thigh0=inp(timer0)
      out control,&h40         'latch timer1
      tlow1=inp(timer1)
      thigh1=inp(timer1)
      out control,&h80         'latch timer2
      tlow2=inp(timer2)
      thigh2=inp(timer2)
      locate 8,1
      print "timer0: ";tlow0+thigh0*16;tab(20);"      timer1: ";tlow1+thigh1*16;
      print tab(40);"timer2: ";tlow2+thigh2*16
      return ' set up the heart rate variations
      '     respiratory frequency is given by
      '        1280Hz/buffer
      '         length
      '        low frequency is 1280Hz/low frequency
      '          divider
      '
70    if numval<=0 then beep:print "setup analog
            buffer first":return
```

```
71      locate 17,1
        print "present lfa,rfa(bpm)= ";zlfa,zrfa,"at
freqs(Hz):";zfqlow,zfqres
        input "lfa,rfa,low freq: ",zlfan,zrfan,zfqlown
        if zlfan>30. then beep:goto 71 else zlfa=zlfan
        if zrfan>30. then beep:goto 71 else zrfa=zrfan
        if zfqlown<.02 or zfrlown>zfqres then beep:goto
71 else
        zfqlow=zfqlown
        locate 21,1
        print "mean heart rate(bpm)= ";hrbpm
72      locate 22,1
        input "new mean heart rate(bpm): ",newhrbpm
        if newhrbpm>150 or newhrbpm<30 then beep:goto 72
else
        hrbpm=newhrbpm
            'clear screen after input
        locate 17,1
        print space$(72)
        print space$(72)
        print space$(72)
        print space$(72)
        print space$(72)

' now compute values for hrsetup subroutine
        meandiv=76800#/hrbpm    '1280*60 ticks/min gives
                                '    ticks/beat
        rfascal=76800#/(hrbpm-zrfa)-76800#/(hrbpm+zrfa)
                ' rfascal is the total excursion
                '     of respiration
        lfascal=76800#/(hrbpm-zlfa)-76800#/(hrbpm+zlfa)
                ' lfascal is the total excursion
                '     of low frequency
        lowdiv=meandiv-(rfascal+lfascal)/2# tbaserst=1280#/zfqlow
        locate 17,1
```

```
           print "tbaserst,rfascal,lfascal,lowdiv:
               ";tbaserst;rfascal;lfascal;
           print lowdiv
           call hrsetup(tbaserst,rfascal,lfascal,lowdiv)

return

' print out interrupt controller parameters
80         locate 10,1
           mask=inp(&h21)
           mask=maskx or 24
           out &h21,mask
           mask=inp(&h21)
           print "8259 IMR(interrupt mask regsiter)=
";mask;"
               =";hex$(mask)
           return ' this subroutine will change the analog buffer
90         locate 12,1
           input "enter breathing rate (bpm): ",brate
           if brate>75 or brate<7 then beep:goto 90
           zfqres=brate/60#
           numval=76800#/brate
           ztincr=8*ATN(1#)/numval
           locate 12,40
           color 31:print "calculating respiratory
signal...":color
               7
           call exstint              ' turn off interrupts
                                     '     while
               resetting buffer
           reseter=256
           call wrbuffer(reseter)
```

```
            for itime=0 to numval
                ztnow=ztnow+ztincr
                analogval=127*(1#+SIN(ztnow))
                call wrbuffer(analogval)
            next itime
            call instint
            locate 12,40
            print "respiratory signal active now      "
            return ' exstall the interrupt and print vector
9996        cls
            locate 4,1
            gosub 10000
            call exstint
            locate 5,1
            gosub 10000
            locate 21,1
9999        stop ' subroutine to print out the interrupt vectors
10000       def seg=0
            print "IRQ3 @0B*4H: ";hex$(peek(&h2C));"
                ";hex$(peek(&h2D));" ";
            print hex$(peek(&h2E));"
";hex$(peek(&h2F));tab(40);
            print "IRQ4 @0C*4H: ";hex$(peek(&h30));"
                ";hex$(peek(&h31));" ";
            print hex$(peek(&h32));" ";hex$(peek(&h33))
            return end
                page    66,80
; bdzint.asm - an assembler routine to handle interrupts
;               from IRQ3
```

```
; Last revision:  1 April 1985
;
;
                        ;--------------------------------;
                        ; 8088 interrupt location        ;
                        ;--------------------------------;

abs0            segment at 0    ;absolute memory segment
                                ;allows placement of
                                ;interrupt address
                                ;future timebase
                                ;  interrupt handler
                                ;  resides at int 0B
IRQ3_int        dw      2 dup(?);offset value is a word org     0CH*4   ;heart beat interrupt
                                ;handler resides at int
                                ; 0C
IRQ4_int        dw      2 dup(?);offset value is a word abs0            ends            ;

;--------------------------------;
                        ; int_buffer: area to save DOS   ;
                        ;      dummy interrupt ptr       ;
                        ;--------------------------------;

int_buffer      segment         ;data segment containing
                                ;user interrupt buffer
save_int        dw      4 dup(?);offset for two DOS
                                ;interrupts saved
                                ;to be restored using
                                ;exstint int_buffer      ends            ;
```

```
;----------------------------;
; working storage for        ;
; time base interrupts       ;
;----------------------------;

dseg_tbase      segment             ;data segment for timebase
                                    ; interrupt
heartbeats      dw      ?           ;keep track of heart beats
                                    ; here (for debugging)
base_rate       dw      ?           ;lowest divisor for heart
                                    ; rate
lfa_scal        db      ?           ;low frequency modulation
rfa_scal        db      ?           ;high frequency modulation
tbase_ctr       dw      ?           ;counter for timebase
                                    ; interrupt
                                    ;(use for low frequency
                                    ;  generation)
tbase_rst       dw      ?           ;reset value for tbase_ctr
                                    ; used to set low frequency
tbase_ptr       dw      ?           ;pointer to present analog
                                    ; value
tbase_len       dw      ?           ;length of analog data buffer
tbase_buffer    db   2800dup(?)     ;buffer for A/D values
dseg_tbase      ends        ;
                ;---------------------------------------;
                ; setup structures to allow access to;
                ; arguments pased by BASIC              ;
                ;---------------------------------------;

; subroutine rdbeat(BASIC_beats)
frame_rd        struc               ;define the stack
                                    ;structure for passing
                                    ;arguments to BASIC
savebp1         dw      ?           ;caller's base pointer
saveret1        dd      ?           ;return offset and
                                    ;segment pushed by BASIC
```

```
BASIC_beats      dw      ?         ;place to return heart
                                   ;beats to BASIC
frame_rd         ends ;subroutine wrbuffer (analog)
frame_wr         struc             ;define the stack structure
                                   ;   for passing
                                   ;arguments from BASIC to
                                   ;   analog buffer
savebp2          dw      ?         ;caller's base pointer
saveret2         dd      ?         ;return offset and segment
                                   ;   pushed by BASIC
analog           dw      ?         ;place to receive analog value
                                   ;   from BASIC
frame_wr         ends ;subroutine hrsetup(B_lreset,
                 ;   Brfa_scal,Blfa_scal,Bbase_
                 ;   rate)
frame_hr         struc             ;define the stack structure for
                                   ;   passing
                                   ;arguments from BASIC to heart
                                   ;   rate controls
savebp3          dw      ?         ;caller's base pointer
saveret3         dd      ?         ;return offset and segment pushed
                                   ;   by BASIC
Bbase_rate       dw      ?         ;BASIC's lowest divider for heart
                                   ;   rate
Blfa_scal        dw      ?         ;BASIC's low frequency scaler
                                   ;   (amplitude)
Brfa_scal        dw      ?         ;BASIC's high frequency scaler
                                   ;   (amplitude)
B_lreset         dw      ?         ;BASIC's low frequency timer
                                   ;   reset value
frame_hr         ends ;..........code segment begins here
```

```
cseg_calibs        segment 'code'
basic_dgroup       group    data,stack,const,heap,memory
                                     ;defining link to BASIC
porta              equ      0700H    ;port definitions for
                                     ;8255 port expander
portb              equ      0708H    ;these addresses are
                                     ;decoded on the homemade
portc              equ      0710H    ;board
control            equ      0718H    ;control word in the
                                     ;8255
timer0             equ      0720H    ;8253 timer0 register
timer1             equ      0721H    ;8253 timer1 register
timer2             equ      0722H    ;8253 timer2 register
con8253            equ      0723H    ;8253 control register ;-----------------------------------------------------;
; timebase interrupt handler (not accessible to;
; BASIC)                                              :
;-----------------------------------------------------;
                   ;this routine reads the A/D every timer)
                   ;tick
                   ;with the next point in the analog
                   ;buffer tbase_int          proc     far      ;this procedure is not
                                     ;made public
                   assume   cs:csey_sync,ds:dseg_
                      base,es:nothing,ss:nothing
                   push     ax       ;save registers used
                                     ;during interrupt
                   push     bx       ;
                   push     dx       ;
                   push     ds       ;

mov      ax,dseg_base   ;set up segment
                                     ;register for data area
```

```
            mov     ds,ax           ;

;..........increment counter used for
            ;low frequency generation
    dec     tbase_ctr   ;decrement
                        ; interrupt counter
    jnz     ctr_ok      ;if not zero then
                        ;  continue
    mov     ax,tbase_rst ;else reload reset
                        ;value
    mov     tbase_ctr,ax ;
ctr_ok:
;..........get analog value from
;buffer and send to DAC mov     bx,tbase_ptr ;get pointer to
                        ;analog data
    dec     bx          ;
    mov     al,tbase_buffer[bx]   ;get analog
                        ;         value mov     dx,porta    ;send analog value
                        ;to DAC
    out     dx,al       ;

mov     dx,control  ;toggle the write
                        ;latch for the DAC
    mov     al,6        ;by using direct bit
                        ;reset
    out     dx,al       ;and
    inc     al          ;reset commands
    out     dx,al       ;

dec     tbase_ptr   ;point to next
                        ;value
```

```
                jnz     tbase_eoi       ;if zero, reset
                                        ;pointer
                mov     ax,tbase_len    ;reset with buffer
                                        ;length
                mov     tbase_ptr,ax    ;

;..........acknowledge interrupt to
                ;              8259A
tbase_eoi:      mov     al,20H          ;send EOI to 8259A
                out     20H,al          ;

pop     ds              ;restore registers which
                                        ;were used
                pop     dx              ;
                pop     bx              ;
                pop     ax              ;
                iret                    ;return to place where
                                        ;interrupt occurred debugmsg1       db      'this is the end of the time
                        base interrupt' tbase_int       endp

;------------------------------------------------;
; heart beat interrupt handler (not accessible   ;
; to BASIC)                                      ;
;------------------------------------------------;

;this routine updates the timer1 rate generator
;every heart beat with the divider necessary to
;generate the next heart beat
;
;the respiratory modulation is given by a scaler
;   (0-255)
```

```
                ;times the present value of the respiratory
                ;   signal.
                ;the low frequency modulation is given by scaler
                ;   (0-255)
                ;times a value selected from the respiratory
                ;   buffer.
                ;the value selected is the
                ;   (tbase_ctr/tbase_rst)*buffer_length
                ;element hbeat_int       proc    far         ;this procedure is not
                                    ;made public
                assume  cs:cseg_calibs,ds:dseg_tbase
                assume  es:nothing,ss:nothing
                push    ax          ;save registers during
                                    ;interrupt
                push    bx          ;
                push    cx          ;
                push    dx          ;
                push    ds          ;

mov     ax,dseg_tbase   ;set up segment
                                        ;register for data area
                mov     ds,ax           ;

inc     heartbeats  ;increment heart
                                    ;   beat counter ;........calculate low frequency
                ;           modulation
                ; (the tbase buffer is used as a trig
                ;   table here)
                mov     ax,tbase_ctr    ;get number of
                                        ;1280Hz pulses
                dec     ax              ;
                mul     tbase_len       ;scale by length
                                        ;of respiratory
                                        ;   buffer
```

```
        div     tbase_rst       ;divided by reset
                                ;value to get
                                        pointer
        mov     bx,ax           ;to low frequency
                                ; modulation
        mov     al,tbase_buffer[bx]   ;get
                                ; sinusoidal
                                ; modulation
        mul     lfa_scal        ;and scale
                                ; appropriately
        mov     cx,ax           ;cx accumulate
                                ;divider for
                                ; 1280Hz clock ;........calculate respiratory
;              modulation
        mov     bx,tbase_ptr    ;get present
                                ;respiration
                                ;signal
        mov     al,tbase_buffer[bx]   ;from
                                ;buffer
        mul     rfa_scal        ;scale with rfa
                                ;scaler
        add     cx,ax           ;and add to cx add     cx,base_rate    ;finally add base
                                ;rate to get
                                ;  value for
                                ;timer1 (heart
                                ;rate
                                ;   on generator
                                ;  8253)

;............... send new divider to 8253
;       timer
        mov     al,76H          ;set timer 1 to
                                ;square wave
                                ;  generator
```

```
            mov     dx,con8253      ;
            out     dx,al           ;

mov     dx,timer1       ;send divider to
                                    ;time1
            mov     al,cl           ;low byte first
            out     dx,al           ;
            mov     al,ch           ;high byte next
            out     dx,al           ;
            ;..........acknowledge interrupt to
            ;          8259A
            mov     al,20H          ;send EOI to 8259A
            out     20H,al          ;

pop     ds              ;restore registers and
            pop     dx              ;
            pop     cx              ;
            pop     bx              ;
            pop     ax              ;
            iret                    ;return to place where
                                    ;interrupt occurred debugmsg2   db      'this is the end of the heart
                    beat interrupt' hbeat_int   endp

;-------------------------------------------------;
; subroutine instint (install_interrupts)         ;
;-------------------------------------------------;

instint     proc    far
            public  instint
            ;public symbol allows external references
            ;es,ds used to access interrupt and must
```

```
;    be restored movsw
;uses (ds:si)(es:di) addr
    assume  cs:cseg_calibs,ss:basic_
        dgroup,ds:basic_dgroup
    assume  es:int_buffer ;..........save registers
    push    ds          ;save ds register on the
                        ;   stack
    push    es          ;save es register on the
                        ;   stack push    bp          ;save BASIC base pointer
                        ;    for return to BASIC
    mov     bp,sp       ;point stack pointer at
                        ;frame reference to
                        ;address of BASIC analog
                        ;data buffer push    ax          ;save additional
                        ;registers
    push    si          ;
    push    di          ;

;set up the segment registers as assumed mov     ax,int_buffer   ;
;es points to buffer area to save
;DOS dummy interrupt vector
    mov     es,ax           ;
    mov     ax,0            ;ds points to
                            ;abs0 (interrupt table)
    mov     ds,ax           ;
    assume  ds:abs0         ;

;setup access to interrupt vectors
    lea     di,save_int     ;load offset of
                            ;save_int in es,di
```

```
            lea     si,IRQ3_int     ;load offset of
                                    ;IRQ3_int in ds,si
            movsw                   ;save DOS dummy
                                    ;interrupt vectors to be
            movsw                   ;restored later
            movsw                   ;now saving IRQ4
            movsw                   ;

;install the DAC timebase (IRQ3)
            mov     IRQ3_int+2,cseg_calibs
            mov     IRQ3_int,offset tbase_int;
                                    ;interrupt handler now
;install the heart beat (IRQ4) interrupt handler now
            mov     IRQ4_int+2,cseg_calibs;
            mov     IRQ4_int,offset hbeat_int;

;..........return to BASIC pop     di      ;restore additional
                              registers
            pop     si      ;
            pop     ax      ;

pop     bp      ;restore BASIC's base
                            ;pointer a..u
            pop     es      ;segment registers
                              before returning
            pop     ds      ;
            ret     0       ;delete 0 parameters (0
                            ;bytes) from the stack
                            ;and return to the
                            ;calling routine debugmsg3   db      'this is the end of the
                    interrupt installation'
instint     endp
```

;----------------------------------;
; subroutine exstint (exstall_     ;
; interrupts)                      ;
;----------------------------------;

```
exstint         proc    far
                public  exstint  ;public symbol allows
                                 ;external references
                assume  cs:cseg_calibs,ss:basic_dgroup
                assume  ds:int_buffer,es:abs0
                ;es,ds used to access interrupt
                ;vectors and must be restored
                ;movsw uses (ds:si)(es:di) addr ;..........save registers push    ds      ;save ds register on the
                                ; stack
                push    es      ;save es register on the
                                ; stack
                push    bp      ;save BASIC base pointer
                                ;   for return to BASIC
                mov     bp,sp   ;point stack pointer at
                                ;   frame reference to
                                ;access arguments passed
                                ;   by BASIC (none here)

push    ax      ;save additional
                                ;registers
                push    si      ;
                push    di      ;
                                ;set up the segment
                                ; registers as assumed
                mov     ax,0            ;es points to
                                ;abs0 (interrupt table)
                mov     es,ax           ;
                mov     ax,int_buffer   ;ds points to
```

```
                    ;buffer area to save
    mov    ds,ax    ;DOS dummy
                    ;interrupt vector ;setup access to interrupt vectors
    lea    di,IRQ3_int   ;load offset of
                         ;IRQ3_int in es,di
    lea    si,save_int   ;load offset of
                         ;save_int in ds,si
    movsw                ;restore DOS
                    ;dummy interrupt vectors
    movsw           ;for IRQ3
    movsw           ;and IRQ4
    movsw           ;

;..........return to BASIC pop    di       ;restore additional
                        registers
    pop    si       ;
    pop    ax       ;

pop    bp       ;restore BASIC's base
    pop    es       ;pointer and segment
    pop    ds       ;registers before
                    ;returning
    ret    0        ;delete 0 parameters (0
                    ;bytes) from the stack
                    ;and return to the
                    ;calling routine
debugmsg4  db       'this is the end of the
                    interrupt exstallation' exstint    endp
```

```
;----------------------------------------;
; subroutine rdbeat (read_heart_beats    ;
;----------------------------------------;

rdbeat          proc    far
                public  rdbeat          ;public symbol allows
                                        ;external references
                assume  cs:cseg_calibs,es:dseg_tbase
                assume  ds:basic_dgroup,ss:basic_dgroup ;..........save registers push    bp              ;save BASIC base pointer
                                        ;for return to BASIC
                mov     bp,sp           ;point stack pointer at
                                        ;frame reference to
                                        ;access arguments passed
                                        ;by BASIC (one here)

push    ax              ;save additional
                                        ;registers
                push    es              ;
                push    di              ;

mov     ax,dseg_tbase   ;set up segment
                                        ;register for data area
                mov     es,ax           ;

mov     ax,heartbeats           ;get
                                        ;beats from local memory
                mov     di,[bp].BASIC_beats     ;
                mov     [di],ax                 ;send
                                        ;beats to BASIC
```

;..........return to BASIC

```
        pop     di          ;restore additional
                            ;   registers
        pop     es          ;
        pop     ax          ;

pop     bp          ;restore BASIC's base
                            ;pointer,
        ret     2           ;delete 2 parameters (4
                            ;bytes) from the stack
                            ;and return to the
                            ;calling routine debugmsg5   db  'this is the end of the heart
                beat read routine' rdbeat  endp

;----------------------------------------;
; subroutine wrbuffer(analog)            ;
;----------------------------------------;

wrbuffer    proc    far
        public wrbuffer     ;public symbol allows
                            ;external references
        assume cs:cseg_calibs,es:dseg_tbase
        assume ds:basic_dgroup,ss:basic_dgroup ;..........save registers push    bp          ;save BASIC base pointer
                            ;for return to BASIC
        mov     bp,sp       ;point stack pointer at
                            ;frame reference to
                            ;access arguments passed
```

```
                           ;by BASIC (one here)

push    ax              ;save additional
                                ;registers
        push    bx              ;
        push    es              ;
        push    si              ;
        mov     ax,dseg_tbase   ;set up segment
                                ;register for data area
        mov     es,ax           ;

mov     si,[bp].analog  ;get analog value
                                ;from BASIC
        mov     ax,[si]         ;
        test    ah,0FFH         ;if upper byte is
                                ;zero
        jz      new_buff        ;then install a
                                ;new point in the
                                ;buffer
        mov     tbase_len,0     ;otherwise reset
                                ;the buffer
        mov     tbase_ptr,1     ;
        jmp     wr_ret          ;
        mov     bx,tbase_len    ;get present
                                ;pointer and use
                                ;it
        mov     tbase_buffer[bx],al ;to store
                                ;buffer value
        inc     tbase_len       ;point to next
                                ;buffer value ;..........return to BASIC pop     si              ;restore additional
                                ;registers
wr_ret: pop     es              ;wr_ret:
        pop     bx              ;
```

```
                pop     ax      ;

pop     bp      ;restore BASIC's base
                                ;pointer,
                ret     2       ;delete 1 parameters (2
                                ;bytes) from the stack
                                ;and return to the
                                ;calling routine debugmsg6       db      'this is the end of the buffer
                         write routine' wrbuffer        endp

;--------------------------------------------------------;
; subroutine hrsetup(B_lreset,Brfa_scal,Blfa_scal,       ;
; Bbase_rate)                                            ;
;--------------------------------------------------------;

proc    far
                public  hrsetup ;public symbol allows
                                        external references
                assume  cs:cseg_calibs,es:dseg_tbase
                assume  ds:basic_dgroup,ss:basic_dgroup ;...........save registers push    bp      ;save BASIC base
                                ;pointer for return
                                ;to BASIC
                mov     bp,sp   ;point stack pointer
                                ;at frame
                                ;reference to
                                ;access arguments
                                ;passed by BASIC
                                ;(one here)
```

```
    push    ax              ;save additional
                            ;registers
    push    es              ;
    push    si              ;

mov     ax,dseg_tbase   ;set up segment
                            ;register for
                            ;data area
    mov     es,ax           ;

mov     si,[bp].Bbase_rate  ;get lowest
                            ;divisor for heart
    mov     ax,[si]         ;rate from BASIC
    mov     base_rate,ax    ;and save in local
                            ;      data
                            ;      segment
    mov     si,[bp],Blfa_sacl   ;get low freq
                            ;      modulation
                            ;      scale
    mov     ax,[si]         ;      from BASIC
    mov     lfa_scal,al     ;and save LSbyte in
                            ;local data
                            ;  segment mov     si,[bp].Brfa_scal   ;get high freq
                            ;   modulation scale
    mov     ax,[si]         ;from BASIC
    mov     rfa_scal,al     ;and save
                            ;LSbyte in local data
                            ;segment
    mov     si,[bp].B_lreset    ;get low freq
                            ;   timer reset value
    mov     ax,[si]         ;from BASIC
    mov     tbase_rst,ax    ;and save in
                            ;  local data segment ;...........return to BASIC
```

```
                pop     si          ;restore additional
                                    ;registers
                pop     es          ;
                pop     ax          ;

pop     bp          ;restore BASIC's base
                                    ;pointer,
                ret     8           ;delete 4 parameters (8
                                    ; bytes) from the stack
                                    ;and return to the
                                    ; calling routine debugmsg 7      db      'this is the end of the heart rate
                        setup routine' hrsetup         endp cseg_calibs     ends end
```

What is claimed is:

1. An apparatus for correcting artifacts in a series of heartbeats comprising:
   means for collecting a series of heartbeat samples;
   means, coupled to said means for collecting, for selecting an appropriate interval between heartbeats;
   means, coupled to said means for selecting, for identifying a mean variance among the intervals between heartbeat samples;
   means, coupled to said means for identifying, for establishing an acceptable range of slewing rates as a function of the means variance;
   means, coupled to said means for selecting, for particularizing the absolute value of the slewing rate of a heartbeat sample relative to the mean interval; and
   means, coupled to said means for particularizing, for substituting the appropriate interval between heartbeats for all heartbeat interval samples having an absolute value outside the range of acceptable slewing rates.

2. The apparatus as recited in claim 1 wherein said means for selecting an appropriate interval comprises means for dividing intervals having a length equal to a multiple of the appropriate interval by the multiple.

3. The apparatus as recited in claim 1 wherein said means for selecting an appropriate interval comprises means for discarding interval shorter than a predetermined length.

4. The apparatus as recited in claim 1 wherein said means for selecting an appropriate interval comprises means for determining a mean interval and means for substituting a mean interval for intervals having preceded by a preselected number of intervals having an absolute value outside the range of acceptable slewing rates and having an absolute value outside of the range of acceptable slewing rates.

5. A method for correcting artifacts in a series of heartbeats comprising the steps of:
   collecting a series of heartbeat samples;
   selecting an appropriate interval between heartbeats;
   identifying variances in the intervals between heartbeats;
   establishing an acceptable range of slewing rates as a function of a mean variance;
   particularizing the absolute value of the slewing rate of a heartbeat sample relative to the mean interval; and
   substituting the selected interval for all heartbeat interval samples having an absolute value outside the range of acceptable slewing rates.

6. The method as recited in claim 5 wherein said selecting step comprises the step of dividing intervals having a length equal to a multiple of the appropriate interval by the multiple.

7. The method as recited in claim 5 wherein said selecting step comprises the steps of determining a mean interval and substituting a mean interval for intervals having preceded by a preselected number of intervals having an absolute value outside the range of acceptable slewing rates and having an absolute value outside of the range of acceptable slewing rates.

8. The method as recited in claim 5 wherein said selecting step comprises the step of discarding an interval shorter than a predetermined length.

9. Apparatus for calibrating a heart rate power spectrum monitor comprising:
   means for supplying a signal simulating a heart rate;
   means for generating a signal simulating a respiratory frequency fluctuation in heart rate;
   means for providing a signal simulating a low frequency fluctuation in heart rate; and
   means for applying signals from said means for supplying, said means for generating and said means for providing to a power spectrum monitor.

10. Apparatus for heart rate fluctuation power spectral analysis comprising:
    means for providing an electrocardiogram signal;
    means for supplying an electroplethysmogram signal;
    means, coupled to said means for providing and to said means for supplying, for obtaining a heart rate fluctuation power spectrum from an electrocardiogram signal and an electroplethysmogram signal; and
    relative means, coupled to said means for obtaining, for displaying a heart rate fluctuation power spectrum.

11. Apparatus for trending heart rate fluctuation power spectral data comprising:
    means for providing an electrocardiogram signal;
    means for supplying an electroplethysmogram signal;
    means, coupled to said means for providing and to said means for supplying, for obtaining a heart rate fluctuation power spectrum from an electrocardiogram signal and from an electroplethysmogram signal; and
    means, coupled to said means for obtaining, for storing heart rate fluctuation power spectral data;
    addressable means, coupled to said means for storing, for transmitting stored heart rate fluctuation power spectral data;
    means, coupled to said addressable means for transmitting, for converting heart rate fluctuation power spectral data into graphic form; and
    real time means, coupled to said means for converting, for displaying heart rate fluctuation power spectra.

12. The apparatus according to claim 11 further comprising:
    means, coupled between said means for obtaining and said means for storing, for segmenting data into overlapping samples.

13. A method for treatment of a condition related to malfunctions of the cardiovascular control system in a patient comprising the steps of:
    monitoring a power spectrum of heart rate fluctuations in the patient;
    identifying a level below about 0.1 (beats/min.)$^2$ in the power spectrum of heart rate fluctuations at a frequency between about 0.04 and about 0.10 Hz as indicative of cardiovascular stress; and
    applying a procedure to treat the condition and thereby to increase the level of heart rate fluctuations between about 0.04 and about 0.10 Hz.

14. A method for treatment of a condition related to malfunctions of the cardiovascular control system in a patient comprising the steps of:
    monitoring a power spectrum of heart rate fluctuations in the patient; and
    identifying a marked increase to above about 10 (beats/min.)$^2$ in heart rate fluctuations at a frequency between about 0.04 to about 0.10 Hz as indicative of cardiovascular instability; and
    applying a procedure to treat the condition and thereby to decrease the level of heart rate fluctuations between about 0.04 and 0.10 Hz.

15. A method for treatment of a condition related to cardiovascular control system in a patient comprising the steps of:
    monitoring a power spectrum of heart rate fluctuations in the patient; and
    identifying a ratio of the area under a heart rate fluctuation power spectrum of a peak at a frequency between about 0.04 and about 0.1 Hz to the area under a peak in the heart rate fluctuation power spectrum centered at the mean respiratory rate about 0.1 Hz as having an absolute value less than 2.0 as indicative of cardiac instability; and
    applying a procedure to treat the condition and thereby to increase the ratio.

16. A method for treatment of a condition related to cardiovascular control system in a patient comprising the steps of:
    monitoring a power spectrum of heart rate fluctuations in the patient; and
    identifying a ratio of the area under a heart rate fluctuation power spectrum of a peak at a frequency between about 0.04 and about 0.1 Hz to the area under a peak in the heart rate fluctuation power spectrum centered at the mean respiratory rate about 0.1 Hz as having an absolute value greater than or about 50 as indicative of cardiovascular stress; and
    applying a procedure to treat the condition and thereby to increase the ratio.

* * * * *